United States Patent
Le Tiran et al.

(10) Patent No.: US 10,688,101 B2
(45) Date of Patent: *Jun. 23, 2020

(54) PYRROLE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Arnaud Le Tiran, Croissy sur Seine (FR); Thierry Le Diguarher, Saint Denis de l'Hôtel (FR); Jérôme-Benoît Starck, Rueil-Malmaison (FR); Jean-Michel Henlin, Suresnes (FR); Anne-Françoise Guillouzic, Nanterre (FR); Guillaume De Nanteuil, Suresnes (FR); Olivier Geneste, Rueil-Malmaison (FR); Imre Fejes, Budapest (HU); János Tatai, Budapest (HU); Miklós Nyerges, Leányfalu (HU); James Edward Paul Davidson, Great Shelford (GB); James Brooke Murray, Linton (GB); I-Jen Chen, Cambridge (GB); Didier Durand, Chambourcy (FR)

(73) Assignees: LES LABORATORIES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,171

(22) Filed: Feb. 8, 2019

(65) Prior Publication Data

US 2019/0192528 A1    Jun. 27, 2019

Related U.S. Application Data

(60) Continuation of application No. 15/419,228, filed on Jan. 30, 2017, now Pat. No. 10,265,323, which is a (Continued)

(30) Foreign Application Priority Data

Jul. 23, 2013 (FR) ...................... 13 57258

(51) Int. Cl.
    *A61K 31/5383* (2006.01)
    *A61K 45/06* (2006.01)
    (Continued)

(52) U.S. Cl.
    CPC ........ *A61K 31/5383* (2013.01); *A61K 9/2059* (2013.01); *A61K 31/4725* (2013.01);
    (Continued)

(58) Field of Classification Search
    None
    See application file for complete search history.

(56) References Cited

U.S. PATENT DOCUMENTS

| 8,557,812 B2 | 10/2013 | Wang et al. |
| 9,108,983 B2 * | 8/2015 | Le Tiran ............. C07D 401/14 |

(Continued)

FOREIGN PATENT DOCUMENTS

| RU | 2009105196 | 8/2010 |
| WO | WO2002/46171 | 6/2002 |

(Continued)

OTHER PUBLICATIONS

French Preliminary Search Report for FR 13/57258 of Feb. 17, 2014.
Ashkenazi, A., "Directing cancer cells to self-destruct with pro-apoptotic receptor agonists", Nature Reviews Drug Discovery, Focus on Apoptosis, vol. 7, Dec. 2008, pp. 1001-1012.
Bardwell, et al., Journal of Immunology, 2009, 182, 7482-7489.
Collison, Nature Reviews Rheumatology, 2016, doi:10.1038/nrrheum.2016.90.
Deng, et al., Cancer Cell, 2007, 12, 171-185.
Hanada, et al.. Blood, 1993, 82, 1820-1828.
Hockenbery, et al., Proc. Natl. Acad. Sci. USA, 1991, 88, 6961-6965.
Juin, et al., Nature Reviews Cancer 2013, 13, 455-465.
Kelly, et al., Cell Death and Differentiation, 2011, 18, 1414-1424.
Kirkin, et al., Biochimica et Biophysica Acta, 2004, 1644, 229-249.
(Continued)

*Primary Examiner* — Zinna Northington Davis
(74) *Attorney, Agent, or Firm* — Hueschen and Sage

(57) ABSTRACT

Compounds of formula (I):

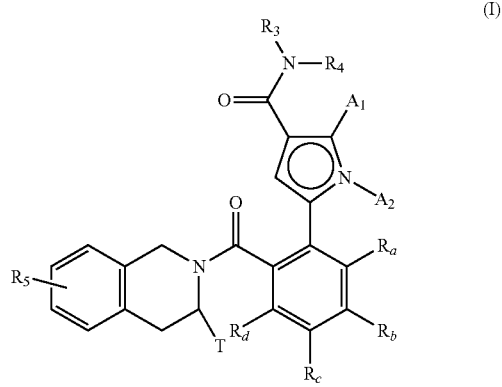

wherein $A_1$, $A_2$, $R_a$, $R_b$, $R_c$, $R_d$, $R_3$, $R_4$, $R_5$ and T are as defined in the description. Medicinal products containing the same which are useful in treating pathologies involving a deficit in apoptosis, such as cancer, auto-immune diseases, and diseases of the immune system.

15 Claims, No Drawings

Related U.S. Application Data continuation of application No. 14/797,532, filed on Jul. 13, 2015, now Pat. No. 9,598,427, which is a division of application No. 14/336,311, filed on Jul. 21, 2014, now Pat. No. 9,108,983.

(51) Int. Cl.

| | | |
|---|---|---|
| *A61K 31/4725* | (2006.01) | |
| *A61K 31/5377* | (2006.01) | |
| *A61K 9/20* | (2006.01) | |
| *C07D 401/14* | (2006.01) | |
| *C07D 405/14* | (2006.01) | |
| *C07D 401/10* | (2006.01) | |
| *C07D 471/04* | (2006.01) | |
| *C07D 491/10* | (2006.01) | |
| *C07D 498/04* | (2006.01) | |
| *A61K 31/496* | (2006.01) | |
| *A61K 31/506* | (2006.01) | |
| *C07D 491/107* | (2006.01) | |
| *C07D 498/14* | (2006.01) | |

(52) U.S. Cl.
CPC .......... *A61K 31/496* (2013.01); *A61K 31/506* (2013.01); *A61K 31/5377* (2013.01); *A61K 45/06* (2013.01); *C07D 401/10* (2013.01); *C07D 401/14* (2013.01); *C07D 405/14* (2013.01); *C07D 471/04* (2013.01); *C07D 491/10* (2013.01); *C07D 491/107* (2013.01); *C07D 498/04* (2013.01); *C07D 498/14* (2013.01)

(56) References Cited

U.S. PATENT DOCUMENTS

| | | |
|---|---|---|
| 9,598,427 B2 | 3/2017 | Le Tiran |
| 10,265,323 B2 * | 4/2019 | Le Tiran .............. C07D 401/14 |

FOREIGN PATENT DOCUMENTS

| | | |
|---|---|---|
| WO | WO2006/023778 | 3/2006 |
| WO | WO2006/087309 A1 | 8/2006 |
| WO | WO2008/008912 | 1/2008 |
| WO | WO2009/073545 | 6/2009 |
| WO | WO2010/080503 | 7/2010 |
| WO | WO2012/162365 | 11/2012 |
| WO | WO2013/096055 A1 | 6/2013 |
| WO | WO2013/096060 | 6/2013 |
| WO | WO2013/110890 | 8/2013 |

OTHER PUBLICATIONS

Ko, et al.: Arthritis & Rheumatology, 2016, 68, 2740-2751.
Letai, et al., Blood, 2005, 106, 5008.
Monni, et al.. Blood, 1997, 90, 1168-1174.
Slavov, et al., Proc. Natl. Acad. Sci. USA, 2009, 106, 4079-4084.
Strasser, et al., Nature Reviews Immunology, 2005, 5, 189-200.
Strasser, et al., Proc. Natl. Acad. Sol. USA, 1991, 88, 8661-8665.
Tsujimoto, et al., Science, 1985, 228, 1440-1443.
Vaux, et al., Nature, 1988, 335, 440-442.
Yip, et al., Oncogene, 2008, 27, 6398-6406.

* cited by examiner

PYRROLE COMPOUNDS, A PROCESS FOR THEIR PREPARATION AND PHARMACEUTICAL COMPOSITIONS CONTAINING THEM

The present invention relates to new pyrrole compounds, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colorectal cancer, breast cancer, small-cell lung cancer, non-small-cell lung cancer, bladder cancer, ovarian cancer, prostate cancer, chronic lymphoid leukaemia, follicular lymphoma, myeloma, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer, autoimmune diseases and diseases of the immune system.

The present invention relates more especially to compounds of formula (I):

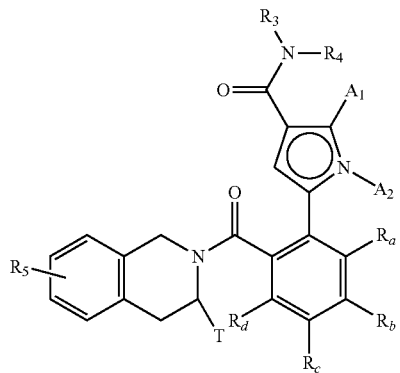

wherein:
$A_1$ and $A_2$, each independently of the other, represent a hydrogen or halogen atom, a linear or branched ($C_1$-$C_6$)polyhaloalkyl group, a linear or branched ($C_1$-$C_6$) alkyl group or a cycloalkyl group, T represents a hydrogen atom, a linear or branched ($C_1$-$C_6$)alkyl group optionally substituted by from one to three halogen atoms, a group ($C_1$-$C_4$)alkyl—$NR_1R_2$, or a group ($C_1$-$C_4$)alkyl—$OR_6$, $R_1$ and $R_2$, each independently of the other, represent a hydrogen atom or a linear or branched ($C_1$-$C_6$)alkyl group, or $R_1$ and $R_2$ form with the nitrogen atom carrying them a heterocycloalkyl, $R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl moiety is linear or branched, a heterocycloalkyl group, an aryl group or a heteroaryl group, it being understood that one or more of the carbon atoms of the preceding groups, or of their possible substituents, may be deuterated, $R_4$ represents an aryl group, a heteroaryl group, a cycloalkyl group or a linear or branched ($C_1$-$C_6$)alkyl group, it being understood that one or more of the carbon atoms of the preceding groups, or of their possible substituents, may be deuterated, $R_5$ represents a hydrogen or halogen atom, a linear or branched ($C_1$-$C_6$)alkyl group, or a linear or branched ($C_1$-$C_6$)alkoxy group, $R_6$ represents a hydrogen atom or a linear or branched ($C_1$-$C_6$)alkyl group, $R_a$, $R_b$, $R_c$ and $R_d$, each independently of the others, represent $R_7$, a halogen atom, a linear or branched ($C_1$-$C_6$)alkoxy group, a hydroxy group, a linear or branched ($C_1$-$C_6$)polyhaloalkyl group, a trifluoromethoxy group, —$NR_7R_7'$, nitro, $R_7$—CO—($C_0$-$C_6$) alkyl-, $R_7$—CO—NH—($C_0$-$C_6$)alkyl-, $NR_7R_7'$—CO—($C_0$-$C_6$)alkyl-, $NR_7R_7'$—CO—($C_0$-$C_6$)alkyl-O—, $R_7$—$SO_2$—NH—($C_0$-$C_6$)alkyl-, $R_7$—NH—CO—NH—($C_0$-$C_6$)alkyl-, $R_7$—O—CO—NH—($C_0$-$C_6$) alkyl-, a heterocycloalkyl group, or the substituents of one of the pairs ($R_a$,$R_b$), ($R_b$,$R_c$) or ($R_c$,$R_d$) form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched $(C_1\text{-}C_6)$alkyl, $R_7$ and $R_7'$, each independently of the other, represent a hydrogen, a linear or branched $(C_1\text{-}C_6)$alkyl, a linear or branched $(C_2\text{-}C_6)$alkenyl, a linear or branched $(C_2\text{-}C_6)$alkynyl, an aryl or a heteroaryl, or $R_7$ and $R_7'$, together with the nitrogen atom carrying them, form a heterocycle composed of from 5 to 7 ring members, it being understood that:

"aryl" means a phenyl, naphthyl, biphenyl or indenyl group,

"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens), "cycloalkyl" means any mono- or bi-cyclic, non-aromatic, carbocyclic group containing from 3 to 10 ring members, "heterocycloalkyl" means any mono- or bi-cyclic, non-aromatic, condensed or spiro group composed of from 3 to 10 ring members and containing from 1 to 3 hetero atoms selected from oxygen, sulphur, SO, $SO_2$ and nitrogen, it being possible for the aryl, heteroaryl, cycloalkyl and heterocycloalkyl groups so defined and the groups alkyl, alkenyl, alkynyl and alkoxy to be substituted by from 1 to 3 groups selected from optionally substituted, linear or branched $(C_1\text{-}C_6)$alkyl, $(C_3\text{-}C_6)$spiro, optionally substituted, linear or branched $(C_1\text{-}C_6)$alkoxy, $(C_1\text{-}C_6)$alkyl-S-, hydroxy, oxo (or N-oxide where appropriate), nitro, cyano, —COOR', —OCOR', NR'R", linear or branched $(C_1\text{-}C_6)$polyhaloalkyl, trifluoromethoxy, $(C_1\text{-}C_6)$alkylsulphonyl, halogen, optionally substituted aryl, heteroaryl, aryloxy, arylthio, cycloalkyl, heterocycloalkyl optionally substituted by one or more halogen atoms or alkyl groups, it being understood that R' and R", each independently of the other, represent a hydrogen atom or an optionally substituted, linear or branched $(C_1\text{-}C_6)$alkyl group, to their enantiomers and diastereoisomers, and to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Advantageously, $A_1$ represents a hydrogen atom or a methyl group.

Furthermore, $A_2$ preferably represents a linear or branched $(C_1\text{-}C_6)$alkyl group optionally substituted by a group selected from halogen, hydroxy, linear or branched $(C_1\text{-}C_6)$alkoxy, NR'R" and morpholine.

In another embodiment of the invention, $A_2$ represents a linear or branched $(C_1\text{-}C_6)$polyhaloalkyl group or a cyclopropyl group.

Even more preferably, $A_1$ and $A_2$ both represent a methyl group.

In a preferred embodiment of the invention, T represents a linear or branched $(C_1\text{-}C_6)$alkyl. In another preferred embodiment, T represents a group alkyl$(C_1\text{-}C_4)$—$NR_1R_2$, and more particularly a group alkyl$(C_1\text{-}C)$—$NR_1R_2$ wherein $R_1$ and $R_2$ form with the nitrogen atom carrying them a heterocycloalkyl.

In preferred compounds of the invention, T represents a methyl, aminomethyl, (morpholin-4-yl)methyl, (4-methylpipérazin-1-yl)methyl, 2-(morpholin-4-yl)ethyl, [2-(morpholin-4-yl)ethoxy]methyl, hydroxymethyl, [2-(dimethylamino)ethoxy]methyl, hexahydropyrazino[2,1-c][1,4]oxazin-8(1H)-ylmethyl, 1-oxa-6-azaspiro[3.3]hept-6-ylmethyl, 3-(morpholin-4-yl)propyl or trifluoromethyl group. Even more preferably, T represents a (morpholin-4-yl)methyl, methyl or 3-(morpholin-4-yl)propyl group.

Preferably, $R_a$ and $R_d$ each represent a hydrogen atom and ($R_b$,$R_c$), together with the carbon atoms carrying them, form a 1,3-dioxolane group or a 1,4-dioxane group; or $R_a$, $R_c$ and $R_d$ each represent a hydrogen atom and $R_b$ represents a hydrogen or halogen atom or a methoxy group. Even more preferably, $R_a$ and $R_d$ each represent a hydrogen atom and ($R_b$,$R_c$), together with the carbon atoms carrying them, form a 1,3-dioxolane group; or $R_a$, $R_c$ and $R_d$ each represent a hydrogen atom and $R_b$ represents a halogen, preferably a chlorine or fluorine atom.

In another embodiment of the invention, $R_a$ and $R_d$ each represent a hydrogen atom, $R_b$ represents a hydrogen or halogen atom and $R_c$ a hydroxy or methoxy group, or: $R_a$ and $R_d$ each represent a hydrogen atom, $R_b$ represents a hydroxy or methoxy group and $R_c$ a halogen atom.

Alternatively, $R_a$, $R_b$ and $R_d$ advantageously each represent a hydrogen atom and $R_c$ represents a group selected from $R_7$—O—NH—$(C_0\text{-}C_6)$alkyl-, $R_7$—$SO_2$—NH—$(C_0\text{-}C_6)$alkyl-, $R_7$—NH— CO—NH—$(C_0\text{-}C_6)$alkyl- and $R_7$—O—CO—NH—$(C_0\text{-}C_6)$alkyl-. For those specific compounds, $R_3$ preferably represents a linear or branched $(C_1\text{-}C_6)$alkyl or a heteroaryl optionally substituted by a linear or branched $(C_1\text{-}C_6)$alkyl, and $R_4$ represents a 4-hydroxyphenyl group. Even more preferably, $R_3$ represents a methyl.

Preferred $R_4$ groups are as follows: phenyl; 4-hydroxyphenyl; 3-fluoro-4-hydroxyphenyl; 2-hydroxypyrimidine; 3-hydroxypyridine. Even more preferably, $R_4$ represents a 4-hydroxyphenyl group.

In preferred compounds of the invention, $R_3$ represents a linear or branched $(C_1\text{-}C_6)$alkyl group (preferably methyl), aryl or heteroaryl, all being optionally substituted. The groups aryl and heteroaryl are more especially preferred. Finally, $R_3$ preferably represents a group selected from phenyl, 1H-pyrazole, 1H-indole, 1H-indazole, pyridine, pyrimidine, 1H-pyrrolo[2,3-b]pyridine, 2,3-dihydro-1H-pyrrolo[2,3-b]pyridine, 1H-benzimidazole, 1H-pyrrole, 1H-pyrrolo[2,3-c]pyridine, 1H-pyrrolo[3,2-b]pyridine, 5H-pyrrolo[3,2-d] pyrimidine, thiophene, pyrazine, 1H-pyrazolo[3,4-b]pyridine, 1,2-oxazole, and 1H-pyrazolo[1,5-a]pyrimidine, those groups optionally having one or more substituents selected from halogen, linear or branched $(C_1\text{-}C_6)$alkyl, linear or branched $(C_1\text{-}C_6)$alkoxy, cyano, cyclopropyl, oxetane, tetrahydrofuran, —CO—O—$CH_3$, trideuteriomethyl, 2-(morpholin-4-yl)ethyl and 2-(morpholin-4-yl)ethoxy. More preferably, $R_3$ represents a group 1-methyl-1H-pyrazol-4-yl, pyridin-4-yl, 1-methyl-1H-pyrrolo[2,3-b]pyridin-5-yl, 5-cyano-1-methyl-1H-pyrrol-3-yl, 5-cyano-1,2-dimethyl-1H-pyrrol-3-yl, 1-methyl-2,3-dihydro-1H-pyrrolo[2,3-b]pyridin-5-yl, 5-cyano-2-methyl-1-(trideuteriomethyl)-1H-pyrrol-3-yl.

Preferred compounds according to the invention are included in the following group:

5-(5-chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide,
5-(5-chloro-2-{[(3R)-3-methyl-3,4-dihydroisoquinolin-2 (1H)-yl]carbonyl}phenyl)-N-(4-hydroxyphenyl)-1,2-dimethyl-N-(pyridin-4-yl)-1H-pyrrole-3-carboxamide,
N-(4-hydroxyphenyl)-1,2-dimethyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide,
N-(4-hydroxyphenyl)-1,2-dimethyl-5-(6-{[(3R)-3-methyl-3,4-dihydroisoquinolin-2(1H)-yl]carbonyl}-1,3-benzodioxol-5-yl)-N-(pyridin-4-yl)-1H-pyrrole-3-carboxamide,
5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide,
5-(5-chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide,
5-(5-chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide,
5-(5-chloro-2-{[(3S)-3-(morpholin-4-ylmethyl)-3,4-dihydroisoquinolin-2(1H)-yl]carbonyl}phenyl)-N-(5-cyano-1-methyl-1H-pyrrol-3-yl)-N-(4-hydroxyphenyl)-1,2-dimethyl-1H-pyrrole-3-carboxamide,
N-(5-cyano-1-methyl-1H-pyrrol-3-yl)-5-(5-fluoro-2-{[(3S)-3-(morpholin-4-yl-methyl)-3,4-dihydroisoquinolin-2(1H)-yl]carbonyl}phenyl)-N-(4-hydroxyphenyl)-1,2-dimethyl-1H-pyrrole-3-carboxamide,
5-(5-chloro-2-{[(3S)-3-(morpholin-4-ylmethyl)-3,4-dihydroisoquinolin-2(1H)-yl]-carbonyl}phenyl)-N-(5-cyano-1,2-dimethyl-1H-pyrrol-3-yl)-N-(4-hydroxyphenyl)-1,2-dimethyl-1H-pyrrole-3-carboxamide,
5-(5-chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide,
N-(5-cyano-1,2-dimethyl-1H-pyrrol-3-yl)-5-(5-fluoro-2-{[(3S)-3-(morpholin-4-yl-methyl)-3,4-dihydroisoquinolin-2(1H)-yl]carbonyl}phenyl)-N-(4-hydroxyphenyl)-1,2-dimethyl-1H-pyrrole-3-carboxamide,
5-(5-chloro-2-{[(3S)-3-(morpholin-4-ylmethyl)-3,4-dihydroisoquinolin-2(1H)-yl]carbonyl}phenyl)-N -[5-cyano-2-methyl-1-(trideuteriomethyl)-1H-pyrrol-3-yl]-N-(4-hydroxyphenyl)-1,2-dimethyl-1H-pyrrole-3-carboxamide, their enantiomers and diastereoisomers, and addition salts thereof with a pharmaceutically acceptable acid or base.

The invention relates also to a process for the preparation of compounds of formula (I), which process is characterised in that there is used as starting material the compound of formula (II):

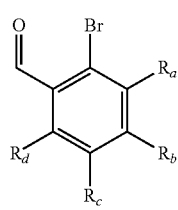

wherein $R_a$, $R_b$, $R_c$ and $R_d$ are as defined for formula (I), which compound of formula (II) is subjected to a Heck reaction, in an aqueous or organic medium, in the presence of a palladium catalyst, of a base, of a phosphine and of the compound of formula (III):

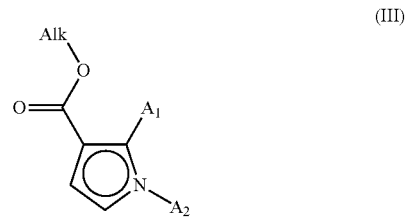

wherein the groups $A_1$ and $A_2$ are as defined for formula (I) and Alk represents a linear or branched $(C_1\text{-}C_6)$alkyl, to obtain the compound of formula (IV):

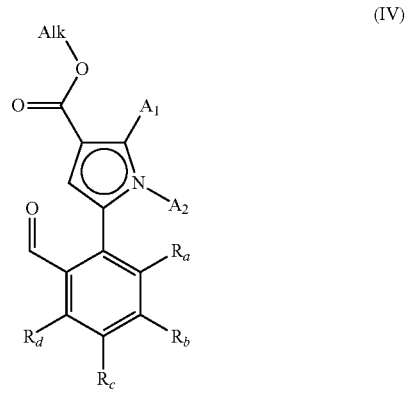

wherein $A_1$, $A_2$, $R_a$, $R_b$, $R_c$ and $R_d$ are as defined for formula (I) and Alk is as defined hereinbefore, the aldehyde function of which compound of formula (IV) is oxidised to a carboxylic acid to form the compound of formula (V):

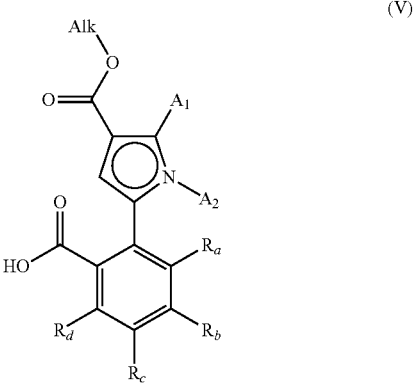

wherein $A_1$, $A_2$, $R_a$, $R_b$, $R_c$ and $R_d$ are as defined for formula (I) and Alk is as defined hereinbefore, which compound of formula (V) is then subjected to peptide coupling with a compound of formula (VI):

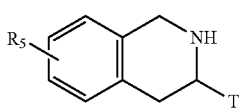
(VI)

wherein T and $R_5$ are as defined for formula (I), to yield the compound of formula (VII):

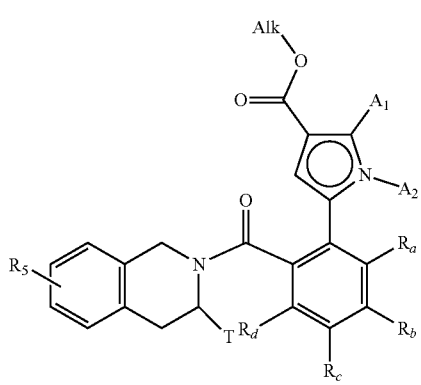
(VII)

wherein $A_1$, $A_2$, $R_a$, $R_b$, $R_c$, $R_d$, T and $R_5$ are as defined for formula (I) and Alk is as defined hereinbefore, the ester function of which compound of formula (VII) is hydrolysed to yield the corresponding carboxylic acid or carboxylate, which may be converted into an acid derivative such as the corresponding acyl chloride or anhydride before being coupled with an amine $NHR_3R_4$ wherein $R_3$ and $R_4$ have the same meanings as for formula (I), to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, it being understood that, at any time considered appropriate in the course of the above-described process, certain groups (hydroxy, amino . . . ) of the reagents or intermediates of synthesis may be protected and then deprotected according to the requirements of synthesis.

More particularly, when one of the groups $R_3$ or $R_4$ of the amine $NHR_3R_4$ is substituted by a hydroxy function, the latter may be subjected beforehand to a protection reaction prior to any coupling with the carboxylic acid formed from the compound of formula (VII), or with a corresponding acid derivative thereof, the resulting protected compound of formula (I) subsequently undergoes a deprotection reaction and is then optionally converted into one of its addition salts with a pharmaceutically acceptable acid or base.

The present invention relates also to an alternative process for the preparation of compounds of formula (I'), which are particular cases of the compounds of formula (I) as defined hereinbefore:

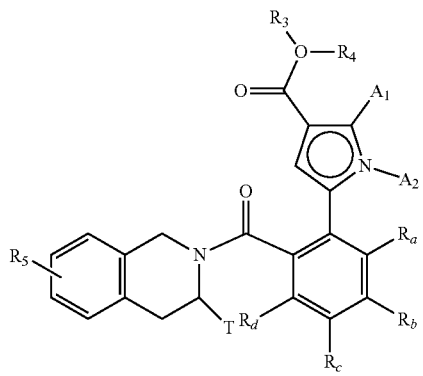
(I')

wherein:
$A_1$, $A_2$, $R_a$, $R_d$, $R_3$, $R_4$, T and $R_5$ are as defined for formula (I),
$R_b$ and $R_c$ are such that one represents a hydrogen and the other a group selected from $R_7$—O—NH—($C_0$-$C_6$)alkyl-, $R_7$—$SO_2$—NH—($C_0$-$C_6$)alkyl-, $R_7$—NH—CO—NH—($C_0$-$C_6$)alkyl- and $R_7$—O—CO—NH—($C_0$-$C_6$)alkyl-, which preparation process uses as starting material a compound of formula (II'):

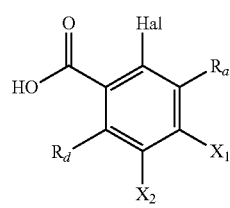
(II')

wherein:
$R_a$ and $R_d$ are as defined for formula (I),
Hal represents a halogen atom,
$X_1$ and $X_2$ are such that one represents a ($C_0$-$C_6$)alkyl-$NH_2$ group while the other represents a hydrogen atom,
which compound of formula (II') is then subjected to peptide coupling with a compound of formula (VI):

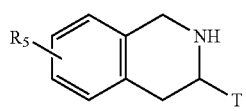
(VI)

wherein T and $R_5$ are as defined for formula (I), to yield the compound of formula (III'):

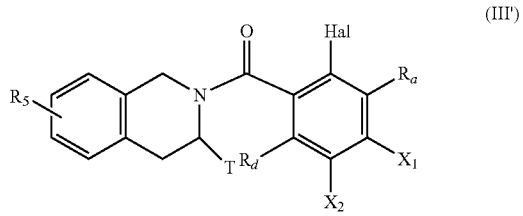
(III')

wherein:

R$_a$, R$_d$, T and R$_5$ are as defined for formula (I),

Hal represents a halogen atom,

X$_1$ and X$_2$ are such that one represents a (C$_0$-C$_6$)alkyl-NH$_2$ group while the other represents a hydrogen atom, which compound of formula (III') is subjected to a Heck reaction, in an aqueous or organic medium, in the presence of a palladium catalyst, of a base, of a phosphine and of a compound of formula (IV'):

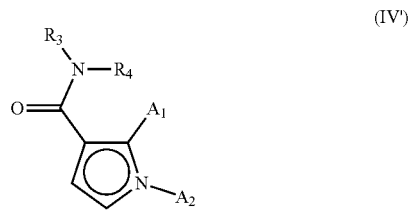

wherein A$_1$, A$_2$, R$_3$ and R$_4$ are as defined for formula (I), to form the compound of formula (V'):

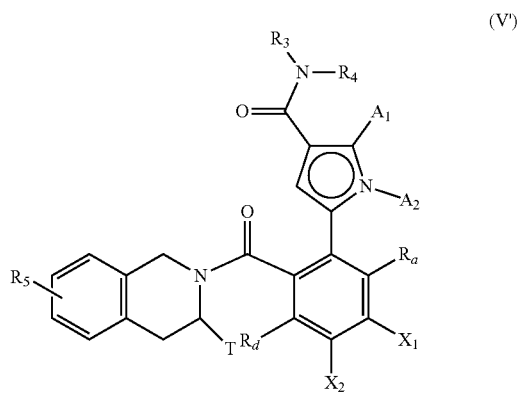

wherein:

A$_1$, A$_2$, R$_a$, R$_d$, R$_3$, R$_4$, T and R$_5$ are as defined for formula (I), X$_1$ and X$_2$ are such that one represents a (C$_0$-C$_6$)alkyl—NH$_2$ group while the other represents a hydrogen atom, which compound of formula (V') is then subjected to an acylation or sulphonylation reaction to yield the compound of formula (I'), which compound of formula (I') may be purified according to a conventional separation technique, which is converted, if desired, into its addition salts with a pharmaceutically acceptable acid or base and which is optionally separated into its isomers according to a conventional separation technique, it being understood that, at any time considered appropriate in the course of the above-described process, certain groups (hydroxy, amino . . . ) of the reagents or intermediates of synthesis may be protected and then deprotected according to the requirements of synthesis.

The compounds of formulae (II), (III), (II'), (IV'), (VI) and the amine NHR$_3$R$_4$ are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers, auto-immune diseases and diseases of the immune system.

More especially, the compounds according to the invention will be useful in the treatment of chemo- or radio-resistant cancers, and in malignant haemopathies and small-cell lung cancer.

Among the cancer treatments envisaged there may be mentioned, without implying any limitation, cancers of the bladder, brain, breast and uterus, chronic lymphoid leukaemias, colorectal cancer, cancers of the oesophagus and liver, lymphoblastic leukaemias, non-Hodgkin lymphomas, melanomas, malignant haemopathies, myelomas, ovarian cancer, non-small-cell lung cancer, prostate cancer and small-cell lung cancer. Among non-Hodgkin lymphomas, there may be mentioned more preferably follicular lymphomas, mantle cell lymphomas, diffuse large B-cell lymphomas, small lymphocytic lymphomas and marginal zone B-cell lymphomas.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, antimetabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn., 13, 2000, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol., 2001, 74(4):257-75), the protein Z derivative from the domain B of staphylococcal protein A, thioredoxin A or any protein with a repeated domain such as an "ankyrin repeat" (Kohl et al., PNAS, 2003, vol.100, No.4, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention without limiting it in any way.

Preparation 1: 4-Chloro-2-[4-(ethoxycarbonyl)-1,5-dimethyl-1H-pyrrol-2-yl]benzoic acid Step A: Ethyl 1,2-dimethyl-1H-pyrrole-3-carboxylate To a solution of 10 g of ethyl 2-methyl-1H-pyrrole-3-carboxylate (65.3 mmol) and 8.95 mL (130.6 mmol) of methyl iodide in 70 mL of dimethylformamide placed at 0° C. there are added, in three portions, 2.61 g (65.3 mmol) of sodium hydride (NaH) 60% . The batch is then stirred at 0° C. for 1 hour. Then, the reaction mixture is hydrolysed by the addition of 420 mL of ice-cold water. The reaction mixture is then diluted with ethyl acetate, successively washed with 0.1M aqueous hydrochloric acid (HCl) solution, saturated aqueous LiCl solution and then brine. The organic phase is then dried over $MgSO_4$, filtered, concentrated to dryness and purified by chromatography over silica gel (petroleum ether/AcOEt gradient).

$^1$H NMR: δ (400 MHz; dmso-d6; 300K): 6.65 (d, 1H pyrrole); 6.3 (1d, 1H pyrrole); 4.1 (1q, 2H, $OCH_2CH_3$); 3.5 (s, 3H N-pyrrole); 2.4 (s, 3H pyrrole); 1.5 (1t, 3H $OCH_2CH_3$)
IR: v: >C=O: 1688 cm$^{-1}$; v: C—O—C: 1172 cm$^{-1}$ Step B: Ethyl 5-(5-chloro-2-formylphenyl)-1,2-dimethyl-1H-pyrrole-3-carboxylate To a solution of 10.5 g of the compound obtained in Step A (62,8 mmol) in 65 mL of N,N-dimethylacetamide there are successively added 15.2 g of 2-bromo-4-chlorobenzaldehyde (69 mmol), 12.3 g of potassium acetate (125.6 mmol) and then the batch is stirred under argon for 20 minutes. There are then added 2.2 g of palladium catalyst $PdCl_2(PPh_3)_2$ (3.14 mmol). The reaction mixture is then heated at 130° C. overnight. The mixture is allowed to return to ambient temperature and it is then diluted with dichloromethane. Animal charcoal is added (2 g per g of product) and the batch is stirred at ambient temperature for 1 hour and then filtered. The organic phase is then washed with water, dried over $MgSO_4$ and concentrated to dryness. The crude product thereby obtained is purified by chromatography over silica gel (petroleum ether/AcOEt gradient). The title product is obtained in the form of a solid.

$^1$H NMR: δ (400 MHz; dmso-d6; 300K): 9.8 (s, 1H, formyl); 7.91-7.69-7.61 (d, 3H, aromatic Hs); 6.5 (s, 1H pyrrole); 4.2 (q, 2H, $OCH_2CH_3$); 3.4 (s, 3H, $CH_3$—N-pyrrole); 2.55 (s, 3H pyrrole); 1.28 (t, 3H, $OCH_2CH_3$)

Step C: 4-Chloro-2[4-(ethoxycarbonyl)-1,5-dimethyl-1H-pyrrol-2-yl]benzoic acid

A solution is prepared containing 12.85 g of the compound obtained in Step B (42 mmol) and 35.7 mL (336 mmol) of 2-methyl-2-butene in a mixture containing 20 mL of acetone and 20 mL of tetrahydrofuran. There are added, dropwise, 200 mL of an aqueous solution containing a mixture of 13.3 g of sodium chlorite ($NaClO_2$) (147 mmol) and 14.5 g of sodium hydrogen phosphate ($NaHPO_4$) (105 mmol). The batch is then vigorously stirred at ambient temperature for 7 hours. The reaction mixture is then concentrated to remove the acetone. Ethyl acetate is added, and the organic phase is washed with water, dried over $MgSO_4$ and then concentrated to dryness. The residue is then taken up in a minimum of ethyl ether. The solid then obtained is filtered off, washed with ether and then dried in vacuo at 40° C. overnight. The title product is obtained in the form of a solid, which is subsequently used without being otherwise purified.

$^1$H NMR: δ (400 MHz; dmso-d6; 300K): 13 (m, 1H COOH); 7.85-7.6-7.41(d,dd, wd, 3H, aromatic Hs); 6.3 (s, 1H, H pyrrole); 4.15 (q, 2H, $OCH_2CH_3$); 3.25 (s, 3H, $CH_3$—N-pyrrole); 2.5 (s, 3H, $CH_3$-pyrrole); 1.25 (t, 3H, $OCH_2CH_3$)
IR: v: —OH: 3100-2500 cm$^{-1}$ acid; v: >C=O: 1681 cm$^{-1}$ester+acid Preparation 2: 2-[4-(Ethoxycarbonyl)-1-methyl-1H-pyrrol-2-yl]benzoic acid The procedure is in accordance with the process of Preparation 1, replacing, on the one hand, the ethyl 2-methyl-1H-pyrrole-3-carboxylate used in Step A by ethyl 1H-pyrrole-3-carboxylate and, on the other hand, the 2-bromo-4-chlorobenzaldehyde used in Step B by 2-bromobenzaldehyde.

Preparation 3: 4-Chloro-2-[4-(ethoxycarbonyl)-1-methyl-1H-pyrrol-2-yl]benzoic acid The procedure is in accordance with the process of Preparation 1, replacing the ethyl 2-methyl-1H-pyrrole-3-carboxylate used in Step A by ethyl 1H-pyrrole-3-carboxylate.

Preparation 4: 6-[4-(Ethoxycarbonyl)-1-methyl-1H-pyrrol-2-yl]-1,3-benzodioxole-5-carboxylic acid The procedure is in accordance with the process of Preparation 1, replacing, on the one hand, the ethyl 2-methyl-1H-pyrrole-3-carboxylate used in Step A by ethyl 1H-pyrrole-3-carboxylate and, on the other hand, the 2-bromo-4-chlorobenzaldehyde used in Step B by 6-bromo-1,3-benzodioxole-5-carbaldehyde.
IR: v: —OH: 3500-2300 cm$^{-1}$ acid; v: >C=O: 1688-1670 cm$^{-1}$ ester+acid Preparation 5: 4-Chloro-2-[4-(ethoxycarbonyl)-1-ethyl-1H-pyrrol-2-yl]benzoic acid The procedure is in accordance with the process of Preparation 1, replacing in Step A, on the one hand, the ethyl 2-methyl-1H-pyrrole-3-carboxylate by ethyl 1H-pyrrole-3-carboxylate and, on the other hand, the methyl iodide by ethyl iodide (see the protocol described in U.S. Pat. No. 6,258,805 B1).

Preparation 6: 4-Chloro-2-[1-cyclopropyl-4-(ethoxycarbonyl)-1H-pyrrol-2-yl]benzoic acid The procedure is in accordance with the process of Preparation 1, replacing in Step A, on the one hand, the ethyl 2-methyl-1H-pyrrole-3-carboxylate by ethyl 1H-pyrrole-3-carboxylate and, on the other hand, the methyl iodide by cyclopropylboronic acid (see the protocol described in Bénard S. et al, Journal of Organic Chemistry 73(16), 6441-6444, 2008).

Preparation 7: 4-Chloro-2-[4-(ethoxycarbonyl)-1-(propan-2-)-1H-pyrrol-2-yl]-benzoic acid The procedure is in accordance with the process of Preparation 1, replacing in Step A, on the one hand, the ethyl 2-methyl-1H-pyrrole-3-carboxylate by ethyl 1H-pyrrole-3-carboxylate and, on the other hand, the methyl iodide by isopropyl iodide (see the protocol described in Okada E. et al, Heterocycles 34(7), 1435-1441, 1992).

Preparation 8: 4-Fluoro-2-[4-(methoxycarbonyl)-1,5-dimethyl-1H-pyrrol-2-yl]benzoic acid The procedure is in accordance with the process of Preparation 1, replacing, in Step A, the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-4-fluorobenzaldehyde.
IR: v: —OH: 2727-2379 cm$^{-1}$ acid; v: >C=O: 1687 cm$^{-1}$ Preparation 9: 6-{1-[2-(Benzyloxy)ethyl]-4-(ethoxycarbonyl)-5-methyl-1H-pyrrol-2-yl}-1,3-benzodioxole-5-carboxylic acid Step A: Ethyl 1-[2-(benzyloxy)ethyl]-2-methyl-1H-pyrrole-3-carboxylate The procedure is in accordance with the process of Step A of Preparation 1, replacing the methyl iodide used as alkylating agent by benzyl 2-bromoethyl ether.
$^1$H NMR: δ (400 MHz; dmso-d6; 300K): 7.32 (t, 2H, aromatic Hs, H meta benzyl ether); 7.3 (t, 1H, aromatic H, H para benzyl ether); 7.23 (d, 2H, aromatic Hs, H ortho benzyl ether); 6.72 (d, 1H, H-pyrrole); 6.35 (d, 1H, H-pyrrole); 4.48 (s, 2H, aliphatic Hs, O—CH$_2$-Ph); 4.15 (q, 2H, aliphatic Hs, O—CH$_2$—CH$_3$); 4.1 (t, 2H, aliphatic Hs, CH$_2$—O—CH$_2$-Ph); 3.7 (t, 2H, aliphatic Hs, CH$_2$—CH$_2$—O—CH$_2$-Ph); 2.45 (s, 3H, CH$_3$-pyrrole); 1.25 (t, 3H, aliphatic Hs, O—CH$_2$—CH$_3$)
IR: v: >C=O: 1689 cm$^{-1}$ Step B: 6-{1-[2-(Benzyloxy)ethyl]-4-(ethoxycarbonyl)-5-methyl-1H-pyrrol-2-yl}-1,3-benzodioxole-5-carboxylic acid The procedure is in accordance with the processes of Steps B and C of Preparation 1, replacing the 2-bromo-4-chlorobenzaldehyde by 6-bromo-1,3-benzodioxole-5-carbaldehyde.
$^1$H NMR: δ (400 MHz; dmso-d6; 300K): 7.35 (s, 1H, aromatic H, H benzodioxole); 7.30 (m, 3H, aromatic Hs, H benzyl ether); 7.25 (s, 1H, aromatic H, H benzodioxole); 7.10 (d, 2H, aromatic Hs, H ortho benzyl ether); 12.55 (broad s, 1H, COOH); 6.75 (s, 1H, H-pyrrole); 6.15 (broad s, 2H, aliphatic Hs, O—CH$_2$—O); 4.30 (s, 2H, aliphatic Hs, O—CH$_2$-Ph); 4.15 (q, 2H, aliphatic Hs, O—CH$_2$—CH$_3$); 3.9 (m, 2H, aliphatic Hs, CH$_2$—CH$_2$—O—CH$_2$-Ph); 3.40 (t, 2H, aliphatic Hs, CH$_2$—CH$_2$—O—CH$_2$-Ph); 2.50 (s, 3H, CH$_3$-pyrrole); 1.25 (t, 3H, aliphatic Hs, O—CH$_2$—CH$_3$)
IR: v: —OH: 3200-2300 cm$^{-1}$ acid; v: >C=O: 1687 cm$^{-1}$ acid Preparation 10: 2-{1-[3-(Benzyloxy)propyl]-4-(ethoxycarbonyl)-5-methyl-1H-pyrrol-2-yl}-4-fluorobenzoic acid The procedure is in accordance with the process of Preparation 9, replacing the benzyl 2-bromoethyl ether used in Step A by benzyl 3-bromopropyl ether and also the 6-bromo-1,3-benzodioxole-5-carbaldehyde used in Step B by 2-bromo-4-fluorobenzaldehyde.
IR: v: —OH: 3200-2305 cm$^{-1}$ acid; v: >C=O: 1690 cm$^{-1}$ acid Preparation 11: 6-[4-(Ethoxycarbonyl)-1,5-dimethyl-1H-pyrrol-2-yl]-3-benzo-dioxole-5-carboxylic acid The procedure is in accordance with the process of Preparation 1, replacing the 2-bromo-4-chlorobenzaldehyde used in Step B by 6-bromo-1,3-benzodioxole-5-carbaldehyde.

Preparation 12: 4-Methoxy-2-[4-(methoxycarbonyl)-1,5-dimethyl-1H-pyrrol-2-yl]-benzoic acid The procedure is in accordance with the process of Preparation 1, replacing the ethyl 2-methyl-1H-pyrrole-3-carboxylate used in Step A by methyl 2-methyl-1H-pyrrole-3-carboxylate and also the 2-bromo-4-chlorobenzaldehyde used in Step B by 2-bromo-4-methoxybenzaldehyde.
IR: v: —OH: 3000-2500 cm$^{-1}$ acid; v: >C=O: 1693+1670 cm$^{-1}$ acid+ester Preparation 13: 7-[4-(Methoxycarbonyl)-1,5-dimethyl-1H-pyrrol-2-yl]-2,3-dihydro-1,4-benzodioxin-6-carboxylic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 7-bromo-2,3-dihydro-1,4-benzodioxin-6-carbaldehyde.
IR: v: —OH: 3100-2500 cm$^{-1}$ acid; v: >C=O: 1690+1674 cm$^{-1}$ acid+ester Preparation 14: 4-Fluoro-5-methoxy-2-[4-(methoxycarbonyl)-1,5-dimethyl-1H-pyrrol-2-yl]benzoic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-4-fluoro-5-methoxybenzaldehyde.

Preparation 15: 4-Fluoro-5-hydroxy-2-[4-(methoxycarbonyl)-1,5-dimethyl-1H-pyrrol-2-yl]benzoic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-4-fluoro-5-hydroxy-benzaldehyde.

Preparation 16: 6-[4-(Ethoxycarbonyl)-1-methyl-5-trifluoromethyl-1H-pyrrol-2-yl]-1,3-benzodioxole-5-carboxylic acid The procedure is in accordance with the process of Preparation 1, replacing in Step A the ethyl 2-methyl-1H-pyrrole-3-carboxylate by ethyl 2-(trifluoromethyl)-1H-pyrrole-3-carboxylate and also the 2-bromo-4-chlorobenzaldehyde used in Step B by 6-bromo-1,3-benzodioxole-5-carbaldehyde.

Preparation 17: 6-[4-(Ethoxycarbonyl)-1-ethyl-5-methyl-1H-pyrrol-2-yl]-1,3-benzodioxole-5-carboxylic acid The procedure is in accordance with the process of Preparation 11, replacing the methyl iodide by ethyl iodide (see the protocol described in U.S. Pat. No. 6,258,805 B1).

Preparation 18: 6-[4-(Ethoxycarbonyl)-1-methyl-5-(trifluoromethyl)-1H-pyrrol-2-yl]-1,3-benzodioxole-5-carboxylic acid

Step A: Ethyl 1-methyl-2-(trifluoromethyl)pyrrole-3-carboxylate

Ethyl 4,4,4-trifluoro-3-oxo-butanoate (29 ml, 0.219 mmol) is added to methylamine (40% solution in water) (50 ml, 0.580 mmol) cooled to 10° C.; a white precipitate forms. 1,2-Dibromoethyl acetate (prepared according to *Molecules*, 16, 9368-9385; 2011) is added dropwise. The reactor is then sealed and heated at 70° C. for 45 minutes. The reaction mixture is cooled, then extracted with ethyl acetate, dried over sodium sulphate ($Na_2SO_4$) and evaporated to dryness. The crude reaction product obtained is purified by chromatography over silica gel using heptane and ethyl acetate as eluants. The expected compound is obtained in the form of crystals.

$^1$H NMR (400 MHz, dmso-d6) δ ppm: 7.11 (d, 1H), 6.52 (d, 1H), 4.21 (quad, 2H), 3.8 (s, 3H), 1.27 (t, 3H)

$^{19}$F NMR (400 MHz, dmso-d6) δ ppm: −53.9

IR (ATR) cm$^{-1}$: 3145+3128 v —CH, 1711 v >C=O, 1183+1117+1078 v —CF3

Step B: 6-[4-(Ethoxycarbonyl)-1-methyl-5-(trifluoromethyl)-1H-pyrrol-2-yl]-1,3-benzodioxole-5-carboxylic acid The procedure is in accordance with the protocol described in Steps B and C of Preparation 1, replacing the 2-bromo-4-chlorobenzaldehyde used in Step B by 6-bromo-1,3-benzodioxole-5-carbaldehyde.

Preparation 19: 6-[1-(2-Benzyloxyethyl)-4-ethoxycarbonyl-5-methyl-1H-pyrrol-2-yl]-1,3-benzodioxole-5-carboxylic acid

Step A: Ethyl 1-(2-benzyloxyethyl)-2-methyl-pyrrole-3-carboxylate

Ethyl 2-methyl-1H-pyrrole-3-carboxylate (10 g, 65.3 mmol) is dissolved in 100 mL of dimethylformamide under argon cooled to 0° C., and then 2-bromoethoxymethylbenzene (28.1 g, 130.6 mmol) is added all at once. The reaction mixture is placed under stirring. There is then added thereto, at 0° C., in three portions, NaH (1.72 g, 71.83 mmol) over a period of 15 minutes. The reaction mixture is stirred for 15 minutes at 0° C., and then for 15 hours at ambient temperature. It is then poured into an ice bath and then extracted 3 times with ethyl acetate. The organic phase is washed 3 times with saturated aqueous lithium chloride solution, dried over $MgSO_4$, filtered and then evaporated to dryness. The residue thereby obtained is purified by chromatography over silica gel using petroleum ether and ethyl acetate as eluants. The expected compound is obtained in the form of an oil.

$^1$H NMR (400 MHz, dmso-d6) δ ppm: 7.32 (t, 2H), 7.3 (t, 1H), 7.23 (d, 2H), 6.72 (d, 1H), 6.35 (d, 1H), 4.48 (s, 2H), 4.15 (quad., 2H), 4.1 (t, 2H), 3.7 (t, 2H), 2.45 (s, 3H), 1.25 (t, 3H)

IR (ATR) cm$^{-1}$: 1689 v —C=O

Step B: Ethyl 1-(2-benzyloxyethyl)-5-(6-formyl-1,3-benzodioxol-5-yl)-2-methyl-pyrrole-3-carboxylate The procedure is in accordance with the process of Step B of Preparation 1, replacing the 2-bromo-4-chlorobenzaldehyde by 6-bromo-1,3-benzodioxole-5-carbaldehyde.

$^1$H NMR (400 MHz, dmso-d6) δ ppm: 9.5 (s, 1H), 7.3 (s, 1H), 7.25 (m, 3H), 7.05 (m, 2H), 7 (s, 1H), 6.4 (s, 1H), 6.2 (bs, 2H), 4.25 (s, 2H), 4.2 (quad., 2H), 4.05 (m, 2H), 3.4 (m, 2H), 2.55 (s, 3H), 1.25 (t, 3H)

Step C: 6-[1-(2-Benzyloxyethyl)-4-ethoxycarbonyl-5-methyl-1H-pyrrol-2-yl]-1,3-benzodioxole-5-carboxylic acid The procedure is in accordance with the process of Step C of Preparation 1.

$^1$H NMR (400 MHz, dmso-d6) δ ppm: 12.55 (bs, 1H), 7.35 (s, 1H), 7.3 (m, 3H), 7.2 (m, 3H), 6.75 (s, 1H), 6.15 (s, 2H), 4.3 (s, 2H), 4.15 (quad., 2H), 3.9 (m, 2H), 3.4 (t, 2H), 2.5 (s, 3H), 1.25 (t, 3H)

IR (ATR) cm$^{-1}$:3200-2300 v —OH, 1687 (+shoulder) v—C=O carboxylic acid+conjugated ester

Preparation 20: 6-[4-(Ethoxycarbonyl)-1-ethyl-5-methyl-1H-pyrrol-2-yl]-1,3-benzodioxole-5-carboxylic acid The procedure is in accordance with the protocol described in Preparation 11, replacing the methyl iodide by ethyl iodide.

$^1$H NMR (400 MHz, dmso-d6) δ ppm: 12.49 (bs, 1H), 7.33 (s, 1H), 6.89 (s, 1H), 6.17 (s, 2H), 6.13 (s, 1H), 4.15 (quad, 2H), 3.69 (quad, 2H), 2.51 (s, 3H), 1.24 (t, 3H), 1.01 (t, 3H)

Preparation 21: 6-[4-(Ethoxycarbonyl)-1-(2-fluoro-ethyl)-5-methyl-1H-pyrrol-2-yl]-1,3-benzodioxole-5-carboxylic acid The procedure is in accordance with the process of Preparation 11, replacing the methyl iodide by 1-bromo-2-fluoroethane.

$^1$H NMR (400 MHz, dmso-d6, 300K) δ ppm: 12.53 (bs, 1H), 7.34 (s, 1H), 6.9 (s, 1H), 6.16 (s, 1H), 6.16 (s, 2H), 4.4 (dt, 2H), 4.15 (quad, 2H), 4.01 (m, 2H), 2.51 (s, 3H), 1.24 (t, 3H)

$^{19}$F NMR (400 MHz, dmso-d6, 300 K) δ ppm: −222

IR: v: —OH: 3700-2400 cm$^{-1}$ acid; v: >C═O: 1689 cm$^{-1}$ acid; v: >CF: 1213 cm$^{-1}$

Preparation 22: 6-{4-(Ethoxycarbonyl)-1-methyl-5-[2-(morpholin-4-yl)ethyl]-1H-pyrrol-2-yl}-1,3-benzodioxole-5-carboxylic acid

Step A: 3,3-Diethoxypropanoic acid

To a solution of 25 g of ethyl 3,3-diethoxypropionate (131 mmol) in 79 mL of methanol there are added 13.1 mL of aqueous 35% sodium hydroxide solution (452 mmol). The reaction mixture is stirred at ambient temperature for 3 hours. The reaction mixture is then concentrated to remove the methanol. After dissolving the undissolved material by adding water, aqueous 5N HCl solution is added to obtain a pH of 5. Dichloromethane is added and then the organic phase is washed with brine. After drying over MgSO$_4$ and concentrating to dryness, the title product is obtained in the form of an oil which is used in the next Step without being otherwise purified.

$^1$H NMR (400 MHz, dmso-d6) δ ppm: 12.2 (s, 1H), 4.8 (t, 1H), 3.58/3.47 (2m, 4H), 2.5 (d, 2H), 1.09 (t, 6H)

Step B: Ethyl 5,5-diethoxy-3-oxo-pentanoate

To a solution of 16 mL of 3-ethoxy-3-oxomalonic acid (135 mmol) in 40 mL of tetrahydrofuran there are added, under argon, 21.9 g of powdered magnesium (90.4 mmol). The mixture obtained is then heated at 80° C. for 7 hours. After returning to ambient temperature, this mixture is transferred by cannula to a solution of 10 g of the compound obtained in Step A (61.7 mmol) in 64 mL of tetrahydrofuran to which there has previously been added, in portions, 11 g of carbonyldiimidazole (66 mmol). The reaction mixture is stirred for 3 days at ambient temperature. After concentration, the residue is taken up in a mixture of ethyl acetate and aqueous sodium hydrogen sulphate (NaHSO$_4$) solution. The mixture is stirred vigorously until no more gas is evolved. After separation of the phases, the organic phase is washed successively with water, saturated aqueous NaHCO$_3$ solution and finally brine. After drying over MgSO$_4$ and concentrating to dryness, the title product is obtained in the form of an oil which is used in the next Step without being otherwise purified.

$^1$H NMR (400 MHz, dmso-d6) δ ppm: 4.84 (t, 1H), 4.08 (q, 2H), 3.59 (s, 2H), 3.56/3.46 (2m, 4H), 2.8 (d, 2H), 1.18 (t, 3H), 1.09 (t, 6H)

Step C: Ethyl 2-(2,2-diethoxyethyl)-1-methyl-pyrrole-3-carboxylate

To a solution of 11.8 g of the compound obtained in Step B (50.8 mmol) in 76 mL of water there are added, dropwise at 0° C., 6.6 ml of aqueous 40% methylamine solution (76.2 mmol). The reaction mixture is stirred and gently reheated to ambient temperature over 5 hours. After returning to 0° C., 8.8 mL of aqueous 40% methylamine solution (102 mmol) and then 16.6 mL of aqueous 50% chloroacetaldehyde solution (127 mmol) are each added dropwise at a temperature of less than 10° C. The reaction mixture is stirred at ambient temperature for 16 hours and then diluted with ethyl acetate. The organic phase is washed with brine, dried over MgSO$_4$ and concentrated to dryness. The crude product thereby obtained is purified by chromatography over silica gel using petroleum ether and ethyl acetate as eluants. The title product is obtained in the form of an oil.

$^1$H NMR (400 MHz, dmso-d6) δ ppm: 6.7 (d, 1H), 6.33 (d, 1H), 4.55 (t, 1H), 4.15 (q, 2H), 3.6 (m, 2H), 3.6 (s, 3H), 3.3 (m, 2H), 3.15 (d, 2H), 1.25 (t, 3H), 1.05 (t, 6H)

Step D: Ethyl 1-methyl-2-(2-morpholinoethyl)pyrrole-3-carboxylate

To a solution of 3.8 g of the compound obtained in Step C (14.05 mmol) in 28 mL of tetrahydrofuran there are added 58 mL of aqueous 10% sulphuric acid solution. The reaction mixture is stirred at ambient temperature for 2 hours and then diluted with a mixture of ethyl acetate and water. After separation, the organic phase is washed with brine, dried over MgSO$_4$ and concentrated to dryness. To a solution of the residue thereby obtained in 70 mL of dichloroethane there are added a solution of 13.5 mL of morpholine (14.5 mmol) in a mixture composed of 30 mL of dichloroethane and 3.6 mL of 4N aqueous HCL solution in dioxane (14.5 mmol), and then 7.4 g of sodium triacetoxyborohydride (NaBH(OAc)$_3$) (35.13 mmol). The reaction mixture is stirred at ambient temperature for 3 hours and then diluted with a mixture of dichloromethane and saturated aqueous NaHCO$_3$ solution. After separation of the phases and extraction of the aqueous phase with dichloromethane, the organic phases are dried over MgSO$_4$ and concentrated to dryness. The crude product thereby obtained is purified by chromatography over silica gel using dichloromethane and methanol as eluants. The title product is isolated in the form of an oil.

$^1$H NMR (400 MHz, dmso-d6) δ ppm: 6.66 (d, 1H), 6.31 (d, 1H), 4.14 (q, 2H), 3.58 (s, 3H), 3.57 (m, 4H), 3.05 (m, 2H), 2.45-2.38 (m, 6H), 1.24 (t, 3H)

Step E: 6-{4-(Ethoxycarbonyl)-1-methyl-5-[2-(morpholin-4-yl)ethyl]-1H-pyrrol-2-yl}-1,3-benzodioxole-5-carboxylic acid The procedure is in accordance with Steps B and C of Preparation, 1 replacing the 2-bromo-4-chlorobenzaldehyde used in Step B by 6-bromo-1,3-benzodioxole-5-carbaldehyde.

Preparation 23: 6-[4-(Ethoxycarbonyl)-1-methyl-5-(morpholin-4-ylmethyl)-1H-pyrrol-2-yl]-1,3-benzodioxole-5-carboxylic acid

Step A: Ethyl 4,4-diethoxy-3-oxo-butanoate

To a solution of 40 g of ethyl diethoxyacetate (227 mmol) in 67 mL of ethyl acetate there are added under argon, in portions, 6 g of sodium (261 mmol). The reaction mixture is then stirred at ambient temperature for 48 hours. There are added 10 mL of methanol, and then the mixture is hydrolysed with 65 mL of water. The pH of the reaction mixture is adjusted to pH 6 by adding 1N aqueous HCl solution. The mixture is separated and then extracted with ethyl acetate. The organic phases are combined, washed with brine, dried over MgSO$_4$, filtered and concentrated to dryness. The title product is obtained in the form of an oil which is used in the next Step without being otherwise purified.

$^1$H NMR (400 MHz, CDCl$_3$) δ ppm: 3.6 (s, 2H), 1.28 (t, 9H), 3.7-3.6 (2m, 4H), 4.7 (s, 1H), 4.2 (quad, 2H)

Step B: Ethyl 2-(2,2-diethoxymethyl)-1-methyl-pyrrole-3-carboxylate

The title compound is obtained in accordance with the process described in Step C of Preparation 22, starting from the ethyl 4,4-diethoxy-3-oxo-butanoate obtained in the preceding Step.

$^1$H NMR (400 MHz, dmso-d6) δ ppm: 6.73 (d, 1H), 6.32 (d, 1H), 6.23 (s, 1H), 4.17 (q, 2H), 3.7 (s, 3H), 3.68/3.43 (2m, 4H), 1.26 (t, 3H), 1.13 (t, 6H)

Step C: Ethyl 1-methyl-2-(2-morpholinomethyl) pyrrole-3-carboxylate

The title compound is obtained in accordance with the process described in Step D of Preparation 22, starting from the ethyl 2-(2,2-diethoxymethyl)-1-methyl-pyrrole-3-carboxylate obtained in the preceding Step.

$^1$H NMR (400 MHz, dmso-d6) δ ppm: 6.74 (d, 1H), 6.32 (d, 1H), 4.15 (q, 2H), 3.8 (s, 2H), 3.65 (s, 3H), 3.5 (m, 4H), 2.32 (m, 4H), 1.22 (t, 3H)

Step D: 6-[4-(Ethoxycarbonyl)-1-methyl-5-(morpholin-4-ylmethyl)-1H-pyrrol-2-yl]-1,3-benzodioxole-5-carboxylic acid The procedure is in accordance with the protocol described in Steps B and C of Preparation 1, replacing the 2-bromo-4-chlorobenzaldehyde used in Step B by 6-bromo-1,3-benzodioxole-5-carbaldehyde.

Preparation 24: 6-[4-(Methoxycarbonyl)-5-(2-methoxyethyl)-1-methyl-1H-pyrrol-2-yl]-1,3-benzo-dioxole-5-carboxylic acid Step A: Methyl 2-(2-methoxyethyl)-1-methyl-pyrrole-3-carboxylate The title compound is obtained in accordance with the protocol of Step C of Preparation 22, using methyl 5-methoxy-3-oxovalerate.

$^1$H NMR (400 MHz, dmso-d6) δ ppm: 6.69 (wd, 1H), 6.31 (wd, 1H), 3.69 (s, 3H), 3.59 (s, 3H), 3.49 (t, 2H), 3.2 (s, 3H), 3.11 (t, 2H)

Step B: 6-[4-(Methoxycarbonyl)-5-(2-methoxy-ethyl)-1-methyl-1H-pyrrol-2-yl]-1,3-benzo-dioxole-5-carboxylic acid The procedure is in accordance with the protocol described in Steps B and C of Preparation 1, replacing the 2-bromo-4-chlorobenzaldehyde used in Step B by 6-bromo-1,3-benzodioxole-5-carbaldehyde.

Preparation 25: 2-[4-(Ethoxycarbonyl)-1,5-dimethyl-1H-pyrrol-2-yl]benzoic acid

The procedure is in accordance with the process of Preparation 1, replacing the 2-bromo-4-chlorobenzaldehyde used in Step B by 2-bromobenzaldehyde.

$^1$H NMR (400 MHz, dmso-d6) δ ppm: 12.81 (m, 1H), 7.84 (m, 1H), 7.59 (m, 1H), 7.51 (m, 1H), 7.35 (m, 1H), 6.23 (s, 1H), 4.16 (q, 2H), 3.24 (s, 3H), 2.5 (s, 3H), 1.25 (t, 3H)

Preparation 26: 5-Fluoro-2-[4-(methoxycarbonyl)4,5-dimethyl-1H-pyrrol-2-yl]-benzoic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-5-fluoro-benzaldehyde.

$^1$H NMR (400 MHz, dmso-d6) δ ppm: 7.6 (dd, 1H), 7.42 (m, 2H), 6.22 (s, 1H), 4.15 (q, 2H), 3.21 (s, 3H), 2.5 (s, 3H), 1.23 (t, 3H)

$^{19}$F NMR (400 MHz, dmso-d6) δ ppm: −113

Preparation 27: 2-[4-(Ethoxycarbonyl)1,5-dimethyl-1H-pyrrol-2-yl]-5-fluoro-4-methoxybenzoic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-4-methoxy-5-fluorobenzaldehyde.

$^1$H NMR (400 MHz, dmso-d6) δ ppm: 9.65 (d, 1H), 7.67 (d, 1H), 7.24 (d, 1H), 6.48 (s, 1H), 4.19 (q, 2H), 3.97 (s, 3H), 3.38 (s, 3H), 2.56 (s, 3H), 1.26 (t, 3H).

Preparation 28: 2-(4-Ethoxycarbonyl-1,5-dimethyl-1H-pyrrol-2-yl)-4-fluoro-5-methoxybenzoic acid The procedure is in accordance with Preparation 1, replacing the 2-bromo-4-chlorobenzaldehyde used in Step B by 4-fluoro-5-methoxybenzaldehyde.

$^1$H NMR (400 MHz, dmso-d6) δ ppm: 12.9 (m, 1H), 7.6 (d, 1H), 7.22 (d, 1H), 6.23 (s, 1H), 4.2 (quad, 2H), 3.95 (s, 3H), 3.25 (s, 3H), 2.5 (s, 3H), 1.25 (t, 3H)

Preparation 29: 5-Chloro-2-[4-(ethoxycarbonyl)-1,5-dimethyl-1H-pyrrol-2-yl]benzoic acid The procedure is in accordance with the process of Preparation 1, replacing the 2-bromo-4-chlorobenzaldehyde used in Step B by 2-bromo-5-chlorobenzaldehyde.

Preparation 30: 2-{1-[2-(Benzyloxy)ethyl]-4-(ethoxycarbonyl)-5-methyl-1H-pyrrol-2-yl}-4-chlorobenzoic acid The procedure is in accordance with the process of Preparation 19, replacing the 6-bromo-1,3-benzodioxole-5-carbaldehyde by 2-bromo-4-chlorobenzaldehyde.

Preparation 31: 5-Methoxy-2-[4-(methoxycarbonyl)-1,5-dimethyl-1H-pyrrol-2-yl]-benzoic acid The procedure is in accordance with the process of Preparation 1, replacing in Step A the ethyl 2-methyl-1H-pyrrole-3-carboxylate by methyl 2-methyl-1H-pyrrole-3-carboxylate and also the 2-bromo-4-chlorobenzaldehyde used in Step B by 2-bromo-5-methoxy-benzaldehyde.

$^1$H NMR (400 MHz, dmso-d6) δ ppm: 12.8 (bs, 1H), 7.34 (wd, 1H), 7.26 (d, 1H), 7.15 (dd, 1H), 6.19 (s, 1H), 3.84 (s, 3H), 3.69 (s, 3H), 3.22 (s, 3H), 2.5 (s, 3H)

Preparation 32: 6-[1-(2,2-Difluoroethyl)-4-(ethoxycarbonyl)-5-methyl-1H-pyrrol-2-yl]-1,3-benzodioxole-5-carboxylic acid The procedure is in accordance with the protocol of Preparation 19, replacing the 2-bromoethoxymethylbenzene used in Step A by 2-bromo-1,1-difluoro-ethane.

Preparation 1': (3R)-3-Methyl-1,2,3,4-tetrahydroisoquinoline hydrochloride

Step A: {(3S)-2-[(4-Methylphenyl)sulphonyl]-1,2,3,4-tetrahydroisoquinolin-3-yl}methyl 4-methylbenzenesulphonate To a solution of 30.2 g of [(3S)-1,2,3,4-tetrahydroisoquinolin-3-yl]methanol (185 mmol) in 750 mL of dichloromethane there are successively added 91.71 g of tosyl chloride (481 mmol) and then, dropwise, 122.3 mL of N,N,N-triethylamine (740 mmol). The reaction mixture is then stirred at ambient temperature for 20 hours. It is then diluted with dichloromethane, washed successively with 1M HCl solution, saturated aqueous NaHCO$_3$ solution and then brine until neutral. The organic phase is then dried over MgSO$_4$, filtered and concentrated to dryness. The solid obtained is then dissolved in a minimum volume of dichloromethane and then cyclohexane is added until a precipitate is formed. This precipitate is then filtered off and washed with cyclohexane. After drying, the title product is obtained in the form of crystals.

$^1$H NMR: δ (400 MHz; dmso-d6; 300K): 7.75 (d, 2H, aromatic Hs, ortho O-tosyl); 7.6 (d, 2H, aromatic Hs, ortho N-tosyl); 7.5 (d, 2H, aromatic Hs, meta O-tosyl); 7.3 (d, 2H, aromatic Hs, meta N-tosyl); 7.15-6.9 (m, 4H, aromatic Hs, tetrahydroisoquinoline); 4.4-4.15 (dd, 2H, aliphatic Hs, tetrahydroisoquinoline); 4.25 (m, 1H, aliphatic H, tetrahydroisoquinoline); 4.0-3.8 (2dd, 2H, aliphatic Hs, CH$_2$—O-tosyl); 2.7 (2dd, 2H, aliphatic Hs, tetrahydroisoquinoline); 2.45 (s, 3H, O—SO$_2$-Ph-CH$_3$); 2.35 (s, 3H, N—SO$_2$-Ph-CH$_3$)

IR: ν: —SO$_2$: 1339-1165 cm$^{-1}$

Step B: (3R)-3-Methyl-2-[(4-methylphenyl)sulphonyl]-1,2,3,4-tetrahydroisoquinoline To a suspension of 8.15 g (214.8 mmol) of lithium aluminium hydride (LiAlH$_4$) in 800 mL of methyl tert-butyl ether (MTBE) there are added 101.2 g of the ditosyl compound obtained in Step A (214.8 mmol) dissolved in 200 mL of MTBE. The batch is then heated at 50° C. for 2 hours. It is allowed to cool and placed at 0° C., and there are then added, dropwise, 12 mL of 5N NaOH solution. The batch is stirred at ambient temperature for 45 minutes. The solid thereby obtained is then filtered off and washed with MTBE and then with dichloromethane. The filtrate is then concentrated to dryness. The title product is then obtained in the form of a solid.

$^1$H NMR: δ (400 MHz; dmso-d6; 300K): 7.70 (d, 2H, aromatic Hs, ortho N-tosyl); 7.38 (d, 2H, aromatic Hs, meta N-tosyl); 7.2-7.0 (m, 4H, aromatic Hs, tetrahydroisoquinoline); 4.4 (m, 2H, aliphatic Hs, tetrahydroisoquinoline); 4.3 (m, 1H, aliphatic H, tetrahydroisoquinoline); 2.85-2.51 (2dd, 2H, aliphatic Hs, tetrahydroisoquinoline); 2.35 (s, 3H, N—SO$_2$-Ph—CH$_3$); 0.90 (d, 3H, tetrahydroisoquinoline-CH$_3$)

IR: ν: —SO$_2$: 1332-1154 cm$^{-1}$

Step C: (3R)-3-Methyl-1,2,3,4-tetrahydroisoquinoline

To a solution of 31.15 g (103.15 mmol) of the monotosyl compound obtained in Step B in 500 mL of anhydrous methanol there are added, in portions, 3.92 g (161 mmol) of magnesium turnings. The batch is stirred in the presence of ultrasound for 96 hours. The reaction mixture is then filtered and the solid is washed several times with methanol. The filtrate is then concentrated to dryness. After purification by chromatography over silica gel using dichloromethane and ammonia-in-ethanol as eluants, the title product is obtained in the form of an oil.

$^1$H NMR: δ (400 MHz; dmso-d6; 300K): 7.05 (m, 4H, aromatic Hs, tetrahydroisoquinoline); 3.90 (m, 2H, aliphatic Hs, tetrahydroisoquinoline); 2.85 (m, 1H, aliphatic H, tetrahydroisoquinoline); 2.68-2.4 (2dd, 2H, aliphatic Hs, tetrahydro-isoquinoline); 1.12 (d, 3H, tetrahydroisoquinoline-CH$_3$); 2.9-2.3 (m, broad, 1H, HN (tetrahydroisoquinoline))

IR: ν: —NH: 3248 cm$^{-1}$

Step D: (3R)-3-Methyl-1,2,3,4-tetrahydroisoquinoline hydrochloride

To a solution of 14.3 g (97.20 mmol) of the compound obtained in Step C in 20 mL of anhydrous ethanol there are added, dropwise, 100 mL of a 1M solution of HCl in ether. The batch is stirred at ambient temperature for 1 hour and then filtered. The crystals thereby obtained are washed with ethyl ether. After drying, the title product is obtained in the form of crystals.

$^1$H NMR: δ (400 MHz; dmso-d6; 300K): 9.57 (m, broad, 2H, NH$_2^+$ (tetrahydroisoquinoline)); 7.22 (m, 4H, aromatic Hs, tetrahydroisoquinoline); 4.27 (s, 2H, aliphatic Hs, tetrahydroisoquinoline); 3.52 (m, 1H, aliphatic H, tetrahydroisoquinoline); 3.03-2.85 (2dd, 2H, aliphatic Hs, tetrahydroisoquinoline); 1.39 (d, 3H, tetrahydroisoquinoline-CH$_3$)

IR: ν: —NH$_2^+$: 3000-2300 cm$^{-1}$; ν: aromatic —CH: 766 cm$^{-1}$

Preparation 2': tert-Butyl [(3S)-1,2,3,4-tetrahydroisoquinolin-3-ylmethyl]-carbamate

Step A: Benzyl (3S)-3-(hydroxymethyl)-3,4-dihydro-1H-isoquinoline-2-carboxylate This compound is obtained using a protocol from the literature (R. B. Kawthekar et al *South Africa Journal of Chemistry* 63, 195, 2009) starting from 15 g of (3S)-1,2,3,4-tetrahydroisoquinolin-3-ylmethanol (91,9 mmol) in the presence of benzyl chloroformate and triethylamine in solution in dichloromethane. After purification by chromatography over silica gel using petroleum ether and ethyl acetate as eluants, the title product is obtained in the form of an oil.

$^1$H NMR: δ (300 MHz; DMSO-d6; 300K): 7.33 (m, 5H, aromatic Hs, O-benzyl); 7.15 (s, 4H, aromatic Hs, H tetrahydroisoquinoline); 5.13 (s, 2H, CH$_2$-Ph); 4.73 (d, 1H, H tetrahydroisoquinoline); 4.47 (m, H, CH$_2$OH); 4.36 (m, 1H, H tetrahydroisoquinoline); 4.28 (d, 1H, H tetrahydroisoquinoline); 3.39 (dd, 1H, CH$_2$OH); 3.23 (dd, 1H, CH$_2$OH); 2.93 (dd, 1H, H tetrahydroisoquinoline); 2.86 (dd, 1H, H tetrahydroisoquinoline)

IR: v: OH: 3416 cm$^{-1}$; v: <C=O 1694 cm$^{-1}$; v:aromatic >C—H: 754 cm$^{-1}$

Step B: Benzyl (3S)-3-(azidomethyl)-3,4-dihydroisoquinoline-2(1H)-carboxylate This compound is obtained using a protocol from the literature (D. Pagé et al *J. Med. Chem*, 44, 2387, 2001) starting from 23 g of the compound obtained in Step A (77.3 mmol) in the presence of diphenylphosphoryl azide and triphenylphosphine in solution in THF. After purification by chromatography over silica gel using petroleum ether and ethyl acetate as eluants, the title product is obtained in the form of an oil.

$^1$H NMR: δ (400 MHz; DMSO-d6; 300K): 7.36 (m, 5H, aromatic Hs, O-benzyl); 7.19 (m, 4H, aromatic Hs, H tetrahydroisoquinoline); 5.16 (s, 2H, CH$_2$-Ph); 4.76 (d, 1H, H tetrahydroisoquinoline); 4.53 (m, 1H, H tetrahydroisoquinoline); 4.30 (m, 1H, H tetrahydroisoquinoline); 3.28 (m, 2H, CH$_2$N$_3$); 3.06 (dd, 1H, H tetrahydroisoquinoline); 2.78 (dd, 1H, H tetrahydroisoquinoline)

IR: v: N$_3$: 2095 cm$^{-1}$; v: <C=O:1694 cm$^{-1}$; v: aromatic >C—H: 754 cm$^{-1}$

Step C: Benzyl (3S)-3-(aminomethyl)-3,4-dihydroisoquinoline-2(1H)-carboxylate To a solution of 20.9 g (64.5 mmol) of the azido compound obtained in Step B in 650 mL of THF, there are successively added 25.5 g (97.2 mmol) of triphenylphosphine and 157 mL of water. The batch is refluxed for 2 hours 30 minutes. The reaction mixture is then concentrated to dryness and the residue oil is then taken up in isopropyl ether. A white precipitate appears; it is filtered off and washed with isopropyl ether. The filtrate is then concentrated to dryness and then purified by chromatography over silica gel using dichloromethane and methanol as eluants. The title product is obtained in the form of an oil.

$^1$H NMR: δ (400 MHz; DMSO-d6; 300K): 7.40 (m, 5H, aromatic Hs, O-benzyl); 7.20 (m, 4H, aromatic Hs, H tetrahydroisoquinoline); 5.15 (s, 2H, CH$_2$-Ph); 4.75-43 (m, 2H, H tetrahydroisoquinoline); 4.30 (d, 1H, H tetrahydroisoquinoline); 2.90 (m, 2H, CH$_2$NH$_2$); 2.45 (m, 2H, H tetrahydroisoquinoline); 1.40 (m, 2H, NH$_2$)

IR: v: NH$_2$: 3400-3300 cm$^{-1}$; v: <C=O: 1688 cm$^{-1}$

Step D: Benzyl (3S)-3-{[(tert-butoxycarbonyl)amino]methyl}-3,4-dihydroisoquinoline-2(1H)-carboxylate To a solution of 18.4 g (62.1 mmol) of the compound obtained in Step C in 630 mL of dichloromethane there are successively added 17.5 mL (124 mmol) of triethylamine and, in portions, 14.9 g (68.3 mmol) of di-tert-butyl dicarbonate. The batch is stirred at ambient temperature for 2 h. The reaction mixture is then concentrated and ethyl acetate is then added. The organic phase is successively washed with 1M HCl solution, brine, saturated aqueous NaHCO$_3$ solution and then brine. After drying, concentrating to dryness and purifying by chromatography over silica gel using petroleum ether and ethyl acetate as eluants, the title product is obtained in the form of an oil.

$^1$H NMR: δ (400 MHz; DMSO-d6; 300K): 7.35 (m, 5H, aromatic Hs, O-benzyl); 7.15 (m, 4H, aromatic Hs, H tetrahydroisoquinoline); 6.51 (m, 1H, NHBoc); 5.12 (s, 2H, CH$_2$-Ph); 4.76 (d, 1H, H tetrahydroisoquinoline); 4.51 (m, 1H, H tetrahydroisoquinoline); 4.36 (d, 1H, H tetrahydroisoquinoline); 2.95 (m, 3H, H tetrahydroisoquinoline+ CH$_2$NHBoc); 2.71 (d, 1H, H tetrahydroisoquinoline); 1.34 (s, 9H, NHBoc)

IR: v: NH: 3351 cm$^{-1}$; v: <C=O: 1686 cm$^{-1}$

Step E: tert-Butyl [(3S)-1,2,3,4-tetrahydroisoquinolin-3-ylmethyl]carbamate

To a solution of 21 g (53 mmol) of the compound obtained in Step D in 600 mL of ethyl acetate there are added 2.1 g of palladium-on-carbon 10%. The batch is stirred at ambient temperature under a pressure of 1.3 bars of dihydrogen for 5 hours. The reaction mixture is then filtered and then concentrated to dryness. The title product is obtained in the form of a solid.

$^1$H NMR: δ (400 MHz; DMSO-d6; 300K): 7.15 (m, 4H, aromatic Hs, H tetrahydroisoquinoline); 6.85 (t, 1H, NHBoc); 3.90 (m, 2H, H tetrahydroisoquinoline); 3.00 (m, 2H, CH$_2$NHBoc); 2.80 (m, 1H, H tetrahydroisoquinoline); 2.65 (dd, 1H, H tetrahydroisoquinoline); 2.40 (dd, 1H, H tetrahydroisoquinoline); 1.40 (s, 9H, NHBoc)

IR: v: NH: 3386-3205 cm$^{-1}$ (NH amide); v: <C=O: 1688 cm$^{-1}$; v: NH: 1526 cm$^{-1}$ (NH amine)

Preparation 3': (3S)-3-(4-Morpholinylmethyl)-2,3,4-tetrahydroisoquinoline

Step A: Benzyl (3S)-3-(4-morpholinylcarbonyl)-3,4-dihydro-2(1H)-isoquinolinecarboxylate To a solution of 5 g of (3S)-2-[(benzyloxy)carbonyl]-1,2,3,4-tetrahydro-3-isoquinolinecarboxylic acid (16 mmol) in 160 mL of dichloromethane there are added 1.5 mL of morpholine (17.6 mmol), then 9 mL of N,N,N-triethylamine (64 mmol), 3.3 g of 1-ethyl-3-(3'-dimethylaminopropyl)-carbodiimide (EDC) (19.2 mmol) and 2.6 g of hydroxybenzotriazole (HOBt) (19.2 mmol). The reaction mixture is stirred at ambient temperature overnight; it is then poured into ammonium chloride solution and extracted with ethyl acetate. The organic phase is then dried over MgSO$_4$, and then filtered and evaporated to dryness. The crude product thereby obtained is then purified by chromatography over silica gel using dichloromethane and methanol as eluants. The product is obtained in the form of a foam.

$^1$H NMR: δ (400 MHz; dmso-d6; 353K): 7.30 (m, 5H benzyl); 7.15 (m, 4H, aromatic Hs); 5.2-5.0 (m, 3H, 2H benzyl, 1H dihydroisoquinoline); 4.75-45 (2d, 2H dihydroisoquinoline); 3.55-3.3 (m, 8H morpholine); 3.15-2.9 (2dd, 2H dihydroisoquinoline)

IR: v: >C=O: 1694;1650 cm$^{-1}$

Step B: Benzyl (3S)-3-(4-morpholinylmethyl)-3,4-dihydro-2(1H)-isoquinolinecarboxylate To a solution of 5.3 g of the product obtained in Step A (13.9 mmol) in 278 mL of tetrahydrofuran there are added 14 mL of borane-dimethylsulphide complex (BH$_3$Me$_2$S) (27.8 mmol) at ambient temperature. The batch is heated for 4 hours at 80° C. It is allowed to return to ambient temperature and there are then added 7 mL (14 mmol) of BH$_3$Me$_2$S. The reaction mixture is again heated at 80° C. for 2 hours. The tetrahydrofuran is then evaporated off and then there is slowly added methanol and then 5.6 mL of 5N aqueous HCl solution (27.8 mmol). The mixture is stirred at ambient temperature overnight, and then at 80° C. for 1 hour. Saturated aqueous NaHCO$_3$ solution is then added to the reaction mixture placed at 0° C. until a pH of 8 is obtained, and extraction with ethyl acetate is then carried out. The organic phase is then dried over MgSO$_4$, and then filtered and evaporated to dryness. The title product is obtained in the form of an oil.

$^1$H NMR: δ (400 MHz; dmso-d6; 353K): 7.43-7.30 (unresolved peak, 5H benzyl); 7.19 (m, 4H, aromatic Hs); 5.16 (m, 2H, 2H benzyl); 4.79-429 (d, 2H dihydroisoquinoline); 4.58 (m, 1H dihydroisoquinoline); 3.50 (m, 4H morpholine); 3.02-2.80 (dd, 2H dihydroisoquinoline); 2.42-2.28 (unresolved peak, 5H, 4H morpholine, 1H morpholine); 2.15 (dd, 1H morpholine)

IR: v: >CH: 2810 cm$^{-1}$; v: >C=O: 1694 cm$^{-1}$; v: >C—O—C<: 1114 cm$^{-1}$; v: >CH—Ar: 751; 697 cm$^{-1}$

Step C: (3S)-3-(4-Morpholinylmethyl)-1,2,3,4-tetrahydroisoquinoline

To a solution of 4.9 g of the compound of Step B (13,4 mmol) in 67 mL of ethanol there is added 0.980 g of palladium dihydroxide (20% by weight) at ambient temperature. The reaction mixture is placed under 1.2 bars of hydrogen at ambient temperature for 4 hours. It is then passed through a Whatman filter and the palladium is then rinsed several times with ethanol. The filtrate is evaporated to dryness. The title product is obtained in the form of an oil.

$^1$H NMR: δ (400 MHz; dmso-d6; 300K): 7.12-7.0 (unresolved peak, 4H, aromatic Hs); 3.92 (s, 2H tetrahydroisoquinoline); 3.60 (t, 4H morpholine); 2.98 (m, 1H tetrahydroisoquinoline); 2.68 (dd, 1H tetrahydroisoquinoline); 2.5-2.3 (unresolved peak, 8H, 1H tetrahydroisoquinoline, 6H morpholine, 1H NH)

IR: v: >NH: 3322 cm$^{-1}$; v: >C—O—C<: 1115 cm$^{-1}$; v: >CH—Ar: 742 cm$^{-1}$

Preparation 4': (3S)-3-[(4-Methyl-1-piperazinyl)methyl]-1,2,3,4-tetrahydroisoquinoline The procedure is in accordance with the process of Preparation 3', replacing the morpholine used in Step A by 1-methyl-piperazine.

Preparation 5': (3S)-3-[2-(Morpholin-4-yl)ethyl]-1,2,3,4-tetrahydroisoquinoline hydrochloride Step A: tert-Butyl (3S)-3-(2-morpholino-2-oxo-ethyl)-3,4-dihydro-1H-isoquinoline-2-carboxylate To a solution of 3 g (10.30 mmol) of [(3S)-2-(tert-butoxycarbonyl)-1,2,3,4-tetrahydroisoquinolin-3-yl]acetic acid in 100 mL of dichloromethane, there are added dropwise 1.10 mL (11.32 mmol) of morpholine, still dropwise 4.3 mL (30.9 mmol) of triethylamine, 2.20 g (12.40 mmol) of EDC and 1.70 g (1.68 mmol) of HOBt (hydroxybenzotriazole). The batch is stirred at ambient temperature for 15 hours. The reaction mixture is then diluted with dichloromethane, successively washed with 1M HCl solution, saturated aqueous NaHCO$_3$ solution and then brine until neutral. The organic phase is then dried over MgSO$_4$, filtered and concentrated to dryness. After purification by chromatography over silica gel using dichloromethane and methanol as eluants, the title product is obtained in the form of an oil.

$^1$H NMR: δ (400 MHz; dmso-d6; 300K): 7.20-7.10 (m, 4H, aromatic Hs, tetrahydroisoquinoline); 4.70 (m, 1H, aliphatic Hs, CH tetrahydroisoquinoline); 4.75-420 (2m, 2H, aliphatic Hs, CH$_2$ alpha to N tetrahydroisoquinoline); 3.60 (m, 8H, aliphatic Hs, morpholine); 3.00 and 2.70 (2dd, 2H, aliphatic H, tetrahydroisoquinoline); 2.50-2.20 (2d, 2H, aliphatic Hs, CH$_2$CO); 1.40 (s, 9H, $^t$Bu)

IR: v: C=O: 1687; 1625 cm$^{-1}$

Step B: 1-(Morpholin-4-yl)-2-[(3S)-1,2,3,4-tetrahydroisoquinolin-3-yl]ethanone hydrochloride To a solution of 2.88 g (7.18 mmol) of the compound obtained in Step A in 16 mL of dichloromethane, there are added dropwise 80 mL (80 mmol) of 1M solution of HCl in ether. The batch is stirred at ambient temperature for 15 hours, and then the suspension is filtered and the precipitate washed with ether. After drying, the title product is obtained in the form of a solid.

$^1$H NMR: δ (400 MHz; dmso-d6; 300K): 9.80-9.50 (m, 2H, NH$_2^+$); 7.30-7.10 (m, 4H, aromatic Hs, tetrahydroisoquinoline); 4.30 (m, 2H, aliphatic Hs, CH$_2$ alpha to N tetrahydroisoquinoline); 3.80 (m, 1H, aliphatic Hs, CH tetrahydroisoquinoline); 3.70-3.40 (2m, 8H, aliphatic Hs, morpholine); 3.15 and 2.8 (m, 4H, aliphatic H, CH$_2$ tetrahydroisoquinoline and CH$_2$CO)

IR: v: —NH$_2^+$: 2800-1900 cm$^{-1}$; v: C=O: 1620 cm$^{-1}$

Step C: (3S)-3-[2-(Morpholin-4-yl)ethyl]-1,2,3,4-tetrahydroisoquinoline hydrochloride A solution of 2.2 g (7.44 mmol) of the compound obtained in Step B in 22 mL of MTBE and 5 mL of dichloromethane is prepared. After cooling in an ice bath at 0° C., there are added thereto, dropwise, 15 mL (15 mmol) of 1M LiAlH$_4$ solution in tetrahydrofuran. The batch is then stirred at ambient temperature for 6 hours. It is placed at 0° C., and there is then added, dropwise, 1 mL of 5N NaOH solution. The batch is stirred at ambient temperature for 45 minutes. The solid is then filtered off and washed with MTBE and then with dichloromethane and the filtrate is concentrated to dryness. The oil thereby obtained is diluted with dichloromethane and there are added, dropwise, 6.3 mL of a 1M solution of HCl in ether. The batch is stirred at ambient temperature for 1 hour and then filtered. The crystals thereby obtained are washed with ethyl ether. After drying, the title product is obtained in the form of a solid.

$^1$H NMR: δ (400 MHz; dmso-d6; 300K): 11.35+9.80 (2m, 2H, NH$_2^+$); 10.00 (m, H, NH$^+$); 7.20 (m, 4H, aromatic Hs, tetrahydroisoquinoline); 4.30 (s, 2H, aliphatic Hs, CH$_2$ alpha to N tetrahydroisoquinoline); 4.00+3.85 (2m, 4H, aliphatic Hs, CH$_2$ alpha to N morpholine); 3.70 (m, 1H, aliphatic Hs, CH tetrahydroisoquinoline); 3.55-3.30 (m, 4H, aliphatic Hs, CH alpha to O morpholine and CH$_2$-morpholine); 3.15 (dd, 1H, aliphatic H, CH$_2$ tetrahydroisoquinoline); 3.10 (m, 2H, aliphatic H, CH alpha to O morpholine); 2.90 (dd, 1H, aliphatic H, CH$_2$ tetrahydroisoquinoline); 2.30+2.15 (2m, 2H, aliphatic H, CH$_2$-tetrahydroisoquinoline)

IR: v: NH$^+$/—NH$_2^+$: between 3500 and 2250 cm$^{-1}$; v: C=C: weak 1593 cm$^{-1}$; v: aromatic C—H: 765 cm$^{-1}$ Preparation 6': (3R)-3-[3-(Morpholin-4-yl)propyl]-1,2,3,4-tetrahydroisoquinoline Step A: {(3S)-2-[(4-Methylphenyl)sulphonyl]-1,2,3,4-tetrahydroisoquinolin-3-yl}methyl 4-methylbenzenesulphonate The process is the same as that of Step A of Preparation 1'.

Step B: tert-Butyl 2-({(3R)-2-[(4-methylphenyl)sulphonyl]-1,2,3,4-tetrahydroisoquinolin-3-yl}methyl)-3-(morpholin-4-yl)-3-oxopropanoate To a suspension of 1 g of NaH (60%) (25.08 mmol) in 30 mL of MTBE there are added, dropwise, a solution of 5 g of tert-butyl 3-morpholino-3-oxopropanoate (21.81 mmol) in 20 mL of anhydrous MTBE. This suspension stirred at ambient temperature for 1 hour and then the compound obtained in Step A is added in the form of a powder. The batch is stirred at 60° C. for 30 hours. 100 mL of saturated aqueous ammonium chloride solution are added. The resulting solution is extracted with dichloromethane. The organic phase is then dried over $MgSO_4$, filtered and concentrated to dryness. After purification by chromatography over silica gel using dichloromethane and MeOH as eluants, the expected product is obtained in the form of an oil.

$^1$H NMR (500 MHz, dmso-d6) δ ppm: 7.63/7.59 (2d, 2H), 7.3/7.26 (2d, 2H), 7.13 (m, 2H), 7.09/6.97 (2t, 2H), 4.64/4.55/4.36/4.28 (2AB, 2H), 4.25/4.11 (2m, 1H), 3.81 (m, 1H), 3.73-3.48 (m, 4H), 3.57-3.32 (m, 4H), 2.51 (m, 2H), 2.32/2.31 (2s, 3H), 1.88/1.79 (2m, 2H), 1.39/1.38 (2s, 9H)

IR (ATR) cm$^{-1}$: v: >C=O: 1731 (ester); v: >C=O: 1644 (amide); v: —SO2: 1334-1156; v: >C—O—C<: 1115; γ: >CH—Ar: 815-746-709

Step C: 2-({(3R)-2-[(4-Methylphenyl)sulphonyl]-1,2,3,4-tetrahydroisoquinolin-3-yl}methyl)-3-(morpholin-4-yl)-3-oxopropanoic acid To a solution of 9.5 g (17.97 mmol) of the compound obtained in Step B in 40 mL of dioxane there are added, dropwise, 20 mL of a 4M solution of HCl in dioxane. The batch is stirred at ambient temperature for 48 hours and then the solution is concentrated to dryness. After drying, the expected product is obtained in the form of an oil.

$^1$H NMR (400 MHz, dmso-d6) δ ppm: 12.75 (m, 1H), 7.6 (2*d, 2H), 7.3 (2*d, 2H), 7.1/6.95 (2*m, 4H), 4.7-42 (d, 2H), 4.25/4.12 (2*m, 1H), 3.9-3.3 (m, 9H), 2.55 (d, 2H), 2.3 (2*s, 3H), 1.8 (t, 2H)

IR (ATR) cm$^{-1}$: v: —OH: 3500 to 2000; v: >C=O: 1727 (acid); v: >C=O: 1634 (amide); v: —SO2: 1330-1155

Step D: 3-{(3R)-2-[(4-Methylphenyl)sulphonyl]-1,2,3,4-tetrahydroisoquinolin-3-yl}-1-(morpholin-4-yl)propan-1-one To a solution of 7.80 g (16.51 mmol) of the compound obtained in Step C in 100 mL of DMSO there are added 1.16 g (19.83 mmol) of solid sodium chloride (NaCl) and then, dropwise, 5 mL of water. The batch is stirred at 130° C. for 1 hour and then the solution is concentrated to ¾. The reaction mixture is then diluted with dichloromethane and washed successively with saturated aqueous lithium chloride solution and then with brine. The organic phase is then dried over $MgSO_4$, filtered and concentrated to dryness. After purification by chromatography over silica gel using cyclohexane and ethyl acetate as eluants, the expected product is obtained in the form of an oil.

$^1$H NMR (400 MHz, dmso-d6) δ ppm: 7.65 (d, 2H), 7.3 (d, 2H), 7.15/7 (2 m, 4H), 4.6 (d, 1H), 4.25 (d, 1H), 4.2 (m, 1H), 3.5 (m, 4H), 3.4 (2 m, 4H), 2.6 (2 dd, 2H), 2.35 (s, 3H), 2.3 (m, 2H), 1.5 (quad., 2H)

IR (ATR) cm$^{-1}$: v: >C=O: 1639; v: —SO2: 1331-1156; γ: >CH—Ar: 815-675

Step E: (3R)-2-[(4-Methylphenyl)sulphonyl]-3-[3-(morpholin-4-yl)propyl]-1,2,3,4-tetrahydroisoquinoline To a solution of 6.0 g (14.0 mmol) of the compound obtained in Step D in 60 mL of MTBE and 14 mL of dichloromethane there are added 1.06 g (28 mmol) of LAH in portions over 5 minutes. The batch is stirred at ambient temperature for 15 hours. There are added, dropwise, 1.5 mL of water and stirring is carried out for 15 minutes. There are then added, dropwise, 1.5 mL of 5M sodium hydroxide solution and stirring is carried out for 15 minutes. The reaction mixture is then diluted with MTBE and dichloromethane. The suspension is then filtered and the precipitate is washed with MTBE and dichloromethane. The organic phase is then dried over $MgSO_4$, filtered and concentrated to dryness. After purification by chromatography over silica gel using dichloromethane and ammonia-in-ethanol as eluants, the expected product is obtained in the form of an oil.

$^1$H NMR (400 MHz, dmso-d6) δ ppm: 7.68 (d, 2H), 7.32 (d, 2H), 7.1 (unresolved peak, 4H), 4.65/4.23 (AB, 2H), 4.2 (m, 1H), 3.55 (t, 4H), 2.7/2.6 (ABX, 2H), 2.35 (s, 3H), 2.25 (t, 4H), 2.2 (t, 2H), 1.4/1.3 (2m, 4H).

IR (ATR) cm$^{-1}$: v: —SO2: 1333-1158

Step F: (3R)-3-[3-(Morpholin-4-yl)propyl]-1,2,3,4-tetrahydroisoquinoline

To a solution of 1.50 g (3.62 mmol) of the compound obtained in Step E in 20 mL of anhydrous methanol there are added 2.0 g (82.3 mmol), in portions, of magnesium turnings. The batch is stirred in the presence of ultrasound for 96 hours. The reaction mixture is then filtered, the solid is washed several times with methanol, and the filtrate is concentrated to dryness. After purification by chromatography over silica gel using dichloromethane and ammonia-in-ethanol as eluants, the expected product is obtained in the form of an oil.

$^1$H NMR (400 MHz, dmso-d6) δ ppm: 7.3 (d, 2H), 7.1 (t, 2H), 7.1 (d+t, 3H), 7 (d, 2H), 3.9 (s, 2H), 3.55 (t, 4H), 2.75 (m, 1H), 2.72/2.45 (dd, 2H), 2.35 (t, 4H), 2.25 (t, 2H), 1.6 (m, 2H), 1.45 (m, 2H)

IR (ATR) cm$^{-1}$: v: >NH2+/NH+: 3500-2300; v: >C—O—C<: 1115

High-Resolution Mass Spectrometry (ESI+−/FIA/HR):
Empirical formula: $C_{16}H_{24}N_2O$
[M+H]$^+$ calculated: 261.1961
[M+H]$^+$ measured: 261.1959

Preparation 7': (3S)-3-[(9aS)-Octahydropiperazino[2,1-c]morpholin-8-ylmethyl]-1,2,3,4-tetrahydroisoquinoline trihydrochloride

Step A: tert-Butyl (9aS)-4-oxo-octahydropiperazino[2,1-c]morpholine-8-carboxylate The synthesis of this compound is known in the literature (*J. Med. Chem.* 2012, 55, 5887 for the opposite enantiomer).

Step B: (9aS)-Octahydropiperazino[2,1-c]morpholin-4-one hydrochloride

A 4M solution of HCl in dioxane (60 mL, 240 mmol) is added to the compound tert-butyl (9aS)-4-oxo-octahydropiperazino [2,1-c] morpholine-8-carboxylate (11.8 g, 46.0 mmol) cooled using an ice bath. The solution is then stirred at ambient temperature for 2 hours, and then at 50-60° C. for 1.5 hours. The solution is then evaporated to dryness. The residue is co-evaporated with dioxane (3×20 mL) and then dried in vacuo to obtain the expected compound in the form of a solid.

$^1$H NMR (400 MHz, dmso-d6) δ ppm: 2.80-2.94 (m, 2H), 2.94-3.05 (m, 1H), 3.23-3.37 (m, 2H), 3.59-3.69 (m, 1H), 3.83-3.93 (m, 1H), 3.95-404 (m, 1H), 4.02-413 (m, 2H), 4.45-455 (m, 1H), 9.58 (br s, 2H)

Step C: tert-Butyl (3S)-3-[(9aS)-4-oxo-octahydropiperazino[2,1-c]morpholine-8-carbonyl]-1,2,3,4-tetrahydroisoquinoline-2-carboxylate EDC (3.90 g, 20.3 mmol) is added to a solution of the compound of Step B (3.02 g, 15.7 mmol), (3S)-2-[(tert-butoxy)carbonyl]-1,2,3,4-tetrahydroisoquinoline-3-carboxylic acid (4.6 g, 16.6 mmol), triethylamine (8.0 mL, 57.4 mmol) and HOBt (2.72 g, 20.1 mmol) in dichloromethane (150 mL). The mixture is stirred at ambient temperature for 21 hours. 1N aqueous HCl solution (105 mL) is added and the precipitate formed is filtered off using a Buchner funnel. The phases of the filtrate are separated. The aqueous phase is extracted with dichloromethane (2×10 mL). The combined organic phases are washed with 3N aqueous HCl solution (35 mL), then with aqueous 5% potassium bicarbonate solution (2×35 mL) and finally with brine (35 mL). The organic phase is dried over Na$_2$SO$_4$, filtered and then concentrated under reduced pressure. The product is purified by chromatography over silica gel using ethyl acetate and heptane as eluants to obtain the expected compound in the form of a solid.

$^1$H NMR (400 MHz, CDCl$_3$) δ ppm: 1.38-1.57 (m, 9H), 2.39-2.89 (m, 2H), 2.89-3.34 (m, 3H), 3.34-3.70 (m, 2H), 3.90-406 (m, 1H), 4.09-427 (m, 2H), 4.30-5.00 (m, 5H), 5.20-5.37 (m, 1H), 7.03-7.24 (m, 4H)

Step D: (3S)-3-[(9aS)-Octahydropiperazino[2,1-c]morpholin-8-ylmethyl]-1,2,3,4-tetrahydroisoquinoline trihydrochloride 4M HCl solution in dioxane (45 mL, 180 mmol) is added to the compound of Step C (6.6 g, 46.0 mmol) cooled in an ice bath. The suspension is then stirred at ambient temperature for 24 hours and then it is evaporated to dryness. The residue is co-evaporated with MTBE and then dried in vacuo. The solid thereby obtained is suspended in tetrahydrofuran (160 mL), and then LiAlH$_4$ (3,0 g, 79.1 mmol) is added. The suspension is refluxed for 6.5 hours, and it is then cooled in an ice bath. Water (3 mL) is then added over a period of 7 minutes. After 0.5 hours, 2N aqueous sodium hydroxide solution (6 mL) is added. Water (6 mL) is again added 0.25 hours later. Finally, Celite (7 g) and Na$_2$SO$_4$ (25 g) are added 0.5 hours later. The suspension is filtered over Celite and rinsed with tetrahydrofuran (2×100 mL). The filtrate is concentrated to dryness. The oil thereby obtained is dissolved in MTBE (50 mL). The resulting solution is filtered and the filtrate concentrated. The residue is dissolved in methanol (60 mL), and then 4M HCl solution in dioxane (20 mL) is added. The solution is heated to 40° C. and treated with activated charcoal (0.66 g), with stirring, for 1 hour. The suspension is filtered over Celite and rinsed with warm methanol. The filtrate is concentrated until the product starts to crystallise out. Crystallisation is allowed to continue for 16 hours at ambient temperature. The solid obtained is filtered off and rinsed with a mixture of 2-propanol/MTBE (4/6) (2×20 mL), and then with MTBE (2×20 mL). After drying, the expected compound is obtained.

$^1$H NMR (400 MHz, D$_2$O) δ ppm: 2.28-2.44 (m, 1H), 2.74-3.00 (m, 4H), 3.08-3.27 (m, 3H), 3.27-3.42 (m, 2H), 3.43-3.56 (m, 2H), 3.56-3.69 (m, 2H), 3.76-3.95 (m, 2H), 4.00-422 (m, 2H), 4.35-450 (m, 2H), 7.20-7.41 (m, 4H)

$^{13}$C NMR (100 MHz, D$_2$O) δ ppm: 29.00, 44.58, 50.30, 51.08, 51.17, 52.75, 53.17, 58.08, 61.60, 64.61, 66.37, 127.14, 127.71, 128.00, 128.77, 129.55, 131.15

MS (ESI): [M+H]$^+$ 288.16

Preparation 8': (3S)-3-(1-Oxa-6-azaspiro[3.3]hept-6-ylmethyl)-1,2,3,4-tetrahydroisoquinoline Step A: (3S)-3-(Iodomethyl)-2-[(4-methylphenyl)sulphonyl]-1,2,3,4-tetrahydroisoquinoline The compound of Step A of Preparation 6' (4.0 g; 8.48 mmol) in acetonitrile (10 mL) is placed in a 27-ml microwave tube and then sodium iodide (1.40 g; 9.33 mmol) is added. The reaction mixture is heated for 5 hours at 100° C. using microwaves (200 W). It is then filtered and the solid is washed with dichloromethane. The filtrate is evaporated to dryness and then the residue is purified by chromatography over silica gel using heptane and ethyl acetate as eluants. The title compound is obtained in the form of an oil.

$^1$H NMR (400 MHz, dmso-d6) δ ppm: 7.64 (d, 2H), 7.28 (d, 2H), 7.15-7 (m, 4H), 4.5/4.3 (2d, 2H), 4.14 (m, 1H), 3.22 (m, 2H), 2.82 (m, 2H), 2.31 (s, 3H)

IR (ATR) cm$^{-1}$: 1897 v —Ar, 1333+1156 v —SO2

Step B: (3S)-2-[(4-Methylphenyl)sulphonyl]-3-(1-oxa-6-azaspiro[3.3]hept-6-ylmethyl)-1,2,3,4-tetrahydroisoquinoline The iodinated compound (2.5 g; 5.85 mmol) obtained in the preceding Step is dissolved in acetonitrile (50 mL). 1-Oxa-6-azaspiro[3.3]heptane oxalate (1.21 g; 6.36 mmol) is added, followed by potassium carbonate (1.61 g; 11.7 mmol). The reaction mixture is heated for 15 hours at reflux. The reaction mixture is filtered and washed with acetonitrile, and then is evaporated to dryness.

The compound is purified by chromatography over silica gel using dichloromethane and ammonia-in-methanol as eluants. The title compound is obtained in the form of an oil.

$^1$H NMR (400 MHz, dmso-d6) δ ppm: 7.68 (d, 2H), 7.32 (d, 2H), 7.14-7 (m, 4H), 4.53/4.2 (dd, 2H), 4.34 (t, 2H), 3.95 (m, 1H), 3.5/3.4/2.98 (3m, 4H), 2.7 (t, 2H), 2.68-2.58 (m, 2H), 2.34 (s, 3H), 2.31-2.24 (m, 2H)

IR (ATR) cm$^{-1}$: 1333+1156 v —SO2

Step C: (3S)-3-(1-Oxa-6-azaspiro[3.3]hept-6-ylmethyl)-1,2,3,4-tetrahydroisoquinoline The tosylated compound of the above Step (1.3 g; 3.26 mmol) is dissolved in 10 mL of methanol. Powdered magnesium (633 mg; 26.08 mmol) is added in portions of 160 mg every 3 hours. The reaction mixture is stirred in an ultrasound bath 15 hours. It is then filtered over Celite, washed with copious amounts of methanol, and then evaporated to dryness. The compound is purified by chromatography over silica gel using dichloromethane and ammonia-in-methanol as eluants. The compound is obtained in the form of an oil.

¹H NMR (400 MHz, dmso-d6) δ ppm: 7.01 (m, 4H), 4.46 (t, 2H), 3.85 (s, 2H), 3.51/3.05 (dd, 2H), 2.73 (t, 2H), 2.61/2.4 (m, 4H), 2.4 (m, 1H), 2.4 (m, 1H)
IR (ATR) cm$^{-1}$: 3325 v >NH

Preparation 9': (3S)-3-[(9aR)-Octahydropiperazino[2,1-c]morpholin-8-ylmethyl]-1,2,3,4-tetrahydroisoquinoline trihydrochloride

Step A: tert-Butyl (9aR)-4-oxo-octahydropiperazino[2,1-c]morpholine-8-carboxylate Synthesis of this compound is described in the literature (*J. Med. Chem.* 2012, 55, 5887).

Step B: (9aR)-Octahydropiperazino[2,1-c]morpholin-4-one hydrochloride

A 4M solution of HCl in dioxane (39 mL, 154 mmol) is added to the compound of Step A (11.3 g, 44.1 mmol). The solution is then stirred at ambient temperature for 5 hours, and then a 4M solution of HCl in dioxane (12 mL, 48 mmol) is added again. The mixture is stirred for 16 hours. The solution is then evaporated to dryness to yield the expected product in the form of a solid.
¹H NMR (400 MHz, dmso-d6) δ ppm: 2.79-2.93 (m, 2H), 3.02 (td, J=13.1, 2.7 Hz, 1H), 3.22-3.34 (m, 2H), 3.59-3.67 (m, 1H), 3.86-3.96 (m, 1H), 3.96-401 (m, 1H), 4.05 (AB q, J=13.3 Hz, 2H), 4.48 (dd, J=14.1, 2.5 Hz, 1H), 9.71 (br. s, 1H), 9.91 (br. s, 1H)

Step C: tert-Butyl (3S)-3-[(9aR)-4-oxo-octahydropiperazino[2,1-c]morpholine-8-carbonyl]-1,2,3,4-tetrahydroisoquinoline-2-carboxylate EDC (5.17 g, 27.0 mmol) is added to a solution of the compound of the above Step (4.0 g, 20.7 mmol), (3S)-2-[(tert-butoxy)carbonyl]-1,2,3,4-tetrahydroisoquinoline-3-carboxylic acid (6.04 g, 21.8 mmol), triethylamine (11.6 mL, 83.1 mmol) and HOBt (3.65 g, 27.0 mmol) in dichloromethane (100 mL). The mixture is stirred at ambient temperature for 16 hours. 1N aqueous HCl solution (70 mL) is added and the precipitate formed is filtered off using a Buchner funnel. The phases of the filtrate are separated. The organic phase is washed with saturated aqueous potassium carbonate solution and is then concentrated under reduced pressure. The residue is pre-absorbed onto silica gel and is purified by chromatography over silica gel using ethyl acetate and heptane as eluants to yield the expected compound in the form of a solid.
¹H NMR (400 MHz, dmso-d6) δ ppm: 1.25-1.58 (m, 9H), 2.50-2.76 (m, 2H), 2.76-3.25 (m, 3H), 3.37-3.76 (m, 2H), 3.92-450 (m, 5H), 4.06 (s, 2H), 4.66 (d, J=15.6 Hz, 1H), 4.76-5.28 (m, 1H), 7.05-7.31 (m, 4H)

Step D: (3S)-3-[(9aR)-Octahydropiperazino[2,1-c]morpholin-8-ylmethyl]-1,2,3,4-tetrahydroisoquinoline trihydrochloride A 4M solution of HCl in dioxane (24.0 mL, 96.2 mmol) is added to a solution of the compound of Step C (8.00 g, 12.25 mmol) in dichloromethane (25 mL). The mixture is stirred at ambient temperature for 16 hours and is then concentrated to dryness. The crude product obtained is added to a suspension of LiAlH$_4$ (1.97 g, 51.91 mmol) in tetrahydrofuran (140 mL). The mixture is refluxed until the reaction (monitored by LC-MS) is complete and it is then cooled to 0° C. Water (2.5 mL) is added dropwise. After stirring for 10 minutes, aqueous 2M sodium hydroxide solution (5 mL) is added dropwise. Water (5 mL) is again added after stirring for 10 minutes. There are finally added Celite (4 g) and Na$_2$SO$_4$ (12 g) after stirring for an additional 10 minutes. The suspension is filtered over Celite and the filtrate is concentrated to dryness. The crude residue thereby obtained is dissolved in methanol (80 mL), and then a 4M solution of HCl in dioxane (16.75 mL, 67.0 mmol) is added. The mixture is stirred at ambient temperature for 3 hours, and then concentrated to dryness. The residue is dissolved in a minimum of warm methanol (70 mL), and then MTBE (3-5 mL) is added. The solution is cooled at 0° C. for 1 hour in an ice-cold water bath, and the product precipitates out. A little MTBE (2-3 mL) is again added and the mixture is allowed to stand for a further 1 hour at 0° C. The solid obtained is filtered over a Buchner funnel and dried in vacuo to yield the expected compound in the form of a solid.
¹H NMR (400 MHz, CD$_3$OD) δ ppm: 2.65 (t, J=11.1 Hz, 1H), 2.74-2.97 (m, 4H), 3.10 (d, J=12.5 Hz, 1H), 3.19 (dd, J=17.6, 4.8 Hz, 1H), 3.25-3.55 (m, 5H), 3.59-3.74 (m, 2H), 3.82-415 (m, 4H), 4.45 (AB q, J=15.9 Hz, 2H), 7.21-7.35 (m, 4H).
¹³C NMR (100 MHz, CD$_3$OD) δ ppm: 30.21, 45.67, 50.22, 51.99, 52.90, 53.58, 53.71, 59.25, 62.58, 65.30, 67.07, 127.76, 128.40, 129.08, 129.36, 130.16, 131.95
MS (ESI): [M+H]$^+$ 288.2

Preparation 1'': N-[4-[tert-Butyl(dimethyl)silyl]oxyphenyl]-1-methyl-pyrazol-4-amine

Step A: 4-{[tert-Butyl(dimethyl)silyl]oxy}aniline

The title compound is obtained starting from 4-aminophenol in THF in the presence of imidazole and tert-butyl (dimethyl)silyl chloride in accordance with the protocol described in the literature (S. Knaggs et al, *Organic & Biomolecular Chemistry*, 3(21), 4002-4010; 2005).
¹H NMR: δ (400 MHz; dmso-d6; 300K): 6.45-6.55 (dd, 4H, aromatic Hs); 4.60 (m, 2H, NH$_2$-Ph); 0.90 (s, 9H, Si (CH$_2$)$_2$CH(CH$_3$)$_2$); 0.10 (s, 6H, Si (CH$_2$)$_2$CH(CH$_3$)$_2$)
IR: v: —NH$_2$$^+$: 3300-3400 cm$^{-1}$

Step B: N-[4-[tert-Butyl(dimethyl)silyl]oxyphenyl]-1-methyl-pyrazol-4-amine To a solution of 30.8 g (0.137 mol) of the compound of Step A in 525 mL of anhydrous toluene there are successively added 29.8 g of sodium tert-butylate (0.310 mol), 4.55 g of Pd$_2$(dba)$_3$ (also referred to as tris(dibenzylideneacetone) dipalladium(0)) (4.96 mmol), 4.81 g of 2-di-tert-butylphosphino-2',4',6'-tri-isopropyl-1,1'-biphenyl (9.91 mmol) and 12.8 mL of 4-bromo-1-methyl-1H-pyrazole (0.124 mol). The batch is degassed under argon for 30 minutes and then refluxed for 3 hours. It is allowed to cool. The reaction mixture is concentrated to dryness and then taken up in dichloromethane, filtered over Celite and then concentrated to dryness again. The residue is then purified by chromatography over silica gel using dichloromethane and ethyl acetate as eluants to provide the expected product in the form of a solid.

¹H NMR: δ (400 MHz; dmso-d6; 300K): 7.55 (s, 1H, pyrazole); 7.23 (s, 1H, pyrazole); 7.18 (broad s, 1H, NH$_2$-Ph);6.64 (m, 4H, aromatic Hs); 3.77 (s, 3H, CH$_3$-pyrazole); 0.90 (s, 9H, Si (CH$_2$)$_2$CH(CH$_3$)$_2$); 0.12 (s, 6H, Si (CH$_2$)$_2$CH(CH$_3$)$_2$)

IR: ν —NH$^+$: 3275 cm$^{-1}$; ν Ar and C═N: 1577 and 1502 cm$^{-1}$; ν —Si—C—: 1236 cm$^{-1}$; ν —Si—O—: 898 cm$^{-1}$; ν —Si—C—: 828, 774 cm$^{-1}$ Preparation 2": 4{[tert-Butyl(dimethyl)silyl]oxy}-N-phenylaniline To a solution of 12 g of 4-anilinophenol (64.7 mmol) in 200 mL of acetonitrile there are added, at ambient temperature, 6.7 g of imidazole (97.05 mmol) and 11.7 g of tert-butyl(dimethyl)silyl chloride (77.64 mmol). The batch is stirred at 70° C. for 4 hours. The reaction mixture is then poured into water and extracted with ether. The organic phase is then dried over MgSO$_4$, then filtered and evaporated to dryness. The crude product thereby obtained is then purified by chromatography over silica gel using petroleum ether and dichloromethane as eluants. The title product is obtained in the form of a powder.

¹H NMR: δ (400 MHz; dmso-d6; 300K): 7.84 (s, 1H NH); 7.17 (t, 2H aniline); 6.98 (d, 2H phenoxy); 6.94 (d, 2H aniline); 6.76 (d, 2H phenoxy); 6.72(t, 1H aniline); 0.95 (s, 9H tert-butyl); 0.15 (s, 6H dimethyl)

IR: ν: >NH: 3403 cm$^{-1}$; ν:>Ar: 1597 cm$^{-1}$

Preparation 3": tert-Butyl 5[(4-{[tert-butyl(dimethyl)silyl]oxy}phenyl)amino]-1H-indole-1-carboxylate The procedure is in accordance with the process of Preparation 1", replacing the 4-bromo-1-methyl-1H-pyrazole used in Step B by tert-butyl 5-bromo-1H-indole-1-carboxylate.

¹H NMR: δ (400 MHz; dmso-d6; 300K): 7.85 (d, 1H); 7.78 (s, 1H); 7.55 (d, 1H); 7.15 (d, 1H); 6.95 (m, 3H); 6.75 (d, 2H); 6.58 (d, 1H); 1.65 (s, 9H); 1.00 (s, 9H); 0.2 (s, 6H)

Preparation 4": N-(4-{[tert-Butyl(dimethyl)silyl]oxy}phenyl)-1-methyl-1H-indol-5-amine The procedure is in accordance with the process of Preparation 1", replacing the 4-bromo-1-methyl-1H-pyrazole used in Step B by 5-bromo-1-methyl-1H-indole.

Preparation 5": N-(4-{[tert-Butyl(dimethyl)sily]oxy}phenyl)-1-methyl-1H-indazol-5-amine The procedure is in accordance with the process of Preparation 1", replacing the 4-bromo-1-methyl-1H-pyrazole used in Step B by 5-bromo-1-methyl-1H-indazole.

Preparation 6": N-(4-{[tert-Butyl(dimethyl)sily]oxy}phenyl)-3-fluoro-4-methylaniline The procedure is in accordance with the process of Preparation 1''', replacing the 4-bromo-1-methyl-1H-pyrazole used in Step B by 4-bromo-2-fluoro-1-methylbenzene.

Preparation 7": N-(4-{[tert-Butyl(dimethyl)silyl]oxy}phenyl)-3-fluoroaniline

The procedure is in accordance with the process of Preparation 1", replacing the 4-bromo-1-methyl-1H-pyrazole used in Step B by 1-bromo-3-fluorobenzene.

Preparation 8": 4-Benzyloxy-N-phenyl-aniline

To a solution of 4-hydroxy-N-phenyl-aniline (30 g; 162 mmol) in acetonitrile (400 mL) there are added 58 g of Cs$_2$CO$_3$ (178 mmol) and stirring is carried out for 15 minutes at ambient temperature. Benzyl bromide (22.5 mL; 178 mmol) is then added dropwise and then the reaction mixture is refluxed for 4 hours. After filtering and rinsing with acetonitrile, the filtrate is concentrated and purified by chromatography over silica gel using petroleum ether and ethyl acetate as eluants. The title product is then obtained in the form of a colourless solid.

¹H NMR: δ (400 MHz; dmso-d6; 300K): 7.80 (m, 1H, NH); 7.45 (m, 2H, aryl); 7.40 (m, 2H, aryl); 7.30 (m, 1H, aryl); 7.15 (s, 2H, aryl); 7.05 (d, 2H, aryl); 6.9-7.0 (m, 4H, aryl); 6.70 (t, 1H, aryl); 5.05 (s, 2H, benzyl).

IR: ν: >NH: 3408 cm$^{-1}$

Preparation 9": N-(4-{[tert-Butyl(dimethyl)silyl]oxy}phenyl)pyridin-4-amine

The procedure is in accordance with the process of Preparation 1", replacing the 4-bromo-1-methyl-1H-pyrazole used in Step B by 4-bromopyridine.

IR: ν —NH—: 3200 and 2500 cm$^{-1}$; ν:-Si—O—: 902 cm$^{-1}$; ν:—Si—C—: 820 cm$^{-1}$ Preparation 10": N-(4-{[tert-Butyl(dimethyl)silyl]oxy}phenyl)-4-fluoroaniline The procedure is in accordance with the process of Preparation 1", replacing the 4-bromo-1-methyl-1H-pyrazole used in Step B by 1-bromo-4-fluorobenzene.

Preparation 11": N-(4-{[tert-Butyl(dimethyl)silyl]oxy}phenyl)-1-methyl-1H-pyrrolo[2,3-b]pyridin-5-amine The procedure is in accordance with the process of Preparation 1", replacing the 4-bromo-1-methyl-1H-pyrazole used in Step B by 5-bromo-1-methyl-1H-pyrrolo[2,3-b]pyridine (obtained in accordance with a protocol from the literature: Heterocycles, 60(4), 865, 2003).

IR: ν:-NH—: 3278 cm$^{-1}$; ν: aromatic —C═C— moieties: 1605 cm$^{-1}$

Preparation 12": N-(4-{[tert-Butyl(dintethyl)silyl]oxy}phenyl)-2-methoxy-pyrimidin-5-amine The procedure is in accordance with the process of Preparation 1", replacing the 4-bromo-1-methyl-1H-pyrazole used in Step B by 5-bromo-2-methoxypyrimidine.

Preparation 13": N-(4-{[tert-Butyl(dimethyl)silyl]oxy}phenyl)-1-methyl-2,3-dihydro-1H-pyrrolo[2,3-b]pyridin-5-amine The procedure is in accordance with the process of Preparation 1", replacing the 4-bromo-1-methyl-1H-pyrazole used in Step B by 5-bromo-1-methyl-2,3-dihydro -1H-pyrrolo-[2,3-b]pyridine.

Preparation 14": N-(4-{[tert-Butyl(dimethyl)silyl]oxy}phenyl)-1-methyl-1H-benzimidazol-5-amine The procedure is in accordance with the process of Preparation 1", replacing the 4-bromo-1-methyl-1H-pyrazole used in Step B by 5-bromo-1-methyl-1H-benzimidazole.

Preparation 15": N⁴-(4-{[tert-Butyl(dimethyl)silyl]oxy}phenyl)-N²,N²-dimethylpyridine-2,4-diamine The procedure is in accordance with the process of Preparation 1", replacing the 4-bromo-1-methyl-1H-pyrazole used in Step B by 4-bromo-N,N-dimethylpyridin-2-amine.

Preparation 16": N-(4-{[tert-Butyl(dimethyl)silyl]oxy}phenyl)pyrazolo[1,5-a]-pyrimidin-6-amine The procedure is in accordance with the process of Preparation 1", replacing the 4-bromo-1-methyl-1H-pyrazole used in Step B by 6-bromopyrazolo[1,5-a]pyrimidine.
IR: ν —NH—: 3272 cm⁻¹; ν —C=N—: 1634 cm⁻¹; ν —C=C—: 1616 cm⁻¹

Preparation 17": N-[4-[tert-Butyl(dimethyl)silyl]oxyphenyl]-1-methyl-pyrazolo-[3,4-b]pyridin-5-amine The procedure is in accordance with the process of Preparation 1", replacing the 4-bromo-1-methyl-1H-pyrazole used in Step B by 5-bromo-1-methyl-pyrazolo [3,4-b]pyridine (obtained in accordance with a protocol from the literature: WO 2006/052568 starting from 2-methyl-pyrazol-3-amine and 2-bromopropanedial).

Preparation 18": 4-({4[(tert-Butyldimethylsilyl)oxy]phenyl}amino)-1 5-dimethyl-1H-pyrrole-2-carbonitrile

Step A: 4-Bromo-1,5-dimethyl-1H-pyrrole-2-carbonitrile

A solution of bromine (6.58 mL, 0.13 mol) in acetic acid (60 mL) is added dropwise, with the aid of a dropping funnel, to a solution of 1,5-dimethyl-1H-pyrrole-2-carbonitrile (15.0 g, 0.12 mol) in acetic acid (300 mL). The batch is stirred at ambient temperature for 24 hours. The reaction mixture is then poured into a beaker containing 300 mL of water. The solid formed is filtered off and rinsed with water. It is then dissolved in dichloromethane (300 mL) and the organic phase is washed with brine, dried over Na₂SO₄, filtered and concentrated in vacuo to yield the expected product in the form of a solid.
¹H NMR (CDCl₃) δ ppm: 2.25 (s, 3H), 3.67 (s, 3H), 6.74 (s, 1H)

Step B: 4-({4-[(tert-Butyldimethylsilyl)oxy]phenyl}amino)-1,5-dimethyl-1H-pyrrole-2-carbonitrile A solution of the compound of the above Step (1.5 g, 7.53 mmol), 4-[(tert-butyldimethylsilyl)oxy]aniline (2.02 g, 9.04 mmol), sodium tert-butylate (1.45 g, 15.06 mmol) and 2-di-tert-butylphosphino-2',4',6'-triisopropylbiphenyl (0.13 g, 0.30 mmol) in toluene (20 mL) is purged with nitrogen. Tris(dibenzylideneacetone)-dipalladium(0) (0.28 g, 0.30 mmol) is added, and then the reaction mixture is heated at 90° C. until the reaction is complete (monitored by TLC). Heating is stopped and the mixture is allowed to return to ambient temperature. Water (75 mL) is added and the mixture is extracted with ethyl acetate (3×75 mL). The combined organic phases are washed with brine and then concentrated. The crude product is absorbed onto silica gel and purified by chromatography over silica gel using ethyl acetate and heptane as eluants. The product thereby obtained is dissolved in heptane in the warm state and is allowed to precipitate, with stirring, at ambient temperature, and then at 0° C. The solid is filtered off and the operation is repeated on the filtrate to yield the expected compound in the form of a solid.
¹H NMR (400 MHz, CDCl₃) δ ppm: 0.15 (s, 6H), 0.97 (s, 9H), 2.13 (s, 3H), 3.66 (s, 3H), 4.68 (br. s, 1H), 6.49 (d, J=8.5 Hz, 2H), 6.64 (s, 1H), 6.66 (d, J=8.7 Hz, 2H)
¹³C NMR (100 MHz, CDCl₃) δ ppm: 4.34, 9.72, 18.30, 25.88, 32.94, 101.27, 114.37, 114.70, 116.41, 120.73, 124.52, 131.23, 141.54, 148.27
MS (ESI+): [M+H]⁺ measured: 342.3

Preparation 19": 4-[(4-{[tert-Butyl(dimethyl)silyl]oxy}phenyl)amino]-1-methyl-1H-pyrrole-2-carbonitrile

Step A: 1-Methyl-1H-pyrrole-2-carbonitrile

N,N-Dimethylformamide (3 mL) and 1,4-diazabicyclo[2.2.2]octane (0.49 g, 4.3 mmol) are added to a solution of pyrrole-2-carbonitrile (4 g, 43.4 mmol) in dimethyl carbonate (56 mL). The solution is stirred at 90° C. for 15 hours, and is then heated at 110° C. for 8 hours. The mixture is cooled to ambient temperature, and then ethyl acetate (80 mL) is added. The phases are separated and the organic phase is washed with water (2×80 mL) and 1N aqueous HCl solution (1×80 mL). The combined aqueous phases are extracted again with ethyl acetate (1×80 mL). The combined organic phases are washed with brine (1×80 mL), dried over MgSO₄, filtered and concentrated in vacuo to obtain the expected product in the form of a liquid.
¹H NMR (400 MHz, CDCl₃) δ ppm: 3.78 (m, 2H), 6.12-6.18 (m, 1H), 6.74-6.82 (m, 1H)

Step B: 4-Bromo-1-methyl-1H-pyrrole-2-carbonitrile

N-Bromosuccinimide (6.2 g, 34.9 mmol) is added to a solution of 1-methyl-1H-pyrrole-2-carbonitrile (3.7 g, 34.9 mmol) in N,N-dimethylformamide (150 mL). The solution is stirred for 15 hours at ambient temperature. Another amount of N-bromosuccinimide (2.0 g, 11 mmol) is added and the mixture is stirred for 3 hours. Silica (7 g) is then added and the suspension is then evaporated to dryness. The material pre-absorbed onto the silica is placed on a silica gel column and the product is purified by chromatography over silica gel using ethyl acetate and heptane as eluants to obtain the expected product in the form of a solid.
¹H NMR (400 MHz, CDCl₃) δ ppm: 3.77 (s, 3H), 6.75 (d, J=1.7 Hz, 1H), 6.80 (d, J=1.7 Hz, 1H)

Step C: 4-[(tert-Butyldimethylsilyl)oxy]phenyl}amino)-1-methyl-1H-pyrrole-2-carbonitrile Nitrogen is bubbled through a solution of 4-bromo-1-methyl-1H-pyrrole-2-carbonitrile (2.82 g, 15.2 mmol) and 4-[(tert-butyldimethylsilyl)oxy]aniline (4.08 g, 18.3 mmol) in toluene (55 mL) for 5 minutes. Sodium tert-butylate (2.92 g, 30.4 mmol), tris(dibenzylideneacetone)dipalladium(0) (556 mg, 0.6 mmol) and 2-di-tert-butylphosphino-2',4',6'-triisopropylbiphenyl (255 mg, 0.6 mmol) are then added to the reaction mixture. The mixture is stirred for 1 hour at 80° C. under nitrogen. The suspension is then cooled to ambient temperature and filtered over Celite. The Celite cake is then rinsed with ethyl acetate. The filtrate is washed with water and then with brine. The organic phase is dried over MgSO$_4$, filtered and concentrated in vacuo. The product is purified twice by chromatography over silica gel using ethyl acetate and heptane as eluants, and then by trituration in heptane to obtain the expected product in the form of a solid.

$^1$H NMR (400 MHz, CDCl$_3$) δ ppm: 0.16 (s, 6H), 0.97 (s, 9H), 3.73 (s, 3H), 6.57 (d, J=1.9 Hz, 1H), 6.64-6.66 (m, 1H), 6.70 (s, 4H); NMR $^{13}$C NMR (100 MHz, CDCl$_3$) δ ppm: −4.48, 18.17, 25.72, 35.46, 103.01, 113.56, 113.69, 115.92, 119.55, 120.67, 129.04, 139.94, 148.85

MS (ESI+): [M+H]$^+$ 328.25

Preparation 20": N-[4-[tert-Butyl(dimethyl)silyl]oxy-3-fluoro-phenyl]-1-methyl-1H-pyrazol-4-amine The procedure is in accordance with the protocol of Preparation 1", replacing the 4-aminophenol used in Step A by 2-fluoro-4-aminophenol.

$^1$H NMR (400 MHz, dmso-d6) δ ppm: 7.59 (bs, 1H), 7.39 (m, 1H), 7.24 (d, 1H), 6.74 (dd, 1H), 6.52 (dd, 1H), 6.42 (ddd, 1H), 3.76 (s, 3H), 0.92 (s, 9H), 0.1 (d, 6H)

Preparation 21": 2-({4-[(tert-Butyldimethylsilyl)oxy]phenyl}amino)pyridine-4-carbonitrile A solution composed of 2-bromo-4-pyridinecarbonitrile (5.00 g, 36.1 mmol), 4-[(tert-butyldimethylsilyl)oxy]aniline (8.06 g, 36.1 mmol), sodium tert-butylate (4.50 g, 46.9 mmol) and 2-di-tert-butylphosphino-2',4',6'-triisoprobylbiphenyl (0.458 g, 1.08 mmol) in toluene (50 mL) is purged with nitrogen. Tris(dibenzylideneacetone)-dipalladium(0) (0.99 g, 1.08 mmol) is then added to the reaction mixture, and then the batch is heated at 50° C. for 1.5 hours. The mixture is then allowed to cool to ambient temperature. Water is added and the reaction mixture is extracted with ethyl acetate (3×20 mL). The combined organic phases are washed with brine, and then concentrated under reduced pressure. The crude product is absorbed onto silica gel and purified by chromatography over silica gel using ethyl acetate and heptane as eluants. The product obtained is dissolved in the warm state in heptane and precipitates, with stirring, at ambient temperature, and then at 0° C. After filtration, the expected compound is obtained in the form of a solid.

$^1$H NMR (400 MHz, CDCl$_3$) δ ppm: 0.22 (s, 6H), 1.00 (s, 9H), 6.61 (br. s, 1H), 6.81-6.84 (m, 2H), 6.84-6.89 (m, 2H), 7.12-7.17 (m, 2H), 8.26 (dd, J=5.1, 0.9 Hz, 1H)

$^{13}$C NMR (100 MHz, CDCl$_3$) δ ppm: −4.29, 18.31, 25.78, 109.11, 114.73, 117.23, 121.17, 121.74, 124.93, 132.12, 149.79, 153.45, 158.00

MS (ESI+): [M+H]$^+$ 326.19

Preparation 22": N-[4[tert-Butyl(dimethyl)silyl]oxyphenyl]-1-tetrahydrofuran-3-yl-pyrazol-4-amine 4-[tert-Butyl(dimethyl)silyl]oxyaniline (0.92 g, 3.48 mmol) and 4-iodo-1-tetrahydrofuran-3-yl-pyrazole (0.78 g, 3.48 mmol) dissolved in anhydrous tetrahydrofuran (20 mL) are stirred for one hour at ambient temperature in the presence of sodium tert-butylate (1.7 mL, 2M solution in THF) and chloro(2-di-tert-butylphosphino-2',4',6'-triisopropyl-1,1'-biphenyl)[2-(2-aminoethyl)phenyl]palladium(II) (84 mg, 0.122 mmol). The reaction mixture is filtered over Celite and then evaporated to dryness. The residue is crystallised from a mixture of heptane/ethyl acetate, filtered and washed with heptane and then purified by chromatography over silica gel using dichloromethane and methanol as eluants to yield the expected product.

$^1$H NMR (500 MHz, dmso-d6, 300 K) δ ppm: 7.62 (d, 1H, pyrazole-H5), 7.29 (d, 1H, pyrazole-H3), 7.26 (s, 1H, NH), 6.68 (d, 2H, Ar—H), 6.64 (d, 2H, Ar—H), 4.93 (m, 1H, THF-3'H), 3.95 (m, 1H, THF-5'H), 3.94 (m, 1H, THF-2'H), 3.87 (m, 1H, THF-2'H), 3.80 (m, 1H, THF-5'H), 2.33 (m, 1H, THF-4'H), 2.27 (m, 1H, THF-4'H), 0.93 (s, 9H, $^t$Bu), 0.12 (s, 6H, Me)

IR: ν C—H: 2857 cm$^{-1}$; ν aromatic: 1505 cm$^{-1}$; ν Si—C: 1249 cm$^{-1}$

Preparation 23": 6-({4-[(tert-Butyldimethylsilyl)oxy]phenyl}amino)pyridine-2-carbonitrile 4-Aminophenol (3.3 g, 30.2 mmol) is added to a solution of 6-chloropyridine-2-carbonitrile (3.5 g, 25.3 mmol) in 1-methyl-2-pyrrolidinone (70 mL). The reaction mixture is heated at 140-150° C. for 16 hours in a sealed flask. The batch is then cooled to ambient temperature. Imidazole (3.4 g, 49.9 mmol) and tert-butyl(dimethyl)silyl chloride (7.6 g, 50.4 mmol) are subsequently added and the mixture is stirred for 16 hours at ambient temperature. The mixture is diluted with water (140 mL) and the product is extracted with AcOEt (4×50 mL). The organic phases are combined and washed with water (3×50 mL), and then brine (1×50 mL). The organic phase is then dried over MgSO$_4$, filtered and concentrated in vacuo. The crude product is purified by chromatography over silica gel using ethyl acetate and heptane as eluants to obtain the title product.

$^1$H NMR (400 MHz, CDCl$_3$) δ ppm: 0.20 (s, 6H), 0.99 (s, 9H), 6.74 (dd, J=7.6, 4.9 Hz, 1H), 6.81-6.88 (m, 3H), 7.36-7.42 (m, 2H), 7.74 (dd, J=7.6, 1.9 Hz, 1H), 8.34 (dd, J=4.9, 1.9 Hz, 1H)

$^{13}$C NMR (100 MHz, CDCl$_3$) δ ppm: −4.38, 18.21, 25.73, 92.58, 113.50, 116.53, 120.30, 123.20, 131.97, 141.67, 152.42, 152.45, 156.51

MS (ESI): [M+H]$^+$ 326.24

Preparation 24": 4-({4-[(tert-Butyldimethylsilyl)oxy]phenyl}amino)pyrimidine-2-carbonitrile Step A: N-{4-[(tert-Butyldimethylsilyl)oxy]pheny}-2-chloropyrimidin-4-amine 4-Aminophenol (8.8 g, 80.6 mmol) and triethylamine (18.6 mL, 133.4 mmol) are added to a solution of 2,4-dichloropyrimidine (10.0 g, 67.1 mmol) in ethanol (150 mL). The reaction mixture is heated at 150° C. for 14 hours in a sealed flask. The batch is then cooled to ambient temperature and the solvent is evaporated off in vacuo. Dichloromethane (200 mL) is added to the residue, and then imidazole (9.1 g, 133.7 mmol) and tert-butyl(dimethyl)silyl chloride (12.1 g, 80.3 mmol) are added. The mixture is stirred for 15 hours at ambient temperature. The reaction mixture is diluted with water (200 mL). The phases are separated and the organic phase is washed with brine (1×100 mL). It is then dried over MgSO$_4$, filtered and concentrated in vacuo. The residue is purified by chromatography over silica gel using ethyl acetate and heptane as eluants to obtain a solid. The latter is triturated in heptane, filtered off and rinsed with heptane to yield the expected compound in the form of a solid.

$^1$H NMR (400 MHz, dmso-d6) δ ppm: 0.22 (s, 6H), 0.99 (s, 9H), 6.42 (d, J=5.9 Hz, 1H), 6.81 (br. s, 1H), 6.85-6.90 (m, 1H), 7.13 (d, J=8.7 Hz, 2H), 8.07 (d, J=5.9 Hz, 2H)

Step B: 4-({4-[(tert-Butyldimethylsilyl)oxy]phenyl}amino)pyrimidine-2-carbonitrile Anhydrous N,N-dimethylformamide (10 mL) is placed under nitrogen in a flask and then the compound of Step A (670 mg, 2.0 mmol) is added. Zinc cyanide (468 mg, 4.0 mmol) and tetrakis(triphenylphosphine)palladium(0) (404 mg, 0.3 mmol) are subsequently added. Nitrogen is bubbled through the solution for 5 minutes and then the reaction mixture is stirred at 120° C. for 2 hours under a nitrogen atmosphere. The reaction, monitored by LC-MS, is complete. The mixture is cooled to ambient temperature, and then water (15 mL) is added thereto. The product is extracted with AcOEt (3×25 mL). The organic phases are combined and washed with water (4×25 mL), and then with brine (1×25 mL). The organic phase is dried over $MgSO_4$, filtered and concentrated in vacuo. The residue is purified by chromatography over silica gel using ethyl acetate and heptane as eluants to obtain the expected compound in the form of a solid.

$^1$H NMR (400 MHz, $CDCl_3$) δ ppm: 0.22 (s, 6H), 0.99 (s, 9H), 6.63 (d, J=6.1 Hz, 1H), 6.86-6.92 (m, 2H), 7.03 (br. s, 1H), 7.17 (d, J=8.5 Hz, 2H), 8.22 (d, J=6.1 Hz, 1H)

$^{13}$C NMR (100 MHz, $CDCl_3$) δ ppm: −4.51, 18.10, 25.55, 106.32, 115.92, 121.00, 125.22, 129.73, 144.55, 154.16, 156.07, 161.56

Preparation 25'': N-{4-[(tert-Butyldimethylsilyl)oxy]phenyl}-1-trideuteriomethyl-1H-pyrazol-4-amine

Step A: 4-Bromo-1-trideuteriomethyl-1H-pyrazole

4-Bromo-1H-pyrazole (9.05 g, 61.6 mmol) is added in portions to a suspension of NaH (60% in oil) (2.83 g, 70.8 mmol) in tetrahydrofuran (90 mL) cooled in an ice bath. After having taken away the ice bath, the solution is stirred at ambient temperature for 0.5 hours. It is again cooled in an ice bath and iodomethane-$d_3$ (5.0 mL, 80.3 mmol) is added. The solution is stirred at ambient temperature for 19 hours. The suspension is then concentrated. The evaporation residue is triturated with MTBE (90 mL) and filtered. The filtrate is concentrated in vacuo to obtain the expected compound in the form of an oil.

$^1$H NMR (400 MHz, $CDCl_3$) δ ppm: 7.37 (s, 1H), 7.43 (s, 1H)

Step B: N-{4-[(tert-Butyldimethylsilyl)oxy]phenyl}-1-trideuteriomethyl-1H-pyrazol-4-amine 4-Bromo-1-trideuteriomethyl-1H-pyrazole (9.6 g, 58.5 mmol), 4-[(tert-butyldimethyl-silyl)oxy]aniline (14.4 g, 64.6 mmol) and toluene (150 mL) are added to a 500-ml three-necked flask. The solution is degassed with nitrogen for 15 minutes, and then sodium tert-butylate (11.4 g, 0.12 mol), 2-di-tert-butylphosphino-2',4',6'-triisopropylbiphenyl (0.77 g, 1.81 mmol) and tris(dibenzylideneacetone)dipalladium(0) (1.64 g, 1.79 mmol) are successively added. The suspension is heated at 85° C. for 1.5 hours. The reaction mixture is then cooled to ambient temperature and water (270 mL) is added. The mixture is stirred for 30 minutes. Celite (30 g) is then added and the suspension is filtered on a bed of Celite.

The phases of the filtrate are separated and the aqueous phase is extracted with ethyl acetate (3×200 mL). The combined organic phases are dried over $Na_2SO_4$ and filtered. Silica (36 g) is added to the filtrate and the batch is evaporated to dryness. The product is purified by chromatography over silica gel using ethyl acetate and heptane as eluants. The product obtained is recrystallised from heptane (80 mL) to obtain the expected compound.

$^1$H NMR (400 MHz, $CDCl_3$) δ ppm: 0.16 (s, 6H), 0.97 (s, 9H), 4.92 (s, 1H), 6.61-6.73 (m, 4H), 7.25 (s, 1H), 7.36 (s, 1H)

$^{13}$C NMR (100 MHz, $CDCl_3$) δ ppm: −4.37, 18.28, 25.86, 38.67 (sept., $^1J_{C\text{-}D}$ =21.0 Hz), 115.12, 120.73, 123.76, 126.52, 134.74, 141.07, 148.43

MS (ESI): $[M+H]^+$ 307.08

Preparation 26'': N-[4-[tert-Butyl(dimethyl)silyl]oxyphenyl]-1-(oxetan-3-yl)-1H-pyrazol-4-amine

Step A: 4-Bromo-1-(oxetan-3-yl)-1H-pyrazole

4-Bromo-1H-pyrazole (1.53 g, 10.7 mmol) is dissolved in anhydrous dimethylformamide (15 mL). 3-Bromooxetane (2.0 g, 14.6 mmol) and caesium carbonate (4.7 g, 14 mmol) are successively added thereto. The reaction mixture is heated for 8 hours at 130° C. in a sealed flask. At the end of the reaction, the solvent is evaporated off in vacuo and the residue is purified by chromatography over silica gel using dichloromethane containing diethylamine and methanol as eluants to yield the expected compound.

Step B: N-[4-[tert-Butyl(dimethyl)silyl]oxyphenyl]-1-(oxetan-3-yl)-1H-pyrazol-4-amine 4-[tert-Butyl(dimethyl)silyl]oxyaniline (1.5 g, 7.2 mmol) and 4-bromo-1-(oxetan-3-yl)-pyrazole (1.6 g, 7.2 mmol) dissolved in anhydrous tetrahydrofuran (25 mL) are stirred for 3 hours at ambient temperature in the presence of sodium tert-butylate (3.7 mL, 2M solution in THF) and chloro(2-di-tert-butylphosphino-2',4',6'-triisoprop yl-1,1'-biphenyl)[2-(2-aminoethyl)phenyl]palladium(II) (101 mg, 0.145 mmol). The reaction mixture is filtered over Celite and then evaporated to dryness. The residue is purified by chromatography over silica gel using dichloromethane containing diethylamine and ethyl acetate as eluants to yield the expected product.

$^1$H NMR (500 MHz, dmso-d6, 300 K) δ ppm: 7.76 (s, 1H, pyrazole-5'H), 7.40 (s, 1H, pyrazole-3'H), 7.34 (br s, 1H, NH), 6.70 (d, 2H, Ar—H), 6.65 (d, 2H, Ar—H), 5.49 (m, 1H, oxetane), 4.89 (d, 4H, oxetane), 0.93 (s, 9H, $^t$Bu), 0.13 (s, 6H, Me)

IR: v: C—H: 2955 $cm^{-1}$; aromatic: 1505 $cm^{-1}$; Si—C: 1237 $cm^{-1}$

Preparation 27'': Mixture of N-(4-{[tert-butyl(dimethyl)silyl]oxy}phenyl)-1,5-dimethyl-1H-pyrazol-4-amine and N-(4-{[tert-butyl(dimethyl)silyl]oxy}phenyl)-1,3-dimethyl-1H-pyrazol-4-amine

Step A: Mixture of 4-bromo-1,5-dimethyl-1H-pyrazole and 4-bromo-1,3-dimethyl-1H-pyrazole To a suspension of NaH 60% in oil (0.3 g; 7.45 mmol) in tetrahydrofuran (150 mL) there is added, at 10° C., 4-bromo-3-methyl-1H-pyrazole dissolved in 15 mL of tetrahydrofuran dropwise, over 15 minutes. After stirring for 40 minutes at ambient temperature, iodomethane (0.45 mL; 7.45 mmol) is added dropwise, and then the reaction mixture is stirred overnight. After adding water, the reaction mixture is evaporated and taken up in dichloromethane. The organic phase is separated off and dried over $MgSO_4$, filtered and concentrated to dryness. The residue is purified by chromatography over silica gel to yield a mixture of the title compounds (4-bromo-1,3-dimethyl-pyrazole and 4-bromo-1,5-dimethyl-pyrazole respectively in a ratio of 4:6).

4-bromo-1,5-dimethyl-1H-pyrazole:
$^1$H NMR (500 MHz, dmso-d6) δ ppm: 7.41 (s, 1H), 3.76 (s, 3H), 2.22 (s, 3H) 4-bromo-1,3-dimethyl-1H-pyrazole:
$^1$H NMR (500 MHz, dmso-d6) δ ppm: 7.81 (s, 1H), 3.74 (s, 3H), 2.09 (s, 3H)

Step B: Mixture of N-(4-{[tert-butyl(dimethyl)silyl]oxy}phenyl)-1,5-dimethyl-1H-pyrazol-4-amine and N-(4-{[tert-butyl(dimethyl)silyl]oxy}phenyl)-1,3-dimethyl-1H-pyrazol-4-amine The procedure is in accordance with Step B of Preparation 1″, replacing the 4-bromo-1-methyl-1H-pyrazole by the mixture of isomers from Step A. A mixture of isomers in a ratio of 4:6 is obtained (respectively N-(4-{[tertbutyl(dimethyl)silyl]oxy}phenyl)-1,5-dimethyl-1H-pyrazol-4-amine and N-(4-{[tert-butyl(dimethyl)silyl]oxy}phenyl)-1,3-dimethyl-1H-pyrazol-4-amine.

Preparation 28″: N-[4-[tert-Butyl(dimethyl)silyl]oxyphenyl]-1-cyclopropyl-1H-pyrazol-4-amine Step A: 4-Bromo-1-cyclopropyl-1H-pyrazole 4-Bromo-1H-pyrazole (1.76 g, 12 mmol) is dissolved in anhydrous dimethylformamide (15 mL). Cyclopropyl bromide (2.9 mL, 36 mmol) and caesium carbonate (7.8 g, 24 mmol) are successively added thereto. The reaction mixture is heated for 15 hours at 160° C. in a sealed flask. At the end of the reaction, the solvent is evaporated off in vacuo and the residue is purified by chromatography over silica gel using heptane and dichloromethane as eluants to yield the expected compound.

Step B: N-[4-[tert-Butyl(dimethyl)silyl]oxyphenyl]-1-cyclopropyl-1H-pyrazol-4-amine 4-[tert-Butyl(dimethyl)silyl]oxyaniline (1.64 g, 7.3 mmol) and 4-bromo-1-cyclopropyl-1H-pyrazole (1.4 g, 7.3 mmol) dissolved in anhydrous tetrahydrofuran (30 mL) are stirred for 3 hours at ambient temperature in the presence of sodium tert-butylate (3.7 mL, 2M solution in THF) and chloro(2-di-tert-butylphosphino-2',4',6'-triisopropyl-1,1'-biphenyl)[2-(2-aminoethyl)phenyl]palladium(II) (101 mg, 0.146 mmol). The reaction mixture is filtered over Celite and then evaporated to dryness. The residue is purified by chromatography over silica gel using heptane and ethyl acetate as eluants to yield the expected product.

$^1$H NMR (500 MHz, dmso-d6, 300 K) δ ppm: 7.61 (s, 1H, pyrazole-5'H), 7.23 (s, 1H, pyrazole-3'H), 7.22 (br s, 1H, NH), 6.65 (d, 2H, Ar—H), 6.63 (d, 2H, Ar—H), 3.64 (m, 1H, cyclopropyl-H), 1.00-0.91 (m, 4H, cyclopropyl), 0.93 (s, 9H, $^t$Bu), 0.12 (s, 6H, Me)

IR: v: C—H: 2930 cm$^{-1}$; aromatic: 1504 cm$^{-1}$; Si—C: 1237 cm$^{-1}$

High-Resolution Mass Spectrometry (ESI+):
Empirical formula: $C_{18}H_{27}N_3OSi$
[M+H]$^+$ calculated: 330.2003
[M+H]$^+$ measured: 330.1989

Preparation 29″: 1,5-Dimethyl-4-(phenylamino)-1H-pyrrole-2-carbonitrile

The procedure is in accordance with the protocol of Preparation 1″, replacing the 4-{[tert-butyl(dimethyl)silyl]oxy}aniline used in Step B by aniline.
$^1$H NMR (400 MHz, dmso-d6) δ ppm: 7.19 (s, 1H), 7.05 (t, 2H), 6.79 (s, 1H), 6.6 (m, 3H), 3.61 (s, 3H), 2.1 (s, 3H)

Preparation 30″: 1-Methyl-N-phenyl-1H-pyrrolo[2,3-b]pyridin-6-amine

The procedure is in accordance with the protocol of Step B of Preparation 1″ using aniline and 5-bromo-1-methyl-1H-pyrrolo[2,3-b]pyridine (obtained in accordance with a protocol from the literature: *Heterocycles*, 60(4), 865, 2003).
$^1$H NMR (400 MHz, dmso-d6) δ ppm: 8.1 (d, 1H), 7.9 (s, 1H), 7.7 (d, 1H), 7.45 (d, 1H), 7.17 (t, 2H), 6.9 (d, 2H), 6.7 (t, 1H), 6.38 (d, 1H), 3.8 (s, 3H)

Preparation 31″: N-(4-{[tert-Butyl(dimethyl)silyl]oxy}phenyl)-1-trideuteriomethyl-1H-pyrrolo[2,3-b]pyridin-5-amine The procedure is in accordance with the process of Preparation 1″, replacing the 4-bromo-1-methyl-1H-pyrazole used in Step B by 5-bromo-1-(trideuteriomethyl)-1H-pyrrolo[2,3-b]pyridine (obtained in accordance with a protocol from the literature *Heterocycles*, 60(4), 865, 2003, replacing the methyl iodide by trideuterated methyl iodide).
$^1$H NMR (400 MHz, dmso-d6) δ ppm: 8.05 (d, 1H), 7.6 (m+d, 2H), 7.4 (d, 1H), 6.85/6.7 (2d, 4H), 6.3 (d, 1H), 0.95 (s, 9H), 0.15 (s, 6H)

Preparation 32″: 4-({4-[(tert-Butyldimethylsilyl)oxy]phenyl}amino)-1-trideuteriomethyl-1H-pyrrole-2-carbonitrile Step A: 1-Trideuteriomethyl-1H-pyrrole-2-carbonitrile NaH (60% in oil) (2.61 g, 65.2 mmol) is suspended in tetrahydrofuran (110 mL) at 0° C. 1H-Pyrrole-2-carbonitrile (5 g, 54.3 mmol) is added dropwise over 10 minutes. The reaction mixture is then warmed up to ambient temperature over 30 minutes. It is again cooled to 0° C., and then iodomethane-d$_3$ (10.23 g, 70.6 mmol) is added. The reaction mixture is stirred for 16 hours under nitrogen at ambient temperature. The reaction mixture is then evaporated under reduced pressure, and then ethyl acetate (200 mL) and water (200 mL) are added. The phases are separated, and the aqueous phase is extracted with ethyl acetate (2×200 mL). The combined organic phases are washed with brine (1×80 mL), dried over MgSO$_4$, filtered and concentrated in vacuo. The residue is purified by chromatography over silica gel using ethyl acetate and heptane as eluants. The fractions are combined and evaporated in vacuo to obtain the expected compound.

$^1$H NMR (400 MHz, CDCl$_3$) δ ppm: 6.13 (dd, J=2.7, 3.9 Hz, 1H), 6.75 (dd, J=1.5, 4.1 Hz, 1H), 6.79 (dd, J=1.7, 2.6 Hz, 1H)

Step B: 4-Bromo-1-trideuteriomethyl-1H-pyrrole-2-carbonitrile

N-Bromosuccinimide (6.68 g, 37.5 mmol) is added to a solution of the compound of the above Step (4.09 g, 37.5 mmol) in N,N-dimethylformamide (188 mL). The solution is stirred for 16 hours at ambient temperature. The residue is purified by chromatography using ethyl acetate and heptane as eluants to obtain the expected compound in the form of a solid.

$^1$H NMR (400 MHz, CDCl$_3$) δ ppm: 6.75 (d, J=1.7 Hz, 1H), 6.80 (d, J=1.7 Hz, 1H)

Step C: 4-({4-[(tert-Butyldimethylsilyl)oxy]phenyl}amino)-1-trideuteriomethyl-1H-pyrrole-2-carbonitrile Nitrogen is bubbled through a solution composed of the compound obtained in the above Step (5.85 g, 31.1 mmol), 4-[(tert-butyldimethylsilyl)oxy]aniline (8 g, 35.8 mmol), sodium tert-butylate (3.88 g, 40.4 mmol) and 2-di-tert-butylphosphino-2',4',6'-triisopropylbiphenyl (662 mg, 1.56 mmol) in toluene (260 mL) for 5 minutes. Tris(dibenzylideneacetone)-dipalladium(0) (1.43 g, 1.56 mmol) is then added. The mixture is stirred for 1 hour at 70° C. under nitrogen. The suspension is then cooled to ambient temperature, diluted with ethyl acetate and filtered over Celite. The Celite cake is then rinsed with ethyl acetate. The filtrate is washed with water (3 times), and then brine (once). The organic phase is dried over Na$_2$SO$_4$, filtered and concentrated in vacuo. The product is purified twice by chromatography over silica gel using ethyl acetate and heptane as eluants, and then by reverse-phase chromatography using methanol and water as eluants to obtain the expected compound in the form of a powder.
$^1$H NMR (400 MHz, CDCl$_3$) δ ppm: 0.17 (s, 6H), 0.98 (s, 9H), 4.96 (br. s, 1H), 6.57 (d, J=1.9 Hz, 1H), 6.64 (d, J=1.8 Hz, 1H), 6.70 (br. s, 4H)
$^{13}$C NMR (100 MHz, CDCl$_3$) δ ppm: −4.38, 18.26, 25.83, 34.83, 102.96, 113.69, 113.71, 115.95, 119.58, 120.75, 129.14, 140.10, 148.84
MS (ESI): [M+H]$^+$ 331.09

Preparation 33''': 4-({4-[(tert-Butyldimethylsilyl)oxy]phenyl}amino)-1-trideuteriomethyl-5-methyl-1H-pyrrole-2-carbonitrile Step A: 5-Methyl-1H-pyrrole-2-carbonitrile The compound is prepared in accordance with the protocol described in *Heterocycles* 2011, 82, 1503.

Step B: 1-Trideuteriomethyl-5-methyl-1H-pyrrole-2-carbonitrile

A solution of 5-methyl-1H-pyrrole-2-carbonitrile (0.30 g, 2.82 mmol) in N,N-dimethyl-formamide (5 mL) is cooled to 0° C. NaH (60% in oil) (0.118 g, 2.96 mmol) is added in portions, and the reaction mixture is stirred at 0° C. for 30 minutes. Iodomethane-d$_3$ (4.15 mL, 67.2 mmol) is added in a single portion, and the reaction mixture is stirred at ambient temperature until the reaction is complete. It is then diluted with water (30 mL) and ethyl acetate (15 mL). The phases are separated and the aqueous phase is extracted a second time with ethyl acetate (15 mL). The combined organic phases are washed with water (1×50 mL), and then brine, and dried over Na$_2$SO$_4$. After filtration and concentration under reduced pressure, the residue is purified by chromatography over silica gel using ethyl acetate and heptane as eluants to yield the expected compound in the form of a solid.
$^1$H NMR (400 MHz, CDCl$_3$) δ ppm: 2.25 (s, 3H), 5.91 (dd, J=3.9, 0.6 Hz, 1H), 6.69 (d, J=3.9 Hz, 1H)

Step C: 4-Bromo-1-trideuteriomethyl-5-methyl-1H-pyrrole-2-carbonitrile

A solution of bromine (0.133 mL, 2.60 mmol) in acetic acid (1.5 mL) is added dropwise to a solution of the compound obtained in the above Step (0.305 g, 2.48 mmol) in acetic acid (5.5 mL) previously cooled to 0° C. The reaction mixture is stirred and gradually warmed up to ambient temperature over a period of 20 hours. The reaction mixture is poured into water (50 mL) and the mixture is extracted with dichloromethane (2×50 mL). The organic phase is dried over Na$_2$SO$_4$, filtered and concentrated under reduced pressure to yield the expected compound in the form of a solid.
$^1$H NMR (400 MHz, CDCl$_3$) δ ppm: 2.24 (s, 3H), 6.73 (s, 1H)

Step D: 4-({14-[(tert-Butyldimethylsilyl)oxy]phenyl}amino)-1-trideuteriomethyl-5-methyl-1H-pyrrole-2-carbonitrile A solution composed of the compound obtained in the above Step (7.00 g, 34.6 mmol), 4-[(tert-butyldimethylsilyl)oxy]aniline (8.90 g, 39.8 mmol), sodium tert-butylate (4.33 g, 45.0 mmol) and 2-di-tert-butylphosphino-2',4',6'-triisopropylbiphenyl (0.441 g, 1.04 mmol) in toluene (70 mL) is purged with nitrogen. Tris(dibenzylideneacetone)-dipalladium(0) (0.951 g, 1.04 mmol) is added, and then the reaction mixture is heated at 65° C. until the reaction, monitored by TLC, is complete. Heating is stopped and the mixture is cooled to ambient temperature. Water (200 mL) is added and the mixture is extracted with ethyl acetate (3 times). The combined organic phases are washed with brine, and then concentrated. The crude product is purified by chromatography over silica gel using ethyl acetate and heptane as eluants. The product obtained is dissolved in heptane in the warm state; it is allowed to precipitate out at ambient temperature and then at 0° C. to yield the expected product in the form of crystals.
$^1$H NMR (400 MHz, CDCl$_3$) δ ppm: 0.15 (s, 6H), 0.96 (s, 9H), 2.12 (s, 3H), 4.66 (br. s, 1H), 6.46-6.51 (m, 2H), 6.64 (s, 1H), 6.64-6.69 (m, 2H)
$^{13}$C NMR (100 MHz, CDCl$_3$) δ ppm: −4.37, 9.64, 18.26, 25.84, 31.62-32.87 (m), 101.14, 114.35, 114.66, 116.33, 120.68, 124.51, 131.17, 141.53, 148.18
MS (ESI): [M+H]$^+$ 345.13

Preparation 34''': 5-[(4-{[tert-Butyl(dimethyl)silyl]oxy}phenyl)amino]-1-methyl-1H-pyrazole-3-carbonitrile Step A: 5-Amino-1-methyl-1H-pyrazole-3-carbonitrile To a suspension of 1-methyl-5-nitro-1H-pyrazole-3-carbonitrile (2 g; 13.1 mmol) in a mixture of water (14 mL) and ethanol (120 mL) there are added HCl 37% (170 μL) and iron filings (5.1 g; 91 mmol). The reaction mixture is heated for 5 hours at 50° C. After cooling to ambient temperature, the reaction mixture is filtered. The filtrate is concentrated to dryness and then purified by chromatography over silica gel using dichloromethane and ethyl acetate as eluants to yield the expected compound in the form of a solid.
$^1$H NMR (400 MHz, dmso-d6) δ ppm: 5.8 (s, 1H), 5.7 (m, 2H), 3.6 (s, 3H)

Step B: 5-[(4-{[tert-Butyl(dimethyl)silyl]oxy}phenyl)amino]-1-methyl-1H-pyrazole-3-carbonitrile The procedure is in accordance with the protocol of Step B of Preparation 1''', replacing the 4-bromo-1-methyl-1H- pyrazole by (4-bromophenoxy)-(tert-butyl)dimethyl-silane and the 4-{[tert-butyl(dimethyl)silyl]oxy}aniline by the compound from Step A.

$^1$H NMR (400 MHz, dmso-d6) δ ppm: 8.15 (s, 1H), 6.9 (d, 2H), 6.75 (d, 2H), 6.45 (s, 1H), 3.75 (s, 3H), 0.95 (s, 9H), 0.15 (s, 6H)

Preparation 35": 4-[(4-{[tert-Butyl(dimethyl)silyl]oxy}phenyl)amino]-5-methyl-1-[2-(morpholin-4-yl)ethyl]-1H-pyrrole-2-carbonitrile The procedure is in accordance with the process of Preparation 33", replacing the iodomethane-d$_3$ in Step B by 2-(chloroethyl)morpholine hydrochloride.

$^1$H NMR (400 MHz, dmso-d6) δ ppm: 6.85 (s, 1H), 6.75 (s, 1H), 6.6 (d, 2H), 6.5 (d, 2H), 4.1 (t, 2H), 3.55 (t, 4H), 2.6 (t, 2H), 2.4 (t, 4H), 2.1 (s, 3H), 0.9 (s, 9H), 0.1 (s, 6H)

Preparation 36": N-(4-{[tert-Butyl(dimethyl)silyl]oxy}phenyl)-2-[2-(morpholin-4-yl)ethoxy]pyrimidin-5-amine

Step A: 4-[2-(5-Bromopyrimidin-2-yl)oxyethyl]morpholine

NaH (1.0 g, 25.0 mmol, 60% in oil) suspended in anhydrous tetrahydrofuran is cooled at 0° C. in an ice bath under argon, and then 2-morpholinoethanol (2.7 g, 20.7 mmol) is added dropwise. The ice bath is withdrawn and the suspension is stirred for 1 hour at ambient temperature. 5-Bromo-2-chloro-pyrimidine (4.0 g, 20.7 mmol) is then added at ambient temperature and the reaction mixture is stirred for 16 hours at ambient temperature. Saturated aqueous ammonium chloride solution (10 mL) and water (10 mL) are added to the reaction mixture; the pH is adjusted to 9 by adding saturated aqueous NaHCO$_3$ solution. The resulting solution is extracted 3 times with ethyl acetate, the organic phase is then washed with brine, dried over MgSO$_4$, and then evaporated to dryness. The expected compound precipitates out by means of the addition of petroleum ether.

$^1$H NMR (400 MHz, dmso-d6) δ ppm: 8.75 (s, 2H), 4.4 (t, 2H), 3.55 (t, 4H), 2.7 (t, 2H), 2.45 (t, 4H)

IR (ATR) cm$^{-1}$: 1562 ν >C=C< and C=N, 787 ν —C—H Ar

Step B: N-(4-{[tert-Butyl(dimethyl)silyl]oxy}phenyl)-2-[2-(morpholin-4-yl)ethoxyl]-pyrimidin-5-amine The procedure is in accordance with the protocol of Step B of Preparation 1", replacing the 4-bromo-1-methyl-1H-pyrazole by the compound from Step A.

$^1$H NMR (400 MHz, dmso-d6) δ ppm: 8.3 (s, 2H), 7.8 (s, 1H), 6.9/6.75 (2d, 4H), 4.35 (t, 2H), 3.55 (t, 4H), 2.7 (t, 2H), 2.45 (t, 4H), 0.95 (s, 9H), 0.15 (s, 6H)

IR (ATR) cm$^{-1}$: 3300 ν —NH, 1506 ν —NH, 837 ν —Si-Me, 837 and 778 ν —CH Ar

Preparation 37": 4-({4-[(tert-Butyldimethylsilyl)oxy]phenyl}amino)-1,3-dimethyl-1H-pyrrole-2-carbonitrile

Step A: 4-Methyl-N-(prop-2-en-1-yl)benzene-1-sulphonamide

Allylamine (10.6 mL, 0.14 mol) is added over a period of 4 minutes to a solution of tosyl chloride (25.1 g, 0.13 mol) in dichloromethane (250 mL) cooled in an ice bath. Triethylamine (24 mL, 0.18 mol) is added and then the solution is stirred at ambient temperature for 1.25 hours. Aqueous 3N HCl solution (60 mL) is added and the phases are then separated. The organic phase is washed with another amount of aqueous 3N HCl solution (60 mL) and then with 5% aqueous sodium bicarbonate solution (60 mL). The organic phase is dried over Na$_2$SO$_4$, filtered and concentrated to obtain the expected compound in the form of a solid.

$^1$H NMR (400 MHz, CDCl$_3$) δ ppm: 2.43 (s, 3H), 3.54-3.63 (m, 2H), 4.50 (1s, 1H), 5.05-5.22 (m, 2H), 5.66-5.79 (m, 1H), 7.31 (d, J=8.1 Hz, 2H), 7.76 (d, J=8.1 Hz, 2H)

Step B: 4-Methyl-N-(2-methylprop-2-en-1-yl)-N-(prop-2-en-1-yl)benzene-1-sulphonamide 3-Chloro-2-methylpropene (20 mL, 0.20 mol) is added over a period of 5 minutes to a suspension of 4-methyl-N-(prop-2-en-1-yl)benzene-1-sulphonamide (27.9 g, 0.13 mol) and potassium carbonate (28.1 g, 0.20 mol) in N,N-dimethylformamide (200 mL) cooled in an ice bath. After 20 minutes, the suspension is stirred at ambient temperature for 18 hours. The suspension is concentrated to dryness. The residue is taken up in ethyl acetate (250 mL) and water (110 mL). The aqueous phase is extracted with ethyl acetate (2×50 mL). The combined organic phases are washed successively with aqueous 3N HCl solution (50 mL), water (3×50 mL), aqueous 5% potassium bicarbonate solution (50 mL), and finally brine (50 mL). The organic phase is dried over Na$_2$SO$_4$, filtered and concentrated to obtain the expected compound in the form of an oil.

$^1$H NMR (400 MHz, CDCl$_3$) δ ppm: 1.69 (s, 3H), 2.43 (s, 3H), 3.70 (s, 2H), 3.75-3.79 (m, 2H), 4.87 (d, J=25.1 Hz, 1H), 5.04-5.09 (m, 1H), 5.09-5.12 (m, 1H), 5.45-5.59 (m, 1H), 7.29 (d, J=8.1 Hz, 2H), 7.71 (d, J=8.1 Hz, 2H)

Step C: 3-Methyl-1-(4-methylbenzenesulphonyl)-1H-pyrrole

A solution of the compound obtained in Step B (15.2 g, 57.3 mmol) in toluene (550 mL) is heated at 80° C. in the presence of (1,3-bis(2,4,6-trimethylphenyl)-2-imidazolidinylidene)-dichloro(phenylmethylene)(tricyclohexylphosphine)ruthenium (Grubbs' catalyst, 2nd generation) (150 mg, 0.18 mmol) for 1 hour. 2,3-Dichloro-5,6-dicyano-p-benzoquinone (16.1 g, 70.9 mmol) is then added in one portion, and the solution is heated at 80° C. for 24 hours. The solution is filtered over Celite, and the filtrate is concentrated in vacuo. The product is purified by chromatography over silica gel using ethyl acetate and heptane as eluants to obtain the expected compound in the form of a solid.

$^1$H NMR (400 MHz, CDCl$_3$) δ ppm: 2.02 (d, J=1.0 Hz, 3H), 2.39 (s, 3H), 6.09-6.13 (m, 1H), 6.85-6.90 (m, 1H), 7.03-7.07 (m, 1H), 7.27 (d, J=8.4 Hz, 2H), 7.72 (d, J=8.4 Hz, 2H)

Step D: 3-Methyl-1-(4-methylbenzenesulphonyl)-1H-pyrrole-2-carbonitrile

Aluminium chloride (19.4 g, 0.15 mol) is added all at once to a solution of 3-methyl-1-(4-methylbenzenesulphonyl)-1H-pyrrole (13.0 g, 55.3 mmol) in 1,2-dichloroethane (230 mL) at ambient temperature. After stirring for 20 minutes, cyanogen bromide (11.11 g, 0.10 mol) is added in portions over a period of 20 minutes. After 4.5 hours, an additional amount of cyanogen bromide (1.94 g, 18.3 mmol) is added. After stirring for 17 hours at ambient temperature, the reaction mixture is poured slowly into a mixture of dichloromethane (300 mL) and water (600 mL) cooled to 0° C. The resulting mixture is stirred for 1 hour. Subsequently the phases are separated and the aqueous phase is extracted with dichloromethane (3×150 mL). The combined organic phases are washed with water (2×150 mL) and brine (150 mL). The organic phase is dried over $Na_2SO_4$, filtered and concentrated in vacuo to obtain the expected compound in the form of a solid.

$^1$H NMR (400 MHz, $CDCl_3$) δ ppm: 2.18 (s, 3H), 2.43 (s, 3H), 6.17 (d, J=3.2 Hz, 1H), 7.33-7.39 (m, 3H), 7.90 (d, J=8.5 Hz, 2H)

Step E: 4-Bromo-3-methyl-1-(4-methylbenzenesulphonyl)-1H-pyrrole-2-carbonitrile N-Bromosuccinimide (12.0 g, 67.4 mmol) is added all at once to a suspension of 3-methyl-1-(4-methylbenzenesulphonyl)-1H-pyrrole-2-carbonitrile (14.45 g, 55.6 mmol) in N,N-dimethylformamide (60 mL) at ambient temperature. The mixture is stirred at ambient temperature for 29 hours and is then cooled in an ice bath. Saturated aqueous sodium bisulphite solution (90 mL), water (90 mL) and ethyl acetate (250 mL) are then added. The phases are separated, and then the aqueous phase is extracted with ethyl acetate (2×70 mL). The combined organic phases are washed with 5% aqueous potassium bicarbonate solution (90 mL), water (3×90 mL), and then brine (3×90 mL). The organic phase is dried over $Na_2SO_4$, filtered and concentrated in vacuo. The crude product is purified by chromatography over silica gel using toluene and heptane as eluants to obtain the expected compound in the form of a solid.

$^1$H NMR (400 MHz, $CDCl_3$) δ ppm: 2.13 (s, 3H), 2.45 (s, 3H), 7.38 (d, J=8.4 Hz, 2H), 7.43 (s, 1H), 7.92 (d, J=8.4 Hz, 2H)

Step F: 4-Bromo-1,3-dimethyl-1H-pyrrole-2-carbonitrile

Potassium hydroxide (3.65 g, 65.1 mmol) is added all at once to a suspension of 4-bromo-3-methyl-1-(4-methylbenzenesulphonyl)-1H-pyrrole-2-carbonitrile (4.66 g, 13.7 mmol) in methanol (95 mL) cooled using an ice bath. After 15 minutes, the suspension is stirred at ambient temperature for 17 hours. The methanol is evaporated to dryness. The evaporation residue is taken up in MTBE (25 mL) and washed with water (25 mL). The aqueous phase is extracted with MTBE (2×25 mL). The combined organic phases are dried over $Na_2SO_4$, filtered and concentrated in vacuo. The residue obtained is dissolved in tetrahydrofuran (50 mL) and the solution is cooled using an ice bath. NaH (60% in oil) (1.02 g, 25.5 mmol) is added. After 10 minutes, iodomethane (2.4 mL, 38.6 mmol) is also added. The mixture is stirred at ambient temperature for 1.5 hours. The tetrahydrofuran is evaporated to dryness. The residue is taken up in dichloromethane and washed with water. The aqueous phase is extracted with dichloromethane. The combined organic phases are dried over $Na_2SO_4$, filtered and concentrated in vacuo to obtain the expected compound in the form of a solid.

$^1$H NMR (400 MHz, $CDCl_3$) δ ppm: 2.16 (s, 3H), 3.71 (s, 3H), 6.74 (s, 1H)

Step G: 4-({4-[(tert-Butyldimethylsilyl)oxy]phenyl}amino)-1,3-dimethyl-1H-pyrrole-2-carbonitrile 4-Bromo-1,3-dimethyl-1H-pyrrole-2-carbonitrile (2.03 g, 10.2 mmol) and 4-[(tert-butyldimethylsilyl)oxy]aniline (3.41 g, 15.3 mmol) are dissolved in toluene (40 mL). The solution is degassed with nitrogen for 10 minutes. Sodium tert-butylate (1.18 g, 12.2 mmol), 2-di-tert-butylphosphino-2', 4', 6'-triisopropylbiphenyl (0.17 g, 0.41 mmol) and tris (dibenzylideneacetone)dipalladium(0) (0.187 g, 0.2 mmol) are then added. The mixture is heated at 100° C. for 30 minutes and then cooled to ambient temperature. Water (50 mL) and Celite (6 g) are added. The suspension is filtered over Celite, and the filtrate is diluted with MTBE. The phases are separated and the aqueous phase is extracted with MTBE (2×50 mL). The combined organic phases are dried over $Na_2SO_4$ and filtered. The residue is purified by chromatography over silica gel using ethyl acetate and heptane as eluants followed by reverse-phase chromatography using methanol and water as eluants. The product obtained is lyophilised to provide the expected compound in the form of a solid.

$^1$H NMR (400 MHz, $CDCl_3$) δ ppm: 0.15 (s, 6H), 0.98 (s, 9H), 2.05 (s, 3H), 3.70 (s, 3H), 4.69 (br. s, 1H), 6.55-6.57 (m, 2H), 6.64-6.69 (m, 3H)

$^{13}$C NMR (100 MHz, $CDCl_3$) δ ppm: −4.37, 9.42, 18.27, 25.84, 35.50, 102.59, 113.77, 115.13, 120.72, 121.91, 126.77, 126.94, 140.98, 148.39

Preparation 38'': 4-[(4-{[tert-Butyl(dimethyl)silyl]oxy}phenyl)amino]-1-ethyl-5-methyl-1H-pyrrole-2-carbonitrile The procedure is in accordance with the process of Preparation 33'', replacing the iodomethane-$d_3$ in Step B by iodoethane.

$^1$H NMR (400 MHz, dmso-d6) δ ppm: 6.85 (s, 1H), 6.75 (s, 1H), 6.6/6.5 (2d, 4H), 4 (quad, 2H), 2.1 (s, 3H), 1.3 (s, 3H), 0.9 (s, 9H), 0.1 (s, 6H)

Preparation 39'': N-[4-[tert-Butyl(dimethyl)silyl]oxyphenyl]-2-ethoxy-pyrimidin-5-amine

Step A: 5-Bromo-2-ethoxy-pyrimidine

5-Bromo-2-chloro-pyrimidine (5.0 g, 25 mmol) is dissolved in ethanol (55 mL) and sodium ethylate (1.81 g, 26.6 mmol) is added in portions. The reaction mixture is stirred for 15 hours at ambient temperature. When the reaction is complete, the solvent is evaporated off, water (200 mL) is added, and then the reaction mixture is extracted with dichloromethane (2×100mL). The organic phase is dried over $Na_2SO_4$, and then evaporated to dryness to yield 5-bromo-2-ethoxy-pyrimidine.

Step B: N-[4-[tert-Butyl(dimethyl)silyl]oxyphenyl]-2-ethoxy-pyrimidin-5-amine 4-[tert-Butyl(dimethyl)silyl]oxyaniline (1.8 g, 8 mmol) and 5-bromo-2-ethoxy-pyrimidine (1.6 g, 8 mmol) dissolved in anhydrous tetrahydrofuran (30 mL) are stirred for 1 hour at ambient temperature in the presence of sodium tert-butylate (4 mL, 2M solution in THF) and chloro(2-di-tert-butylphosphino-2',4',6'-triisopropyl-1,1'-biphenyl)[2-(2-aminoethyl)-phenyl]palladium(II) (111 mg, 0.16 mmol). The reaction mixture is filtered over Celite and then evaporated to dryness. The residue is triturated in heptane to obtain the expected compound after filtration.

$^1$H NMR (500 MHz, dmso-d6, 300 K) δ ppm: 8.31 (s, 2H, pyrimidine-H), 7.80 (s, 1H, NH), 6.73 (d, 2H, Ar—H), 6.68 (d, 2H, Ar—H), 4.26 (q, 2H, $CH_2CH_3$), 1.31 (t, 3H, $CH_2CH_3$), 0.94 (s, 9H, $^t$Bu), 0.15 (s, 6H, Me)

IR: v: aromatic: 1504 $cm^{-1}$; Si—C: 1247 $cm^{-1}$; C—O—C: 1057 $cm^{-1}$

Preparation 40": tert-Butyl 6-[(1-methyl-1H-pyrrolo[2,3-b]pyridin-5-yl)amino]-pyridin-3-yl carbonate Step A: 6-Bromopyridin-3-yl tert-butyl carbonate To a solution of 5 g of 6-bromopyridin-3-ol (28.7 mmol) and 7.53 g of di-tert-butyl dicarbonate (34.5 mmol) in 50 mL of tetrahydrofuran there is added 0.18 g of 4-dimethylaminopyridine (1.4 mmol). The mixture is stirred at ambient temperature for 6 hours and then concentrated. The residue obtained is dissolved in a mixture of ethyl ether and water. After separation of the phases, the separated-off organic phase is dried over $MgSO_4$ and concentrated to dryness. The title product is obtained in the form of a solid which is used in the next Step without being otherwise purified.

$^1$H NMR (400 MHz, dmso-d6) δ ppm: 8.4 (s, 1H), 7.71 (s, 2H), 1.5 (s, 9H)

Step B: tert-Butyl 6-[(1-methyl-1H-pyrrolo[2,3-b]pyridin-5-yl)amino]pyridin-3-yl carbonate To a solution of 2.79 g of the compound obtained in Step A (10.2 mmol) in 15 mL of toluene and 15 mL of tetrahydrofuran there are added 1.18 g of sodium tert-butylate (12.2 mmol), and then the batch is stirred under argon for 15 minutes. There is then added 0.35 g of palladium catalyst (0.5 mmol). The reaction mixture is then stirred at ambient temperature for 16 hours and then filtered. The filtrate is concentrated and taken up in a mixture of dichloromethane and water. The organic phase is separated off and then washed with water, dried over $MgSO_4$, filtered and concentrated to dryness. The crude product thereby obtained is purified by chromatography over silica gel using dichloromethane and ethyl acetate as eluants. The residue is then taken up in a minimum of isopropyl ether. The solid then obtained is filtered off, washed with ether and then dried. The title product is obtained in the form of a solid, which is subsequently used without being otherwise purified.

$^1$H NMR (400 MHz, dmso-d6) δ ppm: 9 (s, 1H), 8.35 (wd, 1H), 8.3 (wd, 1H), 8 (wd, 1H), 7.45 (dd, 1H), 7.45 (wd, 1H), 6.8 (d, 1H), 6.4 (wd, 1H), 3.8 (s, 3H), 1.5 (s, 9H)

Preparation 41": 3-[4-[tert-Butyl(dimethyl)silyl]oxyanilino]benzonitrile

The procedure is in accordance with the process of Preparation 1", replacing the 4-bromo-1-methyl-1H-pyrazole used in Step B by 3-bromobenzonitrile.

$^1$H NMR (400 MHz, dmso-d6) δ ppm: 8.3 (s, 1H), 7.3 (t, 1H), 7.2/7.1 (2 dd, 2H), 7.15 (t, 1H), 7.05 (d, 2H), 6.8 (d, 2H), 0.95 (s, 9H), 0.2 (s, 6H)

Preparation 42": 4-[4-[tert-Butyl(dimethyl)silyl]oxyanilino]thiophene-2-carbonitrile The procedure is in accordance with the process of Preparation 1", replacing the 4-bromo-1-methyl-1H-pyrazole used in Step B by 4-bromothiophene-2-carbonitrile.

$^1$H NMR (400 MHz, dmso-d6) δ ppm: 8.35 (s, 1H), 7.59 (wd, 1H), 7.08 (wd, 1H), 6.95 (d, 2H), 6.75 (d, 2H), 0.94 (s, 9H), 0.16 (s, 6H)

The amines $NHR_3R_4$ wherein $R_3$ and $R_4$, each independently of the other, represent an aryl or heteroaryl group are obtained in accordance with processes described in the literature (Surry D. S. et al., *Chemical Science*, 2011, 2, 27-50, Charles M. D. et al., *Organic Letters*, 2005, 7, 3965-3968). The reaction protecting the hydroxy function of the 4-anilinophenol described in Preparation 2" can be applied to various secondary amines $NHR_3R_4$ (as defined hereinbefore) having one or more hydroxy functions, when they are available commercially. Alternatively, the secondary amines having at least one hydroxy substituent may be synthesised directly in a protected form, i.e. starting from reagents whose hydroxy function has been protected beforehand. Among the protecting groups, tert-butyl(dimethyl)silyloxy and benzyloxy are especially preferred.

Among the amines $NHR_3R_4$ having a hydroxy substituent that are used for synthesising the compounds of the invention there may be mentioned: 4-(4-toluidino)phenol, 4-(4-chloroanilino)phenol, 4-(3-fluoro-4-methylanilino)phenol, 4-[4-trifluoromethoxy)anilinol]-phenol, 4-[4-hydroxyanilino]phenol, {4-[(1-methyl-1H-indol-6-yl)amino]phenyl}-methanol, 4-(2,3-dihydro-1H-indol-6-ylamino)phenol, 4-[(1-methyl-2,3-dihydro-1H-indol-6-yl)amino]phenol, 4-[(1-methyl-1H-indol-6-yl)amino]phenol, 4-[(1-methyl-1H-indol-6-yl)amino]cyclohexanol, 4-[(1-methyl-1,2,3,4-tetrahydro-6-quinolinyl)amino]phenol, 4-[(4-methyl-3,4-dihydro-2H-1,4-benzox azin-7-yl)amino]phenol, 4-[4-(diethylamino)anilino]-phenol, 4-(2,3-dihydro-1H-inden-5-ylamino)phenol, 4-[(1-methyl-1H-indazol-5-yl)amino]-phenol, 4-[(1'-methyl-1',2'-dihydro spiro [cyclopropane-1,3'-indol]-5'-yl)amino]phenol, 4-[(1,3 ,3-trimethyl-2,3-dihydro-1H-indol-5-yl)amino]phenol, 4-[4-methoxy-3-(trifluoro-methyl)anilino]phenol, 4-[4-(methylsulphanyl)-3-(trifluoromethyl)anilino]phenol, 2-fluoro-4-[(1-methyl-1H-indol-5-yl)amino]phenol, 4-[(1-ethyl-1H-indol-5-yl)amino]phenol, 4-[(1-ethyl-2,3-dihydro-1H-indol-5-yl)amino]phenol, 4-[(1-isopropyl-2,3-dihydro -1H-indol-5-yl)amino]phenol, 4-(butylamino)phenol, 3-[(1-methyl-1H-indol-5-yl)amino]-1-propanol, 4-[(1-methyl-1H-indol-5-yl)amino]-1-butanol, 4-[(3-fluoro-4-methylphenyl)-amino]phenol, 4-[(3-chloro-4-methylphenyl)amino]phenol, 4-[(4-fluorophenyl)amino]-phenol, 4-[(1-methyl-1H-pyrrolo[2,3-b]pyridin-5-yl)amino]phenol, 4-[(4-fluorophenyl)-amino]phenol, 4-[(2-fluorophenyl)amino]phenol, 4-[(3-fluorophenyl)amino]phenol, 4-[(2,4-difluorophenyl)amino]phenol, 4-[(3,4-difluorophenyl)amino]phenol, 3-[(4-hydroxy-phenyl)amino]benzonitrile, 4-[(3-methoxyphenyl)amino]phenol, 4-[(3,5-difluorophenyl)-amino]phenol, 4-[(3-methylphenyl)amino]phenol, 4-[(4-hydroxyphenyl)amino]benzo-nitrile, 4-[(3-chlorophenyl)amino]phenol, 4-(pyrimidin-2-ylamino) phenol, 4-[(cyclobutyl-methyl)amino]phenol, 2-[(4-hydroxyphenyl)amino]benzonitrile, 4-{[(1-methyl-1H-pyrazol-4-yl)methyl]amino}phenol, 4-[(cycloprop ylmethyl)amino]phenol, 4-{[(1-methyl-1H-pyrazol-3-yl)methyl]amino }phenol, 4-(but-2-yn-1-ylamino)phenol, 4-(pyrazin-2-yl-amino)phenol, 4-(pyridin-2-ylamino)phenol, 4-(pyridazin-3-ylamino)phenol, 4-(pyrimidin-5-ylamino) phenol, 4-(pyridin-3-ylamino)phenol, 4-[(3,5-difluoro-4-methoxyphenyl)-amino]phenol, 4-(pyridin-4-ylamino)phenol, 4-[(3-fluoro-4-methoxyphenyl)amino]phenol, 2-(phenylamino)pyrimidin-5-ol, 5-[(4-hydroxyphenyl)amino]-2-methoxybenzonitrile, 4-{[3-(trifluoromethyl)phenyl]amino }phenol and 4-(methylamino)phenol.

The hydroxy function(s) of the secondary amines listed above is (are) protected beforehand by a suitable protecting group prior to any coupling to an acid derivative of the compound of formula (VII) as defined in the preceding general process.

Preparation I: tert-Butyl [2-(3-iodo-4-{[(3R)-3-methyl-3,4-dihydroisoquinolin-2(1H)-yl]carbonyl}phenyl)ethyl]carbamate Step A: 4-[2-(tert-Butoxycarbonylamino)ethyl]benzoic acid tert-Butyl dicarbonate (1.64 g; 7.5 mmol) is dissolved in 1,4-dioxane (5 mL) and the solution is added to a well-stirred solution of 4-(2-aminoethyl)benzoic acid (1.0 g; 5 mmol) in 1M aqueous sodium hydroxide solution (25 mL) and 1,4-dioxane (10 mL), and the mixture is then stirred at ambient temperature for 3 hours. The 1,4-dioxane is removed by evaporation in vacuo, and then ethyl acetate (200 mL) is added to the residue. The pH of the aqueous phase is adjusted to 1.5 with 2M aqueous HCl solution. The organic phase is separated off and the aqueous phase is then extracted with ethyl acetate (100 mL). The combined organic extracts are washed with water, dried over $Na_2SO_4$ and evaporated to a volume of 10 mL. Heptane is added to the residue and then the solid precipitate is filtered off to yield the title compound.

$^1$H NMR (500 MHz, dmso-d6, 300K): 12.81 (br s, 1H, COOH), 7.85 (m, 2H, Ar-2' and 6'H), 7.31 (m, 2H, Ar-3' and 5'H), 6.91 and 6.51 (2×br s, 1H, NH), 3.16 (m, 2H, $CH_2$), 2.75 (t, 2H, $CH_2$), 1.35 and 1.31 (2×br s, 9H, Bu$^t$); $^{13}$C NMR (125 MHz, dmso-d6, 300 K): 167.8 (q), 156.0 (CH), 145.3 (q), 129.8 (2×CH), 129.3 (2×CH), 129.1 (q), 78.0 (q), 41.5 ($CH_2$), 35.9 ($CH_2$), 28.7 ($CH_3$)

Step B: 4-[2-(tert-Butoxycarbonylamino)ethyl]-2-iodo-benzoic acid

The compound of the above Step (0.88 g; 3.31 mmol), iodobenzene diacetate (1.07 g; 3.31 mmol), tetrabutylammonium iodide (1.22 g; 3.31 mmol), iodine (0.84 g; 3.31 mmol) and diacetoxypalladium (0.04 g; 0.165 mmol) are dissolved in 1,2-dichloroethane (8 mL), and the mixture is then heated in a microwave reactor at 80° C. for 90 minutes. The cooled mixture is partitioned between saturated aqueous $Na_2CO_3$ solution (30 mL) and the original solvent. The organic phase is separated off and the aqueous residue is extracted with diethyl ether (2×15 mL). The pH of the resulting aqueous solution is adjusted to 2 with 2M aqueous HCl solution and the product is then extracted with ethyl acetate (2×75 mL). The organic phase is dried over $Na_2SO_4$ and evaporated. The crude product is purified by chromatography over silica gel to yield the mixture of regioisomers, which are separated by preparative HPLC using water-TFA and acetonitrile as eluants. The pH of the appropriate combined fractions is adjusted to 5 with $NaHCO_3$, and then the acetonitrile is evaporated off under reduced pressure. The precipitate is recovered by filtration and then dried to yield the title compound.

$^1$H NMR (500 MHz, dmso-d6, 300K): 13.16 (broad s, 1H, COOH), 7.81 (s, 1H, Ar-3'H), 7.66 (d, 1H, Ar-6'H), 7.29 (d, 1H, Ar-5'H), 6.89 (t, 1H, NH), 3.14 (t, 1H, $CH_2$), 2.69 (t, 1H, $CH_2$), 1.35 (s, 9H, Boc)

Step C: tert-Butyl [2-(3-iodo-4-{[(3R)-3-methyl-3,4-dihydroisoquinolin-2(1H)-yl]-carbonyl}phenyl)ethyl]carbamate The compound of the above Step (0.714 g; 1.82 mmol), TBTU (0.73 g; 2.28 mmol), N-ethyl-N-isopropyl-propan-2-amine (0.94 mL; 5.46 mmol) and N,N-dimethylpyridin-4-amine (22 mg) are stirred in dichloromethane (20 mL) for 5 minutes, and then (3R)-3-methyl-1,2,3,4-tetrahydroisoquinoline (0.282 g; 1.92 mmol) (cf. Preparation 1') is added. The mixture is stirred for three more hours. The reaction mixture is diluted with dichloromethane (150 mL) and then washed with water (25 mL), dried over $Na_2SO_4$ and evaporated. The crude product is purified by chromatography over silica gel using dichloromethane and methanol as eluants to yield the title compound.

High-Resolution Mass Spectrometry (ESI+):
Empirical formula: $C_{24}H_{29}IN_2O_3$
[M+H]$^+$ calculated: 521.1303
[M+H]$^+$ measured: 521.1282
IR: ν: C—H: 2931 cm$^{-1}$; >C=O: 1706, 1627 cm$^{-1}$; amide: 1505 cm$^{-1}$; C—O—C: 1248, 1166 cm$^{-1}$ Preparation II: tert-Butyl (4-Iodo-3-{[(3R)-3-methyl-3,4-dihydroisoquinolin-2(1H)-yl]carbonyl}benzyl)carbamate Step A: 2-Iodo-5-methyl-benzoic acid 3-Methylbenzoic acid (6.12 g; 45 mmol), iodobenzene diacetate (14.49 g; 45 mmol), tetrabutylammonium iodide (16.62 g, 45 mmol), iodine (11.43 g; 45 mmol) and diacetoxypalladium (0.5 g; 2.2 mmol) are dissolved in 1,2-dichloroethane, and then the mixture is heated in a sealed tube at 85° C. for 1 hour and 45 minutes. The cooled solution is purified by chromatography over silica gel using dichloromethane and methanol as eluants to yield the title compound.

Step B: Methyl 2-iodo-5-methyl-benzoate

The compound of the above Step (6.25 g, 23.9 mmol) is dissolved in anhydrous methanol (100 mL), and then $SOCl_2$ (3.6 mL, 49 mmol) is added dropwise to the well-stirred solution. The solution is refluxed for 18 hours and then evaporated to a volume of 25 mL and then poured into crushed ice (100 g). The resulting mixture is extracted with diethyl ether (2×75 mL). The organic phase is washed with saturated aqueous $NaHCO_3$ solution and then brine, dried over $Na_2SO_4$ and evaporated to dryness to yield the title compound.

Step C: Methyl 5-(bromomethyl)-2-iodo-benzoate

The compound of the above Step (5.7 g; 20.7 mmol), N-bromo-succinimide (3.67 g; 20.7 mmol) and dibenzoyl peroxide (0.24 g; 1 mmol) are dissolved in carbon tetrachloride (40 mL) and then refluxed for 5 hours. New portions of N-bromosuccinimide (1.0 g; 5.6 mmol) and dibenzoyl peroxide (0.05 g; 0.2 mmol) are then added and heating is continued for 4 more hours. The reaction mixture is cooled to ambient temperature. The insoluble parts are removed by filtration, and the concentrated filtrate is then purified by chromatography over silica gel using heptane and ethyl acetate as eluants to yield the title compound.

Step D: Methyl 5-(aminomethyl)-2-iodo-benzoate

The compound of the above Step (0.53 g; 1.5 mmol) is dissolved in 7M methanolic ammonia (20 mL) and then stirred at ambient temperature for 1 hour. The solution is evaporated to dryness to yield the title compound, which was used in the next Step without purification.

Step E: 5-[(tert-Butoxycarbonylamino)methyl]-2-iodo-benzoic acid

Methyl 5-(aminomethyl)-2-iodo-benzoate hydrobromide (0.56 g; 1.5 mmol) was dissolved in pyridine (10 mL), then di-tert-butyl dicarbonate (0.80 g; 3.6 mmol) is added and the mixture is stirred at ambient temperature for 30 minutes and then evaporated to dryness. The residue is redissolved in methanol (10 mL), and then 2M aqueous NaOH solution (3 mL) and 2 mL of water are added. The resulting solution is stirred for 2 hours at 50° C., then diluted with water (20 mL), and the methanol is evaporated off under reduced pressure. The pH of the resulting aqueous solution is adjusted to 3 with 2M aqueous HCl solution; the product is then extracted with ethyl acetate. The organic phase is washed with brine, and then dried over $Na_2SO_4$ and evaporated to dryness. The crude product is triturated with DCM. The solid formed is recovered by filtration to yield the title compound.

$^1$H NMR (500 MHz, dmso-d6, 300 K): 13.24 (broad s, 1H, COOH), 7.91 (d, 1H, Ar-3'H), 7.58 (d, 1H, Ar-6'H), 7.47 (t, 1H, NH), 7.09 (d, 1H, (Ar-5'H), 4.09 (d, 2H, $CH_2$), 1.38 (s, 9H, Boc); $^{13}$C NMR (125 MHz, dmso-d6, 300K): 168.6 (q), 156.3 (q), 141.1 (q), 140.9 (CH), 137.1 (q), 131.6 (CH), 129.1 (CH), 92.2 (q), 78.5 (q), 28.7 ($CH_3$)

Step F: tert-Butyl (4-iodo-3-{[(3R)-3-methyl-3,4-dihydroisoquinolin-2(1H)-yl]carbonyl}-benzyl)carbamate The compound of the above Step (1.62 g; 4.3 mmol), TBTU (2.76 g; 8.59 mmol), N-ethyl-N-isopropyl-propan-2-amine (1.48 mL; 8.59 mmol) and N,N-dimethylpyridin-4-amine (10 mg) are stirred in DCM (50 mL) for 5 minutes; (3R)-3-methyl-1,2,3,4-tetrahydroisoquinoline (0.76 g; 5.15 mmol) (cf. Preparation 1') is then added and the mixture is stirred for 15 minutes more. The insoluble parts are removed by filtration, and then the concentrated filtrate is purified by chromatography over silica gel using dichloromethane and methanol as eluants to yield the title compound.

Preparation III: tert-Butyl (3-bromo-4-{[(3R)-3-methyl-3,4-dihydroisoquinolin-2(1H)-yl]carbonyl}benzyl)carbamate Step A: Methyl 4-(aminomethyl)-2-bromo-benzoate A solution of methyl 2-bromo-4-(bromomethyl)benzoate (4.57 g; 14.84 mmol) in 50 mL of methanol is added dropwise to a well-stirred solution of ammonia in methanol (7M; 315 mL) at ambient temperature, and the solution is then stirred for 3 hours. All the solvents are evaporated off and the residue is purified by chromatography over silica gel using dichloromethane-methanol as eluants to yield the title compound.

Step B: 2-Bromo-4-[(tert-butoxycarbonylamino)methyl]benzoic acid

The compound of the above Step (4.04 g; 16.6 mmol) is dissolved in pyridine (55 mL) and then di-tert-butyl dicarbonate (5.43 g; 24.9 mmol) is added and the mixture is stirred at ambient temperature for 16 hours; it is then evaporated to dryness. The residue is redissolved in methanol (100 mL), and then 1M aqueous NaOH solution (54 mL) is added. The resulting solution is stirred for 1.5 hours at 50° C. and is then allowed to cool to ambient temperature. The pH of the solution is adjusted to 7 using 2M aqueous HCl solution; the methanol is then evaporated off under reduced pressure. The resulting aqueous solution is diluted with water (50 mL), and then the pH is adjusted to 3 using 2M aqueous HCl solution. The product is extracted with dichloromethane (2×100 mL). The organic phase is washed with brine, then dried over $Na_2SO_4$ and evaporated to dryness to yield the title compound which is used in the next Step without purification.

IR: v: N—H: 3359 $cm^{-1}$; C—H: 2983 $cm^{-1}$; >C=O: 1685, 1603 $cm^{-1}$; amide: 1519 $cm^{-1}$; C—O—C: 1248, 1162, 1057 $cm^{-1}$ Step C: tert-Butyl (3-bromo-4-{[(3R)-3-methyl-3,4-dihydroisoquinolin-2(1H)-yl]-carbonyl}benzyl)carbamate The compound of the above Step (3.7 g; 11.2 mmol), TBTU (7.19 g; 22.4 mmol), N-ethyl-N-isopropyl-propan-2-amine (3.86 mL; 22.4 mmol) and N,N-dimethylpyridin-4-amine (48 mg) are stirred in dichloromethane (100 mL) for 5 minutes, and then (3R)-3-methyl-1,2,3,4-tetrahydroisoquinoline (1.98 g, 13.44 mmol) (cf. Preparation 1') is added, and the mixture is stirred for 1 hour more. The insoluble parts are removed by filtration, and then the concentrated filtrate is purified by chromatography over silica gel using dichloromethane and methanol as eluants to yield the title compound.

High-Resolution Mass Spectrometry (ESI+):
Empirical formula: $C_{23}H_{27}BrN_2O_3$
$[M+H]^+$ calculated: 459.1285
$[M+H]^+$ measured: 459.1282
$^1$H NMR (500 MHz, dmso-d6, 300K, presence of amide rotamers): 7.66-6.87 (m, 7H, aromatic), 5.34 and 4.12 (d, 2H, $CH_2$-isoquinoline), 5.02 and 4.97 and 3.87 and 3.83 (m, 1H, $CH_2$-isoquinoline), 4.17 (d, 2H, $CH_2$-benzyl), 3.18-2.48 (m, 1H, $CH_2$-isoquinoline), 1.16 and 1.14 and 1.10 and 0.98 (d, 3H, isoquinoline $CH_3$), 1.31 and 1.41 (s, 9H, Boc).

Example 1. 5-(5-Chloro-2-{[(3R)-3-methyl-3,4-dihydroisoquinolin-2(1H)-yl]carbonyl}phenyl)-N-(4-hydroxyphenyl)-14-dimethyl-N-(1-methyl-1H-pyrazol-4-yl)-1H-pyrrole-3-carboxamide Step A: Ethyl 5-(5-chloro-2-{[(3R)-3-methyl-3,4-dihydroisoquinolin-2(1H)-yl]carbonyl} phenyl)-1,2-dimethyl-1H-pyrrole-3-carboxylate To a solution of 1.4 g of the compound obtained in Preparation 1 (4.35 mmol) in 50 mL of dichloromethane there are successively added 0.7 g of the compound obtained in Preparation 1' (4.79 mmol), 0.7 g of HOBT (5.22 mmol), 0.81 g of EDC (5.22 mmol) and 1.6 mL of triethylamine (21.7 mmol). The batch is then stirred overnight at ambient temperature. The reaction mixture is then diluted with dichloromethane and washed 3 times with saturated aqueous $NaHCO_3$ solution. The organic phase is then dried over $MgSO_4$, filtered, concentrated to dryness, and then purified by chromatography over silica gel using dichloromethane and methanol as eluants.

$^1$H NMR: δ (500 MHz; dmso-d6; 300K): 7.6-7.3 (m, 3H, aromatic Hs, 4-chlorophenyl); 7.2-6.85 (m, 4H, aromatic Hs, tetrahydroisoquinoline); 6.45-6.3 (m, 1H, H pyrrole); 5.0-4.8-3.8 (m, 1H, aliphatic H, tetrahydroisoquinoline); 5.3-3.75 (dd, 2H, aliphatic Hs tetrahydroisoquinoline); 4.2-4.0 (m, 2H, $OCH_2CH_3$); 3.25 (s, 3H, $CH_3$—N-pyrrole); 3.0-2.2 (m, 2H, aliphatic Hs, tetrahydroisoquinoline); 2.5 (s, 3H, $CH_3$-pyrrole); 1.25 (t, 3H, $OCH_2CH_3$); 1.05 (d, 3H, tetrahydroisoquinoline-$CH_3$)

IR: v: >C=O: 1693 $cm^{-1}$ ester; v: >C=O: 1625 $cm^{-1}$ amide

Step B: 5-(5-Chloro-2-{[(3R)-3-methyl-3,4-dihydroisoquinolin-2(1H)-yl]carbonyl}-phenyl)-1,2-dimethyl-1H-pyrrole-3-carboxylic acid To a solution of 1.7 g of the compound obtained in Step A (3.77 mmol) in 5 mL of dioxane there is added 0.317 g of LiOH (7.5 mmol) dissolved in 5 mL of water. The batch is heated in a microwave apparatus for 4 hours at 100° C. (power 140 W). The reaction mixture is then filtered and concentrated to dryness. The residue thereby obtained is taken up in dichloromethane (50 mL) and then saturated aqueous $NH_4Cl$ solution is added thereto. The organic phase is washed with water and then with brine, dried over $MgSO_4$, filtered and concentrated to dryness. The title product is obtained in the form of a solid and is used directly in the next Step.

$^1$H NMR: δ (500 MHz; dmso-d6; 300K): 11.05 (broad s, 1H, COOH), 7.5-7.2 (m, 3H, aromatic Hs, 4-chlorophenyl); 7.2-6.9 (m, 4H, aromatic Hs, tetrahydroisoquinoline); 6.45-6.2 (m, 1H, aliphatic H, H pyrrole); 5.3-3.75 (dd, 2H, aliphatic Hs, tetrahydroisoquinoline); 5.0-48-3.8 (m, 1H, aliphatic H, tetrahydroisoquinoline); 3.5-3.2 (s, 3H, $CH_3$—N-pyrrole); 3.0-2.1 (aliphatic Hs, $CH_3$-tetraisoquinoline); 2.5-2.4-1.98 (m, 3H, $CH_3$-pyrrole); 1.05-0.52 (m, 3H, aliphatic Hs, $CH_3$-tetraisoquinoline)

IR: v: —OH: 3500-2000 $cm^{-1}$ carboxylic acid; v: >C=O: 1699+1658 $cm^{-1}$ carboxylic acid; v: >C=N—: 1625 $cm^{-1}$ amide

Step C: N-(4-{[tert-Butyl(dimethyl)silyl]oxy}phenyl)-5-(5-chloro-2-{[(3R)-3-methyl-3,4-dihydroisoquinolin-2(1H)-yl]carbonyl}phenyl)-1,2-dimethyl-N-(1-methyl-1H-pyrazol-4-yl)-1H-pyrrole-3-carboxamide To a solution of 0.65 g of the compound obtained in Step B (1.54 mmol) in 15 mL of dichloroethane there is added, dropwise, 0.244 mL of 1-chloro-N,N,2-trimethyl-prop-1-en-1-amine. The reaction mixture is stirred at ambient temperature for 1 hour, and there are then added 0.56 g of the compound of Preparation 1" (1.84 mmol), 10 mL of dichloroethane and 0.376 g of 4-dimethylaminopyridine (DMAP) (3.07 mmol). The batch is stirred at 110° C. overnight. The reaction mixture is concentrated, dissolved in dichloromethane and washed with saturated aqueous $NaHCO_3$ solution. The title product is obtained in the form of an oil and is used directly in the next Step.

Step D: 5-(5-Chloro-2-{[(3R)-3-methyl-3,4-dihydroisoquinolin-2(1H)-yl]carbonyl}-phenyl)-N-(4-hydroxyphenyl)-1,2-dimethyl-N-(1-methyl-1H-pyrazol-4-yl)-1H-pyrrole-3-carboxamide To a solution of 0.8 g of the compound obtained in Step C (1.03 mmol) in 2 mL of methanol, there are added 1.55 mL of a 1M solution of potassium hydroxide in methanol (1.55 mmol). The batch is stirred at ambient temperature for 30 minutes. The reaction mixture is then diluted with dichloromethane and successively washed with 1M aqueous HCl solution, saturated aqueous $NaHCO_3$ solution and then brine until neutral. The organic phase is then dried over $MgSO_4$, filtered and evaporated. The crude product thereby obtained is purified by chromatography over silica gel using dichloromethane and methanol as eluants. The solid thereby obtained is dissolved in a mixture of water/acetonitrile until dissolution is complete, filtered and then lyophilised.

Elemental Microanalysis: (%, Theoretical:Measured)
% C=68.74:68.25; % H=5.43:5.69; % N=11.79:11.66; % Cl=5.97:5.95

High-Resolution Mass Spectrometry (ESI+):
Empirical formula: $C_{34}H_{32}ClN_5O_3$
$[M+H]^+$ calculated: 594.2266
$[M+H]^+$ measured: 594.2289

Example 2. 5-(2-{[(3S)-3-(Aminomethyl)-3,4-dihydroisoquinolin-2(1H)-yl]carbonyl}phenyl)-1-methyl-N,Ndiphenyl-1H-pyrrole-3-carboxamide

Step A: tert-Butyl {[(3S)-2-{2-[4-(diphenykarbamoyl)-1-methyl-1H-pyrrol-2-yl]benzoyl}-1,2,3,4-tetrahydroisoquinolin-3-yl]methyl}carbamate The title compound is obtained in accordance with the process of Example 1 using the acid of Preparation 2 and tert-butyl [(3S)-1,2,3,4-tetrahydroisoquinolin-3-ylmethyl]carbamate (see Preparation 2') in Step A, and N-phenylaniline in Step C.

Step B: 5-(2-{[(3S)-3-(Aminomethyl)-3,4-dihydroisoquinolin-2(1H)-yl]carbonyl} phenyl)-1-methyl-N,N-diphenyl-1H-pyrrole-3-carboxamide A solution of the NH-Boc compound of Step A in dichloromethane is placed at 0° C. 10 molar equivalents of trifluoroacetic acid are added thereto dropwise. The batch is stirred at ambient temperature for 4 hours until the starting material has disappeared completely. The reaction mixture is then concentrated to dryness, taken up again and co-evaporated twice with toluene, then taken up in a mixture of acetonitrile/$H_2O$ and finally lyophilised. The title product is then obtained after a neutralisation step.

Elemental Microanalysis: (%, Theoretical:Measured)
% C=77.75:77.27; % H=5.97:5.73; % N=10.36:10.44

Example 3. 5-(5-Chloro-2-{[(3S)-3-[(4-methylpiperazin-1-yl)methyl]-3,4-dihydro-isoquinolin-2(1H)-yl]carbonyl}phenyl)-N-(4-hydroxyphenyl)-N-(1H-indol-5-yl)-1-methyl-1H-pyrrole-3-carboxamide

Step A: tert-Butyl 5-[(4-{[tert-butyl(dimethyl)silyl]oxy}phenyl){[5-(5-chloro-2-{[(3S)-3-[(4-methylpiperazin-1-yl)methyl]-3,4-dihydroisoquinolin-2(1H)-yl]carbonyl}phenyl)-1-methyl-1H-pyrrol-3-yl]carbonyl}amino]-1H-indole-1-carboxylate The title compound is obtained in accordance with the process of Example 1 using the acid of Preparation 3 and (3S)-3-[(4-methyl-1-piperazinyl)methyl]-1,2,3,4-tetrahydro-isoquinoline (see Preparation 4') in Step A, and the compound of Preparation 3" in Step C.

Step B: 5-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1H-indol-5-yl)-1-methyl-1H-pyrrole-3-carboxamide To a solution of 455 mg (0.49 mmol) of the product obtained in Step A in 5 mL of methanol there are added 135 mg (2.5 mmol) of KOH. After stirring for 3 hours at ambient temperature, the reaction mixture is concentrated, treated with saturated aqueous $NaHCO_3$ solution and extracted with methylene chloride. The organic phase is then dried over $MgSO_4$, filtered and evaporated to dryness. The crude product thereby obtained is then purified by chromatography over silica gel using dichloromethane and methanol as eluants to yield the expected product in the form of a foam.
Elemental Microanalysis: (%, Theoretical:Measured)
% C=70.72:68.54; % H=5.79:5.37; % N=11.78:11.41; % Cl=4.97:4.79
High-Resolution Mass Spectrometry (ESI+):
Empirical formula: $C_{42}H_{41}ClN_6O_3$
[M+H]$^+$ calculated: 713.3007
[M+H]$^+$ measured: 713.2973

Example 4. N-(4-Hydroxyphenyl)-N-(1H-indol-5-yl)-1-methyl-5-(6-{[(3S)-3-[(4-methylpiperazin-1-yl)methyl]-3,4-dihydroisequinolin-2(1H)-yl]carbonyl}-1,3-benzodioxol-5-yl)-1H-pyrrole-3-carboxamide The title compound is obtained in accordance with the process of Example 3 using the compound of Preparation 4 in Step A.
Elemental Microanalysis: (%, Theoretical:Measured)
% C=71.45:69.32; % H=5.86:5.22; % N=11.63:11.08
High-Resolution Mass Spectrometry (ESI+):
Empirical formula: $C_{43}H_{42}N_6O_5$
[M+H]$^+$ calculated: 723.3295
[M+H]$^+$ measured: 723.3262

Unless otherwise mentioned, the compounds of the following Examples are synthesised in accordance with the process of Example 1 using, in Step A: (i) the appropriate acid obtained according to one of Preparations 1 to 32 and (ii) the appropriate tetrahydroisoquinoline compound obtained according to one of Preparations 1' to 9' and, in Step C: (iii) the suitable NHR$_3$R$_4$ amine (a non-exhaustive list is proposed in Preparations 1" to 42"). The compounds thereby obtained are optionally subjected to a step of conversion into salt form in the presence of HCl in ether. After filtration and lyophilisation in a mixture of acetonitrile/water, the hydrochloride of the expected compound is obtained.

Example 5. 5-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-1-methyl-N-(1-methyl-1H-indol-5-1)-1H-pyrrole-3-carboxamide hydrochloride Elemental Microanalysis: (%, Theoretical:Measured)
% C=64.54:64.9; % H=5.67:5.49; % N=10.5:10.4; % Cl=13.29:12.52; % Cl−=8.86:7.39

Example 6. 5-(5-Chloro-2-{[(3S)-3-[(4-methylpiperazin-1-yl)methyl]-3,4-dihydroisoquinolin-2(1H)-yl]carbonyl}phenyl)-1-ethyl-N-(4-hydroxyphenyl)-N-(1-methyl-1H-indol-5-yl)-1H-pyrrole-3-carboxamide High-Resolution Mass Spectrometry (ESI+):
Empirical formula: $C_{44}H_{45}ClN_6O_3$
[M+H]$^+$ calculated: 741.3320
[M+H]$^+$ measured: 741.3326

Example 7. 5-(5-Chloro-2-{[(3S)-3-[(4-methylpiperazin-1-yl)methyl]-3,4-dihydroisoquinolin-2(1H)-yl]carbonyl}phenyl)-1-cyclopropyl-N-(4-hydroxyphenyl)-N-(1-methyl-1H-indol-5-yl)-1H-pyrrole-3-carboxamide High-Resolution Mass Spectrometry (ESI+):
Empirical formula: $C_{45}H_{45}ClN_6O_3$
[M+H]$^+$ calculated: 753.3320
[M+H]$^+$ measured: 753.3306

Example 8. 5-(5-Chloro-2-{[(3S)-3-[(4-methylpiperazin-1-yl)methyl]-3,4-dihydroisoquinolin-2(1H)-yl]carbonyl}phenyl)-N-(4-hydroxyphenyl)-N-(1-methyl-1H-indol-5-yl)-1-(propan-2-yl)-1H-pyrrole-3-carboxamide High-Resolution Mass Spectrometry (ESI+):
Empirical formula: $C_{45}H_{47}ClN_6O_3$
[M+H]$^+$ calculated: 755.3476
[M+H]$^+$ measured: 755.3466

Example 9. N-(4-Hydroxyphenyl)-1-methyl-N-(1-methyl-1H-indol-5-yl)-5-(6-{[(3S)-3-[(4-methylpiperazin-1-yl)methyl]-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=65.26:65.8; % H=5.73:5.47; % N=10.38:10.48; % Cl=8.76:8.46; % Cl−=8.76:8.02

Example 10. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-phenyl-1H-pyrrole-3-carboxamide hydrochloride Elemental Microanalysis: (%, Theoretical:Measured)
% C=69.11:68.56; % H=5.8:5.31; % N=8.06:8.13; % Cl−=5.1:4.68

Example 11. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-(3-hydroxypropyl)-2-methyl-N-phenyl-1H-pyrrole-3-carboxamide hydrochloride Step A: 1-[3-(Benzyloxy)propyl]-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-phenyl-1H-pyrrole-3-carboxamide The title compound is obtained in accordance with the process of Example 1 using the acid of Preparation 10 and the compound of Preparation 3' in Step A, and the compound of Preparation 2" in Step C.

Step B: 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-(3-hydroxypropyl)-2-methyl-N-phenyl-1H-pyrrole-3-carboxamide hydrochloride The compound of Step A is subjected to a deprotection reaction in accordance with a protocol analogous to that described in Step B of Example 23.

Elemental Microanalysis: (%, Theoretical:Measured)
% C=68.24:67.96; % H=6:5.79; % N=7.58:7.61; % Cl−=4.8:4.75

High-Resolution Mass Spectrometry (ESI+):
Empirical formula: $C_{42}H_{43}FN_4O_5$
[M+H]$^+$ calculated: 703.3296
[M+H]$^+$ measured: 703.33294

Example 12. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-indazol-5-yl)-1H-pyrrole-3-carboxamide hydrochloride Elemental Microanalysis: (%, Theoretical:Measured)
% C=67.33:67.39; % H=5.65:5.18; % N=11.22:11.52; % Cl−=4.73:3.82

Example 13. N-(3-Fluoro-4-methylphenyl)-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=66.97:66.72; % H=5.62:5.21; % N=7.44:7.59; % Cl−=4.71:4.54

Example 14. N-(4-Hydroxyphenyl)-1,2-dimethyl-N-(1-methyl-1H-indazol-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=66.62:66.59; % H=5.59:4.67; % N=10.84:10.85; % Cl−=4.57:4.24

Example 15. N-(4-Hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-phenyl-1H-pyrrole-3-carboxamide hydrochloride Elemental Microanalysis: (%, Theoretical:Measured)
% C=68.28:67.07; % H=5.73:5.09; % N=7.77:7.75; % Cl−=4.92:5.71

High-Resolution Mass Spectrometry (ESI+):
Empirical formula: $C_{41}H_{40}N_4O_6$
[M+H]$^+$ calculated: 685.3026
[M+H]$^+$ measured: 685.3033

Example 16. N-(3-Fluorophenyl)-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=66.62:66.11; % H=5.45:5.2; % N=7.58:7.89; % Cl−=4.8:5.59

Example 17. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-phenyl-1H-pyrrole-3-carboxamide hydrochloride Elemental Microanalysis: (%, Theoretical:Measured)
% C=67.51:66.91; % H=5.66:5.05; % N=7.87:7.88; % Cl−=4.98:5.75

Example 18. 1-(2-Hydroxyethyl)-N-(4-hydroxyphenyl)-2-methyl-5-(6-{[(3S)-3-[2-(morpholin-4-yl)ethyl]-3,4-dihydroisoquinolin-2(1H)-yl]carbonyl}-1,3-benzodioxol-5-yl)-N-phenyl-1H-pyrrole-3-carboxamide hydrochloride Step A: 1-[2-(Benzyloxy)ethyl]-N-[4-(benzyloxy)phenyl]-2-methyl-5-(6-{[(3S)-3-[2-(morpholin-4-yl)ethyl]-3,4-dihydroisoquinolin-2(1H)-yl]carbonyl}-1,3-benzodioxol-5-yl)-N-phenyl-1H-pyrrole-3-carboxamide The title compound is obtained in accordance with the process of Example 1 using the acid of Preparation 9 and (3S)-3-[2-(morpholin-4-yl)ethyl]-1,2,3,4-tetrahydroisoquinoline (see Preparation 5') in Step A, and 4-(benzyloxy)-N-phenylaniline (see Preparation 8") in Step C.

Step B: 1-(2-Hydroxyethyl)-N-(4-hydroxyphenyl)-2-methyl-5-(6-{[(3S)-3-[2-(morpholin-4-yl)ethyl]-3,4-dihydroisoquinolin-2(1H)-yl]carbonyl}-1,3-benzodioxol-5-yl)-N-phenyl-1H-pyrrole-3-carboxamide hydrochloride The compound of Step A is subjected to a deprotection reaction in accordance with a protocol analogous to that described in Step B of Example 23.

High-Resolution Mass Spectrometry (ESI+):
Empirical formula: $C_{38}H_{40}N_6O_5$
[M+H]$^+$ calculated: 729.3283
[M+H]$^+$ measured: 729.3282

Example 19. N-(4-Hydroxyphenyl)-5-(5-methoxy-2-{[(3S)-3-(morpholin-4-ylmethyl)-3,4-dihydroisoquinolin-2(1H)-yl]carbonyl}phenyl)-1,2-dimethyl-N-phenyl-1H-pyrrole-3-carboxamide hydrochloride Elemental Microanalysis: (%, Theoretical:Measured)
% C=69.63:69.45; % H=6.13:5.94; % N=7.92:7.79; % Cl−=5.01:4.58

Example 20. N-(4-Hydroxyphenyl)-5-(5-methoxy-2-{[(3R)-3-methyl-3,4-dihydroisoquinolin-2(1H)-yl]carbonyl}phenyl)-1,2-dimethyl-N-(pyridin-4-yl)-1H-pyrrole-3-carboxamide hydrochloride Elemental Microanalysis: (%, Theoretical:Measured)
% C=69.39:69.66; % H=5.66:5.46; % N=8.99:8.92; % Cl−=5.69:5.29

High-Resolution Mass Spectrometry (ESI+):
Empirical formula: $C_{36}H_{35}N_4O_4$
[M+H]$^+$ calculated: 587.2653
[M+H]$^+$ measured: 587.2649

Example 21. N-(4-Hydroxyphenyl)-1,2-dimethyl-N-(1-methyl-1H-pyrazol-4-yl)-5-7-{[(3S)-3-(morpholin-4-ylmethyl)-3,4-dihydroisoquinolin-2(1H)-yl]carbonyl}-2,3-dihydro-1,4-benzodioxin-6-yl)-1H-pyrrole-3-carboxamide hydrochloride Elemental Microanalysis: (%, Theoretical:Measured)
% C=64.99:64.67; % H=5.86:5.67; % N=11.37:11.27; % Cl−=4.8:4.71
High-Resolution Mass Spectrometry (ESI+):
Empirical formula: $C_{40}H_{43}N_6O_6$
[M+H]$^+$ calculated: 703.3236
[M+H]$^+$ measured: 703.3239

Example 22. N-(4-Hydroxyphenyl)-1,2-dimethyl-5-(7-{[(3S)-3-(morpholin-4-ylmethyl)-3,4-dihydroisoquinolin-2(1H)-yl]carbonyl}-2,3-dihydro-1,4-benzodioxin-6-yl)-N-phenyl-1H-pyrrole-3-carboxamide hydrochloride Elemental Microanalysis: (%, Theoretical:Measured)
% C=68.61:67.97; % H=5.89:5.59; % N=7.62:7.55; % Cl−=4.82:4.27

Example 23. 1-(2-Hydroxyethyl)-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide Step A: 1-[2-(Benzyloxy)ethyl]-N-(4-{[tert-butyl(dimethyl)silyl]oxy}phenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide The title compound is obtained in accordance with the process of Example 1 using the acid of Preparation 9 and the compound of Preparation 1" in Step C.

Step B: N-(4-{[tert-Butyl(dimethyl)silyl]oxy}phenyl)-1-(2-hydroxyethyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide To a solution of 6.86 g (8.19 mmol) of the compound of Step A in 70 mL of anhydrous methanol there are added 1.37 g of Pd/C 10%. The batch is degassed for 0.5 hours and then stirred at ambient temperature under dihydrogen pressure (1.5 bar) for 12 hours. The reaction mixture is then filtered and then concentrated to dryness. The expected product is obtained in the form of a solid.

$^1$H NMR: δ (500 MHz; dmso-d6; 300K): 7.7-7.4 (s, 1H, H pyrazole); 7.1-6.8 (s, 1H, H pyrazole); 7.3-6.9 (m, 4H, aromatic Hs, H tetrahydroisoquinoline); 7.0-6.7 (m, 2H, aromatic Hs); 6.9-6.4 (m, 2H, aromatic Hs); 6.8-6.4 (m, 2H, aromatic Hs); 6.1 (m, 2H, OCH$_2$O); 5.2 , 5.0, 4.7 (4s, H, H-pyrrole (presence of conformational isomers); 5.15 (d, 1H, aliphatic H, H tetrahydroisoquinoline); 4.9 (m, 1H, aliphatic H, H tetrahydroisoquinoline); 4.9-48 (m, 1H, CH$_2$OH); 4.7 (m, 1H, aliphatic H, H tetrahydroisoquinoline); 3.9 (d, 1H, aliphatic H, H tetrahydroisoquinoline); 3.85 (m, 1H, aliphatic H, H tetrahydroisoquinoline); 3.7 (m, 2H, aliphatic Hs, CH$_2$CH$_2$OH); 3.75 (2s, 3H,); 3.5-3.2 (m, 2H, aliphatic Hs, CH$_2$CH$_2$OH); 3.0-2.4 (m, 2H, aliphatic H, H tetrahydroisoquinoline); 2.4-2.3 (4s, 3H, CH$_3$-pyrrole); 1.5, 0.95, 0.75 (4 d, 3H, CH$_3$-THIQ); 0.85 (broad s, 9H, Si(CH$_3$)$_2$(CH(CH$_3$)$_2$); 0.15 (m, 6H, Si(CH$_3$)$_2$(CH(CH$_3$)$_2$)
IR: v: —OH: 3346 cm$^{-1}$ carboxylic acid; v: >C=O: 1621 cm$^{-1}$ Step C: 1-(2-Hydroxyethyl)-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide The phenol function of the compound of Step B is deprotected following the process of Step D of Example 1.
Elemental Microanalysis: (%, Theoretical:Measured)
% C=68.23:68.12; % H=5.57:5.29; % N=11.05:10.79
High-Resolution Mass Spectrometry (ESI+):
Empirical formula: $C_{36}H_{36}N_5O_6$
[M+H]$^+$ calculated: 634.2662
[M+H]$^+$ measured: 634.2660

Example 24. N-(4-Hydroxyphenyl)-5-(5-methoxy-2-{[(3S)-3-(morpholin-4-ylmethyl)-3,4-dihydroisoquinolin-2(1H)-yl]carbonyl}phenyl)-1,2-dimethyl-N-(1-methyl-1H-pyrazol-4-yl)-1H-pyrrole-3-carboxamide hydrochloride Elemental Microanalysis: (%, Theoretical:Measured)
% C=65.86:64.47; % H=6.09:5.88; % N=11.82:11.45; % Cl−=4.98:6.7
High-Resolution Mass Spectrometry (ESI+):
Empirical formula: $C_{39}H_{42}N_6O_5$
[M+H]$^+$ calculated: 675.3289
[M+H]$^+$ measured: 675.3287

Example 25. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride Elemental Microanalysis: (%, Theoretical:Measured)
% C=63.77:62.83; % H=5.63:5.83; % N=11.74:11.29; % Cl−=4.95:5.42

Example 26. N-(4-Hydroxyphenyl)-2-methyl-1-[2-(methylamino)ethyl]-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide hydrochloride The procedure is in accordance with Steps A, B and C of the process of Example 30 replacing the sodium azide used in Step B by methylamine. After purification over silica gel (CH$_2$Cl$_2$/MeOH/NH$_3$ gradient), the compound obtained, 0.3 g (0.46 mmol), is dissolved in 5 mL of anhydrous methanol and there is added, dropwise, 0.464 mL (0.47 mmol) of 1M HCl solution in ether. The batch is stirred for 0.5 hours at ambient temperature. The precipitate thereby obtained is filtered off and dried and then dissolved in a mixture of CH$_3$CN/H$_2$O before being lyophilised at low temperature. The expected product is obtained in the form of a solid.
Elemental Microanalysis: (%, Theoretical:Measured)
% C=65.05:64.64; % H=5.75:5.43; % N=12.3:12.3; % Cl−=5.19:5.39
High-Resolution Mass Spectrometry (ESI+):
Empirical formula: $C_{37}H_{38}N_6O_5$
[M+H]$^+$ calculated: 647.2903
[M+H]$^+$ measured: 647.2922

Example 27. 1-[2-(Dimethylamino)ethyl]-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide hydrochloride The procedure is in accordance with the process of Example 26, replacing the methylamine in Step B by dimethylamine.

Elemental Microanalysis: (%, Theoretical:Measured)
% C=65.46:65.07; % H=5.93:5.87; % N=12.05:12.06; % Cl−=5.08:5.55

High-Resolution Mass Spectrometry (ESI+):
Empirical formula: $C_{38}H_{40}N_6O_5$
[M+H]+ calculated: 661.3060
[M+H]+ measured: 661.3045

Example 28. 5-(5-Chloro-2-{[(3R)-3-methyl-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide hydrochloride Elemental Microanalysis: (%, Theoretical:Measured)
% C=66.99:66.88; % H=5.14:5.28; % N=8.93:8.87; % Cl−=5.65:4.98

High-Resolution Mass Spectrometry (ESI+):
Empirical formula: $C_{35}H_{32}ClN_4O_3$
[M+H]+ calculated: 591.2157
[M+H]+ measured: 591.2178

Example 29. 5-(5-Chloro-2-{[(3S)-3-{[2-(morpholin-4-yl)ethoxy]methyl}-3,4-dihydroisoquinolin-2(1H)-yl]carbonyl}phenyl)-N-(4-hydroxyphenyl)-1,2-dimethyl-N-phenyl-1H-pyrrole-3-carboxamide hydrochloride

Step A: Methyl 5-(5-chloro-2-{[(3S)-3-(hydroxymethyl)-3,4-dihydroisoquinolin-2(1H)-yl]carbonyl}phenyl)-1,2-dimethyl-1H-pyrrole-3-carboxylate To a solution of 4.9 g of the compound of Preparation 1 in a mixture of 40 mL of dimethylformamide and 40 mL of tetrahydrofuran there are added 2.73 g (1.1 equivalents) of (3S)-3-hydroxymethyl-1,2,3,4-tetrahydroisoquinoline, 7.95 mL of diisopropylethyl-amine and 9.84 g (1.7 equivalents) of HATU. After stirring for 2 hours at ambient temperature, the reaction mixture is dried, taken up in ethyl acetate and then washed with 10% aqueous citric acid solution and water. The combined aqueous phases are extracted with ethyl acetate. The organic phases thereby obtained are combined, dried over $Na_2SO_4$, filtered and concentrated under reduced pressure. The crude product obtained is purified by chromatography over silica gel using dichloromethane and ethanol as eluants to yield the title compound.

1H NMR: δ (500 MHz; dmso-d6; 300K): 7.6-7.4 (m, 3H, Cl-Ph); 7.2-6.9 (m, 4H, Ar(THIQ); 6.5-6.15 (broad 4s, 1H, pyrrole); 4.9-3.8 (6 d, 2H, $NCH_2$ THIQ); 4.85-3.6 (m, 1H, NCH THIQ); 4.2-40 (m, 2H, $OCH_2$ ester), 3.45-3.2 (3s, 3H, N—$CH_3$); 3.35-3.0 (3m, 2H, $HOCH_2$); 3.0-2.0 (m, 2H, THIQ); 2.5-2.1 (m, 3H, $CH_3$ pyrrole); 1.25-1.1 (m, 3H, $CH_3$ ester)

IR: ν —OH: 3388 $cm^{-1}$, ν >C=O: 1693 $cm^{-1}$ (conjugated ester), ν >C=O: 1620 $cm^{-1}$ (amide)

Step B: Methyl 5-(5-chloro-2-{[(3S)-3-{[2-(morpholin-4-yl)ethoxy]methyl}-3,4-dihydroisoquinolin-2(1H)-yl]carbonyl}phenyl)-1,2-dimethyl-1H-pyrrole-3-carboxylate A solution of 1.7 g (3.2 mmol) of the compound obtained in the above Step in 20 mL of dimethylformamide is added, dropwise at 0° C., to a suspension of 0.280 g of NaH 60% in oil (2.2 equivalents) in 10 mL of dimethylformamide. After stirring for 5 minutes at ambient temperature, a suspension of 0.68 g of 4-(2-bromoethyl)morpholine hydrobromide (1.1 equivalents) is added dropwise. The reaction mixture is stirred at ambient temperature for 45 minutes. There are then added, in two steps over 20 hours, 2.2 equivalents of 4-(2-bromoethyl)morpholine hydrobromide, and then 3 equivalents of NaH 60% in oil. The reaction mixture is then poured into a mixture of 10% aqueous ammonium chloride and ethyl acetate. The resulting organic phase is successively washed with water, and then with saturated aqueous LiCl solution and brine. It is then dried over $Na_2SO_4$, filtered and concentrated under reduced pressure. The oil obtained is purified by chromatography over silica gel using dichloromethane and ethanol as eluants to provide the expected product.

1H NMR: δ (500 MHz; dmso-d6; 300K): 7.6-7.3 (m, 3H, Cl-Ph); 7.2-6.85 (m, 4H, Ar(THIQ); 6.5-6.15 (broad s, 1H, pyrrole); 5.25-3.8 (m, 2H, $NCH_2$ THIQ); 5.05-3.75 (m, 1H, NCH THIQ); 4.2-40 (m, 2H, $OCH_2$ ester), 3.5-3.25 (m, 3H, N—$CH_3$); 3.6-2.75 (m, 8H, $OCH_2$ morpholinoethoxymethyl); 2.95-2.05 (m, 2H, THIQ); 2.55-2.15 (m, 6H, $NCH_2$ morpholinoethoxymethyl); 2.55-2.05 (m, 3H, $CH_3$ pyrrole), 1.25-1.1 (m, 3H, $CH_3$ ester)

IR: ν >C=O: 1694 $cm^{-1}$ (conjugated ester), ν >C=O: 1629 $cm^{-1}$ (amide)

Step C: 5-(5-Chloro-2-{[(3S)-3-{[2-(morpholin-4-yl)ethoxy]methyl}-3,4-dihydroisoquinolin-2(1H)-yl]carbonyl}phenyl)-1,2-dimethyl-1H-pyrrole-3-carboxylic acid To a solution of 1.46 g of the compound of the above Step in 5 mL of dioxane there are added 5 mL of 1M aqueous LiOH solution. The batch is heated in a microwave apparatus (100 W) at 100° C. for 2 hours. The reaction mixture is poured into water and then extracted with ethyl ether. The ethereal phase is extracted again with 10 mL of water. The aqueous phases are acidified to pH 5-6 by adding saturated aqueous ammonium chloride solution and then extracted twice with dichloromethane. The dichloromethane phase is dried over $Na_2SO_4$, filtered and concentrated to dryness. The title product is obtained in the form of a meringue.

1H NMR: δ (500 MHz; dmso-d6; 300K): 11.4 (broad s, 1H, $CO_2H$), 7.6-7.3 (m, 3H, Cl-Ph); 7.2-6.8 (m, 4H, Ar(THIQ); 6.5-6.2 (broad 4s, 1H, pyrrole); 5.25-3.75 (m, 2H, $NCH_2$ THIQ); 5.05-3.7 (3m, 1H, NCH THIQ); 3.5-3.2 (3s, 3H, N—$CH_3$); 3.6-2.7 (m, 8H, $OCH_2$ morpholinoethoxymethyl); 2.5-2.2 (m, 6H, $NCH_2$ morpholinoethoxymethyl); 3.0-2.0 (m, 2H, THIQ), 2.5-2.0 (3s, 3H, $CH_3$ pyrrole)

IR: ν —OH: 3300-2200 $cm^{-1}$, ν >C=O: 1697-1662 $cm^{-1}$ (double band, carboxylic acid), ν >C=O: 1628 $cm^{-1}$ (amide)

Step D: N-(4-{[tert-Butyl(dimethyl)silyl]oxy}phenyl)-5-(5-chloro-2-{[(3S)-3-{[2-(morpholin-4-yl)ethoxy]methyl}-3,4-dihydroisoquinolin-2(1H)-yl]carbonyl}phenyl)-1,2-dimethyl-N-phenyl-1H-pyrrole-3-carboxamide The acid obtained in Step C (1.48 g) is suspended in 15 mL of 1,2-dichloroethane. 1.1 equivalents of 1-chloro-N,N,2-trimethylpropenylamine are added thereto. After stirring for 1 hour at ambient temperature, there are added 15 mL of toluene and 1.05 equivalents of the compound of Preparation 2". The reaction mixture is heated for 14 hours at 110° C. and then dried. The crude product thereby obtained is purified by chromatography over silica gel using dichloromethane and ethanol as eluants to yield the expected product.

$^1$H NMR: δ (500 MHz; dmso-d6; 300K): 7.55-7.25 (m, 3H, Cl-Ph); 7.25-6.6 (m, 9H, Ar(THIQ)+phenyl); 6.8-6.5 (m, 2H, phenoxy); 7.0-6.6 (m, 2H, phenoxy); 5.7-5.05 (broad 4s, 1H, pyrrole); 5.2-3.6 (8d, 2H, THIQ); 5.05-3.6 (4m, 1H, NCH THIQ), 3.6-2.9 (m, 8H, aliphatic morpholinoethoxymethyl); 3.4-3.2 (broad 3s, 3H, N—CH$_3$); 3.0-2.1 (m, 2H, THIQ), 2.35 (m, 2H, NCH$_2$ morpholinoethoxymethyl); 2.4-2.2 (m, 4H, NCH$_2$ morpholine); 2.4-2.15 (broad 3s, 3H, CH$_3$ pyrrole); 0.8 (broad 2s, 9H, SiC(CH$_3$)$_3$); 0.1 (4s, 6H, SiCH$_3$)

IR: ν >C=O: 1635-1595 cm$^{-1}$ (double band), ν Si—O: 1117 cm$^{-1}$, ν Si—C: 837 cm$^{-1}$

Step E: 5-(5-Chloro-2-{[(3S)-3-{[2-(morpholin-4-yl)ethoxy]methyl}-3,4-dihydroiso-quinolin-2(1H)-yl]carbonyl}phenyl)-N-(4-hydroxyphenyl)-1,2-dimethyl-N-phenyl-1H-pyrrole-3-carboxamide hydrochloride To a solution of 0.7 g of the compound of Step D in 5 mL of methanol there is added 0.92 mL of a 1M solution of potassium hydroxide in methanol. After stirring for 1 hour 10 minutes at ambient temperature, saturated aqueous sodium bicarbonate solution is added. The product which precipitates is extracted with ethyl acetate and then washed with water and brine. The resulting aqueous phases are extracted again with ethyl acetate. The organic phases thereby obtained are dried over Na$_2$SO$_4$, filtered and concentrated under reduced pressure. The crude product obtained is purified by chromatography over silica gel using dichloromethane and ammonia-in-ethanol as eluants to provide 0.536 g of the title product, in the form of the base. The latter is dissolved in acetonitrile and converted into salt form using 1M aqueous HCl solution. After a lyophilisation step, the expected product is obtained in the form of a solid.

Elemental Microanalysis: (%, Measured(Theoretical))
% C=66.4(66.75); % H=5.98(5.87); % N=7.38(7.41); % Cl=9.42(9.38); % Cl$^-$=4.57(4.69)

Example 30. 1-(2-Aminoethyl)-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide hydrochloride

Step A: 2-{3-[(4-{[tert-Butyl(dimethyl)silyl]oxy}phenyl)(1-methyl-1H-pyrazol-4-yl)carbamoyl]-2-methyl-5-(6-{[(3R)-3-methyl-3,4-dihydroisoquinolin-2(1H)-yl]carbonyl}-1,3-benzodioxol-5-yl)-1H-pyrrol-1-yl}ethyl methanesulphonate A solution of 4.65 g of the compound obtained in Step B of Example 23 (6.22 mmol) in 100 mL of anhydrous THF is placed at 0° C. There are successively added thereto 3.5 mL (12.44 mmol) of triethylamine and then, dropwise, 0.722 mL of methanesulphonic chloride (9.33 mmol) dissolved in 20 mL of THF. The batch is then stirred at ambient temperature for 2 hours. The reaction mixture is hydrolysed by addition of saturated aqueous NaHCO$_3$ solution and then extracted twice with ethyl acetate. The organic phases are combined, dried over MgSO$_4$ and concentrated to dryness. The expected compound is obtained in the form of a glassy solid.

$^1$H NMR: δ (500 MHz; dmso-d6; 300K): 7.7-7.45 (s, 1H, H pyrazole); 7.1-6.9 (s, 1H, H pyrazole); 7.2-6.4 (m, 8H, aromatic Hs); 6.95-6.65 (m, 2H, aromatic Hs); 6.1 (m, 2H, OCH$_2$O); 5.2, 4.6 (4s, H, H-pyrrole (presence of conformational isomers); 4.9, 4.6, 3.9, 3.8 (m, 1H), 5.05-3.75 (m, 1H, aliphatic H, H tetrahydroisoquinoline); 4.3-405 (m, 2H, aliphatic Hs, CH$_2$CH$_2$OSO$_2$CH$_3$); 4.2-3.95 (m, 2H, aliphatic Hs, CH$_2$CH$_2$OSO$_2$CH$_3$); 3.75-2.7 (2s, 3H, CH$_3$-pyrazole); 3.0 (several s, 3H, CH$_2$OSO$_2$CH$_3$); 3.05-2.5 (several m, 2H, aliphatic Hs, H tetrahydroisoquinoline); 2.45-2.3 (several s, 3H, CH$_3$-pyrrole); 1.05, 0.75 (several d, 3H, CH$_3$-tetraisoquinoline); 0.9 (several s, 9H, Si(CH$_3$)$_2$(CH(CH$_3$)$_2$); 0.1 (m, 6H, Si(CH$_3$)$_2$(CH(CH$_3$)$_2$)

IR: ν: >C=O: 1626 cm$^{-1}$, ν: —SO$_2$: 1349 and 1172 cm$^{-1}$

Step B: 1-(2-Azidoethyl)-N-(4-{[tert-butyl(dimethyl)silyl]oxy}phenyl)-2-methyl-5-(6-{[(3R)-3-methyl-3,4-dihydroisoquinolin-2(1H)-yl]carbonyl}-1,3-benzodioxol-5-yl)-N-(1-methyl-M-pyrazol-4-yl)-1H-pyrrole-3-carboxamide To a solution of 2 g (2.42 mmol) of compound of Step A in 20 mL of anhydrous DMF there is added 0.472 g (7.26 mmol) of sodium azide. The batch is stirred at 65° C. for 4 hours 30 minutes. The reaction mixture is poured into saturated aqueous NaHCO$_3$ solution and then extracted twice with ethyl acetate. The organic phases are combined and washed with saturated aqueous LiCl solution, dried over MgSO$_4$ and concentrated to dryness. After purification over silica gel using dichloromethane and ammonia-in-methanol as eluants, the expected product is obtained in the form of a foam.

$^1$H NMR: δ (500 MHz; dmso-d6; 300K): 7.65-7.45 (several s, 1H, H pyrazole); 7.1-6.9 (several s, 1H, H pyrazole); 7.3-6.4 (several m, 6H, aromatic Hs); 7.1-6.9 (several s, 1H, aromatic Hs); 6.8, 6.5 (2m, 2H, aromatic Hs); 6.1 (several s, 2H, OCH$_2$O); 5.25-465 (several s, 1H, H-pyrrole (presence of conformational isomers); 4.9, 4.6,3.8 (several m, 1H); 5.05-3.7 (several m, 4H, aliphatic Hs, H-THIQ+ CH$_2$CH$_2$N$_3$); 3.7 (several s, 3H, H CH$_3$-pyrazole); 3.5-3.25 (m, 2H, CH$_2$CH$_2$N$_3$); 3.1-2.4 (several m, 3H, CH$_3$-pyrrole); 2.45-2.3 (several s, 3H, CH$_3$-pyrrole); 1.0-0.75 (several d, 3H, CH$_3$-THIQ); 0.9 (several s, 9H, Si(CH$_3$)$_2$(CH(CH$_3$)$_2$); 0.1 (several s, 6H, Si(CH$_3$)$_2$(CH(CH$_3$)$_2$)

IR: ν:-N=N=N: 2100 cm$^{-1}$, ν: >C=O: 1630 cm$^{-1}$, ν: —Si—O—: 1035 cm$^{-1}$

Step C: 1-(2-Azidoethyl)-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide To a solution of 1.12 g of the compound obtained in Step B (14.49 mmol) in 5 mL of methanol there are added, dropwise, 7.24 mL of 1M methanolic potassium hydroxide solution (72.45 mmol). The batch is stirred at ambient temperature for 3 hours. The reaction mixture is then concentrated to dryness, taken up in dichloromethane, hydrolysed with saturated aqueous NaHCO₃ solution and then extracted twice with dichloromethane. The organic phases are then combined, washed with water, dried over MgSO₄ and concentrated to dryness. The expected product is obtained in the form of a foam and used directly in the next Step.

¹H NMR: δ (500 MHz; dmso-d6; 300K): 9.60((s, 1H, CH₂CH₂OH); 7.65-7.45 (several s, 1H, H pyrazole); 7.1-6.9 (several s, 1H, H pyrazole); 7.3-6.4 (several m, 6H, aromatic Hs); 7.1-6.9 (several s, 1H, aromatic Hs); 6.8, 6.5 (2m, 2H, aromatic Hs); 6.15 (several s, 2H, OCH₂O); 5.35-48 (several s, 1H, H-pyrrole (presence of conformational isomers); 4.9, 4.6, 3.8 (several m, 1H, aliphatic H, H tetrahydroisoquinoline); 3.7 (several s, 3H, H CH₃-pyrazole); 3.5-3.25 (m, 2H, CH₂CH₂N₃); 3.1-2.4 (several m, 3H, CH₃-pyrrole); 2.45-2.3 (several s, 3H, H THIQ); 2.45-2.3 (several s, 3H, CH₃-pyrrole); 1.0-0.75 (several d, 3H, CH₃-THIQ)

IR: v: —OH: 3171 cm⁻¹, v: —N═N═N: 2100 cm⁻¹, v: >C═O: 1617 cm⁻¹

Step D: 1-(2-Aminoethyl)-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide hydrochloride To a solution of 1.27 g of the compound obtained in the above Step (1.93 mmol) in 15 mL of anhydrous ethanol there is added 0.154 g of Pd/C 10%. The batch is degassed for 0.5 hours. It is then stirred for 12 hours at ambient temperature under hydrogen pressure (1.5 bar). The reaction mixture is then filtered and then concentrated to dryness. After purification by chromatography over silica gel (CH₂Cl₂/MeOH/NH₃ gradient), an oily residue is obtained. The residue is dissolved in 10 mL of anhydrous ethanol and then converted into salt form by adding two molar equivalents of a 1N solution of HCl in ethanol. The product is then dried before being dissolved in a minimum of a mixture of water and acetonitrile. After a lyophilisation step at low temperature, the expected product is obtained in the form of a solid.

Elemental Microanalysis: (%, Theoretical:Measured)
% C=64.62:63.84; % H=5.57:5.55; % N=12.56:12.36; % Cl−=5.3:5.56
High-Resolution Mass Spectrometry (ESI+):
Empirical formula: $C_{36}H_{36}N_6O_5$
[M+H]⁺ calculated: 633.2820
[M+H]⁺ measured: 633.2808

Example 31. N-(4-Hydroxyphenyl)-5-(5-methoxy-2-{[(3R)-3-methyl-3,4-dihydroisaquinolin-2(1H)-yl]carbonyl}phenyl)-1,2-dimethyl-N-(1-methyl-1H-pyrazol-4-yl)-1H-pyrrole-3-carboxamide Elemental Microanalysis: (%, Theoretical:Measured)
% C=71.29:70.17; % H=5.98:5.98; % N=11.88:11.49
High-Resolution Mass Spectrometry (ESI+):
Empirical formula: $C_{35}H_{36}N_5O_4$
[M+H]⁺ calculated: 590.2762
[M+H]⁺ measured: 590.2778

Example 32. Phenyl (4-{4-[(4-hydroxyphenyl)(methyl)carbamoyl]-1,5-dimethyl-1H-pyrrol-2-yl}-3-{[(3R)-3-methyl-3,4-dihydroisoquinolin-2(1H)-yl]carbonyl}benzyl)-carbamate Step A: N-(4-Benzyloxyphenyl)-N,1,2-trimethyl-pyrrole-3-carboxamide The process is analogous to that described in Step A of Example 45.

Step B: tert-Butyl [4-(4-{[4-(benzyloxy)phenyl](methyl)carbamoyl}-1,5-dimethyl-1H-pyrrol-2-yl)-3-{[(3R)-3-methyl-3,4-dihydroisoquinolin-2(1H)-yl]carbonyl}benzyl]-carbamate The compound of Preparation II (1.5 g; 2.96 mmol) and the compound of Step A (1.16 g; 3.44 mmol) are dissolved in dimethylacetamide (25 mL) and then nitrogen is bubbled through the solution for 5 minutes. Potassium acetate (0.586 g; 5.92 mmol) and bis(triphenylphosphine)palladium(II) dichloride (0.2 g; 0.295 mmol) are added to the mixture which is then heated to 100° C. and, after stirring for 20 minutes, water (10 µL) is added. Stirring at 100° C. under a nitrogen atmosphere is continued for 2 hours more. The reaction mixture is allowed to cool to ambient temperature and is then evaporated to a volume of 15 mL. The resulting mixture is filtered over a short Celite column and then purified by preparative HPLC using water-TFA and acetonitrile as eluants. The pH of the appropriate fractions is adjusted to 7 with NaHCO₃, and then the acetonitrile is evaporated off under reduced pressure. The aqueous residue is extracted with DCM. The organic phase is washed with brine, dried over Na₂SO₄ and evaporated to dryness to yield the title compound.
High-Resolution Mass Spectrometry (ESI+):
Empirical formula: $C_{40}H_{41}N_5O_4$
[M+H]⁺ calculated: 713.3705
[M+H]⁺ measured: 713.3709

Step C: 5-[4-(Aminomethyl)-2-{[(3R)-3-methyl-3,4-dihydroisoquinolin-2(1H)-yl]-carbonyl}phenyl]-N-[4-(benzyloxy)phenyl]-N,1,2-trimethyl-1H-pyrrole-3-carboxamide hydrochloride The compound of the above Step (1.18 g, 1.66 mmol) is dissolved/suspended in 4M HCl in dioxane (20 mL). The heterogeneous mixture is stirred for 30 minutes at ambient temperature and then evaporated to dryness to yield 1.19 g of the title compound which is used in the next Step without purification.

Step D: Phenyl (4-{4-[(4-hydroxyphenyl)(methyl)carbamoyl]-1,5-dimethyl-1H-pyrrol-2-yl}-3-{[(3R)-3-methyl-3,4-dihydroisoquinolin-2(1H)-yl]carbonyl}benzyl)carbamate The title compound is obtained starting from the compound of the above Step in accordance with the protocol of Step D of Example 45.
Elemental Microanalysis: (%, Measured(Theoretical))
% C=72.83(72.88); % H=6.01(5.96); % N=8.02(8.72)
High-Resolution Mass Spectrometry (ESI+):
Empirical formula: $C_{39}H_{38}N_4O_5$
[M+H]⁺ calculated: 643.2922
[M+H]⁺ measured: 643.2916

Example 33. 5-(5-Chloro-2-{[(3S)-3-(morpholin-4-ylmethyl)-3,4-dihydroisoquinolin-2(1H)-yl]carbonyl}phenyl)-N-(4-fluorophenyl)-N-(4-hydroxyphenyl)-1,2-dimethyl-1H-pyrrole-3-carboxamide hydrochloride Elemental Microanalysis: (%, Measured(Theoretical))
% C=65.75(65.84); % H=5.38(5.39); % N=7.62(7.68); % Cl=9.77(9.72); % Cl−=4.84(4.86)

Example 34. 5-(5-Chloro-2-{[(3S)-3-(morpholin-4-ylmethyl)-3,4-dihydroisoquinolin-2(1H)-yl]carbonyl}phenyl)-N-(3-fluorophenyl)-N-(4-hydroxyphenyl)-1,2-dimethyl-1H-pyrrole-3-carboxamide hydrochloride Elemental Microanalysis: (%, Measured(Theoretical))
% C=65.61(65.84); % H=5.09(5.39); % N=7.76(7.68); % Cl−=4.83(4.86)

Example 35. N-(4-Hydroxyphenyl)-N,1,2-trimethyl-5-(2-{[(3R)-3-methyl-3,4-dihydroisoquinolin-2(1H)-yl]carbonyl}-4-{[(phenoxyacetyl)amino]methyl}phenyl)-1H-pyrrole-3-carboxamide The title compound is obtained in accordance with the process of Example 32 using 2-phenoxyacetyl chloride as acylating agent in Step D.
Elemental Microanalysis: (%, Measured(Theoretical))
% C=72.53(73.15); % H=5.76(6.14); % N=8.31(8.53)
High-Resolution Mass Spectrometry (ESI+):
Empirical formula: $C_{40}H_{40}N_4O_5$
$[M+H]^+$ calculated: 657.3079
$[M+H]^+$ measured: 657.3061

Example 36. 5-(4-{[(Ethylcarbamoyl)amino]methyl}-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 32 using ethyl isocyanate as acylating agent in Step D.
Elemental Microanalysis: (%, Measured(Theoretical))
% C=70.88(70.8); % H=6.02(6.62); % N=11.17(11.8)
High-Resolution Mass Spectrometry (ESI+):
Empirical formula: $C_{35}H_{39}N_5O_4$
$[M+H]^+$ calculated: 594.3100
$[M+H]^+$ measured: 594.3083

Example 37. 5-(4-{[(Benzylcarbamoyl)amino]methyl}-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 32 using benzyl isocyanate as acylating agent in Step D.
Elemental Microanalysis: (%, Measured(Theoretical))
% C=73.21(73.26); % H=5.98(6.3); % N=10.23(10.68)
High-Resolution Mass Spectrometry (ESI+):
Empirical formula: $C_{40}H_{41}N_5O_4$
$[M+H]^+$ calculated: 656.3239
$[M+H]^+$ measured: 656.3256

Example 38. 5-(5-Chloro2-{[(3S)-3-(hydroxymethyl)-3,4-dihydroisoquinolin-2(1H)-yl]carbonyl}phenyl)-N-(4-hydroxyphenyl)-1,2-dimethyl-N-phenyl-1H-pyrrole-3-carboxamide Elemental Microanalysis: (%, Measured(Theoretical))
% C=70.97(71.34);% H=5.2(5.32);% N=6.96(6.93)

Example 39. N-(4-Hydroxyphenyl)-1,2-dimethyl-5-(6-{[(3R)-3-methyl-3,4-dihydroisaquinolin-2(1H)-yl]carbonyl}-1,3-benzodioxol-5-yl)-N-(1-methyl-1H-pyrazol-4-yl)-1H-pyrrole-3-carboxamide Elemental Microanalysis: (%, Measured(Theoretical))
% C=69.81(69.64); % H=5.6(5.51); % N=11.55(11.6)
High-Resolution Mass Spectrometry (ESI+):
Empirical formula: $C_{35}H_{34}N_5O_5$
$[M+H]^+$ calculated: 604.2554
$[M+H]^+$ measured: 604.2565

Example 40. Phenyl (3-{4-[(4-hydroxyphenyl)(methyl)carbamoyl]-1,5-dimethyl-1H-pyrrol-2-yl}-4-{[(3R)-3-methyl-3,4-dihydroisoquinolin-2(1H)-yl]carbonyl}benzyl)-carbamate Step A: N-(4-Benzyloxyphenyl)-N,1,2-trimethyl-pyrrole-3-carboxamide The process is analogous to that described in Step A of Example 45.

Step B: 5-[5-(Aminomethyl)-2-{[(3R)-3-methyl-3,4-dihydroisoquinolin-2(1H)-yl]-carbonyl}phenyl]-N-[4-(benzyloxy)phenyl]-N,1,2-trimethyl-1H-pyrrole-3-carboxamide hydrochloride The compound of Preparation III (1.84 g; 3.99 mmol) and the compound of Step A (1.60 g; 4.48 mmol) are dissolved in dimethylacetamide (20 mL) and then nitrogen is bubbled through the solution for 5 minutes. Potassium acetate (0.78 g; 7.48 mmol) and bis(triphenylphosphine)palladium(II) dichloride (0.28 g; 0.4 mmol) are added to the mixture which is then heated to 105° C. and, after stirring for 10 minutes, water (11 µL) is added. Stirring at 105° C. under a nitrogen atmosphere is continued for 6 hours more. The reaction mixture is allowed to cool to ambient temperature, the resulting mixture is filtered over a short Celite column and is then purified by preparative HPLC using water-TFA and acetonitrile as eluants. The pH of the appropriate fractions is adjusted to 7 with $NaHCO_3$ and then the acetonitrile is evaporated off under reduced pressure. The solid precipitate is removed by filtration and then dried (5 mbar, 45° C., 16 hours) to form tert-butyl [3-(4-{[4-(benzyloxy)phenyl](methyl)carbamoyl}-1,5-dimethyl-1H-pyrrol-2-yl)-4-{[(3R)-3-methyl-3,4-dihydroisoquinolin-2(1H)-yl]carbonyl}benzyl]carbamate which is dissolved/suspended in 4M HCl in dioxane (35 mL). The heterogeneous mixture is stirred for 30 minutes at ambient temperature and then evaporated to dryness to yield the title compound which is used in the next Step without purification.
High-Resolution Mass Spectrometry (ESI+):
Empirical formula: $C_{39}H_{40}N_4O_3$
$[M+H]^+$ calculated: 613.3180
$[M+H]^+$ measured: 613.3194

IR: ν: N—H+: 2854 cm$^{-1}$; >C=O: 1621 cm$^{-1}$; C—O—C: 1234, 1120, 1011 cm$^{-1}$

Step C: Phenyl (3-{4-[(4-hydroxyphenyl)(methyl)carbamoyl]-1,5-dimethyl-1H-pyrrol-2-yl}-4-{[(3R)-3-methyl-3,4-dihydroisoquinolin-2(1H)-yl]carbonyl}benzyl)carbamate The title compound is obtained starting from the compound of the above Step in accordance with the process of Step D of Example 45.
Elemental Microanalysis: (%, Measured(Theoretical))
% C=73.2(72.88); % H=5.83(5.96); % N=8.13(8.72)
High-Resolution Mass Spectrometry (ESI+):
Empirical formula: $C_{39}H_{38}N_4O_5$
[M+H]$^+$ calculated: 643.2922
[M+H]$^+$ measured: 643.2902

Example 41. N-(3-Fluorophenyl)-N-(4-hydroxyphenyl)-1,2-dimethyl-5-(6-{[(3R)-3-methyl-3,4-dihydroisoquinolin-2(1H)-yl]carbonyl}-1,3-benzodioxol-5-yl)-1H-pyrrole-3-carboxamide Elemental Microanalysis: (%, Measured(Theoretical))
% C=71.44(71.95); % H=4.95(5.22); % N=6.8(6.8)
High-Resolution Mass Spectrometry (ESI+):
Empirical formula: $C_{37}H_{33}FN_3O_5$
[M+H]$^+$ calculated: 618.2399
[M+H]$^+$ measured: 618.2392

Example 42. N-(4-Hydroxyphenyl)-1,2-dimethyl-5-(6-{[(3R)-3-methyl-3,4-dihydroisoquinolin-2(1H)-yl]carbonyl}-1,3-benzodioxol-5-pyrrolo[2,3-b]pyridin-5-yl)-1H-pyrrole-3-carboxamide Elemental Microanalysis: (%, Measured(Theoretical))
% C=71.32(71.65); % H=5.17(5.4); % N=10.67(10.71)
High-Resolution Mass Spectrometry (ESI+):
Empirical formula: $C_{39}H_{36}N_5O_5$
[M+H]$^+$ calculated: 654.2711
[M+H]$^+$ measured: 654.2710

Example 43. N-(4-Hydroxyphenyl)-1,2-dimethyl-5-(6-{[(3R)-3-methyl-3,4-dihydroisoquinolin-2(1H)-yl]carbonyl}-1,3-benzodioxol-5-1)-N-phenyl-1H-pyrrole-3-carboxamide Elemental Microanalysis: (%, Measured(Theoretical))
% C=73.9(74.11); % H=5.16(5.55); % N=6.81(7.01)
High-Resolution Mass Spectrometry (ESI+):
Empirical formula: $C_{37}H_{34}N_3O_5$
[M+H]$^+$ calculated: 600.2493
[M+H]$^+$ measured: 600.2495

Example 44. N-(4-Hydroxyphenyl)-1,2-dimethyl-N-(1-methyl-1H-pyrrolo[2,3-b]-pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Measured(Theoretical))
% C=66.41(66.62); % H=5.08(5.59); % N=10.85(10.84); % Cl-=4.68(4.57)
High-Resolution Mass Spectrometry (ESI+):
Empirical formula: $C_{43}H_{42}N_6O_6$
[M+H]$^+$ calculated: 739.3239
[M+H]$^+$ measured: 739.3246

Example 45. Phenyl [2-(3-{4-[(4-hydroxyphenyl)(methyl)carbamoyl]-1,5-dimethyl-1H-pyrrol-2-yl}-4-{[(3R)-3-methyl-3,4-dihydroisoquinolin-2(1H)-yl]carbonyl}-phenyl)ethyl]carbamate Step A: N-(4-Benzyloxyphenyl)-N,1,2-trimethylpyrrole-3-carboxamide To a suspension of 1,2-dimethylpyrrole-3-carboxylic acid (2.085 g; 15 mmol) in 1,2-dichloroethane (40 mL) there is added 1-chloro-N,N,2-trimethyl-prop-1-en-1-amine (2.37 mL; 17.9 mmol), and the solution formed is stirred for 1 hour. To the resulting solution there is added, dropwise, an ice-cold solution of 4-benzyloxy-N-methyl-aniline (3.73 g; 15 mmol) and N-ethyl-N-isopropyl-propan-2-amine (7.75 mL; 45 mmol) in 1,2-dichloroethane (40 mL). The reaction mixture is stirred at ambient temperature for 1 hour; it is then diluted with dichloromethane (250 mL) and washed with water (2×30 mL), dried over $Na_2SO_4$ and evaporated. The crude product is triturated with diethyl ether and the solid formed is filtered off to yield the title compound.
IR: ν: >C=O: 1616 cm$^{-1}$; amide: 1508 cm$^{-1}$; C—O—C: 1230, 1172, 1009 cm$^{-1}$ Step B: tert-Butyl {2-[3-(4-{[4-(benzyloxy)phenyl](methyl)carbamoyl}-1,5-dimethyl-1H-pyrrol-2-yl)-4-{[(3R)-3-methyl-3,4-dihydroisoquinolin-2(1H)-yl]carbonyl}phenyl]ethyl}-carbamate The compound of Preparation I (0.869 g; 1.67 mmol) and the compound of Step A (0.558 g; 1.67 mmol) are dissolved in dimethylacetamide (8 mL) and then nitrogen is bubbled through the solution for 5 minutes. Potassium acetate (0.33 g; 3.34 mmol) and bis(triphenylphosphine)palladium(II) dichloride (0.117 g; 0.167 mmol) are added to the mixture which is then heated to 140° C. and, after stirring for 10 minutes, water (80 µL) is added. Stirring at 140° C. under a nitrogen atmosphere is continued for 16 hours more. The reaction mixture is allowed to cool to ambient temperature and then evaporated. The residue is partitioned between dichloromethane (100 mL) and water (20 mL). The organic phase is washed with water (20 mL), dried over $Na_2SO_4$ and evaporated. The residue was purified by preparative HPLC using water-TFA and acetonitrile as eluants. The pH of the appropriate fractions is adjusted to 12 using aqueous NaOH solution and then the acetonitrile is evaporated off under reduced pressure. The aqueous residue is extracted with dichloromethane (2×100 mL). The organic phase is dried over $Na_2SO_4$ and evaporated to dryness to yield the title compound.
High-Resolution Mass Spectrometry (ESI+):
Empirical formula: $C_{45}H_{50}N_4O_5$
[M+H]$^+$ calculated: 727.3861
[M+H]$^+$ measured: 727.3852
IR: ν: >C=O: 1705, 1618 cm$^{-1}$; amide: 1509 cm$^{-1}$; C—O—C: 1242, 1166, 1012 cm$^{-1}$ Step C: 5-[5-(2-Aminoethyl)-2-{[(3R)-3-methyl-3,4-dihydroisoquinolin-2(1H)-yl]-carbonyl}phenyl]-N-[4-(benzyloxy)phenyl]-N,1,2-trimethyl-1H-pyrrole-3-carboxamide hydrochloride The compound of Step B (0.35 g; 0.48 mmol) was dissolved/suspended in 4M HCl in dioxane (3 mL). The heterogeneous mixture is stirred for 30 minutes at ambient temperature and then evaporated to dryness to yield the title compound which is used in next Step without being otherwise purified.

High-Resolution Mass Spectrometry (ESI+):
Empirical formula: $C_{40}H_{42}N_4O_3$
$[M+H]^+$ calculated: 627.3337
$[M+H]^+$ measured: 627.3309
IR: v: C—H: 2931 cm$^{-1}$; >C=O: 1608 cm$^{-1}$; amide: 1508 cm$^{-1}$; C—O—C: 1233, 1012 cm$^{-1}$ Step D: Phenyl 2-(3-{4-[(4-hydroxyphenyl)(methyl)carbamoyl]-1,5-dimethyl-1H-pyrrol-2-yl}-4-{[(3R)-3-methyl-3,4-dihydroisoquinolin-2(1H)-yl]carbonyl}phenyl)ethyl]-carbamate The compound of Step C (0.10 g; 0.15 mmol) is dissolved in dichloromethane. Phenyl chloroformate (0.027 g; 0.17 mmol) and diisopropylethylamine (0.097 g, 0.75 mmol) are added thereto. The reaction mixture is stirred at ambient temperature for 30 minutes. After dilution with dichloromethane (100 mL), the organic phase is washed with water (20 mL), evaporated and concentrated. The residue is then dissolved in ethanol and a Pd/C catalyst is added (10 mg). The reaction mixture is hydrogenated at atmospheric pressure at ambient temperature. When the reaction is complete, the catalyst is removed by filtration, the filtrate is concentrated and the crude product is purified by chromatography over silica gel using dichloromethane and methanol as eluants, to yield the title product.

Elemental Microanalysis: (%, Measured(Theoretical))
% C=72.36(73.15);% H=6.15(6.14);% N=8.14(8.53)
High-Resolution Mass Spectrometry (ESI+):
Empirical formula: $C_{40}H_{40}N_4O_5$
$[M+H]^+$ calculated: 657.3077
$[M+H]^+$ measured: 657.3062

Example 46. N-(4-Hydroxyphenyl)-N,1,2-trimethyl-5-(2-{[(3R)-3-methyl-3,4-dihydroisoquinolin-2(1H)-yl]carbonyl}-5-{2-[(phenoxyacetyl)amino]ethyl}phenyl)-1H-pyrrole-3-carboxamide The title compound is obtained in accordance with the process of Example 45 using 2-phenoxyacetyl chloride as acylating agent in Step D.

Elemental Microanalysis: (%, Measured(Theoretical))
% C=72.74(73.41);% H=6.38(6.31);% N=7.65(8.35)
High-Resolution Mass Spectrometry (ESI+):
Empirical formula: $C_{41}H_{42}N_4O_5$
$[M+H]^+$ calculated: 671.3235
$[M+H]^+$ measured: 671.3226

Example 47. N-(4-Hydroxyphenyl)-1,2-dimethyl-N-(1-methyl-1H-pyrazol-4-yl)-5-6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Measured(Theoretical))
% C=64.25(64.59);% H=5.4(5.7);% N=11.41(11.59);% Cl-=4.93(4.89)

Example 48. N-(4-Hydroxyphenyl)-N-(2-methoxypyrimidin-5-yl)-1,2-dimethyl-5-(6-{[(3R)-3-methyl-3,4-dihydroisoquinolin-2(1H)-yl]carbonyl}-1,3-benzodioxol-5-yl)-1H-pyrrole-3-carboxamide Elemental Microanalysis: (%, Measured(Theoretical))
% C=68.07(68.45);% H=5(5.27);% N=10.74(11.09)

Example 49. N-(4-Hydroxyphenyl)-1,2-dimethyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide dihyrochloride Step A: N-(4-{[tert-Butyl(dimethyl)silyl]oxy}phenyl)-1,2-dimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide The title compound is obtained in accordance with the process of Example 1 using the acid of Preparation 11 and (3S)-3-(4-morpholinylmethyl)-1,2,3,4-tetrahydroisoquinoline (see Preparation 3') in Step A, and the compound of Preparation 11" in Step C.

Step B: N-(4-Hydroxyphenyl)-1,2-dimethyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide dihydrochloride To a solution of 0.21 g (0.2 mmol) of the compound of Step A in 3 mL of acetic acid there are added 85 mg of sodium cyanoborohydride (5 equivalents). The reaction mixture is stirred for 3 hours at ambient temperature and then overnight at 50° C. There are then added 2.6 equivalents of sodium cyanoborohydride and the reaction mixture is heated at 50° C. for 3 hours. The operation is repeated for a second time (addition of 2.6 equivalents of sodium cyanoborohydride and then heating at 50° C. for 3 hours). After coevaporation of the acetic acid in the presence of toluene, the residue is taken up in 3 mL of methanol. The pH of the solution is adjusted to 12 using 1M methanolic potassium hydroxide solution. After stirring overnight at ambient temperature, the reaction mixture is poured into saturated aqueous sodium bicarbonate solution and extracted with dichloromethane. The resulting organic phase is washed with brine, dried over $Na_2SO_4$, filtered and concentrated under reduced pressure. The product obtained is purified by chromatography over silica gel (dichloromethane/ethanol/ammonia 94/6/0.6) and then over a Lichroprep RP18 column (water/acetonitrile/trifluoroacetic acid). After evaporation of the acetonitrile, the product is neutralised with sodium bicarbonate. It is then extracted with ethyl acetate. The organic phase is dried over $Na_2SO_4$, filtered and concentrated under reduced pressure. The residue obtained is dissolved in acetonitrile and converted into salt form with 1M aqueous HCl solution. After lyophilisation, the title product is obtained in the form of a solid.

High-Resolution Mass Spectrometry (ESI+):
Empirical formula: $C_{43}H_{44}N_6O_6$
$[M+H]^+$ calculated: 741.3395
$[M+H]^+$ measured: 741.3400

Example 50. N-(4-Hydroxyphenyl)-N-(2-methoxypyrimidin-5-yl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride High-Resolution Mass Spectrometry (ESI+):
Empirical formula: $C_{40}H_{40}N_6O_7$
[M+H]$^+$ calculated: 717.3031
[M+H]$^+$ measured: 717.3031

Example 51. 5-(5-{[(Benzylcarbamoyl)amino]methyl}-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 40 using benzyl isocyanate as acylating agent in Step C.
Elemental Microanalysis: (%, Measured(Theoretical))
% C=73.39(73.26);% H=6.16(6.3);% N=10.08(10.68)
High-Resolution Mass Spectrometry (ESI+):
Empirical formula: $C_{40}H_{41}N_5O_4$
[M+H]$^+$ calculated: 656.3239
[M+H]$^+$ measured: 656.3226

Example 52. 5-(5-{[(Ethylcarbamoyl)amino]methyl}-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 40 using ethyl isocyanate as acylating agent in Step C.
Elemental Microanalysis: (%, Measured(Theoretical))
% C=71.4(70.8); % H=6.41(6.62); % N=11.24(11.8)
High-Resolution Mass Spectrometry (ESI+):
Empirical formula: $C_{35}H_{39}N_5O_4$
[M+H]$^+$ calculated: 594.3082
[M+H]$^+$ measured: 594.3069

Example 53. N-(4-Hydroxyphenyl)-N,1,2-trimethyl-5-(2-{[(3R)-3-methyl-3,4-dihydroisoquinolin-2(1H)-yl]carbonyl}-5-{[(phenoxyacetyl)amino]methyl}phenyl)-1H-pyrrole-3-carboxamide The title compound is obtained in accordance with the process of Example 40 using 2-phenoxyacetyl chloride as acylating agent in Step C.
Elemental Microanalysis: (%, Measured(Theoretical))
% C=72.32(73.15); % H=6.21(6.14); % N=7.84(8.53)
High-Resolution Mass Spectrometry (ESI+):
Empirical formula: $C_{40}H_{40}N_4O_5$
[M+H]$^+$ calculated: 657.3079
[M+H]$^+$ measured: 657.3105

Example 54. N-(4-Hydroxyphenyl)-1,2-dimethyl-5-(2-{[(3R)-3-methyl-3,4-dihydroisoquinolin-2(1H)-yl]carbonyl}-5-{[(phenoxyacetyl)amino]methyl}phenyl)-N-(1-methyl-1H-pyrrole[2,3-b]pyridin-5-yl)-1H-pyrrole-3-carboxamide Elemental Microanalysis: (%, Measured(Theoretical))
% C=73.87(73.04); % H=5.47(5.74); % N=10.26(10.87)

Example 55. 5-(5-[2-({[2-(4-Fluorophenyl)ethyl]sulphonyl}amino)ethyl]-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 45 using 2-(4-fluorophenyl)ethanesulphonyl chloride as acylating agent in Step D.
Elemental Microanalysis: (%, Measured(Theoretical))
% C=67.42(68.12); % H=5.76(6); % N=7.27(7.75); S=3.68(4.44)
High-Resolution Mass Spectrometry (ESI+):
Empirical formula: $C_{41}H_{43}FN_4O_5S$
[M+H]$^+$ calculated: 723.3018
[M+H]$^+$ measured: 723.3011

Example 56. 5-(5-{2-[(Benzylcarbamoyl)amino]ethyl}-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 45 using benzyl isocyanate as acylating agent in Step D.
Elemental Microanalysis: (%, Measured(Theoretical))
% C=71.14(73.52); % H=6.47(6.47); % N=9.42(10.46)
High-Resolution Mass Spectrometry (ESI+):
Empirical formula: $C_{41}H_{43}N_5O_4$
[M+H]$^+$ calculated: 670.3395
[M+H]$^+$ measured: 670.3390

Example 57. N-(4-Hydroxyphenyl)-N,1,2-trimethyl-5-(2-{[(3R)-3-methyl-3,4-dihydroisoquinolin-2(1H)-yl]carbonyl}-5-{2-[(phenylacetyl)amino]ethyl}phenyl)-1H-pyrrole-3-carboxamide The title compound is obtained in accordance with the process of Example 45 using phenylacetyl chloride as acylating agent in Step D.
Elemental Microanalysis: (%, Measured(Theoretical))
% C=75.46(75.21); % H=6.11(6.46); % N=8.31(8.56)
High-Resolution Mass Spectrometry (ESI+):
Empirical formula: $C_{41}H_{42}N_4O_4$
[M+H]$^+$ calculated: 655.3286
[M+H]$^+$ measured: 655.3285

Example 58. N-(4-Hydroxyphenyl)-N,1,2-trimethyl-5-(2-{[(3R)-3-methyl-3,4-dihydroisoquinolin-2(1H)-yl]carbonyl}-5-{2-[(phenylcarbamoyl)amino]ethyl}phenyl)-1H-pyrrole-3-carboxamide The title compound is obtained in accordance with the process of Example 45 using phenyl isocyanate as acylating agent in Step D.
Elemental Microanalysis: (%, Measured(Theoretical))
% C=71.25(73.26); % H=6.12(6.3); % N=9.61(10.68)
High-Resolution Mass Spectrometry (ESI+):
Empirical formula: $C_{40}H_{41}N_5O_4$
[M+H]$^+$ calculated: 656.3239
[M+H]$^+$ measured: 656.3226

Example 59. 5-(4-[({[2-(4-Fluorophenyl)ethyl]sulphonyl}amino)methyl]-2-{[(3R)-3-methyl-3,4-dihydroisoquinolin-2(1H)-yl]carbonyl}phenyl)-N-(4-hydroxyphenyl)-N,1,2-trimethyl-1H-pyrrole-3-carboxamide The title compound is obtained in accordance with the process of Example 32 using 2-(4-fluorophenyl)ethanesulphonyl chloride as sulphonylation agent in Step D.
Elemental Microanalysis: (%, Measured(Theoretical))
% H=5.19(5.83); % N=7.28(7.9); S=4.45(4.52); % C=66.17(67.78)
High-Resolution Mass Spectrometry (ESI+):
Empirical formula: $C_{40}H_{41}FN_4O_5S$
$[M+H]^+$ calculated: 709.2866
$[M+H]^+$ measured: 709.2866

Example 60. 5-(5-Chloro2-{[(3S)-3-{[2-(dimethylamino)ethoxy]methyl}-3,4-dihydroisoquinolin-2(1H)-yl]carbonyl}phenyl)-N-(4-hydroxy phenyl)-1,2-dimethyl-N-phenyl-1H-pyrrole-3-carboxamide hydrochloride The process of Example 29 is used, on the one hand replacing the 4-(2-bromoethyl)morpholine hydrobromide used in Step B by 2-chloroethyldimethylamine hydrochloride and on the other hand adding a catalytic amount of tetrabutylammonium iodide.
High-Resolution Mass Spectrometry (ESI+):
Empirical formula: $C_{40}H_{41}ClN_4O_4$
$[M+H]^+$ calculated: 677.2890
$[M+H]^+$ measured: 677.2887

Example 61. N-(4-Hydroxyphenyl)-1,2-dimethyl-5-(6-{[(3R)-3-methyl-3,4-dihydroisoquinolin-2(1H)-yl]carbonyl}-1,3-benzodioxol-5-yl)-N-(pyridin-4-yl)-1H-pyrrole-3-carboxamide hydrochloride High-Resolution Mass Spectrometry (ESI+):
Empirical formula: $C_{36}H_{32}N_4O_5$
$[M+H]^+$ calculated: 601.2445
$[M+H]^+$ measured: 601.2424

Example 62. 5-(5-Fluoro-4-methoxy-2-{[(3R)-3-methyl-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Elemental Microanalysis: (%, Measured(Theoretical))
% C=68.99(69.18); % H=5.89(5.64); % N=11.35(11.52)
High-Resolution Mass Spectrometry (ESI+):
Empirical formula: $C_{35}H_{34}FN_5O_4$
$[M+H]^+$ calculated: 608.2668
$[M+H]^+$ measured: 608.2640

Example 63. 5-(5-Chloro-2-{[(3R)-3-methyl-3,4-dihydroisoquinolin-2(1H)-yl]-carbonyl}phenyl)-N-(4-hydroxyphenyl)-1,2-dimethyl-N-(1-methyl-1H-pyrrolo[2,3-b]-pyridin-5-yl)-1H-pyrrole-3-carboxamide Elemental Microanalysis: (%, Measured(Theoretical))
% C=70.48(70.85); % H=5.67(5.32); % N=11.2(10.87)
High-Resolution Mass Spectrometry (ESI+):
Empirical formula: $C_{38}H_{34}ClN_5O_3$
$[M+H]^+$ calculated: 666.2242
$[M+H]^+$ measured: 666.2235

Example 64. N,1,2-Trimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride High-Resolution Mass Spectrometry (ESI+):
Empirical formula: $C_{38}H_{40}N_6O_5$
$[M+H]^+$ calculated: 661.3133
$[M+H]^+$ measured: 661.3125

Example 65. 1,2-Dimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-N-phenyl-1H-pyrrole-3-carboxamide hydrochloride High-Resolution Mass Spectrometry (ESI+):
Empirical formula: $C_{43}H_{42}N_6O_5$
$[M+H]^+$ calculated: 723.3289
$[M+H]^+$ measured: 723.3287

Example 66. 4-Methylphenyl (4-{4-[(4-hydroxyphenyl)(methyl)carbamoyl]-1,5-dimethyl-1H-pyrrol-2-yl}-3-{[(3R)-3-methyl-3,4-dihydroisoquinolin-2(1H)-yl]-carbonyl}benzyl)carbamate The title compound is obtained in accordance with the process of Example 32 using 4-methylphenyl chloroformate as acylating agent in Step D.
High-Resolution Mass Spectrometry (ESI+):
Empirical formula: $C_{40}H_{40}N_4O_5$
$[M+H]^+$ calculated: 657.3079
$[M+H]^+$ measured: 657.3076

Example 67. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride Elemental Microanalysis: (%, Measured(Theoretical))
% C=65.69(65.28); % H=5.38(5.77); % N=11.18(12.02); % Cl-=5.61(5.07)

Example 68. 5-(5-Fluoro-4-hydroxy-2-{[(3R)-3-methyl-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide A 1N solution of tribromoborane (1.3 equivalents) in dichloromethane is poured rapidly, at ambient temperature, into a solution of the compound of Example 62 in dichloromethane. This operation is repeated twice in order to complete the reaction in 5 hours. The reaction mixture is poured into anhydrous ethanol at 5° C. After stirring for 10 minutes, saturated aqueous $NaHCO_3$ solution is added. The mixture is extracted with dichloromethane, dried over $Na_2SO_4$ and concentrated to dryness. The crude product obtained is purified by preparative HPLC using water, TFA and acetonitrile as eluants. The pH of the appropriate fractions is adjusted to 12 with saturated aqueous $NaHCO_3$ solution, and then the acetonitrile is evaporated off under reduced pressure. The aqueous residue is extracted with dichloromethane. The organic phase is dried over $Na_2SO_4$ and evaporated to dryness to yield the title compound.

High-Resolution Mass Spectrometry (ESI+):
Empirical formula: $C_{34}H_{32}FN_5O_4$
[M+H]$^+$ calculated: 594.2511
[M+H]$^+$ measured: 594.2517

Example 69. N-(4-Hydroxyphenyl)-1,2-dimethyl-5-(6-{[(2S)-3-[(4-methylpiperazin-1-yl)methyl]-3,4-dihydroisoquinolin-2(1H)-yl]carbonyl}-1,3-benzodioxol-5-yl)-N-(1-methyl-1H-pyrrolo[2,3-b]pyridin-5-yl)-1H-pyrrole-3-carboxamide hydrochloride High-Resolution Mass Spectrometry (ESI+):
Empirical formula: $C_{44}H_{45}N_7O_5$
[M+H]$^+$ calculated: 752.3555
[M+H]$^+$ measured: 752.3552

Example 70. N-(4-Hydroxyphenyl)-1,2-dimethyl-5-(6-{[(3S)-3-[(4-methylpiperazin-1-yl)methyl]-3,4-dihydroisoquinolin-2(1H)-yl]carbonyl}-1,3-benzodioxol-5-yl)-N-(pyridin-4-yl)-1H-pyrrole-3-carboxamide hydrochloride High-Resolution Mass Spectrometry (ESI+):
Empirical formula: $C_{41}H_{42}N_6O_5$
[M+H]$^+$ calculated: 699.3289
[M+H]$^+$ measured: 699.3293

Example 71. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide hydrochloride High-Resolution Mass Spectrometry (ESI+):
Empirical formula: $C_{42}H_{41}ClN_6O_4$
[M+H]$^+$ calculated: 723.3289
[M+H]$^+$ measured: 723.3287

Example 72. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-benzimidazol-5-yl)-1H-pyrrole-3-carboxamide Elemental Microanalysis: (%, Measured(Theoretical))
% C=68.90(69.17); % H=5.32(5.67); % N=11.40(11.52)

Example 73. N-(4-Hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-(pyridin-4-yl)-1H-pyrrole-3-carboxamide dihydrochloride High-Resolution Mass Spectrometry (ESI+):
Empirical formula: $C_{40}H_{39}N_5O_6$
[M+H]$^+$ calculated: 686.2973
[M+H]$^+$ measured: 686.2971

Example 74. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide hydrochloride High-Resolution Mass Spectrometry (ESI+):
Empirical formula: $C_{39}H_{38}ClN_5O_4$
[M+H]$^+$ calculated: 676.2685
[M+H]$^+$ measured: 676.2684

Example 75. N-(4-Hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-2-(trifluoromethyl)-1H-pyrrole-3-carboxamide hydrochloride Elemental Microanalysis: (%, Theoretical:Measured)
% C=60.12:59.77; % H=4.92:4.76; % N=10.79:10.39% Cl-=4.55:5.17

High-Resolution Mass Spectrometry (ESI+):
Empirical formula: $C_{39}H_{37}F_3N_6O_6$
[M+H]$^+$ calculated: 743.2799
[M+H]$^+$ measured: 742.2802

Example 76. 2-(Difluoromethyl)-N-(4-hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 77. N-(4-Hydroxyphenyl)-2-(methoxymethyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 78. 2-(2,2-Difluoroethyl)-N-(4-hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 79. N-(4-Hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-2-(2,2,2-trifluoroethl)-1H-pyrrole-3-carboxamide Example 80. N-(4-Hydroxyphenyl)-2-(2-methoxyethyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 81. N-(4-Hydroxyphenyl)-1-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-2-[2-(morpholin-4-yl)ethyl]-1H-pyrrole-3-carboxamide hydrochloride The procedure is in accordance with the general protocol of Example 1 using the compound of Preparation 22 in Step A. The product obtained is finally dissolved in acetonitrile and converted into salt form using 0.1M aqueous HCl solution. After a lyophilisation step, the expected compound is obtained in the form of a solid.

High-Resolution Mass Spectrometry (ESI+):
Empirical formula: $C_{40}H_{42}N_6O_6$
[M+H]$^+$ calculated: 703.3239
[M+H]$^+$ measured: 703.3236

Example 82. N-(4-Hydroxyphenyl)-1-methyl-5-(6-{[(3R)-3-methyl-3,4-dihydroisoquinolin-2(1H)-yl]carbonyl}-1,3-benzodioxol-5-yl)-N-(1-methyl-1H)-pyrazol-4-yl)-2-(morpotin-4-ylmethyl)-1H-pyrrole-3-carboxamide The procedure is in accordance with the general protocol of Example 1 using the compound of Preparation 23 in Step A.

High-Resolution Mass Spectrometry (ESI+):
Empirical formula: $C_{39}H_{40}N_6O_6$
$[M+H]^+$ calculated: 689.3082
$[M+H]^+$ measured: 689.3085

Example 83. N-(4-Hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-2-(trifluoromethyl)-1H-pyrrole-3-carboxamide Example 84. 2-(Difluoromethyl)-N-(4-hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 85. N-(4-Hydroxyphenyl)-2-(methoxymethyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 86. 2-(2,2-Difluoroethyl)-N-(4-hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 87. N-(4-Hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-2-(2,2,2-trifluoroethyl)-1H-pyrrole-3-carboxamide Example 88. N-(4-Hydroxyphenyl)-2-(2-methoxyethyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The procedure is in accordance with the general protocol of Example 1 using the appropriate Preparations. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)
% C=65.97:66.15; % H=5.78:5.46; % N=10.26:10.24; % Cl-=4.33:4.76

High-Resolution Mass Spectrometry (ESI/FIA/HR and MS/MS):
Empirical formula: $C_{45}H_{46}N_6O_7$
$[M+H]^+$ calculated: 783.3501
$[M+H]^+$ measured: 783.3502

Example 89. N-(4-Hydroxyphenyl)-1-methyl-N-(1-methyl-1H-pyrrolo[2,3-b]pyridin-5-yl)-2-[2-(morpholin-4-yl)ethyl]-5-(6-{[(3R)-3-methyl-3,4-dihydroisoquinolin-2(1H)-yl]carbonyl}-1,3-benzodioxol-5-yl)-1H-pyrrole-3-carboxamide Example 90. N-(4-Hydroxyphenyl)-1-methyl-N-(1-methyl-1H-pyrrolo[2,3-b]pyridin-5-yl)-2-(morpholin-4-ylmethyl)-5-(6-{[(3R)-3-methyl-3,4-dihydroisoquinolin-2(1H)-yl]carbonyl}-1,3-benzodioxol-5-yl)-1H-pyrrole-3-carboxamide Example 91. N-(4-Hydroxyphenyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 92. 1-Ethyl-N-(4-hydroxyphenyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The procedure is in accordance with the protocol described in Example 1, using the compounds from Preparations 20 and 3' in Step A and the compound from Preparation 1" in Step C. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)
% C=64.99:65.61; % H=5.86:5.39; % N=11.37:11.43; % Cl=4.80:4.42
$[M+H]^+$ measured: 703.3236

Example 93. N-(4-Hydroxyphenyl)-1-(2-methoxyethyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=64.01:64.10; % H=5.90:5.63; % N=10.92:10.88; % Cl-=4.61:4.70.

High-Resolution Mass Spectrometry (ESI+):
Empirical formula: $C_{41}H_{44}N_6O_7$
$[M+H]^+$ calculated: 733.3344
$[M+H]^+$ measured: 733.3345

Example 94. 1-(2-Fluoroethyl)-N-(4-hydroxyphenyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The procedure is in accordance with the protocol described in Steps A-D of Example 1, using the compounds from Preparations 21 and 3' in Step A and the compound from Preparation 1" in Step C. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)
% C=63.44:63.25; % H=5.59:5.09; % N=11.10:11.02; % Cl=4.68:4.74

High-Resolution Mass Spectrometry (ESI+):
Empirical formula: $C_{40}H_{41}FN_6O_6$
$[M+H]^+$ calculated: 721.3144
$[M+H]^+$ measured: 721.3147

Example 95. 1-(2,2-Difluoroethyl)-N-(4-hydroxyphenyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The title compound is obtained in accordance with the process of Example 1 using the acid of Preparation 32 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)
% C=61.97:61.89; % H=5.33:5.04; % N=10.84:10.85; % Cl−=4.57:4.55

High-Resolution Mass Spectrometry (ESI+/HR, ESI−/LR):
Empirical formula: $C_{40}H_{40}F_2N_6O_6$
$[M+H]^+$ calculated: 739.3050
$[M+H]^+$ measured: 739.3052

Example 96. N-(4-Hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1-[2-(morpholin-4-yl)ethyl]-1H-pyrrole-3-carboxamide hydrochloride Step A: N-[4-[tert-Butyl(dimethyl)silyl]oxyphenyl]-2-methyl-5-[6-[(3R)-3-methyl-3,4-dihydro-1H-isoquinoline-2-carbonyl]-1,3-benzodioxol-5-yl]-N-(1-methyl-1H-pyrazol-4-yl)-1-(2-morpholinoethyl)pyrrole-3-carboxamide The compound obtained in Step E of Example 99 is dissolved in 6 mL of tetrahydrofuran. Sodium iodide (100 mg, 0.67 mmol) is added, followed by morpholine (0.21 mL, 2.53 mmol) dropwise. The reaction mixture is heated in a sealed flask at 90° C. for 72 hours. After cooling, the solution is evaporated to dryness and the residue is purified by chromatography over silica gel using dichloromethane and methanol as eluants. The expected product is obtained in the form of a foam.

$^1$H NMR (500 MHz, dmso-d6) δ ppm: 7.7-7.45 (4 bs, 1H), 7.2-6.9 (m, 4H), 7.1-6.4 (m, 2H), 7.1-6.9 (4 bs, 1H), 7-6.8 (4 m, 2H), 6.75/6.48 (d+bs, 2H), 6.1 (4 bs, 2H), 5.25-47 (4 bs, 1H), 5.2-3.8 (m, 2H), 4.9/4.65/3.8 (3 m, 1H), 3.75 (4 s, 3H), 3.5 (bs, 4H), 3-2 (m, 10H), 2.41/2.3 (2 bs, 3H), 1.02/0.95/0.78 (3 bd, 3H), 0.88 (m, 9H), 0.1 (m, 6H)
IR (ATR) $cm^{-1}$: 1626 δ>C=O amides Step B: N-(4-Hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1-[2-(morpholin-4-yl)ethyl]-1H-pyrrole-3-carboxamide hydrochloride The procedure is in accordance with the protocol described in Step D of Example 1. The product obtained is finally subjected to a step of conversion into salt form in the presence of HCl in ether. After filtration and lyophilisation in a mixture of acetonitrile/water, the expected compound is obtained.

High-Resolution Mass Spectrometry (ESI+):
Empirical formula: $C_{40}H_{42}N_6O_6$
$[M+H]^+$ calculated: 703.3239
$[M+H]^+$ measured: 703.3238

Example 97. N-(4-Hydroxyphenyl)-2-methyl-5-(6-{[(3R)-3-methyl-3,4-dihydroisoquinolin-2(1H)-yl]carbonyl}-1,3-benzodioxol-5-yl)-1-[2-(morpholin-4-yl)ethyl]-N-phenyl-1H-pyrrole-3-carboxamide hydrochloride The procedure is in accordance with the protocol described in Example 96 replacing the compound of Preparation 1" by that of Preparation 2".

Elemental Microanalysis: (%, Theoretical:Measured)
% C=68.61:68.12; % H=5.89:5.23; % N=7.62:7.54; % Cl−=4.82:4.66

High-Resolution Mass Spectrometry (ESI/FIA/HR and MS/MS):
Empirical formula: $C_{42}H_{42}N_4O_6$
$[M+H]^+$ calculated: 699.3177
$[M+H]^+$ measured: 699.3173

Example 98. 1-[2-(Dimethylamino)ethyl]-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-phenyl-1H-pyrrole-3-carboxamide hydrochloride The procedure is in accordance with the protocol described in Example 27 replacing the compound of Preparation 1" by that of Preparation 2". The product obtained is finally subjected to a step of conversion into salt form in the presence of 1M HCl in ether. After filtration and lyophilisation in a mixture of acetonitrile/water, the expected compound is obtained.

Elemental Microanalysis: (%, Theoretical:Measured)
% C=69.30:69.20; % H=5.96:5.48; % N=8.08:8.08; % Cl−=5.11:5.03

High-Resolution Mass Spectrometry (ESI/FIA/HR and MS/MS):
Empirical formula: $C_{40}H_{40}N_4O_5$
$[M+H]^+$ calculated: 657.3071
$[M+H]^+$ measured: 657.3066

Example 99. N-(4-Hydroxyphenyl)-1-{2-[(2-methoxyethyl)(methyl)amino]ethyl}-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide hydrochloride Step A: Ethyl 1-(2-benzyloxyethyl)-2-methyl-5-[6-[(3R)-3-methyl-3,4-dihydro-1H-isoquinoline-2-carbonyl]-1,3-benzodioxol-5-yl]pyrrole-3-carboxylate The procedure is in accordance with the protocol described in Step A of Example 1 replacing the compound of Preparation 1 by that of Preparation 19.

$^1$H NMR (500 MHz, dmso-d6) δ ppm: 7.35-6.95 (m, 9H), 7-6.8 (several s, 2H), 6.35-5.85 (several s, 1H), 6.15 (several s, 2H), 5.15-3.5 (several m, 4H), 4.9/4.7/3.95 (several m, 1H), 4.4 (m, 2H), 4.2-3.95 (m, 2H), 3.55 (m, 2H), 3.1-2.35 (several m, 2H), 2.5-2.2 (several s, 3H), 1.25-1.1 (several m, 3H), 1.05-0.7 (several d, 3H)

Step B: 1-(2-Benzyloxyethyl)-2-methyl-5-[6-[(3R)-3-methyl-3,4-dihydro-1H-isoquinoline-2-carbonyl]-1,3-benzodioxol-5-yl]pyrrole-3-carboxylic acid The procedure is in accordance with the protocol described in Step B of Example 1.
IR (ATR) cm$^{-1}$: 3000-2500 v —OH, 1675-1625 v —C═O carboxylic acid+amide Step C: 1-(2-Benzyloxyethyl)-N-[4-[tert-butyl(dimethyl)silyl]oxyphenyl]-2-methyl-5-[6-[(3R)-3-methyl-3,4-dihydro-1H-isoquinoline-2-carbonyl]-1,3-benzodioxol-5-yl]-N-(1-methyl-1H-pyrazol-4-yl)pyrrole-3-carboxamide The procedure is in accordance with the protocol described in Step C of Example 1.
$^1$H NMR (500 MHz, dmso-d6) δ ppm:7.7-7.5 (several s, 1H), 7.35-6.5 (several m, 11H), 7.1-6.9 (several s, 1H), 6.95-6.5 (several s, 2H), 6.8/6.5 (m, 2H), 6.05 (several s, 2H), 5.25-47 (several s, 1H), 5.1-3.6 (several m, 4H), 4.85/4.6/3.75 (several m, 1H), 4.3 (m, 2 H), 3.7 (2×s, 3H), 3.4 (m, 2H), 3.05-2.4 (several m, 2H), 2.4-2.25 (several s, 3H), 1-0.75 (several d, 3H), 0.9 (several s, 9H), 0.1 (several s, 6H)
IR (ATR) cm$^{-1}$: 1629 v >C═O amides Step D: N-[4-[tert-Butyl(dimethyl)silyl]oxyphenyl]-1-(2-hydroxyethyl)-2-methyl-5-[6-[(3R)-3-methyl-3,4-dihydro-1H-isoquinoline-2-carbonyl]-1,3-benzodioxol-5-yl]-N-(1-methyl-1H-pyrazol-4-yl)pyrrole-3-carboxamide In a hydrogenating reactor, the compound of the above Step is dissolved in 30 mL of methanol. The solution is degassed by bubbling argon in, and palladium-on-carbon 10% (550 mg) is added. The resulting suspension is stirred under a pressure of 1 bar of hydrogen for 15 hours, and then passed through a Whatman® filter. The catalyst is rinsed with methanol and the filtrate is evaporated in vacuo. The residue thereby obtained is purified by chromatography over silica gel using dichloromethane and methanol as eluants. The expected product is obtained in the form of an oil.
$^1$H NMR (500 MHz, pyridine-d5) δ ppm: 7.7-7.4 (4 s, 1H), 7.3-6.9 (m, 4H), 7.1-6.8 (4 s, 1H), 7-6.7 (m, 2H), 6.9-6.4 (m, 2H), 6.8-6.4 (4 m, 2H), 6.1 (m, 2H), 5.2/5/4.7 (4 s, 1H), 5.15-3.9 (8 d, 2H), 4.9-48 (m, 1H), 4.9/4.7/3.85 (3 m, 1H), 3.9-3.7 (m, 2H), 3.75 (2 s, 3H), 3.5-3.2 (m, 2H), 3-2.4 (m, 2H), 2.4-2.3 (4 s, 3H), 1.05/0.95/0.75 (4 d, 3H), 0.85 (bs, 9H), 0.15-0 (m, 6H)
IR (ATR) cm$^{-1}$:3346 v —OH primary alcohol, 1621v —C═O amides Step E: 2-[3-[[4-[tert-Butyl(dimethyl)silyl]oxyphenyl]-(1-methyl-1H-pyrazol-4-yl)-carbamoyl]-2-methyl-5-[6-[(3R)-3-methyl-3,4-dihydro-1H-isoquinoline-2-carbonyl]-1,3-benzodioxol-5-yl]pyrrol-1-yl]ethyl methanesulphonate The compound of the above Step (2.37 g, 3.17 mmol) is dissolved in 30 mL of tetrahydrofuran. The reaction mixture is cooled to 0° C. and there are successively added triethylamine (1.8 mL, 13.9 mmol) and, dropwise, methanesulphonyl chloride (0.40 mL, 5.17 mmol). The reaction mixture is stirred for 2 hours at 0° C. The reaction mixture is then poured into saturated aqueous sodium hydrogen carbonate solution and extracted 3 times with ethyl acetate. The organic phase is washed 3 times with brine, dried over MgSO$_4$, filtered and then evaporated to dryness. The evaporation residue is used without purification in the next Step.
$^1$H NMR (500 MHz, dmso-d6) δ ppm: 7.7-7.45 (several s, 1H), 7.25-6.4 (m, 8 H), 7.1-6.9 (several s, 1H), 6.95-6.65 (several s, 2H), 6.1 (several s, 2H), 5.2-46 (several s, 1H), 5.05-3.75 (several d, 2H), 4.9/4.6/3.9/3.8 (several m, 1H), 4.3-405 (m, 2H), 4.2-3.95 (m, 2H), 3.75/3.7 (2 s, 3H), 3.05-2.5 (several m, 2H), 3 (several s, 3H), 2.45-2.3 (several s, 3H), 1.05-0.75 (several d, 3H), 0.9 (several s, 9H), 0.1 (several s, 6H)
IR (ATR) cm$^{-1}$: 1626 v —C═O, 1349 v —SO$_2$, 1249 δ —CH3, 1172 v —SO$_2$ Step F: N-[4-[tert-Butyl(dimethyl)silyl]oxyphenyl]-1-[2-[2-methoxyethyl(methyl)amino]-ethyl]-2-methyl-5-[6-[(3R)-3-methyl-3,4-dihydro-1H-isoquinoline-2-carbonyl]-1,3-benzodioxol-5-yl]-N-(1-methyl-1H-pyrazol-4-yl)pyrrole-3-carboxamide The compound of the above Step (1.33 mg, 1.61 mmol) is dissolved in 6 mL of tetrahydrofuran. Sodium iodide (100 mg, 0.67 mmol) is added, followed by dimethylamine (0.172 g, 1.932 mmol) dropwise. The reaction mixture is heated in a sealed flask at 60° C. for 36 hours. After cooling, it is evaporated to dryness and purified by chromatography over silica gel using dichloromethane and ammonia-in-methanol as eluants. The expected product is obtained in the form of a foam.
$^1$H NMR (500 MHz, dmso-d6) δ ppm 7.7-7.45 (4 bs, 1H), 7.2-6.9 (m, 4H), 7.1-6.9 (4 bs, 1H), 7-6.7 (4 m, 2H), 7/6.45 (2 m, 2H), 6.8/6.45 (2 m, 2H), 6.1 (m, 2H), 5.22/5.05/4.7 (4 bs, 1H), 5.2-3.8 (m, 2H), 4.91/4.65/3.9 (3 m, 1H), 3.75 (2 bs, 3H), 3.7 (m, 2H), 3.2 (bs, 3H), 3-2 (m, 2H), 2.7-2 (ml, 6H), 2.7-2 (m, 3H), 2.45/2.35 (2 bs, 3H), 1.05/0.95/0.8 (3 bd, 3H), 0.9 (m, 9H), 0.1 (m, 6H)
IR (ATR) cm$^{-1}$: 1628 (shoulder) δ —C═O amides Step G: N-(4-hydroxyphenyl)-1-[2-[2-methoxyethyl (methyl)amino]ethyl]-2-methyl-5-[6-[(3R)-3-methyl-3,4-dihydro-1H-isoquinoline-2-carbonyl]-1,3-benzodioxol-5-yl]-N-(1-methyl-1H-pyrazol-4-yl)pyrrole-3-carboxamide hydrochloride The procedure is in accordance with the protocol described in Step D of Example 1. The product obtained is finally subjected to a step of conversion into salt form in the presence of 1M HCl in ether. After filtration and lyophilisation in a mixture of acetonitrile/water, the expected compound is obtained.
IR (ATR) cm$^{-1}$: 2000 to 3500 v —NH$^+$/OH, 1615 v >C═O amides, 1237-1161 δ>C—O—C<, 745 v >CH—Ar
High-Resolution Mass Spectrometry (ESI+):
Empirical formula: C$_{40}$H$_{44}$ N$_6$O$_6$
[M+H]$^+$ calculated: 705.3395
[M+H]$^+$ measured: 705.3391

Example 100. 5-(5-Fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride The procedure is in accordance with the general protocol of Example 1 using the appropriate Preparations. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)
% C=64.23:64.31; % H=5.80:5.43; % N=11.52:11.46; % Cl−=4.86:4.95
High-Resolution Mass Spectrometry (ESI+):
Empirical formula: $C_{39}H_{41}FN_6O_5$
$[M+H]^+$ calculated: 693.3195
$[M+H]^+$ measured: 693.3194

Example 101. 5-(4-Fluoro-5-methoxy-2-{[(3S)-3-(morpholin-4-ylmethyl)-3,4-dihydroisoquinolin-2(1H)-yl]carbonyl}phenyl)-N-(4-hydroxyphenyl)1,2-dimethyl-N-(1-methyl-1H-pyrazol-4-yl)-1H-pyrrole-3-carboxamide hydrochloride The title compound is obtained in accordance with the process of Example 1 using the acid of Preparation 27 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)
% C=64.23:63.12; % H=5.80:5.20; % N=11.52:11.38. % Cl−=4.86:5.03
High-Resolution Mass Spectrometry (ESI+/HR, ESI−/LR):
Empirical formula: $C_{39}H_{41}FN_6O_5$
$[M+H]^+$ calculated: 693.3195
$[M+H]^+$ measured: 693.3195

Example 102. 5-(5-Chloro-2-{[(3S)-3-[(4-methyl-piperazin-1-yl)methyl]-3,4-dihydro-isoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide trihydrochloride High-Resolution Mass Spectrometry (ESI+):
Empirical formula: $C_{43}H_{44}ClN_7O_3$
$[M+H]^+$ calculated: 742.3267
$[M+H]^+$ measured: 742.3268

Example 103. 5-(5-Chloro-2-{[(3S)-3-[(4-methyl-piperazin-1-yl)methyl]-3,4-dihydroisoquinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide

Example 104. N-(4-Hydroxyphenyl)-1,2-dimethyl-N-(1-methyl-1H-pyrazolo[3,4-b]-pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide

Example 105. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b pyridin-5-yl)-1H-pyrrole-3-carboxamide

Example 106. 5-(5-Chloro-2-{[(3S)-3-(morpholin-4-ylmethyl)-3,4-dihydroisoquinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide The procedure is in accordance with the general protocol of Example 1 using the appropriate Preparations, it being understood that Step D is not carried out. The expected product is obtained in free base form.

Elemental Microanalysis: (%, Theoretical:Measured)
% C=70.72:69.77; % H=5.79:5.96; % N=11.78:11.43
High-Resolution Mass Spectrometry (ESI+):
Empirical formula: $C_{42}H_{41}ClN_6O_3$
$[M+H]^+$ calculated: 713.3001
$[M+H]^+$ measured: 713.2998

Example 107. 5-(5-Chloro-2-{[(3S)-3-(morpholin-4-ylmethyl)-3,4-dihydroisoquinolin-2(1H)-yl]carbonyl}phenyl)-N-(4-fluorophenyl)-1,2-dimethyl-N-(1-methyl-1H-pyrrolo[2,3-b]pyridin-5-yl)-1H-pyrrole-3-carboxamide

Example 108. 5-(5-Chloro-2-{[(3S)-3-(morpholin-4-ylmethyl)-3,4-dihydroisoquinolin-2(1H)-yl]carbonyl}phenyl)-N-(5-cyano-1-methyl-1H-pyrrol-3-yl)-N-(4-hydroxyphenyl)-1,2-dimethyl-1H-pyrrole-3-carboxamide hydrochloride The title compound is obtained in accordance with the process of Example 1 using the acid of Preparation 1 and (3S)-3-(4-morpholinylmethyl)-1,2,3,4-tetrahydroisoquinoline (see Preparation 3') in Step A, and the compound of Preparation 19" in Step C. The product obtained is finally subjected to a step of conversion into salt form in the presence of HCl in ether. After filtration and lyophilisation in a mixture of acetonitrile/water, the expected compound is obtained.

Elemental Microanalysis: (%, Theoretical:Measured)
% C=64.95:65.09; % H=5.45:5.20; % N=11.36:11.26; % Cl−=4.79:4.62
High-Resolution Mass Spectrometry (ESI/+):
Empirical formula: $C_{40}H_{39}ClN_6O_4$
$[M+H]^+$ calculated: 703.2794
$[M+H]^+$ measured: 703.2789

Example 109. 5-(5-Chloro2-{[(3S)-3-(morpholin-4-ylmethyl)-3,4-dihydroisoquinolin-2(1H)-yl]carbonyl}phenyl)-N-(6-cyanopyridin-2-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 23" in Step C. The compound obtained is converted into salt form and lyophilised as described in the general process to obtain the title compound.

High-Resolution Mass Spectrometry (ESI+−/FIA/HR, ESI−/FIA):
Empirical formula: $C_{40}H_{37}ClN_6O_4$
$[M+H]^+$ calculated: 701.2638
$[M+H]^+$ measured: 701.2639

Example 110. 5-(5-Chloro-2-{[(3S)-3-(morpholin-4-ylmethyl)-3,4-dihydroisoquinolin-2(1H)-yl]carbonyl}phenyl)-N-(4-cyanopyridin-2-yl)-N-(4-hydroxyphenyl)-1,2-dimethyl-1H-pyrrole-3-carboxamide hydrochloride Elemental Microanalysis: (%, Theoretical:Measured)
% C=65.13:65.72; % H=5.19:4.76; % N=11.39:12.04; % Cl−=4.81:4.45

High-Resolution Mass Spectrometry (ESI+−/FIA/HR, ESI−/FIA):
Empirical formula: $C_{40}H_{37}ClN_6O_4$
[M+H]$^+$ calculated: 701.2638
[M+H]$^+$ measured: 701.2643

Example 111. 5-(5-Chloro-2-{[(3S)-3-(morpholin-4-ylmethyl)-3,4-dihydroisoquinolin-2(1H)-yl]carbonyl}phenyl)-N-(4-cyanopyrimidin-2-yl)-N-(4-hydroxyphenyl)-1,2-dimethyl-1H-pyrrole-3-carboxamide Example 112. 5-(5-Chloro-2-{[(3S)-3-(morpholin-4-ylmethyl)-3,4-dihydroisoquinolin-2(1H)-yl]carbonyl}phenyl)-N-[2-(dimethylamino)pyridin-4-yl]-N-(4-hydroxyphenyl)-1,2-dimethyl-1H-pyrrole-3-carboxamide Example 113. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-benzimidazol-5-yl)-1H-pyrrole-3-carboxamide Example 114. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyrazolo[1,5-a]pyrimidin-6-yl)-1H-pyrrole-3-carboxamide Example 115. 5-(5-Chloro-2-{[(3S)-3-[(9aS)-hexahydropyrazino[2,1-c][1,4]oxazin-8(1H)-ylmethyl]-34-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide dihydrochloride The title compound is obtained in accordance with the process of Example 1 using the acid of Preparation 1 and the compound of Preparation 7' in Step A, and the compound of Preparation 1" in Step C. The compound obtained is converted into salt form and lyophilised as described in the general process to obtain the title compound.
Elemental Microanalysis: (%, Theoretical:Measured)
% C=61.01:60.17; % H=5.74:5.09; % N=12.15:12.02; % Cl$^−$=8.78:9.81
High-Resolution Mass Spectrometry (ESI+−/FIA/HR, ESI−/FIA):
Empirical formula: $C_{41}H_{44}ClN_7O_4$
[M+H]$^+$ calculated: 734.3216
[M+H]$^+$ measured: 734.3220

Example 116. 5-(5-Chloro-2-{[(3S)-3-[(9aR)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide dihydrochloride The title compound is obtained in accordance with the process of Example 1 using the acid of Preparation 1 and the compound of Preparation 9' in Step A, and the compound of Preparation 1" in Step C. The compound obtained is converted into salt form and lyophilised as described in the general process to obtain the title compound.
Elemental Microanalysis: (%, Theoretical:Measured)
% C=61.01:61.90; % H=5.74:5.65; % N=12.15:12.14; % Cl=13.15:11.51
High-Resolution Mass Spectrometry (ESI/FIA/HR and MS/MS):
Empirical formula: $C_{41}H_{44}ClN_7O_4$
[M+H]$^+$ calculated: 734.3216
[M+H]$^+$ measured: 734.3218

Example 117. 5-(5-Chloro-2-{[(3S)-3-(fluoromethyl)-3,4-dihydroisequinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 118. 5-(5-Chloro-2-{[(3S)-3-(difluoromethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 119. 5-(5-Chloro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 120. 5-(5-Chloro-2-{[(3S)-3-[(3-cyanoazetidin-1-yl)methyl]-3,4-dihydroisaquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 121. 5-(5-Chloro-2-{[(3S)-3-(morpholin-4-ylmethyl)-3,4-dihydroisoquinolin-2(1H)-yl]carbonyl}phenyl)-N-(1-ethyl-1H-pyrazol-4-yl)-N-(4-hydroxyphenyl)-1,2-dimethyl-1H-pyrrole-3-carboxamide Example 122. 5-(5-Chloro-2-{[(3S)-3-(morpholin-4-ylmethyl)-3,4-dihydroisoquinolin-2(1H)-yl]carbonyl}phenyl)-N-(1-cyclopropyl-1H-pyrazol-4-yl)-N-(4-hydroxyphenyl)-1,2-dimethyl-1H-pyrrole-3-carboxamide The title compound is obtained in accordance with the process of Example 1 using the acid of Preparation 1 and the compound of Preparation 3' in Step A, and the compound of Preparation 28" in Step C.
Elemental Microanalysis: (%, Theoretical:Measured)
% C=68.12:67.94; % H=5.86:5.77; % N=11.92:11.65
High-Resolution Mass Spectrometry (ESI+/HR, ESI−/LR):
Empirical formula: $C_{40}H_{41}ClN_6O_4$
[M+H]$^+$ calculated: 705.2951
[M+H]$^+$ measured: 705.2952

Example 123. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trifluoromethyl)-1H-pyrazol-4-yl]-1H-pyrrole-3-carboxamide Example 124. 5-(5-Chloro-2-{[(3S)-3-(morpholin-4-ylmethyl)-3,4-dihydroisoquinolin-2(1H)-yl]carbonyl}phenyl)-N-[1(difluoromethyl)-1H-pyrazol-4-yl]-N-(4-hydroxyphenyl)-1,2-dimethyl-1H-pyrrole-3-carboxamide Example 125. 5-(5-Chloro2-{[(3S)-3-(morpholin-4-ylmethyl)-3,4-dihydroisoquinolin-2(1H)-yl]carbonyl}phenyl)-N-(4-hydroxyphenyl)-N-[1-(2-methoxyethyl)-1H-pyrazol-4-yl]-1,2-dimethyl-1H-pyrrole-3-carboxamide Example 126. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(oxetan-3-yl)-1H-pyrazol-4-yl]-1H-pyrrole-3-carboxamide The title compound is obtained in accordance with the process of Example 1 using the acid of Preparation 1 and the compound of Preparation 3' in Step A, and the compound of Preparation 26" in Step C.
High-Resolution Mass Spectrometry (ESI+/HR, ESI−/LR):
Empirical formula: $C_{40}H_{41}ClN_6O_5$
[M+H]$^+$ calculated: 721.2900
[M+H]$^+$ measured: 721.2902

Example 127. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(tetrahydrofuran-3-yl)-1H-pyrazol-4-yl]-1H-pyrrole-3-carboxamide hydrochloride The title compound is obtained in accordance with the process of Example 1 using the acid of Preparation 1 and the compound of Preparation 3' in Step A, and the compound of Preparation 22" in Step C. The compound obtained is converted into salt form and lyophilised as described in the general process to obtain the title compound.
Elemental Microanalysis: (%, Theoretical:Measured)
% C=63.81:63.63; % H=5.75:5.74; % N=10.89:10.71; % Cl$^-$=4.59:4.52
High-Resolution Mass Spectrometry (ESI+/HR, ESI−/LR):
Empirical formula: $C_{41}H_{43}ClN_6O_5$
[M+H]$^+$ calculated: 735.3056
[M+H]$^+$ measured: 735.3061

Example 128. 5-(5-Chloro-2-{[(3S)-3-(morpholin-4-ylmethyl)-3,4-dihydroisoquinolin-2(1H)-yl]carbonyl}phenyl)-N-[1-(2-hydroxy-2-methylpropyl)-1H-pyrazol-4-yl]-N-(4-hydroxyphenyl)-1,2-dimethyl-1H-pyrrole-3-carboxamide Example 129. 5-(5-Chloro-2-{[(3S)-3-(morpholin-4-ylmethyl)-3,4-dihydroisoquinolin-2(1H)-yl]carbonyl}phenyl)-1,2-dimethyl-N-(1-methyl-2,3-dihydro-1H-pyrrolo[2,3-b]-pyridin-5-yl)-N-phenyl-1H-pyrrole-3-carboxamide The title compound is obtained in accordance with the process described in Step B of Example 49 using Example 106 as starting material, it being understood that the product is not subjected to the step of conversion into salt form.
Elemental Microanalysis: (%, Theoretical:Measured)
% C=70.53:70.51; % H=6.06:5.81; % N=11.75:11.71
High-Resolution Mass Spectrometry (ESI+−/FIA):
Empirical formula: $C_{42}H_{43}ClN_6O_3$
[M+H]$^+$ calculated: 715.3158
[M+H]$^+$ measured: 715.3159

Example 130. 5-(5-Chloro-2-{[(3S)-3-(morpholin-4-ylmethyl)-3,4-dihydroisoquinolin-2(1H)-yl]carbonyl}phenyl)-N-(4-fluorophenyl)-1,2-dimethyl-N-(1-methyl-2,3-dihydro-1H-pyrrolo[2,3-b]pyridin-5-yl)-1H-pyrrole-3-carboxamide Example 131. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-N,1,2-trimethyl-1H-pyrrole-3-carboxamide Example 132. 5-(5-Chloro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-phenyl-1H-pyrrole-3-carboxamide Example 133. 5-(5-Chloro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-(1-methyl-1H-pyrrolo[2,3-b]pyridin-5-yl)-1H-pyrrole-3-carboxamide Example 134. 5-(5-Chloro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-(1-methyl-2,3-dihydro-1H-pyrrolo[2,3-b]pyridin-5-yl)-1H-pyrrole-3-carboxamide Example 135. 5-(5-Chloro-2-{[(3S)-3-(morpholin-4-ylmethyl)-3,4-dihydroisaquinolin-2(1H)-yl]carbonyl}phenyl)-N-(2-hydroxypyrimidin-5-yl)-1,2-dimethyl-N-(1-methyl-1H-pyrazol-4-yl)-1H-pyrrole-3-carboxamide Example 136. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrazol-4-yl)-1H-pyrrole-3-carboxamide Example 137. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1H-pyrrole-3-carboxamide Example 138. 5-(5-Chloro-2-{[(3S)-3-(morpholin-4-ylmethyl)-3,4-dihydroisequinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 139. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-1H-pyrrole-3-carboxamide Example 140. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-1H-pyrrole-3-carboxamide Example 141. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 142. 5-(5-Chloro-2-{[(3S)-3-(morpholin-4-ylmethyl)-3,4-dihydroisoquinolin-2(1H)-yl]carbonyl}phenyl)-1-ethyl-N-(4-hydroxyphenyl)-2-methyl-N-(1-methyl-1H-pyrazol-4-yl)-1H-pyrrole-3-carboxamide Example 143. 5-(5-Chloro-2-{[(3S)-3-(morpholin-4-ylmethyl)-3,4-dihydroisoquinolin-2(1H)-yl]carbonyl}phenyl)-1-ethyl-N-(4-hydroxyphenyl)-2-methyl-N-(1-methyl-1H-pyrrolo[2,3-b]pyridin-5-yl)-1H-pyrrole-3-carboxamide Example 144. 5-(5-Chloro-2-{[(3S)-3-(morpholin-4-ylmethyl)-3,4-dihydroisoquinolin-2(1H)-yl]carbonyl}phenyl)-1-ethyl-N-(4-hydroxyphenyl)-2-methyl-N-(1-methyl-2,3-dihydro-1H-pyrrolo[2,3-b]pyridin-5-yl)-1H-pyrrole-3-carboxamide Example 145. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-(2-methoxyethyl)-2-methyl-N-(1-methyl-1H-pyrazol-4-yl)-1H-pyrrole-3-carboxamide Example 146. 5-(5-Chloro-2-{[(3S)-3-(morpholin-4-ylmethyl)-3,4-dihydroisequinolin-2(1H)-yl]carbonyl}phenyl)-N-(4-hydroxyphenyl)-1-(2-methoxyethyl)-2-methyl-N-(1-methyl-1H-pyrrolo[2,3-b]pyridin-5-yl)-1H-pyrrole-3-carboxamide Example 147. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-(2-methoxyethyl)-2-methyl-N-(1-methyl-2,3-dihydro-1H-pyrrolo[2,3-b]pyridin-5-yl)-1H-pyrrole-3-carboxamide Example 148. 5-(5-Chloro-2-{[(3S)-3-(morpholin-4-ylmethyl)-3,4-dihydroisoquinolin-2(1H)-yl]carbonyl}phenyl)-1-(2-fluoroethyl)-N-(4-hydroxyphenyl)-2-methyl-N-(1-methyl-1H-pyrazol-4-yl)-1H-pyrrole-3-carboxamide Example 149. 5-(5-Chloro2-{[(3S)-3-(morpholin-4-ylmethyl)-3,4-dihydroisoquinolin-2(1H)-yl]carbonyl}phenyl)-1-(2-fluaroethyl)-N-(4-hydroxyphenyl)-2-methyl-N-(1-methyl-1H-pyrrolo[2,3-b]pyridin-5-yl)-1H-pyrrole-3-carboxamide Example 150. 5-(5-Chloro-2-{[(3S)-3-(morpholin-4-ylmethyl)-3,4-dihydroisoquinolin-2(1H)-yl]carbonyl}phenyl)-1-(2-fluoroethyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 151. 5-(5-Chloro-2-{[(3S)-3-(morpholin-4-ylmethyl)-3,4-dihydroisoquinolin-2(1H)-yl]carbonyl}phenyl)-1-(2,2-difluoroethyl)-N-(4-hydroxyphenyl)-2-methyl-N-(1-methyl-1H-pyrazol-4-yl)-1H-pyrrole-3-carboxamide Example 152. 5-(5-Chloro-2-{[(3S)-3-(morpholin-4-ylmethyl)-3,4-dihydroisoquinolin-2(1H)-yl]carbonyl}phenyl)-1-(2,2-difluoroethyl)-N-(4-hydroxyphenyl)-2-methyl-N-(1-methyl-1H-pyrrolo[2,3-b]pyridin-5-yl)-1H-pyrrole-3-carboxamide Example 153. 5-(5-Chloro-2-{[(3S)-3-(morpholin-4-ylmethyl)-3,4-dihydroisoquinolin-2(1H)-yl]carbonyl}phenyl)-1-(2,2-difluoroethyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 154. 5-(5-Chloro-2-{[(3S)-3-(morpholin-4-ylmethyl)-3,4-dihydroisequinolin-2(1H)-yl]carbonyl}phenyl)-N-(4-hydroxyphenyl)-2-methyl-N-(1-methyl-1H-pyrazol-4-yl)-1-(2,2,2-trifluoroethyl)-1H-pyrrole-3-carboxamide Example 155. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1-(2,2,2-trifluoroethyl)-1H-pyrrole-3-carboxamide Example 156. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1-(2,2,2-trifluoroethyl)-1H-pyrrole-3-carboxamide Example 157. 5-(5-Chloro-2-{[(3R)-3-methyl-3,4-dihydroisoquinolin-2(1H)-yl]carbonyl}phenyl)-N-(4-hydroxyphenyl)-2-methyl-N-(1-methyl-1H-pyrazol-4-yl)-1-[2-(morpholin-4-yl)ethyl]-1H-pyrrole-3-carboxamide Example 158. 5-(5-Chloro-2-{[(3R)-3-methyl-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1-[2-(morpholin-4-yl)ethyl]-1H-pyrrole-3-carboxamide Example 159. 5-(5-Chloro-2-{[(3R)-3-methyl-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1-[2-(morpholin-4-yl)ethyl]-1H-pyrrole-3-carboxamide Example 160. 5-(5-Chloro-2-{[(3R)-3-methyl-3,4-dihydroisoquinolin-2(1H)-yl]carbonyl}phenyl)-N-(4-hydroxyphenyl)-2-methyl-1-[2-(morpholin-4-yl)ethyl]-N-phenyl-1H-pyrrole-3-carboxamide Example 161. 5-(5-Chloro-2-{[(3R)-3-methyl-3,4-dihydroisoquinolin-2(1H)-yl]carbonyl}phenyl)-1-[2-(dimethylamino)ethyl]-N-(4-hydroxyphenyl)-2-methyl-N-(1-methyl-1H-pyrazol-4-yl)-1H-pyrrole-3-carboxamide Example 162. 5-(5-Chloro-2-{[(3R)-3-methyl-3,4-dihydroisoquinolin-2(1H)-yl]carbonyl}phenyl)-1-[2-(dimethylamino)ethyl]-N-(4-hydroxyphenyl)-2-methyl-N-phenyl-1H-pyrrole-3-carboxamide Example 163. 5-(5-Chloro-2-{[(3R)-3-methyl-3,4-dihydroisoquinolin-2(1H)-yl]carbonyl}phenyl)-1-[2-(dimethylamino)ethyl]-N-(4-hydroxyphenyl)-2-methyl-N-(1-methyl-1H-pyrrolo[2,3-b]pyridin-5-yl)-1H-pyrrole-3-carboxamide Example 164. 5-(5-Chloro-2-{[(3R)-3-methyl-3,4-dihydroisoquinolin-2(1H)-yl]carbonyl}phenyl)-1-[2-(dimethylamino)ethyl]-N-(4-hydroxyphenyl)-2-methyl-N-(1-methyl-2,3-dihydro-1H-pyrrolo[2,3-b]pyridin-5-yl)-1H-pyrrole-3-carboxamide Example 165. 5-(5-Chloro-2-{[(3R)-3-methyl-3,4-dihydroisoquinolin-2(1H)-yl]-carbonyl}phenyl)-N-(4-hydroxyphenyl)-1-{2-[(2-methoxyethyl)(methyl)amino]ethyl}-2-methyl-N-(1-methyl-1H-pyrazol-4-yl)-1H-pyrrole-3-carboxamide Example 166. 5-(5-Chloro-2-{[(3R)-3-methyl-3,4-dihydroisoquinolin-2(1H)-yl]-carbonyl}phenyl)-N-(4-hydroxyphenyl)-1-{2-[(2-methoxyethyl)(methyl)amino]ethyl}-2-methyl-N-(1-methyl-1H-pyrrolo[2,3-b]pyridin-5-yl)-1H-pyrrole-3-carboxamide Example 167. 5-(5-Chloro-2-{[(3R)-3-methyl-3,4-dihydroisoquinolin-2(1H)-yl]-carbonyl}phenyl)-N-(4-hydroxyphenyl)-1-{2-[(2-methoxyethyl)(methyl)amino]ethyl}-2-methyl-N-(1-methyl-2,3-dihydro-1H-pyrrolo[2,3-b]pyridin-5-yl)-1H-pyrrole-3-carboxamide Example 168. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-2-(trifluoromethyl)-1H-pyrrole-3-carboxamide Example 169. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-(trifluoromethyl)-1H-pyrrole-3-carboxamide Example 170. 5-(5-Chloro2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(trifluoromethyl)-1H-pyrrole-3-carboxamide Example 171. 5-(5-Chloro-2-{[(3S)-3-(morpholin-4-ylmethyl)-3,4-dihydroisoquinolin-2(1H)-yl]carbonyl}phenyl)-2-(difluoromethyl)-N-(4-hydroxyphenyl)-1-methyl-N-(1-methyl-1H-pyrazol-4-yl)-1H-pyrrole-3-carboxamide Example 172. 5-(5-Chloro-2-{[(3S)-3-(morpholin-4-ylmethyl)-3,4-dihydroisoquinolin-2(1H)-yl]carbonyl}phenyl)-2-(difluoromethyl)-N-(4-hydroxyphenyl)-1-methyl-N-(1-methyl-1H-pyrrolo[2,3-b]pyridin-5-yl)-1H-pyrrole-3-carboxamide Example 173. 5-(5-Chloro-2-{[(3S)-3-(morpholin-4-ylmethyl)-3,4-dihydroisoquinolin-2(1H)-yl]carbonyl}phenyl)-2-(difluoromethyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 174. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-(methoxymethyl)-1-methyl-N-(1-methyl-1H-pyrazol-4-yl)-1H-pyrrole-3-carboxamide Example 175. 5-(5-Chloro-2-{[(3S)-3-(morpholin-4-ylmethyl)-3,4-dihydroisequinolin-2(1H)-yl]carbonyl}phenyl)-N-(4-hydroxyphenyl)-2-(methoxymethyl)-1-methyl-N-(1-methyl-1H-pyrrolo[2,3-b]pyridin-5-yl)-1H-pyrrole-3-carboxamide Example 176. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-(methoxymethyl)-1-methyl-N-(1-methyl-2,3-dihydro-1H-pyrrolo[2,3-b]pyridin-5-yl)-1H-pyrrole-3-carboxamide Example 177. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-2-(2,2,2-trifluoroethyl)-1H-pyrrole-3-carboxamide Example 178. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-(2,2,2-trifluoroethyl)-1H-pyrrole-3-carboxamide Example 179. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(2,2,2-trifluoroethyl)-1H-pyrrole-3-carboxamide Example 180. 5-(5-Chloro-2-{[(3S)-3-(morpholin-4-ylmethyl)-3,4-dihydroisoquinolin-2(1H)-yl]carbonyl}phenyl)-2-(2,2-difluoroethyl)-N-(4-hydroxyphenyl)-1-methyl-N-(1-methyl-1H-pyrazol-4-yl)-1H-pyrrole-3-carboxamide Example 181. 5-(5-Chloro-2-{[(3S)-3-(morpholin-4-ylmethyl)-3,4-dihydroisoquinolin-2(1H)-yl]carbonyl}phenyl)-2-(2,2-difluoroethyl)-N-(4-hydroxyphenyl)-1-methyl-N-(1-methyl-1H-pyrrolo[2,3-b]pyridin-5-yl)-1H-pyrrole-3-carboxamide Example 182. 5-(5-Chloro-2-{[(3S)-3-(morpholin-4-ylmethyl)-3,4-dihydroisoquinolin-2(1H)-yl]carbonyl}phenyl)-2-(2,2-difluoroethyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 183. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl-1H-pyrazol-4-yl)-1H-pyrrole-3-carboxamide Example 184. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl-1H-pyrrolo[2,3-b]pyridin-5-yl)-1H-pyrrole-3-carboxamide Example 185. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl-2,3-dihydro-1H-pyrrolo[2,3-b]pyridin-5-yl)-1H-pyrrole-3-carboxamide Example 186. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrazol-4-yl)-2-(morpholin-4-ylmethyl)-1H-pyrrole-3-carboxamide Example 187. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-(morpholin-4-ylmethyl)-1H-pyrrole-3-carboxamide Example 188. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(morpholin-4-ylmethyl)-1H-pyrrole-3-carboxamide Example 189. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrazol-4-yl)-2-[2-(morpholin-4-yl)ethyl]-1H-pyrrole-3-carboxamide Example 190. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-[2-(morpholin-4-yl)ethyl]-1H-pyrrole-3-carboxamide Example 191. 5-(5-Chloro-2-{[(3R)-3-methyl-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-[2-(morpholin-4-yl)ethyl]-1H-pyrrole-3-carboxamide Example 192. 5-(5-Chloro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 193. 5-(5-Chloro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 194. 5-(5-Chloro2-{[(3S)-3-(difluoromethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 195. 5-(5-Chloro-2-{[(3S)-3-(difluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 196. 5-(5-Chloro-2-{[(3S)-3-(fluoromethyl)-3,4-dihydroisaquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 197. 5-(5-Chloro-2-{[(3S)-3-(fluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 198. 5-(5-Chloro-2-{[(3S)-3-[(9aS)-hexahydropyrazino[2,1-c][1,4]oxazin-(8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 199. 5-(5-Chloro-2-{[(3S)-3-[(9aS)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 200. 5-(5-Chloro-2-{[(3S)-3-[(9aR)-hexahydropyrazine[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 201. 5-(5-Chloro-2-{[(3S)-3-[(9aR)-hexahydropyrazino[2,1-c][1,4] oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 202. 5-(2-{[(3S)-3-(Aminomethyl)-3,4-dihydroisoquinolin-2(1H)-yl]carbonyl}-5-chlorophenyl)-N-(4-hydroxyphenyl)-1,2-dimethyl-N-(1-methyl-1H-pyrazol-4-yl)-1H-pyrrole-3-carboxamide Example 203. 5-(2-{[(3S)-3-(Aminomethyl)-3,4-dihydroisoquinolin-2(1H)-yl]carbonyl}-5-chlorophenyl)-N-(4-hydroxyphenyl)-1,2-dimethyl-N-(1-methyl-1H-pyrrolo[2,3-b]pyridin-5-yl)-1H-pyrrole-3-carboxamide Example 204. 5-(2-{[(3S)-3-(Aminomethyl)-3,4-dihydroisoquinolin-2(1H)-yl]carbonyl}-5-chlorophenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 205. 5-(5-Chloro-2-{[(3S)-3-[(3-cyanoazetidin-1-yl)methyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 206. 5-(5-Chloro-2-{[(3S)-3-[(3-cyanoazetidin-1-yl)methyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 207. 5-(5-Chloro-2-{[(3S)-3-(1-oxa-6-azaspiro[3.3]hept-6-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide The title compound is obtained in accordance with the process of Example 1 using the acid of Preparation 1 and the compound of Preparation 8' in Step A, and the compound of Preparation 1" in Step C.

High-Resolution Mass Spectrometry (ESI+−/FIA/HR, ESI−/FIA):

Empirical formula: $C_{39}H_{39}ClN_6O_4$

[M+H]$^+$ calculated: 691.2794

[M+H]$^+$ measured: 691.2796

Example 208. 5-(5-Chloro-2-{[(3S)-3-(1-oxa-6-azaspiro[3.3]hept-6-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 209. 5-(5-Fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide hydrochloride The procedure is in accordance with the general protocol of Example 1 using the appropriate Preparations. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)

%C=66.27:66.84; % H=5.69:5.15; % N=10.78:10.71; % Cl−=4.55:4.46

High-Resolution Mass Spectrometry (ESI+−/FIA):

Empirical formula: $C_{43}H_{43}FN_6O_5$

[M+H]$^+$ calculated: 743.3352

[M+H]$^+$ measured: 743.3353

Example 210. 5-(5-Fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide hydrochloride Step A: 5-(5-Fluoro-4-methoxy-2-{[(3S)-3-(morpholin-4-ylmethyl)-3,4-dihydroiso-quinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide The title compound is obtained in accordance with the process of Example 1 using the compound of Preparation 14 and (3S)-3-(4-morpholinylmethyl)-1,2,3,4-tetrahydroisoquinoline (see Preparation 3') in Step A, and the compound of Preparation 11" in Step C.

Step B: 5-(5-Chloro-2-{[(3S)-3-(morpholin-4-ylmethyl)-3,4-dihydroisoquinolin-2(1H)-yl]carbonyl}phenyl)-1,2-dimethyl-N-(1-methyl-2,3-dihydro-1H-pyrrolo[2,3-b]pyridin-5-yl)-N-phenyl-1H-pyrrole-3-carboxamide hydrochloride The title compound is obtained in accordance with the process described in Step B of Example 49 starting from compound of the above Step, it being understood that the product is finally subjected to a step of conversion into salt form in the presence of 1M HCl in ether. After filtration and lyophilisation in a mixture of acetonitrile/water, the expected product is obtained.

Elemental Microanalysis: (%, Theoretical:Measured)
% C=60.12:59.77; % H=4.92:4.76; % N=10.79:10.39; % Cl−=4.55:5.17

High-Resolution Mass Spectrometry (ESI/FIA/HR and MS/MS):
Empirical formula: $C_{40}H_{40}N_4O_5$
[M+H]$^+$ calculated: 657.3071
[M+H]$^+$ measured: 657.3066

Example 211. 5-(4-Fluoro-5-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide

Example 212. 5-(4-Fluoro-5-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide

Example 213. N-(1-Ethyl-1H-pyrazol-4-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide

Example 214. N-(1-Cyclopropyl-1H-pyrazol-4-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the compound of Preparation 28" in Step C. The compound obtained is converted into salt form and lyophilised as described in the general process to obtain the title compound.

Elemental Microanalysis: (%, Theoretical:Measured)
% C=66.24:66.53; % H=5.84:5.39; % N=10.59:10.92% Cl−=4.89:5.68

Example 215. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trifluoromethyl)-1H-pyrazol-4-yl]-1H-pyrrole-3-carboxamide

Example 216. N-[1-(Difluoramethyl)-1H-pyrazol-4-yl]-5-(5-fluoro-2-{[(3S)-3-(merpholin-4-ylmethyl)-3,4-dihydroisequinolin-2(1H)-yl]carbonyl}phenyl)-N-(4-hydroxyphenyl)-1,2-dimethyl-1H-pyrrole-3-carboxamide

Example 217. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-N-[1-(2-methoxyethyl)-1H-pyrazol-4-yl]-1,2-dimethyl-1H-pyrrole-3-carboxamide

Example 218. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(oxetan-3-yl)-1H-pyrazol-4-yl]-1H-pyrrole-3-carboxamide

Example 219. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(tetrahydrofuran-3-yl)-1H-pyrazol-4-yl]-1H-pyrrole-3-carboxamide

Example 220. 5-(5-Fluoro-2-{[(3S)-3-(morpholin-4-ylmethyl)-3,4-dihydroisoquinolin-2(1H)-yl]carbonyl}phenyl)-N-[1-(2-hydroxy-2-methylpropyl)-1H-pyrazol-4-yl]-N-(4-hydroxyphenyl)-1,2-dimethyl-1H-pyrrole-3-carboxamide

Example 221. 5-(5-Fluoro-2-{[(3S)-3-(morpholin-4-ylmethyl)-3,4-dihydroisoquinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide

Example 222. 5-(5-Fluoro-2-{[(3S)-3-(morpholin-4-ylmethyl)-3,4-dihydroisoquinolin-2(1H)-yl]carbonyl}phenyl)-1,2-dimethyl-N-(1-methyl-2,3-dihydro-1H-pyrrolo[2,3-b]pyridin-5-yl)-N-phenyl-1H-pyrrole-3-carboxamide Example 223. 5-(5-Fluoro-2-{[(3S)-3-(morpholin-4-ylmethyl)-3,4-dihydroisoquinolin-2(1H)-yl]carbonyl}phenyl)-N-(4-fluorophenyl)-1,2-dimethyl-N-(1-methyl-1H-pyrrolo[2,3-b]pyridin-5-yl)-1H-pyrrole-3-carboxamide Example 224. 5-(5-Fluoro-2-{[(3S)-3-(morpholin-4-ylmethyl)-3,4-dihydroisoquimain-2(1H)-yl]carbonyl}phenyl)-N-(4-fluorophenyl)-1,2-dimethyl-N-(1-methyl-2,3-dihydro-1H-pyrrolo[2,3-b]pyridin-5-yl)-1H-pyrrole-3-carboxamide Example 225. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-N,1,2-trimethyl-1H-pyrrole-3-carboxamide Example 226. 5-(5-Fluoro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-phenyl-1H-pyrrole-3-carboxamide Example 227. 5-(5-Fluoro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-(1-methyl-1H-pyrrolo[2,3-b]pyridin-5-yl)-1H-pyrrole-3-carboxamide Example 228. 5-(5-Fluoro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-(1-methyl-2,3-dihydro-1H-pyrrolo[2,3-b]pyridin-5-yl)-1H-pyrrole-3-carboxamide Example 229. 5-(5-Fluoro-2-{[(3S)-3-(morpholin-4-ylmethyl)-3,4-dihydroisoquinolin-2(1H)-yl]carbonyl}phenyl)-N-(2-hydroxypyrimidin-5-yl)-1,2-dimethyl-N-(1-methyl-1H-pyrazol-4-yl)-1H-pyrrole-3-carboxamide Example 230. N-(5-Cyano-1-methyl-1H-pyrrol-3-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the compound of Preparation 19" in Step C. The compound obtained is converted into salt form and lyophilised as described in the general process to obtain the title compound.

Elemental Microanalysis: (%, Theoretical:Measured)

% C=66.43:67.09; % H=5.57:5.21; % N=11.62:11.48% Cl⁻=4.90:4.75

High-Resolution Mass Spectrometry (ESI+):

Empirical formula: $C_{40}H_{39}FN_6O_4$

[M+H]⁺ calculated: 687.3097

[M+H]⁺ measured: 687.3073

Example 231. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrazol-4-yl)-1H-pyrrole-3-carboxamide Example 232. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1H-pyrrole-3-carboxamide Example 233. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 234. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-1H-pyrrole-3-carboxamide Example 235. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-1H-pyrrole-3-carboxamide Example 236. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 237. 1-Ethyl-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-meth—N-(1-methyl-1H-pyrazol-4-yl)-1H-pyrrole-3-carboxamide Example 238. 1-Ethyl-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1H-pyrrole-3-carboxamide Example 239. 1-Ethyl-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 240. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-(2-methoxyethyl)-2-methyl-N-(1-methyl-1H-pyrazol-4-yl)-1H-pyrrole-3-carboxamide Example 241. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-(2-methoxyethyl)-2-methyl-N-(1-methyl-1H-pyrrolo[2,3-b]pyridin-5-yl)-1H-pyrrole-3-carboxamide Example 242. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-(2-methoxyethyl)-2-methyl-N-(1-methyl-2,3-dihydro-1H-pyrrolo[2,3-b]pyridin-5-yl)-1H-pyrrole-3-carboxamide Example 243 . 1-(2-Fluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrazol-4-yl)-1H-pyrrole-3-carboxamide Example 244. 1-(2-Fluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1H-pyrrole-3-carboxamide Example 245. 1-(2-Fluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 246. 1-(2,2-Difluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl4H-pyrazol-4-yl)-1H-pyrrole-3-carboxamide Example 247. 1-(2,2-Difluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl4H-pyrrolo[2,3-b]pyridin-5-yl)-1H-pyrrole-3-carboxamide Example 248. 1-(2,2-Difluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 249. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrazol-4-yl)-1-(2,2,2-trifluoroethyl)-1H-pyrrole-3-carboxamide Example 250. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-1H-pyrrolo[2,3-b]pyridin-5-yl)-1-(2,2,2-trifluoroethyl)-1H-pyrrole-3-carboxamide Example 251. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1-(2,2,2-trifluoroethyl)-1H-pyrrole-3-carboxamide Example 252. 5-(5-Fluoro-2-{[(3R)-3-methyl-3,4-dihydroisoquinolin-2(1H)-yl]carbonyl}phenyl)-N-(4-hydroxyphenyl)-2-methyl-N-(1-methyl-1H-pyrazol-4-yl)-1-[2-(morpholin-4-yl)ethyl]4H-pyrrole-3-carboxamide Example 253. 5-(5-Fluoro-2-{[(3R)-3-methyl-3,4-dihydroisoquinolin-2(1H)-yl]carbonyl}phenyl)-N-(4-hydroxyphenyl)-2-methyl-N-(1-methyl-1H-pyrrole[2,3-b]pyridin-5-yl)-1-[2-(morpholin-4-yl)ethyl]-1H-pyrrole-3-carboxamide Example 254. 5-(5-Fluoro-2-{[(3R)-3-methyl-3,4-dihydroisoquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1-[2-(morpholin-4-yl)ethyl]-1H-pyrrole-3-carboxamide Example 255. 5-(5-Fluoro-2-{[(3R)-3-methyl-3,4-dihydroisoquinolin-2(1H)-yl]carbonyl}phenyl)-N-(4-hydroxyphenyl)-2-methyl-1-[2-(morpholin-4-yl)ethyl]-N-phenyl-1H-pyrrole-3-carboxamide Example 256. 1-[2-(Dimethylamino)ethyl]-5-(5-fluoro-2-{[(3R)-3-methyl-3,4-dihydroisoquinolin-2(1H)-yl]carbonyl}phenyl)-N-(4-hydroxyphenyl)-2-methyl-N-(1-methyl1H-pyrazol-4-yl)-1H-pyrrole-3-carboxamide Example 257. 1-[2-(Dimethylamino)ethyl]-5-(5-fluoro-2-{[(3R)-3-methyl-3,4-dihydroisoquinolin-2(1H)-yl]carbonyl}phenyl)-N-(4-hydroxyphenyl)-2-methyl-N-phenyl-1H-pyrrole-3-carboxamide Example 258. 1-[2-(Dimethylamino)ethyl]-5-(5-fluoro-2-{[(3R)-3-methyl-3,4-dihydroisaquinolin-2(1H)-yl]carbonyl}phenyl)-N-(4-hydroxyphenyl)-2-methyl-N-(1-methyl-1H-pyrrolo[2,3-b]pyridin-5-yl)-1H-pyrrole-3-carboxamide Example 259. 1-[2-(Dimethylamino)ethyl]-5-(5-fluoro-2-{[(3R)-3-methyl-3,4-dihydroisaquinolin-2(1H)-yl]carbonyl}phenyl)-N-(4-hydroxyphenyl)-2-methyl-N-(1-methyl-2,3-dihydro-1H-pyrrolo[2,3-b]pyridin-5-yl)-1H-pyrrole-3-carboxamide Example 260. 5-(5-Fluoro-2-{[(3R)-3-methyl-3,4-dihydroisoquinolin-2(1H)-yl]-carbonyl}phenyl)-N-(4-hydroxyphenyl)-1-{2-[(2-methoxyethyl)(methyl)amino]ethyl}-2-methyl-N-(1-methyl-1H-pyrazol-4-yl)-1H-pyrrole-3-carboxamide Example 261. 5-(5-Fluoro-2-{[(3R)-3-methyl-3,4-dihydroisoquinolin-2(1H)-yl]-carbonyl}phenyl)-N-(4-hydroxyphenyl)-1-{2-[(2-methoxyethyl)(methyl)amino]ethyl}-2-methyl-N-(1-methyl-1H-pyrrolo[2,3-b]pyridin-5-yl)-1H-pyrrole-3-carboxamide Example 262. 5-(5-Fluoro-2-{[(3R)-3-methyl-3,4-dihydroisoquinolin-2(1H)-yl]-carbonyl}p phenyl)-N-(4-hydroxyphenyl)-1-{2-[(2-methoxyethyl)(methyl)amino]ethyl}-2-methyl-N-(1-methyl-2,3-dihydro-1H-pyrrolo[2,3-b]pyridin-5-yl)-1H-pyrrole-3-carboxamide Example 263. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-2-(trifluoromethyl)-1H-pyrrole-3-carboxamide Example 264. 5-(5-Fluoro-2-{[(3S)-3-(morpliolin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-(trifluoromethyl)-1H-pyrrole-3-carboxamide Example 265. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(trifluoromethyl)-1H-pyrrole-3-carboxamide Example 266. 2-(Difluoromethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl4H-pyrazol-4-yl)-1H-pyrrole-3-carboxamide Example 267. 2-(Difluoromethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-1H-pyrrole-3-carboxamide Example 268. 2-(Difluoromethyl)-5-(5-fluoro-2-{[(3S)-3-(morpholin-4-ylmethyl)-3,4-dihydroisaquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 269. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(methoxymethyl)-1-methyl-N-(1-methyl-1H-pyrazol-4-yl)-1H-pyrrole-3-carboxamide Example 270. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(methoxymethyl)-1-methyl-N-(1-methyl-1H-pyrrolo[2,3-b]pyridin-5-yl)-1H-pyrrole-3-carboxamide Example 271. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(methoxymethyl)-1-methyl-N-(1-methyl-2,3-dihydro-1H-pyrrolo[2,3-b]pyridin-5-yl)-1H-pyrrole-3-carboxamide Example 272. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-2-(2,2,2-trifluoroethyl)-1H-pyrrole-3-carboxamide Example 273. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-(2,2,2-trifluoroethyl)-1H-pyrrole-3-carboxamide Example 274. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(2,2,2-trifluoroethyl)-1H-pyrrole-3-carboxamide Example 275. 2-(2,2-Difluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-1H-pyrazol-4-yl)-1H-pyrrole-3-carboxamide Example 276. 2-(2,2-Difluoroethyl)-5-(5-fluoro-2-{[(3S)-3-(morphan-4-ylmethyl)-3,4-dihydroisoquinolin-2(1H)-yl]carbonyl}-phenyl)-N-(4-hydroxyphenyl)-1-methyl-N-(1-methyl-1H-pyrrolo[2,3-b]pyridin-5-yl)-1H-pyrrole-3-carboxamide Example 277. 2-(2,2-Difluoroethyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-1H-pyrrole-3-carboxamide Example 278. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl4H-pyrazol-4-yl)-1H-pyrrole-3-carboxamide Example 279. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl-1H-pyrrolo[2,3-b]pyridin-5-yl)-1H-pyrrole-3-carboxamide Example 280. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-2-(2-methoxyethyl)-1-methyl-N-(1-methyl-2,3-dihydro-1H-pyrrolo[2,3-b]pyridin-5-yl)-1H-pyrrole-3-carboxamide Example 281. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrazol-4-yl)-2-(morpholin-4-ylmethyl)-1H-pyrrole-3-carboxamide Example 282. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrrole[2,3-b]pyridin-5-yl)-2-(morpholin-4-ylmethyl)-1H-pyrrole-3-carboxamide Example 283. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-(morpholin-4-ylmethyl)-1H-pyrrole-3-carboxamide Example 284. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrazol-4-yl)-2-[2-(morpholin-4-yl)ethyl]-1H-pyrrole-3-carboxamide Example 285. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-1H-pyrrolo[2,3-b]pyridin-5-yl)-2-[2-(morpholin-4-yl)ethyl]-1H-pyrrole-3-carboxamide Example 286. 5-(5-Fluoro-2-{[(3R)-3-methyl-3,4-dihydroisoquinolin-2(1H)-yl]carbonyl}phenyl)-N-(4-hydroxyphenyl)-1-methyl-N-(1-methyl-2,3-dihydro-1H-pyrrolo[2,3-b]pyridin-5-yl)-2-[2-(morpholin-4-yl)ethyl]-1H-pyrrole-3-carboxamide Example 287. 5-(5-Fluoro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 288. 5-(5-Fluoro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 289. 5-(5-Fluoro-2-{[(3S)-3-(trifluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 290. 5-(2-{[(3S)-3-(Difluoromethyl)-3,4-dihydroisoquinolin-2(1H)-yl]carbonyl}-5-fluorophenyl)-N-(4-hydroxyphenyl)-1,2-dimethyl-N-(1-methyl-1H-pyrazol-4-yl)-1H-pyrrole-3-carboxamide Example 291. 5-(2-{[(3S)-3-(Difluoromethyl)-3,4-dihydroisoquinolin-2(1H)-yl]carbonyl}-5-fluorophenyl)-N-(4-hydroxyphenyl)-1,2-dimethyl-N-(1-methyl-1H-pyrrolo[2,3-b]pyridin-5-yl)-1H-pyrrole-3-carboxamide Example 292. 5-(2-{[(3S)-3-(Difluoromethyl)-3,4-dihydroisoquinolin-2(1H)-yl]carbonyl}-5-fluorophenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 293. 5-(5-Fluoro-2-{[(3S)-3-(fluoromethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 294. 5-(5-Fluoro-2-{[(3S)-3-(fluoromethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 295. 5-(5-Fluoro-2-{[(3S)-3-(fluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 296. 5-(5-Fluoro-2-{[(3S)-3-(fluoromethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 297. 5-(5-Fluoro-2-{[(3S)-3-[(9aS)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 298. 5-(5-Fluoro-2-{[(3S)-3-[(9aS)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 299. 5-(5-Fluoro-2-{[(3S)-3-[(9aR)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 300. 5-(5-Fluoro-2-{[(3S)-3-[(9aR)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 301. 5-(5-Fluoro-2-{[(3S)-3-[(9aR)-hexahydropyrazino[2,1-c][1,4]oxazin-8(1H)-ylmethyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 302. 5-(2-{[(3S)-3-(Aminomethyl)-3,4-dihydroisoquinolin-2(1H)-yl]carbonyl}-5-fluorophenyl)-N-(4-hydroxyphenyl)-1,2-dimethyl-N-(1-methyl-1H-pyrazol-4-yl)-1H-pyrrole-3-carboxamide Example 303. 5-(2-{[(3S)-3-(Aminomethyl)-3,4-dihydroisoquinolin-2(1H)-yl]carbonyl}-5-fluorophenyl)-N-(4-hydroxyphenyl)-1,2-dimethyl-N-(1-methyl-1H-pyrrolo[2,3-b]pyridin-5-yl)-1H-pyrrole-3-carboxamide Example 304. 5-(2-{[(3S)-3-(Aminomethyl)-3,4-dihydroisoquinolin-2(1H)-yl]carbonyl}-5-fluorophenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 305. 5-(2-{[(3S)-3-[(3-Cyanoazetidin-1-yl)methyl]-3,4-dihydroisoquinolin-2(1H)-yl]carbonyl}-5-fluorophenyl)-N-(4-hydroxyphenyl)-1,2-dimethyl-N-(1-methyl-1H-pyrazol-4-yl)-1H-pyrrole-3-carboxamide Example 306. 5-(2-{[(3S)-3-[(3-Cyanoazetidin-1-yl)methyl]-3,4-dihydroisoquinolin-2(1H)-yl]carbonyl}-5-fluorophenyl)-N-(4-hydroxyphenyl)-1,2-dimethyl-N-(1-methyl-1H-pyrrolo[2,3-b]pyridin-5-yl)-1H-pyrrole-3-carboxamide Example 307. 5-(2-{[(3S)-3-[(3-Cyanoazetidin-1-ypmethyl]-3,4-dihydroisoquinolin-2(1H)-yl]carbonyl}-5-fluorophenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 308. 5-(5-Fluoro-2-{[(3S)-3-(1-oxa-6-azaspiro[3.3]hept-6-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide Example 309. 5-(5-Fluoro-2-{[(3S)-3-(1-oxa-6-azaspiro[3.3]hept-6-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide Example 310. N-(1-Ethyl-1H-pyrazol-4-yl)-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 311. N-(1-Cyclopropyl-1H-pyrazol-4-yl)-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 312. N-(4-Hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-[1-(trifluoromethyl)-1H-pyrazol-4-yl]-1H-pyrrole-3-carboxamide Example 313. N-[1-(Difluoromethyl)-1H-pyrazol-4-yl]-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 314. N-(4-Hydroxyphenyl)-N-[1-(2-methoxyethyl)-1H-pyrazol-4-yl]-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 315. N-(4-Hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-[1-(oxetan-3-yl)-1H-pyrazol-4-yl]-1H-pyrrole-3-carboxamide Example 316. N-(4-Hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-[1-(tetrahydrofaran-3-yl)-1H-pyrazol-4-yl]-1H-pyrrole-3-carboxamide Example 317. N-[1-(2-Hydroxy-2-methylpropyl)-1H-pyrazol-4-yl]-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 318. 1,2-Dimethyl-N-(1-methyl-1H-pyrrolo[2,3-b]pyridin-5-yl)-5-(6-{[(3S)-3-(morpholin-4-ylmethyl)-3,4-dihydroisequinolin-2(1H)-yl]carbonyl}-1,3-benzodioxol-5-yl)-N-phenyl-1H-pyrrole-3-carboxamide Example 319. 1,2-Dimethyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-N-phenyl-1H-pyrrole-3-carboxamide Example 320. N-(4-Fluorophenyl)-1,2-dimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 321. N-(4-Fluorophenyl)-1,2-dimethyl-N-(1-methyl-2,3-dihydro-1H-pyrrolo[2,3-b]pyridin-5-yl)-5-(6-{[(3S)-3-(morpholin-4-ylmethyl)-3,4-dihydroisaquinolin-2(1H)-yl]carbonyl}-1,3-benzodioxol-5-yl)-1H-pyrrole-3-carboxamide Example 322. N-(4-Hydroxyphenyl)-N,1,2-trimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 323. N-(2-Hydroxypyrimidin-5-yl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-N-phenyl-1H-pyrrole-3-carboxamide Example 324. N-(2-Hydroxypyrimidin-5-yl)-1,2-dimethyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 325. N-(2-Hydroxypyrimidin-5-yl)-1,2-dimethyl-N-(1-methyl-2,3-dihydro-1H-pyrrolo[2,3-b]pyridin-5-yl)-5-(6-{[(3S)-3-(morpholin-4-ylmethyl)-3,4-dihydroiso-quinolin-2(1H)-yl]carbonyl}-1,3-benzodioxol-5-yl)-1H-pyrrole-3-carboxamide Example 326. N-(2-Hydroxypyrimidin-5-yl)-1,2-dimethyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 327. N-(5-Cyano-1-methyl-1H-pyrrol-3-yl)-N-(4-hydroxyphenyl)-1,2-dimethyl-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 328. N-(4-Hydroxyphenyl)-2-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 329. N-(4-Hydroxyphenyl)-2-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 330. N-(4-Hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 331. N-(4-Hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 332. N-(4-Hydroxyphenyl)-1-methyl-N-(1-methyl-2,3-dihydro-1H-pyrrolo-[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 333. 1-Ethyl-N-(4-hydroxyphenyl)-2-methyl-N-(1-methyl-1H-pyrrolo[2,3-b]-pyridin-5-yl)-5-(6-{[(3S)-3-(morpholin-4-ylmethyl)-3,4-dihydroisoquinolin-2(1H)-yl]-carbonyl}-1,3-benzodioxol-5-yl)-1H-pyrrole-3-carboxamide Example 334. 1-Ethyl-N-(4-hydroxyphenyl)-2-methyl-N-(1-methyl-2,3-dihydro-1H-pyrrolo[2,3-b]pyridin-5-yl)-5-(6-{[(3S)-3-(morpholin-4-ylmethyl)-3,4-dihydroiso-quinolin-2(1H)-yl]carbonyl}-1,3-benzodioxot-5-yl)-1H-pyrrole-3-carboxamide Example 335. N-(4-Hydroxyphenyl)-1-(2-methoxyethyl)-2-methyl-N-(1-methyl-1H-pyrrolo[2,3-b]pyridin-5-yl)-5-(6-{[(3S)-3-(morpholin-4-ylmethyl)-3,4-dihydroiso-quinolin-2(1H)-yl]carbonyl}-1,3-benzodioxol-5-1)-1H-pyrrole-3-carboxamide Example 336. N-(4-Hydroxyphenyl)-1-(2-methoxyethyl)-2-methyl-N-(1-methyl-2,3-dihydro-1H-pyrrolo[2,3-b]pyridin-5-yl)-5-(6-{[(3S)-3-(morpholin-4-ylmethyl)-3,4-dihydroisaquinolin-2(1H)-yl]carbonyl}-1,3-benzodioxol-5-yl)-1H-pyrrole-3-carboxamide Example 337. 1-(2-Fluoroethyl)-N-(4-hydroxyphenyl)-2-methyl-N-(1-methyl-1H-pyrrolo[2,3-b]pyridin-5-yl)-5-(6-{[(3S)-3-(morpholin-4-ylmethyl)-3,4-dihydroiso-quinolin-2(1H)-yl]carbonyl}-1,3-benzodioxol-5-yl)-1H-pyrrole-3-carboxamide Example 338. 1-(2-Fluoroethyl)-N-(4-hydroxyphenyl)-2-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 339. 1-(2,2-Difluoroethyl)-N-(4-hydroxyphenyl)-2-methyl-N-(1-methyl-1H-pyrrolo[2,3-b]pyridin-5-yl)-5-(6-{[(3S)-3-(morpholin-4-ylmethyl)-3,4-dihydroiso-quinolin-2(1H)-yl]carbonyl}-1,3-benzodioxol-5-yl)-1H-pyrrole-3-carboxamide Example 340. 1-(2,2-Difluoroethyl)-N-(4-hydroxyphenyl)-2-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 341. N-(4-Hydroxyphenyl)-2-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1-(2,2,2-trifluoroethyl)-1H-pyrrole-3-carboxamide Example 342. N-(4-Hydroxyphenyl)-2-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1-(2,2,2-trifluoroethyl)-1H-pyrrole-3-carboxamide Example 343. N-(4-Hydroxyphenyl)-2-methyl-N-(1-methyl-2,3-dihydro-1H-pyrrolo-[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1-(2,2,2-trifluoroethyl)-1H-pyrrole-3-carboxamide Example 344. N-(4-Hydroxyphenyl)-2-methyl-5-(6-{[(3R)-3-methyl-3,4-dihydroisaquinolin-2(1H)-yl]carbonyl}-1,3-benzodioxol-5-yl)-N-(1-methyl-1H-pyrrolo[2,3-b]pyridin-5-yl)-1-[2-(morpholin-4-yl)ethyl]-1H-pyrrole-3-carboxamide Example 345. N-(4-Hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-2,3-dihydro-1H-pyrrolo[2,3-b]pyridin-5-yl)-1-[2-(morpholin-4-yl)ethyl]-1H-pyrrole-3-carboxamide Example 346. 1-[2-(Dimethylamino)ethyl]-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl-1H-pyrazol-4-yl)-1H-pyrrole-3-carboxamide Example 347. 1-[2-(Dimethylamino)ethyl]-N-(4-hydroxyphenyl)-2-methyl-5-(6-{[(3R)-3-methyl-3,4-dihydroisoquinolin-2(1H)-yl]carbonyl}-1,3-benzodioxol-5-yl)-N-(1-methyl4H-pyrrolo[2,3-b]pyridin-5-yl)-1H-pyrrole-3-carboxamide Example 348. 1-[2-(Dimethylamino)ethyl]-N-(4-hydroxyphenyl)-2-methyl-5-(6-{[(3R)-3-methyl-3,4-dihydroisaquinolin-2(1H)-yl]carbonyl}-1,3-benzodioxol-5-yl)-N-(1-methyl-2,3-dihydro-1H-pyrrolo[2,3-b]pyridin-5-yl)-1H-pyrrole-3-carboxamide Example 349. N-(4-Hydroxyphenyl)-1-{2-[(2-methoxyethyl)(methyl)amino]ethyl}-2-methyl-5-(6-{[(3R)-3-methyl-3,4-dihydroisoquinolin-2(1H)-yl]carbonyl}-1,3-benzo-dioxol-5-yl)-N-(1-methyl-1H-pyrrolo[2,3-b]pyridin-5-yl)-1H-pyrrole-3-carboxamide Example 350. N-(4-Hydroxyphenyl)-1-{2-[(2-methoxyethyl)(methyl)amino]ethyl}-2-methyl-5-(6-{[(3R)-3-methyl-3,4-dihydroisoquinolin-2(1H)-yl]carbonyl}-1,3-benzo-dioxol-5-yl)-N-(1-methyl-2,3-dihydro-1H-pyrrolo[2,3-b]pyridin-5-yl)-1H-pyrrole-3-carboxamide Example 351. N-(4-Hydroxyphenyl)-1-methyl-N-(1-methyl-2,3-dihydro-1H-pyrrolo-[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-2-(trifluoromethyl)-1H-pyrrole-3-carboxamide Example 352. 2-(Difluoromethyl)-N-(4-hydroxyphenyl)-1-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 353. N-(4-Hydroxyphenyl)-2-(methoxymethyl)-1-methyl-N-(1-methyl-2,3-dihydro-1H-pyrrolo[2,3-b ]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 354. N-(4-Hydroxyphenyl)-1-methyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-2-(2,2,2-trilluoroethyl)-1H-pyrrole-3-carboxamide Example 355. N-(4-Hydroxyphenyl)-1-methyl-N-(1-methyl-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-2-(2,2,2-trifluoroethyl)-1H-pyrrole-3-carboxamide Example 356. N-(4-Hydroxyphenyl)-1-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-2-(2,2,2-trifluoroethyl)-1H-pyrrole-3-carboxamide Example 357. 2-(2,2-Difluoroethyl)-N-(4-hydroxyphenyl)-1-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide Example 358. N-(4-Hydroxyphenyl)-2-(2-methoxyethyl)-1-methyl-N-(1-methyl-2,3-dihydro-1H-pyrrolo[2,3-b]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The title compound is obtained in accordance with the process described in Step B of Example 49 using Example 88 as starting material, it being understood that the product is finally dissolved in acetonitrile and converted into salt form in 0.1M aqueous HCl solution. After a lyophilisation step, the expected product is obtained in the form of a solid.

Elemental Microanalysis: (%, Theoretical:Measured)

% C=65.80:64.71; % H=6.01:5.74; % N=10.23:10.03; % Cl−=4.32:6.47

High-Resolution Mass Spectrometry (ESI/+):

Empirical formula: $C_{45}H_{48}N_6O_7$ $[M+H]^+$ calculated: 785.3657

$[M+H]^+$ measured: 785.3658

Example 359. N-(4-Hydroxyphenyl)-1-methyl-5-(6-{[(3R)-3-methyl-3,4-dihydroisoquinolin-2(1H)-yl]carbonyl}-1,3-benzodioxol-5-yl)-N-(1-methyl-2,3-dihydro-1H-pyrrolo[2,3-b]pyridin-5-yl)-2-(morpholin-4-ylmethyl)-1H-pyrrole-3-carboxamide Example 360. N-(4-Hydroxyphenyl)-1-methyl-5-(6-{[(3R)-3-methyl-3,4-dihydroiso-quinolin-2(1H)-yl]carbonyl}-1,3-benzodioxol-5-yl)-N-(1-methyl-2,3-dihydro-1H-pyrrolo[2,3-b]pyridin-5-yl)-2-[2-(morpholin-4-yl)ethyl]-1H-pyrrole-3-carboxamide Example 361. N-(4-Hydroxyphenyl)-1,2-dimethyl-N-(1-methyl-1H-pyrazol-4-yl)-5-6-{[(3S)-3-(trifluoromethyl)-3,4-dihydroisoquinolin-2(1H)-yl]carbonyl}-1,3-benzodioxol-5-yl)-1H-pyrrole-3-carboxamide Example 362. N-(4-Hydroxyphenyl)-1,2-dimethyl-N-(1-methyl-1H-pyrrolo[2,3-b]-pyridin-5-yl)-5-(6-{[(3S)-3-(trifluoromethyl)-3,4-dihydroisoquinolin-2(1H)-yl]carbonyl}-1,3-benzodioxol-5-yl)-1H-pyrrole-3-carboxamide Example 363. N-(4-Hydroxyphenyl)-1,2-dimethyl-N-(1-methyl-2,3-dihydro-1H-pyrrolo[2,3-b]pyridin-5-yl)-5-(6-{[(3S)-3-(trifluoromethyl)-3,4-dihydroisoquinolin-2(1H)-yl]carbonyl}-1,3-benzodioxol-5-yl)-1H-pyrrole-3-carboxamide Example 364. 5-(6-{[(3S)-3-(Difluoromethyl)-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 365. 5-(6-{[(3S)-3-(Difluoromethyl)-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 366. 5-(6-{[(3S)-3-(Difluoromethyl)-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 367. 5-(6-{[(3S)-3-(Fluoromethyl)-3,4-dihydroisoquinotin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 368. 5-(6-{[(3S)-3-(Fluoromethyl)-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 369. 5-(6-{[(3S)-3-(Fluoromethyl)-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 370. 5-(6-{[(3S)-3-[(9aS)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 371. 5-(6-{[(3S)-3-[(9aS)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 372. 5-(6-{[(3S)-3-[(9aS)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 373. 5-(6-{[(3S)-3[(9aR)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 374. 5-(6-{[(3S)-3-[(9aR)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 375. 5-(6{[(3S)-3-[(9aR)-Hexahydropyrazino[2,1-c][1,4]oxazin-8(1H)-ylmethyl]-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 376. 5-(6{[(3S)-3-(Aminomethyl)-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 377. 5-(6-{[(3S)-3-(Aminomethyl)-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 378. 5-(6-{[(3S)-3-(Aminomethyl)-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 379. 5-(6-{[(3S)-3-[(3-Cyanoazetidin-1-yl)methyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrazol-4-yl)-1H-pyrrole-3-carboxamide Example 380. 5-(6-{[(3S)-3-[(3-Cyanoazetidin-1-yl)methyl]-3,4-dihydroisoquinolin-2(1H)-yl]carbonyl}-1,3-benzodioxol-5-yl)-N-(4-hydroxyphenyl)-1,2-dimethyl-N-(1-methyl-1H-pyrrolo[2,3-b]pyridin-5-yl)-1H-pyrrole-3-carboxamide Example 381. 5-(6-{[(3S)-3-[(3-Cyanoazetidin-1-yl)methyl]-3,4-dihydroisoquinolin-2(1H)-yl]carbonyl}-1,3-benzodioxol-5-yl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide Example 382. N-(4-Hydroxyphenyl)-1,2-dimethyl-N-(1-methyl-1H-pyrazol-4-yl)-5-6-{[(3S)-3-(1-oxa-6-azaspiro[3.3]hept-6-ylmethyl)-3,4-dihydroisoquinolin-2(1H)-yl]carbonyl}-1,3-benzodioxol-5-yl)-1H-pyrrole-3-carboxamide Example 383. N-(4-Hydroxyphenyl)-1,2-dimethyl-N-(1-methyl-1H-pyrrolo[2,3-b]-pyridin-5-yl)-5-(6-{[(3S)-3-(1-oxa-6-azaspiro[3.3]hept-6-ylmethyl)-3,4-dihydroiso-quinolin-2(1H)-yl]carbonyl}-1,3-benzodioxol-5-yl)-1H-pyrrole-3-carboxamide Example 384. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide hydrochloride Elemental Microanalysis: (%, Theoretical:Measured)
% C=67.28:67.73; % H=5.65:5.30; % N=10.06:9.41% Cl-=5.09:5.79

Example 385. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)4,2-dimethyl-N-(1-methyl-1H-pyrrolo[2,3-b]pyridin-5-yl)-1H-pyrrole-3-carboxamide hydrochloride High-Resolution Mass Spectrometry (ESI+):
Empirical formula: $C_{41}H_{41}ClN_6O_4$
[M+H]$^+$ calculated: 713.3253
[M+H]$^+$ measured: 713.3272

Example 386. 5-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide hydrochloride Step A: N-[4-[tert-Butyl(dimethyl)silyl]oxyphenyl]-5-[5-chloro-2-[(3S)-3-(morpholinomethyl)-3,4-dihydro-1H-isoquinoline-2-carbonyl]phenyl]-N-(5-cyano-1,2-dimethyl-pyrrol-3-yl)-1,2-dimethyl-pyrrole-3-carboxamide The title compound is obtained in accordance with the process of Example 1 using the acid of Preparation 1 and the compound of Preparation 3' in Step A, and the compound of Preparation 18" in Step C.
IR: v —CN—: 2210 cm$^{-1}$; v —C=O—: 1631 cm$^{-1}$ Step B: 5-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide hydrochloride The compound of Step A is deprotected in accordance with the protocol described in Step D of Example 1. The product thereby obtained is finally subjected to a step of conversion into salt form in the presence of HCl in ether. After filtration and lyophilisation in a mixture of acetonitrile/water, the expected product is obtained.

$^1$H NMR (500 MHz, dmso-d6) δ ppm: 11.2 (bs, 1H), 9.39 (bs,1H), 7.83 (d, 1H), 7.54 (d, 1H), 7.33 (s, 1H), 7.14 (m, 2H), 7 (m, 2H), 6.8 (d, 2H), 6.62 (d, 2H), 6.57 (bs, 1H), 5.26 (s, 1H), 5.26 (m, 1H), 4.64/4.03 (AB, 2H), 4.01/3.92 (2m, 4H), 3.75/3.43/3.15/3.02 (4m, 4H), 3.59 (s, 3H), 3.3/3.15 (2m, 2H), 2.97 (s, 3H), 2.69/2.52 (dd+d, 2H), 2.06 (s, 3H), 1.91 (s, 3H)

Elemental Microanalysis: (%, Theoretical:Measured)
% C=65.34:65.50; % H=5.62:5.15; % N=11.15:10.84% Cl-=4.70:4.44

High-Resolution Mass Spectrometry (ESI+):
Empirical formula: $C_{41}H_{41}ClN_6O_4$
[M+H]$^+$ calculated: 717.2952
[M+H]$^+$ measured: 717.2951

Example 387. N-(4-Hydroxyphenyl)-1,2-dimethyl-N-(1-methyl-1H-pyrrolo[2,3-c]pyridin-5-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride Elemental Microanalysis: (%, Theoretical:Measured)
% C=66.62:66.36; % H=5.59:5.62; % N=10.84:10.72% Cl-=4.57:4.55

High-Resolution Mass Spectrometry (ESI+):
Empirical formula: $C_{43}H_{42}N_6O_6$
[M+H]$^+$ calculated: 739.3239
[M+H]$^+$ measured: 739.3241

Example 388. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide dihydrochloride The title compound is obtained in accordance with the process described in Step B of Example 49 using Example 71 as starting material, it being understood that the product is finally subjected to a step of conversion into salt form in the presence of 1M HCl in ether. After filtration and lyophilisation in a mixture of acetonitrile/water, the expected compound is obtained.

Elemental Microanalysis: (%, Theoretical:Measured)
% C=62.73:62.96; % H=5.64:4.95; % N=10.45:10.32; % Cl=13.23:12.91

High-Resolution Mass Spectrometry (ESI+):
Empirical formula: $C_{42}H_{43}ClN_6O_4$
[M+H]$^+$ calculated: 731.3107
[M+H]$^+$ measured: 731.3111

Example 389. 5-(5-Chloro2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[2,3-c]pyridin-5-yl)-1H-pyrrole-3-carboxamide hydrochloride The procedure is in accordance with the general protocol of Example 1 using the appropriate Preparations. The product obtained is finally dissolved in acetonitrile and converted into salt form using 0.1M aqueous HCl solution. After a lyophilisation step, the expected compound is obtained in the form of a solid.

Elemental Microanalysis: (%, Theoretical:Measured)
% C=65.88:66.28; % H=5.53:5.15; % N=10.98:10.95; % Cl−=4.63:4.47
High-Resolution Mass Spectrometry (ESI/FIA/HR and MS/MS):
Empirical formula: $C_{42}H_{41}ClN_6O_4$
[M+H]$^+$ calculated: 729.2951
[M+H]$^+$ measured: 729.2954

Example 390. 5-(5-Chloro-2-{[(3S)-3-(morpholin-4-ylmethyl)-3,4-dihydroisoquinolin-2(1H)-yl]carbonyl}phenyl)-N-(1-methyl-1H-pyrrolo[2,3-b]pyridin-5-yl)-N-phenyl-1H-pyrrole-3-carboxamide The procedure is in accordance with the general protocol of Example 1 using the appropriate Preparations, it being understood that Step D is not carried out. The expected product is obtained in free base form.
Elemental Microanalysis: (%, Theoretical:Measured)
% C=70.72:69.77; % H=5.79:5.96; % N=11.78:11.43
High-Resolution Mass Spectrometry (ESI+):
Empirical formula: $C_{42}H_{41}ClN_6O_3$
[M+H]$^+$ calculated: 713.3001
[M+H]$^+$ measured: 713.2998

Example 391. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrrolo[3,2-b]pyridin-5-yl)-1H-pyrrole-3-carboxamide hydrochloride Elemental Microanalysis: (%, Theoretical:Measured)
% C=65.88:65.69; % H=5.33:4.87; % N=10.98:10.86; % Cl−=4.63:4.51
High-Resolution Mass Spectrometry (ESI+−/FIA):
Empirical formula: $C_{42}H_{41}ClN_6O_4$
[M+H]$^+$ calculated: 729.2951
[M+H]$^+$ measured: 729.2953

Example 392. 5-(5-Chloro-2-{[(3R)-3-[3-(morpholin-4-yl)propyl]-3,4-dihydroiso-quinolin-2(1H)-yl]carbonyl}phenyl)-N-(4-hydroxyphenyl)-1,2-dimethyl-N-phenyl-1H-pyrrole-3-carboxamide hydrochloride Elemental Microanalysis: (%, Theoretical:Measured)
% C=68.19:68.33; % H=6.00:5.49; % N=10.78:10.71; % Cl−=4.55:4.46; % Cl =9.58:9.78
High-Resolution Mass Spectrometry (ESI+−/FIA):
Empirical formula: $C_{42}H_{43}ClN_4O_4$
[M+H]$^+$ calculated: 703.3046
[M+H]$^+$ measured: 703.3042

Example 393. 5-(5-Chloro-2-{[(3R)-3-[3-(morpholin-4-yl)propyl]-3,4-dihydroisoquinolin-2(1H)-yl]carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide hydrochloride High-Resolution Mass Spectrometry (ESI+−/FIA):
Empirical formula: $C_{44}H_{45}ClN_6O_4$
[M+H]$^+$ calculated: 757.3264
[M+H]$^+$ measured: 757.3263

Example 394. 5-(5-Chloro-2-{[(3R)-3-[3-(morpholin-4-yl)propyl]-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide The title compound is obtained in accordance with the process described in Step B of Example 49 using Example 393 as starting material, it being understood that the product is not subjected to the step of conversion into salt form.
Elemental Microanalysis: (%, Theoretical:Measured)
% C=69.60:69.56; % H=6.21:6.24; % N=11.07:11.08
High-Resolution Mass Spectrometry (ESI+−/FIA):
Empirical formula: $C_{44}H_{47}ClN_6O_4$
[M+H]$^+$ calculated: 759.3420
[M+H]$^+$ measured: 759.3422

Example 395. 5-(5-Chloro-2-{[(3S)-3-(morpholin-4-ylmethyl)-3,4-dihydroisoquinolin-2(1H)-yl]carbonyl}phenyl)-N-(3-cyano-4-methoxyphenyl)-N-(4-hydroxyphenyl)-1,2-dimethyl-1H-pyrrole-3-carboxamide hydrochloride The procedure is in accordance with the general protocol of Example 1 using the appropriate Preparations. The product obtained is finally dissolved in acetonitrile and converted into salt form using 0.1M aqueous HCl solution. After a lyophilisation step, the expected compound is obtained in the form of a solid.
High-Resolution Mass Spectrometry (ESI/FIA/HR and MS/MS):
Empirical formula: $C_{42}H_{40}ClN_5O_5$
[M+H]$^+$ calculated: 730.2791
[M+H]$^+$ measured: 730.2790

Example 396. N-(3-Fluoro-4-hydroxyphenyl)-1,2-dimethyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide hydrochloride The title compound is obtained in accordance with the process of Example 1 using the acid of Preparation 11 and (3S)-3-(4-morpholinylmethyl)-1,2,3,4-tetrahydroisoquinoline (see Preparation 3') in Step A, and the compound of Preparation 20″ in Step C. The product obtained is finally subjected to a step of conversion into salt form in the presence of 1M HCl in ether. After filtration and lyophilisation in a mixture of acetonitrile/water, the expected compound is obtained.
Elemental Microanalysis: (%, Theoretical:Measured)
% C=65.79:65.43; % H=5.39:5.19; % N=11.31:11.21; % Cl=4.77:4.34
High-Resolution Mass Spectrometry (ESI/FIA/HR and MS/MS):
Empirical formula: $C_{39}H_{39}FN_6O_6$
[M+H]$^+$ calculated: 707.2988
[M+H]$^+$ measured: 707.2988

Example 397. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(2-methoxypyrimidin-5-yl)-1,2-dimethyl-1H-pyrrole-3-carboxamide High-Resolution Mass Spectrometry (ESI+):
Empirical formula: $C_{39}H_{39}ClN_6O_5$
[M+H]$^+$ calculated: 707.2743
[M+H]$^+$ measured: 707.2746

Example 398. 5-(5-Chloro-2-{[(3S)-3-(morpholin-4-ylmethyl)-3,4-dihydroisoquinolin-2(1H)-yl]carbonyl}phenyl)-N-(3-cyanophenyl)-N-(4-hydroxyphenyl)-1,2-dimethyl-1H-pyrrole-3-carboxamide hydrochloride Elemental Microanalysis: (%, Theoretical:Measured)
% C=66.85:66.75; % H=5.34:5.42; % N=9.51:9.73; % Cl=9.62:9.67; % Cl$^-$=4.81:4.71

High-Resolution Mass Spectrometry (ESI+–/FIA/HR, ESI–/FIA):
Empirical formula: $C_{41}H_{38}ClN_5O_4$
[M+H]$^+$ calculated: 700.2685
[M+H]$^+$ measured: 700.2686

Example 399. 5-(5-Chloro-2-{[(3S)-3-(morpholin-4-ylmethyl)-3,4-dihydroisoquinolin-2(1H)-yl]carbonyl}phenyl)-N-(3-fluoro-4-hydroxyphenyl)-1,2-dimethyl-N-(1-methyl-1H-pyrazol-4-yl)-1H-pyrrole-3-carboxamide hydrochloride The title compound is obtained in accordance with the process of Example 1 using the acid of Preparation 1 and (3S)-3-(4-morpholinylmethyl)-1,2,3,4-tetrahydroisoquinoline (see Preparation 3') in Step A, and the compound of Preparation 20" in Step C. The product obtained is finally subjected to a step of conversion into salt form in the presence of 1M HCl in ether. After filtration and lyophilisation in a mixture of acetonitrile/water, the expected compound is obtained.

Elemental Microanalysis: (%, Theoretical:Measured)
% C=62.21:61.32; % H=5.36:5.18; % N=11.46:11.14; % Cl=9.66:10.16; % Cl$^-$=4.83:5.23

High-Resolution Mass Spectrometry (ESI+–/FIA/HR, ESI–/FIA):
Empirical formula: $C_{38}H_{38}ClFN_6O_4$
[M+H]$^+$ calculated: 697.2700
[M+H]$^+$ measured: 697.2704

Example 400. Methyl 2-[{[5-(5-chloro-2-{[3S)-3-(morpholin-4-ylmethyl)-3,4-dihydro-isoquinolin-2(1H)-yl]carbonyl}phenyl)-1,2-dimethyl-1H-pyrrol-3-yl]carbonyl}(4-hydroxyphenyl)amino]pyridine-4-carboxylate hydrochloride The title compound is a secondary product which forms in the course of synthesis of Example 110 (in the final Step before the step of conversion into salt form) owing to hydrolysis of the nitrile function into a methyl ester function. The compound is separated from that of Example 110 by chromatography over silica gel in a mixture of methanol and dichloromethane.

Elemental Microanalysis: (%, Theoretical:Measured)
% C=63.90:64.43; % H=5.36:5.01; % N=9.09:9.34; % Cl$^-$=4.60:4.46

High-Resolution Mass Spectrometry (ESI+/HR and ESI–/LR):
Empirical formula: $C_{41}H_{40}ClN_5O_6$
[M+H]$^+$ calculated: 734.2740
[M+H]$^+$ measured: 734.2743

Example 401. 5-(5-Chloro-2-{[(3S)-3-(morpholin-4-ylmethyl)-3,4-dihydroisoquinolin-2(1H)-yl]carbonyl}phenyl)-N-(3-cyano-4-fluorophenyl)-N-(4-hydroxyphenyl)4,2-dimethyl-1H-pyrrole-3-carboxamide hydrochloride Elemental Microanalysis: (%, Theoretical:Measured)
% C=65.25:64.23; % H=5.07:4.71; % N=9.28:9.36; % Cl=9.40:9.59; % Cl$^-$=4.70:4.50

High-Resolution Mass Spectrometry (ESI+–/FIA/HR, ESI–/FIA):
Empirical formula: $C_{41}H_{37}ClFN_5O_4$
[M+H]$^+$ calculated: 718.2591
[M+H]$^+$ measured: 718.2593

Example 402. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-{1-[(3S or R)-tetrahydrofuran-3-yl]-1H-pyrazol-4-yl}-1H-pyrrole-3-carboxamide hydrochloride Elemental Microanalysis: (%, Theoretical:Measured)
% C=65.20:65.92; % H=5.87:5.78; % N=11.13:10.36% Cl$^-$=4.69:4.79)

High-Resolution Mass Spectrometry (ESI+):
Empirical formula: $C_{41}H_{43}FN_6O_5$
[M+H]$^+$ calculated: 719.3359
[M+H]$^+$ measured: 719.3362 and

Example 403. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-{1-[(3R or S)-tetrahydrofuran-3-yl]-1H-pyrazol-4-yl}-1H-pyrrole-3-carboxamide hydrochloride Elemental Microanalysis: (%, Theoretical:Measured)
% C=65.20:66.04; % H=5.87:5.87; % N=11.13:10.62; % Cl$^-$=4.69:4.76

High-Resolution Mass Spectrometry (ESI/+):
Empirical formula: $C_{41}H_{43}FN_6O_5$
[M+H]$^+$ calculated: 719.3359
[M+H]$^+$ measured: 719.3350

The compounds of Examples 402 and 403 are obtained in accordance with the process of Example 1 using the acid of Preparation 8 and the compound of Preparation 3' in Step A, and the compound of Preparation 22" in Step C. The diastereoisomers obtained are separated by chiral chromatography and then converted into salt form and lyophilised as described in the general process to yield the title compounds.

Example 404. 5-(5-Chloro-2-{[(3S)-3-(morpholin-4-ylmethyl)-3,4-dihydroisoquinolin-2(1H)-yl]carbonyl}phenyl)-N-(2-cyanopyrimidin-4-yl)-N-(4-hydroxyphenyl)-1,2-dimethyl4H-pyrrole-3-carboxamide hydrochloride

Example 405. 5-(5-Chloro-2-{[(3S)-3-(morpholin-4-ylmethyl)-3,4-dihydroisoquinolin-2(1H)-yl]carbonyl}phenyl)-1,2-dimethyl-N-(1-methyl-1H-pyrrolo[2,3-b]pyridin-5-yl)-N-(pyridazin-4-yl)-pyrrole-3-carboxamide dihydrochloride The title compound is obtained in accordance with the process of Example 1 using the acid of Preparation 1 and the compound of Preparation 3' in Step A, and the appropriate amine in Step C, it being understood that Step D is not carried out. The compound obtained is converted into salt form and lyophilised as described in the general process to obtain the title compound.

High-Resolution Mass Spectrometry (ESI+−/FIA/HR, ESI−/FIA):
Empirical formula: $C_{40}H_{39}ClN_8O_3$
$[M+H]^+$ calculated: 715.2906
$[M+H]^+$ measured: 715.2909

Example 406. N-(5-Cyano-1,2-dimethyl-1H-pyrrol-3-yl)-N-(4-hydroxyphenyl)-1,2-dimethyl-5-(2-{[(3S)-3-(morpholin-4-ylmethyl)-3,4-dihydroisoquinolin-2(1H)-yl]carbonyl}phenyl)-1H-pyrrole-3-carboxamide hydrochloride The title compound is obtained in accordance with the process of Example 1 using the acid of Preparation 25 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=68.46:68.27; % H=6.03:5.12; % N=11.68:11.75; % Cl⁻=4.93:4.73

High-Resolution Mass Spectrometry (ESI/FIA/HR and MS/MS, ESI−/FIA):
Empirical formula: $C_{41}H_{42}N_6O_4$
$[M+H]^+$ calculated: 683.3340
$[M+H]^+$ measured: 683.3334

Example 407. N-(3-Fluoro-4-hydroxyphenyl)-5-(5-methoxy-2-{[(3S)-3-(morpholin-4-ylmethyl)-3,4-dihydroisoquinolin-2(1H)-yl]carbonyl}phenyl)-1,2dimethyl-N-(1-methyl4H-pyrazol-4-yl)-1H-pyrrole-3-carboxamide hydrochloride The title compound is obtained in accordance with the process of Example 1 using the acid of Preparation 12 and the compound of Preparation 3' in Step A, and the compound of Preparation 20" in Step C. The compound obtained is converted into salt form and lyophilised as described in the general process to obtain the title compound.

Elemental Microanalysis: (%, Theoretical:Measured)
% C=64.23:63.94; % H=5.80:5.00; % N=11.52:11.56; % Cl⁻=4.86:4.99

High-Resolution Mass Spectrometry (ESI+−/FIA/HR and MS/MS, ESI−/FIA):
Empirical formula: $C_{39}H_{41}FN_6O_5$
$[M+H]^+$ calculated: 693.3195
$[M+H]^+$ measured: 693.3191

Example 408. N-(5-Cyano-1,2-dimethyl-1H-pyrrol-3-yl)-N-(4-hydroxyphenyl)-5-(5-methoxy-2-{[(3S)-3-(morpholin-4-ylmethyl)-3,4-dihydroisoquinolin-2(1H)-yl]carbonyl}phenyl)-1,2-dimethyl-1H-pyrrole-3-carboxamide hydrochloride The title compound is obtained in accordance with the process of Example 1 using the acid of Preparation 12 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=67.32:67.30; % H=6.05:5.28; % N=11.22:11.15; % Cl⁻=4.73:4.59

High-Resolution Mass Spectrometry (ESI+−/FIA/HR and ESI−/FIA):
Empirical formula: $C_{42}H_{44}N_6O_5$
$[M+H]^+$ calculated: 713.3446
$[M+H]^+$ measured: 713.3443

Example 409. N-(4-Hydroxyphenyl)-1,2-dimethyl-N-(1-methyl-1H-pyrrolo[2,3-b]-pyridin-5-yl)-5-(2-{[(3S)-3-(morpholin-4-ylmethyl)-3,4-dihydroisoquinolin-2(1H)-yl]-carbonyl}phenyl)-1H-pyrrole-3-carboxamide hydrochloride The title compound is obtained in accordance with the process of Example 1 using the acid of Preparation 25 and the compound of Preparation 3' in Step A, and the compound of Preparation 11" in Step C. The compound obtained is converted into salt form and lyophilised as described in the general process to obtain the title compound.

Elemental Microanalysis: (%, Theoretical:Measured)
% C=68.98:68.95; % H=5.93:4.76; % N=11.49:11.43

High-Resolution Mass Spectrometry (ESI/FIA/HR and MS/MS):
Empirical formula: $C_{42}H_{42}N_6O_4$
$[M+H]^+$ calculated: 695.3340
$[M+H]^+$ measured: 695.3341

Example 410. N-(4-Hydroxyphenyl)-1,2-dimethyl-N-(1-methyl-2,3-dihydro-1H-pyrrolo[2,3-b]pyridin-5-yl)-5-(2-{[(3S)-3-(morpholin-4-ylmethyl)-3,4-dihydroiso-quinolin-2(1H)-yl]carbonyl}phenyl)-1H-pyrrole-3-carboxamide hydrochloride The title compound is obtained in accordance with the process described in Step B of Example 49 using Example 409 as starting material. The compound obtained is converted into salt form and lyophilised as described in the general process to obtain the title compound.

High-Resolution Mass Spectrometry (ESI/FIA/HR and ESI−/FIA):
Empirical formula: $C_{42}H_{44}N_6O_4$
$[M+H]^+$ calculated: 697.3497
$[M+H]^+$ measured: 697.3497

Example 411. 5-(5-Chloro-2-{[(3R)-3-methyl-3,4-dihydroisoquinolin-2(1H)-yl]carbonyl}phenyl)-N-(4-hydroxyphenyl)-2-methyl-N-(1-methyl-1H-pyrazol-4-yl)-[2-(morpholin-4yl)ethyl]-1H-pyrrole-3-carboxamide hydrochloride The title compound is obtained in accordance with the process of Example 96 using the acid of Preparation 30, the compound of Preparation 1', and the compound of Preparation 1". The compound obtained is converted into salt form and lyophilised as described in the general process to obtain the title compound.

High-Resolution Mass Spectrometry (ESI/FIA/HR and MS/MS):
Empirical formula: $C_{39}H_{41}ClN_6O_4$
$[M+H]^+$ calculated: 693.2951
$[M+H]^+$ measured: 693.2947

Example 412. 5-(5-Chloro-2-{[(3R)-3-[3-(morpholin-4-yl)propyl]-3,4-dihydroiso-quinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 6' in Step A, and the compound of Preparation 18" in Step C. The compound obtained is converted into salt form and lyophilised as described in the general process to obtain the title compound.

Elemental Microanalysis: (%, Theoretical:Measured)
% C=66.06:65.61; % H=5.93:5.22; % N=10.75:10.69; % Cl⁻=4.53:4.68

High-Resolution Mass Spectrometry (ESI/FIA/HR and MS/MS, ESI–/FIA):

Empirical formula: $C_{43}H_{45}ClN_6O_4$
$[M+H]^+$ calculated: 745.3264
$[M+H]^+$ measured: 745.3260

Example 413. N-(5-Cyano-1,2-dimethyl-1H-pyrrol-3-yl)-N-(4-hydroxyphenyl)-1,2-dimethyl-5-(7-{[(3S)-3-(morpholin-4-ylmethyl)-3,4-dihydroisoquinolin-2(1H)-yl]-carbonyl}-2,3-dihydro-1,4-benzodioxin-6-yl)-1H-pyrrole-3-carboxamide hydrochloride The title compound is obtained in accordance with the process of Example 1 using the acid of Preparation 13 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=66.44:66.40; % H=5.83:4.84; % N=10.81:10.79; % Cl⁻=4.56:4.22

High-Resolution Mass Spectrometry (ESI/FIA/HR and MS/MS, ESI–/FIA):

Empirical formula: $C_{43}H_{44}N_6O_6$
$[M+H]^+$ calculated: 741.3395
$[M+H]^+$ measured: 741.3397

Example 414. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(5-methyl-5H-pyrrolo[3,2-d]pyrimidin-2-yl)-1H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.

Elemental Microanalysis: (%, Theoretical:Measured)
% C=64.23:64.38; % H=5.39:5.25; % N=12.79:12.62; % Cl⁻=4.62:4.39

High-Resolution Mass Spectrometry (ESI/FIA/HR and MS/MS, ESI–/FIA):

Empirical formula: $C_{41}H_{40}ClN_7O_4$
$[M+H]^+$ calculated: 730.2903
$[M+H]^+$ measured: 730.2904

Example 415. 5-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1-methyl-1H-pyrrole-3-carboxamide hydrochloride The title compound is obtained in accordance with the process of Example 1 using the acid of Preparation 3 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=64.95:65.14; % H=5.45:5.34; % N=11.36:11.36; % Cl⁻=4.79:4.67

High-Resolution Mass Spectrometry (ESI+–/FIA/HR, ESI–/FIA):

Empirical formula: $C_{40}H_{39}ClN_6O_4$
$[M+H]^+$ calculated: 703.2794
$[M+H]^+$ measured: 703.2795

Example 416. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuterio-methyl)-1H-pyrazol-4-yl]-1H-pyrrole-3-carboxamide hydrochloride The title compound is obtained in accordance with the process of Example 1 using the acid of Preparation 1 and the compound of Preparation 3' in Step A, and the compound of Preparation 25" in Step C. The compound obtained is converted into salt form and lyophilised as described in the general process to obtain the title compound.

Elemental Microanalysis: (%, Theoretical:Measured)
% C=63.51:63.41; % H=5.63:5.42; % N=11.69:11.61; % Cl⁻=4.93:4.85

High-Resolution Mass Spectrometry (ESI+–/FIA/HR, ESI–/FIA):

Empirical formula: $C_{38}H_{36}ClD_3N_6O_4$
$[M+H]^+$ calculated: 682.2982
$[M+H]^+$ measured: 682.2986

Example 417. N-(5-Cyano-1,2-dimethyl-1H-pyrrol-3-yl)-N-(4-hydroxyphenyl)-5-(4-methoxy-2-{[(3S)-3-(morpholin-4-ylmethyl)-3,4-dihydroisoquinolin-2(1H)-yl]carbonyl}phenyl)-1,2-dimethyl-1H-pyrrole-3-carboxamide hydrochloride The title compound is obtained in accordance with the process of Example 1 using the acid of Preparation 31 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=67.32:67.56; % H=6.05:5.84; % N=11.22:11.21; % Cl⁻=4.73:4.71

High-Resolution Mass Spectrometry (ESI/FIA/HR and MS/MS, ESI–/FIA):

Empirical formula: $C_{42}H_{44}N_6O_5$
$[M+H]^+$ calculated: 713.3446
$[M+H]^+$ measured: 713.3446

Example 418. N-(4-Hydroxyphenyl)-5-(4-methoxy-2-{[(3S)-3-(morpholin-4-ylmethyl)-3,4-dihydroisoquinolin-2(1H)-yl]carbonyl}phenyl)-1,2dimethyl-N-(1-methyl-1H-pyrazol-4-yl)-1H-pyrrole-3-carboxamide hydrochloride The title compound is obtained in accordance with the process of Example 1 using the acid of Preparation 31 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)
% C=65.86:65.51; % H=6.09:6.09; % N=11.82:11.73; % Cl⁻=4.98:5.14

High-Resolution Mass Spectrometry (ESI/FIA/HR, ESI-/FIA):
Empirical formula: $C_{39}H_{42}N_6O_5$
[M+H]⁺ calculated: 675.3289
[M+H]⁺ measured: 675.3286

Example 419. N-(3-Cyanophenyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the compound of Preparation 41" in Step C. The compound obtained is converted into salt form and lyophilised as described in the general process to obtain the title compound.

High-Resolution Mass Spectrometry (ESI+):
Empirical formula: $C_{41}H_{38}FN_5O_4$
[M+H]⁺ calculated: 684.2988
[M+H]⁺ measured: 684.2975

Example 420. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuterio-methyl)-1H-pyrazol-4-yl]-1H-pyrrole-3-carboxamide hydrochloride The title compound is obtained in accordance with the process of Example 1 using the acid of Preparation 8 and the compound of Preparation 3' in Step A, and the compound of Preparation 25" in Step C. The compound obtained is converted into salt form and lyophilised as described in the general process to obtain the title compound.

High-Resolution Mass Spectrometry (ESI/+):
Empirical formula: $C_{38}D_3H_{36}FN_6O_4$
[M+H]⁺ calculated: 666.3285
[M+H]⁺ measured: 666.3265

Example 421. N-(5-Cyano-1,2-dimethyl-1H-pyrrol-3-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the compound of Preparation 18" in Step C. The compound obtained is converted into salt form and lyophilised as described in the general process to obtain the title compound.

High-Resolution Mass Spectrometry (ESI/FIA/HR and MS/MS):
Empirical formula: $C_{41}H_{41}FN_6O_4$
[M+H]⁺ calculated: 701.3246
[M+H]⁺ measured: 701.3282

Example 422. N-(4-Hydroxyphenyl)-1,2-dimethyl-N-(1-methyl-1H-pyrazol-4-yl)-5-(2-{[(3S)-3-(morpholin-4-ylmethyl)-3,4-dihydroisoquinolin-2(1H)-yl]carbonyl}phenyl)-1H-pyrrole-3-carboxamide hydrochloride The title compound is obtained in accordance with the process of Example 1 using the acid of Preparation 25 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)
% C=67.00:67.47; % H=6.07:5.54; % N=12.34:12.46; % Cl⁻=5.20:4.58

High-Resolution Mass Spectrometry (ESI+-/FIA/HR, ESI-/FIA):
Empirical formula: $C_{38}H_{40}N_6O_4$
[M+H]⁺ calculated: 645.3184
[M+H]⁺ measured: 645.3182

Example 423. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(oxetan-3-yl)-1H-pyrazol-4-yl]-1H-pyrrole-3-carboxamide The title compound is obtained in accordance with the process of Example 1 using the acid of Preparation 8 and the compound of Preparation 3' in Step A, and the compound of Preparation 26" in Step C.

Elemental Microanalysis: (%, Theoretical:Measured)
% C=68.17:67.82; % H=5.86:5.97; % N=11.92:11.48

High-Resolution Mass Spectrometry (ESI/FIA/HR and MS/MS):
Empirical formula: $C_{40}H_{41}FN_6O_5$
[M+H]⁺ calculated: 705.3202
[M+H]⁺ measured: 705.3207

Example 424. N-(4-Hydroxyphenyl)-N-(2-methoxypyrimidin-5-yl)-1,2-dimethyl-5-(2-{[(3S)-3-(morpholin-4-ylmethyl)-3,4-dihydroisoquinolin-2(1H)-yl]carbonyl}phenyl)-1H-pyrrole-3-carboxamide hydrochloride The title compound is obtained in accordance with the process of Example 1 using the acid of Preparation 25 and the compound of Preparation 3' in Step A, and the compound of Preparation 12" in Step C. The compound obtained is converted into salt form and lyophilised as described in the general process to obtain the title compound.

Elemental Microanalysis: (%, Theoretical:Measured)
% C=66.05:65.63; % H=5.83:5.45; % N=11.85:11.93; % Cl⁻=5.00:4.91

High-Resolution Mass Spectrometry (ESI+-/FIA/HR, ESI-/FIA):
Empirical formula: $C_{39}H_{40}N_6O_5$
[M+H]⁺ calculated: 673.3133
[M+H]⁺ measured: 673.3129

Example 425. N-(3-Cyano-5-methoxyphenyl)-5-(5-fluoro-2-{[(3,5)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the appropriate amine in Step C. The compound obtained is converted into salt form and lyophilised as described in the general process to obtain the title compound.
Elemental Microanalysis: (%, Theoretical:Measured)
% C=67.25:66.55; % H=5.51:5.28; % N=9.33:8.55% $Cl^-$=4.73:4.67

Example 426. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-N-(2-methoxypyrimidin-5-yl)-1,2-dimethyl-1H-pyrrole-3-carboxamide The title compound is obtained in accordance with the process of Example 1 using the acid of Preparation 8 and the compound of Preparation 3' in Step A, and the compound of Preparation 12" in Step C.
High-Resolution Mass Spectrometry (ESI/FIA/HR and MS/MS):
Empirical formula: $C_{39}H_{39}FN_6O_5$
[M+H]$^+$ calculated: 691.3038
[M+H]$^+$ measured: 691.3060

Example 427. N-(3-Cyano-4-methoxyphenyl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the appropriate amine in Step C. The compound obtained is converted into salt form and lyophilised as described in the general process to obtain the title compound.
Elemental Microanalysis: (%, Theoretical:Measured)
% C=67.24:66.41; % H=5.51:5.35; % N=9.33:8.97% $Cl^-$=4.73:4.81

Example 428. N-(5-Cyano-1,2-dimethyl-1H-pyrrol-3-yl)-5-(4-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 26 and the compound of Preparation 3' in Step A, and the compound of Preparation 18" in Step C. The compound obtained is converted into salt form and lyophilised as described in the general process to obtain the title compound.
Elemental Microanalysis: (%, Theoretical:Measured)
% C=66.79:66.97; % H=5.74:5.36; % N=11.40:11.45; % $Cl^-$=4.81:4.53
High-Resolution Mass Spectrometry (ESI+-/FIA/HR, ESI-/FIA):
Empirical formula: $C_{41}H_{41}FN_6O_4$
[M+H]$^+$ calculated: 701.3246
[M+H]$^+$ measured: 701.3245

Example 429. N-(5-Cyano-1,2-dimethyl-1H-pyrrol-3-yl)-5-(4-fluoro-5-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 27 and the compound of Preparation 3' in Step A, and the compound of Preparation 18" in Step C. The compound obtained is converted into salt form and lyophilised as described in the general process to obtain the title compound.
Elemental Microanalysis: (%, Theoretical:Measured)
% C=65.75:65.43; % H=5.78:5.57; % N=10.95:10.81; % $Cl^-$=4.62:4.54
High-Resolution Mass Spectrometry (ESI/FIA/HR and MS/MS, ESI-/FIA):
Empirical formula: $C_{42}H_{43}FN_6O_5$
[M+H]$^+$ calculated: 731.3352
[M+H]$^+$ measured: 731.3351

Example 430. 5-(5-Chloro-2-{[3-(trifluoromethyl)-3,4-dihydroisoquinolin-2(1H)-yl]-carbonyl}phenyl)-N-(4-hydroxyphenyl)-1,2-dimethyl-N-(1-methyl-1H-pyrrolo[2,3-b]-pyridin-5-yl)-1H-pyrrole-3-carboxamide The title compound is obtained in accordance with the process of Example 1 using the acid of Preparation 1 and racemic 3-(trifluoromethyl)-1,2,3,4-tetrahydroisoquinoline in Step A, and the compound of Preparation 11" in Step C.
High-Resolution Mass Spectrometry (ESI+-/FIA/HR and MS/MS, ESI-/FIA):
Empirical formula: $C_{38}H_{31}ClF_3N_5O_3$
[M+H]$^+$ calculated: 698.2140
[M+H]$^+$ measured: 698.2144

Example 431. 5-(5-Chloro-2-{[(3S)-3-(morpholin-4-ylmethyl)-3,4-dihydroisoquinolin-2(1H)-yl]carbonyl}phenyl)-N-(1,3-dimethyl-1H-pyrazol-4-yl)-N-(4-hydroxyphenyl)-1,2-dimethyl-1H-pyrrole-3-carboxamide hydrochloride Elemental Microanalysis: (%, Theoretical:Measured)
% C=64.19:64.37; % H=5.80:5.18; % N=11.52:11.55; % $Cl^-$=4.86:4.68
High-Resolution Mass Spectrometry (ESI+-/FIA/HR, ESI-/FIA):
Empirical formula: $C_{39}H_{41}ClN_6O_4$
[M+H]$^+$ calculated: 693.2951
[M+H]$^+$ measured: 693.2952
and

Example 432. 5-(5-Chloro-2-{[(3S)-3-(morpholin-4-ylmethyl)-3,4-dihydroisoquinolin-2(1H)-yl]carbonyl}phenyl)-N-(1,5-dimethyl-1H-pyrazol-4-yl)-N-(4-hydroxyphenyl)-1,2-dimethyl-1H-pyrrole-3-carboxamide hydrochloride Elemental Microanalysis: (%, Theoretical:Measured)
% C=64.19:64.43; % H=5.80:5.22; % N=11.52:11.60; % $Cl^-$=4.86:4.66

High-Resolution Mass Spectrometry (ESI+−/FIA/HR, ESI−/FIA):

Empirical formula: $C_{39}H_{41}ClN_6O_4$
[M+H]$^+$ calculated: 693.2951
[M+H]$^+$ measured: 693.2953

The compounds of Examples 431 and 432 are obtained in accordance with the process of Example 1 using the acid of Preparation 1 and the compound of Preparation 3' in Step A, and the mixture of Preparation 27" in Step C. At the end of Step D, the isomers are separated by preparative HPLC using acetonitrile and water-TFA as eluants. After evaporating off the solvent and neutralising with sodium bicarbonate, the products are subjected to a step of conversion into salt form in the presence of 1M HCl in ether. After filtration and lyophilisation in a mixture of acetonitrile/water, the title products are obtained.

Example 433. N-(5-Cyano-1-methyl-1H-pyrrol-3-yl)-N-(4-hydroxyphenyl)-1,2-dimethyl-5-(2-{[(3S)-3-(morpholin-4-ylmethyl)-3,4-dihydroisoquinolin-2(1H)-yl]carbonyl}phenyl)-1H-pyrrole-3-carboxamide hydrochloride The title compound is obtained in accordance with the process of Example 1 using the acid of Preparation 25 and the compound of Preparation 3' in Step A, and the compound of Preparation 19" in Step C. The compound obtained is converted into salt form and lyophilised as described in the general process to obtain the title compound.

Elemental Microanalysis: (%, Theoretical:Measured)
% C=68.12:68.29; % H=5.86:5.40; % N=11.92:12.05; % Cl$^-$=5.03:4.92

High-Resolution Mass Spectrometry (ESI/FIA/HR and MS/MS):
Empirical formula: $C_{40}H_{40}N_6O_4$
[M+H]$^+$ calculated: 669.3184
[M+H]$^+$ measured: 669.3184

Example 434. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide hydrochloride The title compound is obtained in accordance with the process described in Step B of Example 49 using Example 385 as starting material. The compound obtained is converted into salt form and lyophilised as described in the general process to obtain the title compound.

Elemental Microanalysis: (%, Theoretical:Measured)
% C=67.15:68.03; % H=5.90:5.50; % N=11.19:10.59% Cl$^-$=4.72:5.55

Example 435. N-(4-Cyanopyridin-2-yl)-5-(5-fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 14 and the compound of Preparation 3' in Step A, and the appropriate amine in Step C. The compound obtained is converted into salt form and lyophilised as described in the general process to obtain the title compound.

High-Resolution Mass Spectrometry (ESI+−/FIA/HR, ESI−/FIA):

Empirical formula: $C_{41}H_{39}FN_6O_5$
[M+H]$^+$ calculated: 715.3039
[M+H]$^+$ measured: 715.3040

Example 436. 5-(5-Chloro2-{[(3S)-3-(morpholin-4-ylmethyl)-3,4-dihydroisoquinolin-2(1H)-yl]carbonyl}phenyl)-N-(5-cyanothiophen-2-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.

Elemental Microanalysis: (%, Theoretical:Measured)
% C=63.07:63.09; % H=5.02:4.78; % N=9.43:9.35; %S=4.32:4.09; % Cl$^-$=4.77:4.59

High-Resolution Mass Spectrometry (ESI/FIA/HR and MS/MS, ESI+−/FIA):
Empirical formula: $C_{39}H_{36}ClN_5O_4S$
[M+H]$^+$ calculated: 706.2249:
[M+H]$^+$ measured: 706.2250

Example 437. N-(3-Cyano-4-fluorophenyl)-5-(5-fluoro-2-{[(3S)-3-(morpholin-4-ylmethy3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 8 and the compound of Preparation 3' in Step A, and the appropriate amine in Step C. The compound obtained is converted into salt form and lyophilised as described in the general process to obtain the title compound.

High-Resolution Mass Spectrometry (ES+):
Empirical formula: $C_{41}H_{37}F_2N_5O_4$
[M+H]$^+$ calculated: 702.2894
[M+H]$^+$ measured: 702.2886

Example 438. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(pyrazin-2-yl_-1H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.

Elemental Microanalysis: (%, Theoretical:Measured)
% C=63.95:63.96; % H=5.37:5.17; % N=11.78:11.61; % Cl$^-$=4.97:4.57

High-Resolution Mass Spectrometry (ESI+/HR, ESI−/LR):
Empirical formula: $C_{38}H_{37}ClN_6O_4$
[M+H]$^+$ calculated: 677.2638
[M+H]$^+$ measured: 677.2639

Example 439. 5-(5-Fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-N-(2-methoxypyrimidin-5-yl)-1,2-dimethyl-1H-pyrrole-3-carboxamide hydrochloride The title compound is obtained in accordance with the process of Example 1 using the acid of Preparation 14 and the compound of Preparation 3' in Step A, and the compound of Preparation 12" in Step C. The compound obtained is converted into salt form and lyophilised as described in the general process to obtain the title compound.

High-Resolution Mass Spectrometry (ESI/FIA/HR and MS/MS, ESI−/FIA):

Empirical formula: $C_{40}H_{41}FN_6O_6$ $[M+H]^+$ calculated: 721.3144

$[M+H]^+$ measured: 721.3144

Example 440. N-(5-Cyano-1,2-dimethyl-1H-pyrrol-3-yl)-5-(5-fluoro-4-methoxy-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride The title compound is obtained in accordance with the process of Example 1 using the acid of Preparation 14 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)

% C=65.75:65.98; % H=5.78:5.50; % N=10.95:10.87; % Cl−=4.62:4.42

High-Resolution Mass Spectrometry (ESI+/HR, ESI−/LR):

Empirical formula: $C_{42}H_{43}FN_6O_5$ $[M+H]^+$ calculated: 731.3352

$[M+H]^+$ measured: 731.3353

Example 441. 5-(5-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-1,2-dimethyl-N-phenyl-1H-pyrrole-3-carboxamide hydrochloride The title compound is obtained in accordance with the process of Example 1 using the acid of Preparation 1 and the compound of Preparation 3' in Step A, and the compound of Preparation 29" in Step C, it being understood that Step D is not carried out. The compound obtained is converted into salt form and lyophilised as described in the general process to obtain the title compound.

Elemental Microanalysis: (%, Theoretical:Measured)

% C=66.75:66.44; % H=5.74:5.59; % N=11.39:11.45; % Cl−=4.81:4.43

High-Resolution Mass Spectrometry (ESI+/HR, ESI−/LR):

Empirical formula: $C_{41}H_{41}ClN_6O_3$ $[M+H]^+$ calculated: 701.3001

$[M+H]^+$ measured: 701.2998

Example 442. 5-(5-Chloro-2-{[(3S)-3-(morpholin-4-ylmethyl)-3,4-dihydroisoquinolin-2(1H)-yl]carbonyl}phenyl)-N-(5-cyanothiophen-3-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 42" in Step C. The compound obtained is converted into salt form and lyophilised as described in the general process to obtain the title compound.

Elemental Microanalysis: (%, Theoretical:Measured)

% C=63.07:63.14; % H=5.02:4.87; % N=9.43:9.41; % S=4.32:4.24; % Cl−=4.77:4.57

High-Resolution Mass Spectrometry (ESI+/HR, ESI−/LR):

Empirical formula: $C_{39}H_{36}ClN_5O_4S$ $[M+H]^+$ calculated: 706.2249

$[M+H]^+$ measured: 706.2252

Example 443. 5-(5-Fluoro-4-hydroxy-2-{[(3S)-3-(morpholin-4-ylmethyl)-3,4-dihydroisoquinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide Step A: 5-(5-Fluoro-4-methoxy-2-{[(3S)-3-(morpholin-4-ylmethyl)-3,4-dihydroiso-quinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide The title compound is obtained in accordance with the process of Example 1 (Steps A to C) using the acid of Preparation 28 and the compound from Preparation 3' in Step A, and the compound of Preparation 30" in Step C.

Step B: 5-(5-Fluoro-4-hydroxy-2-{[(3S)-3-(morpholin-4-ylmethyl)-3,4-dihydroiso-quinolin-2(1H)-yl]carbonyl}phenyl)-1,2-dimethyl-N-(1-methyl-1H-pyrrolo[2,3-b]pyridin-5-yl)-N-phenyl-1H-pyrrole-3-carboxamide To a solution of the compound of Step A (1 g; 1.37 mmol) in anhydrous dichloromethane (10 mL) there is added, dropwise at 0° C., a 1M solution of boron tribromide in dichloromethane (1.8 mL; 1.8 mmol). After stirring for 15 hours at ambient temperature, the reaction mixture is poured dropwise into a solution of ethanol (15 mL) at -10° C. After stirring for one hour, saturated aqueous sodium bicarbonate solution is added, and the reaction mixture is extracted with dichloromethane. After drying over MgSO$_4$, the residue is purified on a silica gel column using a mixture of dichloromethane and methanol as eluant to yield the expected product.

High-Resolution Mass Spectrometry (ESI+/HR, ESI−/LR):

Empirical formula: $C_{42}H_{41}FN_6O_4$ $[M+H]^+$ calculated: 713.3246

$[M+H]^+$ measured: 713.3244

Example 444. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-N-(5-methoxypyrazin-2-yl)-1,2-dimethyl4H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.

Elemental Microanalysis: (%, Theoretical:Measured)

% C=62.99:62.72; % H=5.42:5.24; % N=11.30:11.19; % Cl$^-$=4.77:4.67

High-Resolution Mass Spectrometry (ESI+/HR, ESI−/LR):

Empirical formula: $C_{39}H_{39}ClN_6O_5$

[M+H]$^+$ calculated: 707.2743

[M+H]$^+$ measured: 707.2747

Example 445. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuteriomethyl)-2,3-dihydro-1H-pyrrolo[2,3-b]pyridin-5-yl]-1H-pyrrole-3-carboxamide hydrochloride Step A: 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuteriomethyl)-1H-pyrrolo[2,3-b]pyridin-5-yl]-1H-pyrrole-3-carboxamide The intermediate is obtained in accordance with the process of Example 1 using the acid of Preparation 1 and the compound of Preparation 3' in Step A, and the compound of Preparation 31" in Step C.

Step B: 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-[1-(trideuteriomethyl)-2,3-dihydro-1H-pyrrolo[2,3-b]pyridin-5-yl]-1H-pyrrole-3-carboxamide hydrochloride The procedure is in accordance with the protocol described in Step B of Example 49, it being understood that the product is then subjected to a step of conversion into salt form in the presence of 1M HCl in ether. After filtration and lyophilisation in a mixture of acetonitrile/water, the title product is obtained.

Elemental Microanalysis: (%, Theoretical:Measured)

% C=65.45:65.33; % H=5.78:5.59; % N=10.90:10.82; % Cl$^-$=4.60:4.28

High-Resolution Mass Spectrometry (ESI+/HR, ESI−/LR):

Empirical formula: $C_{42}H_{40}ClD_3N_6O_4$

[M+H]$^+$ calculated: 734.3295

[M+H]$^+$ measured: 734.3300

Example 446. 5-(5-Chloro-2-{[(3S)-3-(morpholin-4-ylmethyl)-3,4-dihydroisoquinolin-2(1H)-yl]carbonyl}phenyl)-N-(5-fluoropyrazin-2-yl)-N-(4-hydroxyphenyl)-1,2-dimethyl4H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.

Elemental Microanalysis: (%, Theoretical:Measured)

% C=62.28:62.16; % H=5.10:4.97; % N=11.04:11.35; % Cl$^-$=4.85:4.48

High-Resolution Mass Spectrometry (ESI+/HR, ESI−/LR):

Empirical formula: $C_{38}H_{36}ClFN_6O_4$

[M+H]$^+$ calculated: 695.2543

[M+H]$^+$ measured: 695.2545

Example 447. 5-(4-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazol-4-yl)-1H-pyrrole-3-carboxamide hydrochloride The title compound is obtained in accordance with the process of Example 1 using the acid of Preparation 26 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)

% C=65.28:65.27; % H=5.77:5.51; % N=12.02:1.90; % Cl$^-$=5.07:4.74

High-Resolution Mass Spectrometry (ESI+/HR, ESI−/LR):

Empirical formula: $C_{38}H_{39}FN_6O_4$

[M+H]$^+$ calculated: 663.3090

[M+H]$^+$ measured: 663.3084

Example 448. 5-(5-Chloro-2-{[(3S)-3-(morpholin-4-ylmethyl)-3,4-dihydroisoquinolin-2(1H)-yl]carbonyl}phenyl)-N-[5-cyano-1-(trideuteriomethyl)-1H-pyrrol-3-yl]-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 32" in Step C. The compound obtained is converted into salt form and lyophilised as described in the general process to obtain the title compound.

Elemental Microanalysis: (%, Theoretical:Measured)

% C=64.69:64.23; % H=5.45:5.47; % N=11.32:11.16; % Cl$^-$=4.77:4.56

High-Resolution Mass Spectrometry (ESI+/HR, ESI−/LR):

Empirical formula: $C_{40}H_{36}ClD_3N_6O_4$

[M+H]$^+$ calculated: 706.2982

[M+H]$^+$ measured: 706.2985

Example 449. 5-(5-Chloro-2-{[(3S)-3-(morpholin-4-ylmethyl)-3,4-dihydroisoquinolin-2(1H)-yl]carbonyl}phenyl)-N-[5-cyano-2-methyl-1-(trideuteriomethyl)-1H-pyrrol-3-yl]-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 33" in Step C. The compound obtained is converted into salt form and lyophilised as described in the general process to obtain the title compound.

Elemental Microanalysis: (%, Theoretical:Measured)
% C=65.07:64.55; % H=5.62:5.51; % N=11.11:10.98; % Cl⁻=4.68:4.58

High-Resolution Mass Spectrometry (ESI+/HR, ESI−/LR):
Empirical formula: $C_{41}H_{38}ClD_3N_6O_4$
[M+H]⁺ calculated: 720.3139
[M+H]⁺ measured: 720.3143

Example 450. 5-(5-Chloro-2-{[(3S)-3-(morpholin-4-ylmethyl)-3,4-dihydroisoquinolin-2(1H)-yl]carbonyl}phenyl)-N-(3-cyano-1-methyl-1H-pyrazol-5-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 34" in Step C. The compound obtained is converted into salt form and lyophilised as described in the general process to obtain the title compound.

Elemental Microanalysis: (%, Theoretical:Measured)
% C=63.24:62.62; % H=5.31:5.09; % N=13.24:13.04; % Cl⁻=4.79:4.37

High-Resolution Mass Spectrometry (ESI+/HR, ESI−/LR):
Empirical formula: $C_{39}H_{38}ClN_7O_4$
[M+H]⁺ calculated: 704.2747
[M+H]⁺ measured: 704.2747

Example 451. 5-(5-Fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(1-methyl-1H-pyrazolo[3,4-b]pyridin-5-yl)-1H-pyrrole-3-carboxamide hydrochloride The title compound is obtained in accordance with the process of Example 1 using the acid of Preparation 8 and the compound of Preparation 3' in Step A, and the compound of Preparation 17" in Step C. The compound obtained is converted into salt form and lyophilised as described in the general process to obtain the title compound.

Elemental Microanalysis: (%, Theoretical:Measured)
% C=65.64:66.28; % H=5.51:5.45; % N=13.07:12.17% Cl⁻=4.73:5.51

Example 452. N-(1,3-Dimethyl-1H-pyrazol-4-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride Elemental Microanalysis: (%, Theoretical:Measured)
% C=65.68:64.77; % H=5.94:5.55; % N=11.78:10.69% Cl⁻=4.97:6.48 and

Example 453. N-(1,5-Dimethyl-1H-pyrazol-4-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide hydrochloride Elemental Microanalysis: (%, Theoretical:Measured)
% C=65.68:65.43; % H=5.94:5.62; % N=11.78:10.95% Cl⁻=4.97:5.60

The compounds of Examples 452 and 453 are obtained in accordance with the process of Example 1 using the acid of Preparation 8 and the compound of Preparation 3' in Step A, and the mixture of Preparation 27" in Step C. At the end of Step D, the isomers are separated by preparative HPLC using acetonitrile and water-TFA as eluants. After evaporating off the solvent and neutralising with sodium bicarbonate, the products are subjected to a step of conversion into salt form in the presence of 1M HCl in ether. After filtration and lyophilisation in a mixture of acetonitrile/water, the title products are obtained.

Example 454. 5-(5-Chloro-2-{[3-(trifluoromethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide The title compound is obtained in accordance with the process of Example 1 using the acid from Preparation 1 and racemic 3-(trifluoromethyl)-1,2,3,4-tetrahydroisoquinoline in Step A, and the compound of Preparation 18" in Step C.

Elemental Microanalysis: (%, Theoretical:Measured)
% C=64.77:64.81; % H=4.55:4.52; % N=10.21:10.33
High-Resolution Mass Spectrometry (ESI+/HR):
Empirical formula: $C_{37}H_{31}ClF_3N_5O_3$
[M+H]⁺ calculated: 686.2140
[M+H]⁺ measured: 686.2145

Example 455. 5-(5-Chloro-2-{[(3R)-3-methyl-3,4-dihydroisoquinolin-2(1H)-yl]-carbonyl}phenyl)-N-{5-cyano-2-methyl-1-[2-(morpholin-4-yl)ethyl]-1H-pyrrol-3-yl}-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 1' in Step A, and the compound of Preparation 35" in Step C. The compound obtained is converted into salt form and lyophilised as described in the general process to obtain the title compound.

Elemental Microanalysis: (%, Theoretical:Measured)
% C=65.71:66.07; % H=5.78:5.82; % N=10.95:10.66; % Cl⁻=4.62:4.45
High-Resolution Mass Spectrometry (ESI+/HR, ESI−/LR):
Empirical formula: $C_{42}H_{43}ClN_6O_4$
[M+H]⁺ calculated: 731.3107
[M+H]⁺ measured: 731.3109

Example 456. 5-(5-Chloro-2-{[(3R)-3-methyl-3,4-dihydroisoquinolin-2(1H)-yl]-carbonyl}phenyl)-N-(4-hydroxyphenyl)-1,2-dimethyl-N-{2-[2-(morpholin-4-yl)-ethoxy]pyrimidin-5-yl}-1H-pyrrole-3-carboxamide hydrochloride The title compound is obtained in accordance with the process of Example 1 using the acid of Preparation 1 and the compound of Preparation 1' in Step A, and the compound of Preparation 36" in Step C. The compound obtained is converted into salt form and lyophilised as described in the general process to obtain the title compound.
Elemental Microanalysis: (%, Theoretical:Measured)
% C=63.41:63.51; % H=5.59:5.26; % N=11.09:11.10; % Cl⁻=4.68:4.46
High-Resolution Mass Spectrometry (ESI+/HR, ESI−/LR):
Empirical formula: $C_{40}H_{41}ClN_6O_5$
[M+H]⁺ calculated: 721.2900
[M+H]⁺ measured: 721.2907

Example 457. 5-(5-Chloro-2-{[(3S)-3-(morpholin-4-ylmethyl)-3,4-dihydroisoquinolin-2(1H)-yl]carbonyl}phenyl)-N-(6-cyano-5-methoxypyridin-2-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the appropriate amine in Step C. The compound obtained is converted into salt form and lyophilised as described in the general process to obtain the title compound.
Elemental Microanalysis: (%, Theoretical:Measured)
% C=64.15:63.95; % H=5.25:4.79; % N=10.95:10.97; % Cl⁻=4.62:4.22
High-Resolution Mass Spectrometry (ESI+/HR):
Empirical formula: $C_{41}H_{39}ClN_6O_5$
[M+H]⁺ calculated: 731.2743
[M+H]⁺ measured: 731.2746

Example 458. 5-(5-Chloro-2-{[(3S)-3-(morpholin-4-ylmethyl)-3,4-dihydroisoquinolin-2(1H)-yl]carbonyl}phenyl)-N-(5-cyano-1,4-dimethyl-1H-pyrrol-3-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 37" in Step C. The compound obtained is converted into salt form and lyophilised as described in the general process to obtain the title compound.
Elemental Microanalysis: (%, Theoretical:Measured)
% C=65.34:65.68; % H=5.62:5.31; % N=11.15:11.15; % Cl⁻=4.70:4.33
High-Resolution Mass Spectrometry (ESI+/HR, ESI−/LR):
Empirical formula: $C_{41}H_{41}ClN_6O_4$
[M+H]⁺ calculated: 717.2951
[M+H]⁺ measured: 717.2954

Example 459. 5-(5-Chloro-2-{[(3S)-3-(morpholin-4-ylmethyl)-3,4-dihydroisoquinolin-2(1H)-yl]carbonyl}phenyl)-N-(5-cyano-1-ethyl-2-methyl-1H-pyrrol-3-yl)-N-(4-hydroxyphenyl)-1,2-dimethyl-1H-pyrrole-3-carboxamide hydrochloride The title compound is obtained in accordance with the process of Example 1 using the acid of Preparation 1 and the compound of Preparation 3' in Step A, and the compound of Preparation 38" in Step C. The compound obtained is converted into salt form and lyophilised as described in the general process to obtain the title compound.
Elemental Microanalysis: (%, Theoretical:Measured)
% C=65.71;65.29; % H=5.78:5.51; % N=10.95:10.95; % Cl⁻=4.62:4.39
High-Resolution Mass Spectrometry (ESI+/HR, ESI−/LR):
Empirical formula: $C_{42}H_{43}ClN_6O_4$
[M+H]⁺ calculated: 731.3107
[M+H]⁺ measured: 731.3109

Example 460. 5-(5-Chloro-2-{[(3R)-3-[3-(morpholin-4-yl)propyl]-3,4-dihydroisoquinolin-2(1H)-yl]carbonyl}phenyl)-N-(4-hydroxyphenyl)-1,2-dimethyl-N-[1-(tetrahydrofuran-3-yl)-1H-pyrazol-4-yl]-1H-pyrrole-3-carboxamide hydrochloride The title compound is obtained in accordance with the process of Example 1 using the acid of Preparation 1 and the compound of Preparation 6' in Step A, and the compound of Preparation 22" in Step C. The compound obtained is converted into salt form and lyophilised as described in the general process to obtain the title compound.
Elemental Microanalysis: (%, Theoretical:Measured)
% C=64.58:64.24; % H=6.05:5.88; % N=10.51:10.53; % Cl⁻=4.43:4.39
High-Resolution Mass Spectrometry (ESI+/HR, ESI−/LR):
Empirical formula: $C_{43}H_{47}ClN_6O_5$
[M+H]⁺ calculated: 763.3369
[M+H]⁺ measured: 763.3371

Example 461. 5-(5-Chloro-2-{[(3R)-3-[3-(morpholin-4-yl)propyl]-3,4-dihydroiso-quinolin-2(1H)-yl]carbonyl}phenyl)-N-(5-cyano-1,2-dimethyl-1H-pyrrol-3-yl)-1,2-dimethyl-N-phenyl-1H-pyrrole-3-carboxamide hydrochloride The title compound is obtained in accordance with the process of Example 1 using the acid of Preparation 1 and the compound of Preparation 6' in Step A, and the compound of Preparation 29" in Step C, it being understood that Step D is not carried out. The compound obtained is converted into salt form and lyophilised as described in the general process to obtain the title compound.
Elemental Microanalysis: (%, Theoretical:Measured)
% C=67.44:66.68; % H=6.05:5.80; % N=10.97:10.95; % Cl⁻=4.63:4.57
High-Resolution Mass Spectrometry (ESI+/HR):
Empirical formula: $C_{43}H_{45}ClN_6O_3$
[M+H]⁺ calculated: 729.3314
[M+H]⁺ measured: 729.3316

Example 462. 5-(5-Chloro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-N-(5-methyl-1,2-oxazol-3-yl)-1H-pyrrole-3-carboxamide The title compound is obtained in accordance with the process of Example 1 using the acid of Preparation 1 and the compound of Preparation 3' in Step A, and the appropriate amine in Step C.

Elemental Microanalysis: (%, Theoretical:Measured)
% C=67.10:66.64; % H=5.63:5.40; % N=10.30:10.24
High-Resolution Mass Spectrometry (ESI+/HR, ESI−/LR):
Empirical formula: $C_{38}H_{38}ClN_5O_5$
$[M+H]^+$ calculated: 680.2634
$[M+H]^+$ measured: 680.2637

Example 463. N-(2-Ethoxypyrimidin-5-yl)-5-(5-fluoro-2-{[(3S)-3-(morpholin-4-ylmethyl)-3,4-dihydroisoquinolin-2(1H)-yl]carbonyl}phenyl)-N-(4-hydroxyphenyl)-1,2-dimethyl-1H-pyrrole-3-carboxamide The title compound is obtained in accordance with the process of Example 1 using the acid of Preparation 8 and the compound of Preparation 3' in Step A, and the compound of Preparation 39" in Step C.

Elemental Microanalysis: (%, Theoretical:Measured)
% C=68.17:67.52; % H=5.86:5.60; % N=11.92:11.43

Example 464. 5-(5-Chloro-2-{[(3S)-3-(morpholin-4-ylmethyl)-3,4-dihydroisoquirmlin-2(1H)-yl]carbonyl}phenyl)-N-(5-hydroxypyridin-2-yl)-1,2-dimethyl-N-(1-methyl-1H-pyrrolo[2,3-b]pyridin-5-yl)-1H-pyrrole-3-carboxamide dihydrochloride The title compound is obtained in accordance with the process of Example 1 using the acid of Preparation 1 and the compound of Preparation 3' in Step A, and the compound of Preparation 40" in Step C. The compound obtained is converted into salt form and lyophilised as described in the general process to obtain the title compound.

High-Resolution Mass Spectrometry (ESI+/HR, ESI−/LR):
Empirical formula: $C_{41}H_{40}ClN_7O_4$
$[M+H]^+$ calculated: 730.2903
$[M+H]^+$ measured: 730.2907

Example 465. 5-(4-Chloro-2-{[(3S)-3-(morpholin-4-ylmethyl)-3,4-dihydroisoquinolin-2(1H)-yl]carbonyl}phenyl)-N-(5-cyano-1,2-dimethyl-1H-pyrrol-3-yl)-N-(4-hydroxyphenyl)-1,2-dimethyl-1H-pyrrole-3-carboxamide hydrochloride The title compound is obtained in accordance with the process of Example 1 using the acid of Preparation 29 and the compound of Preparation 3' in Step A, and the compound of Preparation 18" in Step C. The compound obtained is converted into salt form and lyophilised as described in the general process to obtain the title compound.

Elemental Microanalysis: (%, Theoretical:Measured)
% C=65.34:64.81; % H=5.62:5.27; % N=11.15:10.95% Cl−=4.70:5.09
High-Resolution Mass Spectrometry (ESI+):
Empirical formula: $C_{41}H_{41}ClN_6O_4$
$[M+H]^+$ calculated: 717.2951
$[M+H]^+$ measured: 717.2952

Example 466. 5-(4-Chloro-2-{[(3S)-3-(morpholin-4-ylmethyl)-3,4-dihydroisoquinolin-2(1H)-yl]carbonyl}phenyl)-N-(4-hydroxyphenyl)4,2-dimethyl-N-(1-methyl-1H-pyrazol-4-yl)-1H-pyrrole-3-carboxamide hydrochloride The title compound is obtained in accordance with the process of Example 1 using the acid of Preparation 29 and the compound of Preparation 3' in Step A, and the compound of Preparation 1" in Step C. The compound obtained is converted into salt form and lyophilised as described in the general process to obtain the title compound.

Elemental Microanalysis: (%, Theoretical:Measured)
% C=66.77:62.82; % H=5.63:5.29; % N=11.74:11.75; % Cl−=5.01:5.23
High-Resolution Mass Spectrometry (ESI+/HR, ESI−/LR):
Empirical formula: $C_{38}H_{39}ClN_6O_4$
$[M+H]^+$ calculated: 679.2794
$[M+H]^+$ measured: 679.2796

Example 467. 5-(5-Chloro-2-{[3,4-dihydroisoquinolin-2(1H)-yl]carbonyl}phenyl)-N-(4-hydroxyphenyl)-1,2-dimethyl-N-phenyl-1H-pyrrole-3-carboxamide The title compound is obtained in accordance with the process of Example 1 using the acid of Preparation 1 and 1,2,3,4-tetrahydroisoquinoline in Step A, and the compound of Preparation 2" in Step C.

Elemental Microanalysis: (%, Theoretical:Measured)
% C=72.97:72.93; % H=5.25:5.08; % N=7.29:7.34
High-Resolution Mass Spectrometry (ESI/FIA/HR and MS/MS):
Empirical formula: $C_{35}H_{30}ClN_3O_3$
$[M+H]^+$ calculated: 576.2048
$[M+H]^+$ measured: 576.2067

PHARMACOLOGICAL STUDY

EXAMPLE A

Inhibition of Bcl-2 by the Fluorescence Polarisation Technique

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of $2.50 \times 10^{-8}$M, is mixed with a fluorescent peptide (Fluorescein-REIGAQLRRMADDLNAQY), at a final concentration of $1.00 \times 10^{-8}$M in a buffer solution (Hepes 10 mM, NaCl 150 mM, Tween20 0.05%, pH 7.4), in the presence or absence of increasing concentrations of test compounds. After incubation for 2 hours, the fluorescence polarisation is measured.

The results are expressed in $IC_{50}$ (the concentration of compound that inhibits fluorescence polarisation by 50%) and are presented in Table 1 below.

The results show that the compounds of the invention inhibit interaction between the Bcl-2 protein and the fluorescent peptide described hereinbefore.

EXAMPLE B

In Vitro Cytotoxicity

The cytotoxicity studies were carried out on the RS4;11 leukaemia tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Bcl-2 inhibition (fluorescence polarisation test) and of cytotoxicity for RS4; 11 cells

|  | $IC_{50}$ (nM) Bcl-2 FP | $IC_{50}$ (nM) MTT RS4; 11 |
| --- | --- | --- |
| Example 1 | 5.0 | 33.6 |
| Example 2 | ND | 1660 |
| Example 3 | 24.6 | 94.9 |
| Example 4 | ND | 231 |
| Example 5 | 21.2 | 44.8 |
| Example 6 | 25.2 | 69 |
| Example 7 | 25.6 | 90.6 |
| Example 8 | ND | 255 |
| Example 9 | 22.4 | 87.5 |
| Example 10 | 16.2 | 205 |
| Example 11 | 14.2 | 202 |
| Example 12 | 5.5 | 39.6 |
| Example 13 | 4.4 | 19.8 |
| Example 14 | 3.7 | 8.23 |
| Example 15 | 11.1 | 69.4 |
| Example 16 | 12.6 | 22.7 |
| Example 17 | 8.0 | 75.2 |
| Example 18 | 3.9 | 27.6 |
| Example 19 | 6.0 | 65.5 |
| Example 20 | 4.9 | 164 |
| Example 21 | 4.7 | 79.9 |
| Example 22 | 6.6 | 45.7 |
| Example 23 | 3.6 | 25.4 |
| Example 24 | 6.2 | 79.1 |
| Example 25 | 4.0 | 33.3 |
| Example 26 | 4.1 | 541 |
| Example 27 | 5.2 | 93.4 |
| Example 28 | 7.5 | 95.3 |
| Example 29 | 6.6 | 47.5 |
| Example 30 | 4.7 | 771 |
| Example 31 | 7.2 | 89.3 |
| Example 32 | 13.3 | 240 |
| Example 33 | 10.9 | 57.8 |
| Example 34 | 8.2 | 47 |
| Example 35 | 50.0 | 560 |
| Example 36 | 71.4 | >600 |
| Example 37 | 60.4 | >600 |
| Example 38 | 7.5 | 134 |
| Example 39 | 7.2 | 19.7 |
| Example 40 | 64.4 | 431 |
| Example 41 | 10.0 | 22.6 |
| Example 42 | 5.2 | 4.36 |
| Example 43 | 5.1 | 28.9 |
| Example 44 | 3.0 | 5.41 |
| Example 45 | 38.9 | 403 |
| Example 46 | 76.6 | >600 |
| Example 47 | 5.9 | 44.5 |
| Example 48 | 4.4 | 14.9 |
| Example 49 | 4.0 | 14.1 |

TABLE 1-continued $IC_{50}$ of Bcl-2 inhibition (fluorescence polarisation test) and of cytotoxicity for RS4; 11 cells

|  | $IC_{50}$ (nM) Bcl-2 FP | $IC_{50}$ (nM) MTT RS4; 11 |
| --- | --- | --- |
| Example 50 | 5.9 | 33.1 |
| Example 51 | 26.7 | 354 |
| Example 52 | 28.9 | 433 |
| Example 53 | 43.5 | 293 |
| Example 54 | 18.0 | 30.5 |
| Example 55 | 209.6 | >600 |
| Example 56 | 75.0 | >600 |
| Example 57 | 80.0 | >600 |
| Example 58 | 133.3 | >600 |
| Example 59 | 134.0 | >600 |
| Example 60 | ND | 18.3 |
| Example 61 | 4.5 | 37.8 |
| Example 62 | 14.3 | 127 |
| Example 63 | 5.1 | 11.2 |
| Example 65 | 21.9 | 113 |
| Example 66 | 16.9 | 241 |
| Example 67 | 12.5 | 98.6 |
| Example 68 | 2.1 | 20.7 |
| Example 69 | 5.3 | 3.68 |
| Example 70 | 8.5 | 63.5 |
| Example 71 | 6.1 | 12.9 |
| Example 72 | 7.7 | 43.6 |
| Example 73 | 8 | 42.6 |
| Example 74 | 4 | 45.4 |
| Example 75 | 52.9 | 367 |
| Example 81 | ND | 249 |
| Example 82 | 19.5 | 427 |
| Example 88 | 15.9 | 69.6 |
| Example 92 | 8.4 | 37.8 |
| Example 93 | 19.7 | 368 |
| Example 94 | 8.6 | 104 |
| Example 95 | 7 | 174 |
| Example 96 | 13.5 | 161 |
| Example 97 | 19 | 98 |
| Example 98 | 7.6 | 68.3 |
| Example 99 | 6.4 | 108 |
| Example 100 | 22.9 | 193 |
| Example 101 | 21.1 | 743 |
| Example 102 | 2 | 6.51 |
| Example 108 | 3.9 | 15.4 |
| Example 109 | 91.5 | 930 |
| Example 110 | 8.5 | 39.5 |
| Example 115 | 3.6 | 18.3 |
| Example 116 | 3.4 | 47.8 |
| Example 122 | 3.4 | 82.4 |
| Example 126 | 4.2 | 49.2 |
| Example 127 | 5.3 | 111 |
| Example 129 | 18.1 | 275 |
| Example 207 | 4.6 | 32.2 |
| Example 209 | 7.4 | 25.4 |
| Example 210 | 8.8 | 47.2 |
| Example 214 | 6.3 | 236 |
| Example 230 | 5.1 | 18.3 |
| Example 358 | 14.8 | 165 |
| Example 384 | 9.7 | 216 |
| Example 385 | 5.7 | 28.7 |
| Example 386 | 2.6 | 9.23 |
| Example 387 | 20.6 | 243 |
| Example 388 | 3.6 | 16.5 |
| Example 389 | 14.7 | 208 |
| Example 390 | 21.2 | 173 |
| Example 391 | 30.3 | 255 |
| Example 392 | 3.8 | 11.4 |
| Example 393 | 2.1 | 1.95 |
| Example 394 | 2.5 | 2.76 |
| Example 395 | 3.5 | 7.57 |
| Example 396 | 15.7 | 116 |
| Example 397 | 4.5 | 37.1 |
| Example 398 | 3.9 | 13.4 |
| Example 399 | 9.9 | 155 |
| Example 400 | 49 | 469 |
| Example 401 | 8 | 24.3 |
| Example 402 | 26.1 | 241 |
| Example 403 | 24.2 | 289 |
| Example 404 | 24.4 | 85.5 |

TABLE 1-continued

IC$_{50}$ of Bcl-2 inhibition (fluorescence polarisation test) and of cytotoxicity for RS4; 11 cells

| | IC$_{50}$ (nM) Bcl-2 FP | IC$_{50}$ (nM) MTT RS4; 11 |
|---|---|---|
| Example 406 | 4.2 | 10.6 |
| Example 407 | 20.6 | 150 |
| Example 408 | 5.4 | 4.46 |
| Example 409 | 12.2 | 41.9 |
| Example 410 | 9.9 | 61.6 |
| Example 411 | 5.5 | 32.8 |
| Example 412 | 3.1 | 0.398 |
| Example 413 | 3.1 | 9.43 |
| Example 414 | 3.8 | 29.9 |
| Example 416 | 2.9 | 42.5 |
| Example 417 | 3 | 11 |
| Example 418 | 10.1 | 159 |
| Example 419 | 2.8 | 15.8 |
| Example 420 | 6.1 | 51.8 |
| Example 421 | 2.5 | 3.73 |
| Example 422 | 9.2 | 101 |
| Example 423 | 11.7 | 344 |
| Example 424 | 13.6 | 102 |
| Example 425 | 4.2 | 62 |
| Example 426 | 5.2 | 139 |
| Example 427 | 2.2 | 23.3 |
| Example 428 | 3.5 | 59.2 |
| Example 429 | 3.1 | 109 |
| Example 430 | 19.9 | 328 |
| Example 431 | 3 | 89 |
| Example 432 | 3.4 | 76.6 |
| Example 433 | 2.6 | 48.2 |
| Example 434 | 3.5 | 45.7 |
| Example 435 | 14.9 | 441 |
| Example 436 | 49.1 | 338 |
| Example 437 | 4.4 | 70.5 |
| Example 438 | 11.3 | 379 |
| Example 439 | 6.1 | 329 |
| Example 440 | 2.6 | 13.6 |
| Example 441 | 3.5 | 132 |
| Example 442 | 3 | 42.8 |
| Example 443 | ND | 57.9 |
| Example 444 | 5.5 | 181 |
| Example 445 | 2 | 19 |
| Example 446 | 7.8 | 249 |
| Example 447 | 20 | >600 |
| Example 448 | 2.4 | 12.1 |
| Example 449 | 1.7 | 11.9 |
| Example 450 | 2.7 | 53.2 |
| Example 451 | 2.9 | 102 |
| Example 452 | 8.3 | 112 |
| Example 453 | 6.9 | 99.9 |
| Example 454 | 6.5 | 158 |
| Example 455 | 1.9 | 11.8 |
| Example 456 | 2.7 | 80.6 |
| Example 457 | ND | 80.4 |
| Example 458 | 10.5 | 197 |
| Example 459 | 2.5 | 5.93 |
| Example 460 | 2.8 | 22.9 |
| Example 461 | 3.1 | 18.6 |
| Example 462 | 13.3 | 368 |
| Example 463 | ND | 40.8 |
| Example 464 | 36.6 | 723 |
| Example 465 | ND | 50.6 |
| Example 466 | ND | 493 |
| Example 467 | 19.2 | 188 |

ND: not determined

EXAMPLE C

Induction of Caspase Activity In Vivo

The ability of the compounds of the invention to activate caspase 3 is evaluated in a xenograft model of RS4;11 leukaemia cells.

1×10$^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities: the activity for the treated mice divided by the activity for the control mice.

The results obtained show that the compounds of the invention are capable of inducing apoptosis in RS4;11 tumour cells in vivo.

EXAMPLE D

Quantification of the Cleaved Form of Caspase 3 In Vivo

The ability of the compounds of the invention to activate caspase 3 is evaluated in a xenograft model of RS4;11 leukaemia cells.

1×10$^7$ RS4;11 cells are grafted sub-cutaneously into immunosuppressed mice (SCID strain). 25 to 30 days after the graft, the animals are treated orally with the various compounds. After treatment, the tumour masses are recovered and lysed, and the cleaved (activated) form of caspase 3 is quantified in the tumour lysates.

The quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of the invention are capable of inducing apoptosis in RS4;11 tumour cells in vivo.

TABLE 2

Caspase activation factors (cleaved caspase 3 MSD test in the tumours of treated mice versus control mice) in vivo, after treatment by the oral route (exact doses in brackets)

| Compound tested | Time period after which the tumour is removed (T) | Activation factor ± SEM (versus control) |
|---|---|---|
| Example 25 | 2 hours | 45.7 ± 2.0 (25 mg/kg) |
| Example 28 | 2 hours | 72.3 ± 5.4 (12.5 mg/kg) |
| Example 47 | 2 hours | 12.3 ± 2.4 (25 mg/kg) |
| Example 61 | 2 hours | 76.0 ± 5.2 (12.5 mg/kg) |
| Example 67 | 2 hours | 29.8 ± 4.0 (25 mg/kg) |
| Example 71 | 2 hours | 46.8 ± 16.1 (25 mg/kg) |
| Example 74 | 2 hours | 24.5 ± 7.4 (12.5 mg/kg) |
| Example 108 | 2 hours | 22.6 ± 2.4 (12.5 mg/kg) |
| Example 230 | 2 hours | 42.2 ± 9.3 (25 mg/kg) |
| Example 386 | 2 hours | 52.0 ± 8.6 (12.5 mg/kg) |
| Example 388 | 2 hours | 85.7 ± 3.7 (25 mg/kg) |
| Example 421 | 2 hours | 38.7 ± 10.7 (12.5 mg/kg) |
| Example 449 | 2 hours | 50.5 ± 3.4 (12.5 mg/kg) |

EXAMPLE E

Anti-Tumour Activity In Vivo

The anti-tumour activity of the compounds of the invention is evaluated in a xenograft model of RS4;11 leukaemia cells.

$1\times10^7$ RS4;11 cells are grafted sub-cutaneously into immunosuppressed mice (SCID strain). 25 to 30 days after the graft, when the tumour mass has reached about 150 mm$^3$, the mice are treated orally with the various compounds in two different regimes (daily treatment for five days per week for two weeks, or two treatments weekly for two weeks). The tumour mass is measured twice weekly from the start of treatment.

The results obtained accordingly show that the compounds of the invention are capable of inducing significant tumour regression, which can be total, during the treatment period.

EXAMPLE F

Pharmaceutical Composition: Tablets

| 1000 tablets containing a dose of 5 mg of a compound selected from Examples 1 to 467 | 5 g |
|---|---|
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A process for the preparation of a compound of formula (I):

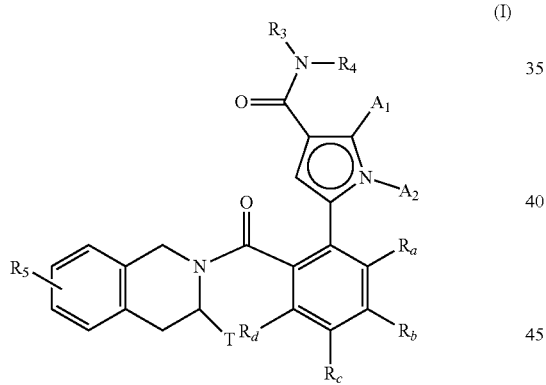

wherein:
- $A_1$ and $A_2$, each independently of the other, represent a hydrogen atom, a halogen atom, a linear or branched ($C_1$-$C_6$)polyhaloalkyl group, a linear or branched ($C_1$-$C_6$)alkyl group or a cycloalkyl group;
- T represents a hydrogen atom, a linear or branched ($C_1$-$C_6$)alkyl group optionally substituted by from one to three halogen atoms, a ($C_1$-$C_4$)alkyl-$NR_1R_2$ group, or a ($C_1$-$C_4$)alkyl-$OR_6$ group;
- $R_1$ and $R_2$, each independently of the other, represent a hydrogen atom or a linear or branched ($C_1$-$C_6$)alkyl group,
or $R_1$ and $R_2$ form with the nitrogen atom carrying them a heterocycloalkyl;
- $R_3$ represents a linear or branched ($C_1$-$C_6$)alkyl group, a linear or branched ($C_2$-$C_6$)alkenyl group, a linear or branched ($C_2$-$C_6$)alkynyl group, a cycloalkyl group, a ($C_3$-$C_{10}$)cycloalkyl-($C_1$-$C_6$)alkyl group wherein the alkyl moiety is linear or branched, a heterocycloalkyl group, an aryl group or a heteroaryl group, wherein one or more of the carbon atoms of the preceding groups, or of their possible substituents, may be deuterated;
- $R_4$ represents an aryl group, a heteroaryl group, a cycloalkyl group or a linear or branched ($C_1$-$C_6$) alkyl group, wherein one or more of the carbon atoms of the preceding groups, or of their possible substituents, may be deuterated;
- $R_5$ represents a hydrogen or halogen atom, a linear or branched ($C_1$-$C_6$)alkyl group, or a linear or branched ($C_1$-$C_6$)alkoxy group;
- $R_6$ represents a hydrogen atom or a linear or branched ($C_1$-$C_6$)alkyl group;
- $R_a$, $R_b$, $R_c$ and $R_d$, each independently of the others, represent a hydrogen atom, a linear or branched ($C_1$-$C_6$)alkyl group, a linear or branched ($C_2$-$C_6$) alkenyl group, a linear or branched ($C_2$-$C_6$)alkynyl group, an aryl group, a heteroaryl group, a halogen atom, a linear or branched ($C_1$-$C_6$)alkoxy group, a hydroxy group, a linear or branched ($C_1$-$C_6$)polyhaloalkyl group, a trifluoromethoxy group, —$NR_7R_7'$, nitro, $R_7$—CO—($C_0$-$C_6$)alkyl-, $R_7$—CO—NH—($C_0$-$C_6$)alkyl-, $NR_7R_7'$—CO—($C_0$-$C_6$)alkyl-, $NR_7R_7'$—CO—($C_0$-$C_6$)alkyl-O—, $R_7$—SO$_2$—NH—($C_0$-$C_6$) alkyl-, $R_7$—NH—CO—NH—($C_0$-$C_6$)alkyl-, $R_7$—O—CO—NH—($C_0$-$C_6$)alkyl-, a heterocycloalkyl group, or the substituents of one of the pairs ($R_a$,$R_b$), ($R_b$,$R_c$), or ($R_c$,$R_d$) form together with the carbon atoms carrying them a ring composed of from 5 to 7 ring members, which ring may have from one to 2 hetero atoms selected from oxygen and sulphur, wherein one or more carbon atoms of the ring defined hereinbefore may be deuterated or substituted by from one to 3 groups selected from halogen and linear or branched ($C_1$-$C_6$)alkyl;
- $R_7$ and $R_7'$, each independently of the other, represent a hydrogen atom, a linear or branched ($C_1$-$C_6$)alkyl group, a linear or branched ($C_2$-$C_6$)alkenyl group, a linear or branched ($C_2$-$C_6$)alkynyl group, an aryl group or a heteroaryl group, or $R_7$ and $R_7'$, together with the nitrogen atom carrying them, form a heterocycle composed of from 5 to 7 ring members;

it being understood that:
- "aryl" means a phenyl, naphthyl, biphenyl or indenyl group,
- "heteroaryl" means any mono- or bi-cyclic group composed of from 5 to 10 ring members, having at least one aromatic moiety and having from 1 to 4 hetero atoms selected from oxygen, sulphur and nitrogen (including quaternary nitrogens),
- "cycloalkyl" means any mono- or bi-cyclic, non-aromatic, carbocyclic group having from 3 to 10 ring members,
- "heterocycloalkyl" means any mono- or bi-cyclic, non-aromatic, condensed or spiro group composed of from 3 to 10 ring members and having from 1 to 3 hetero atoms selected from oxygen, sulphur, SO, SO$_2$ and nitrogen, wherein the aryl, heteroaryl, cycloalkyl and heterocycloalkyl groups so defined and the alkyl, alkenyl, alkynyl and alkoxy groups may be optionally substituted by from 1 to 3 groups selected from optionally substituted, linear or branched ($C_1$-$C_6$)alkyl, ($C_3$-$C_6$) spiro, optionally substituted, linear or branched ($C_1$-$C_6$)alkoxy, ($C_1$-$C_6$)alkyl-S-, hydroxy, oxo (or N-oxide where appropriate), nitro, cyano, —COOR', —OCOR', NR'R", linear or branched (C$_1$-C$_6$)polyhaloalkyl, trifluoromethoxy, (C$_1$-C$_6$)alkylsulphonyl, halogen, optionally substituted aryl, heteroaryl, aryloxy, arylthio, cycloalkyl, heterocycloalkyl optionally substituted by one or more halogen atoms or alkyl groups, wherein R' and R", each independently of the other, represent a hydrogen atom or an optionally substituted, linear or branched (C$_1$-C$_6$)alkyl group, or an enantiomer, a diastereoisomer, or an addition salt thereof with a pharmaceutically acceptable acid or base, which process comprises subjecting a compound of formula (II)

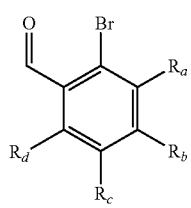

(II)

to a Heck reaction in an aqueous or organic medium, in the presence of a palladium catalyst, a base, a phosphine and a compound of formula (III):

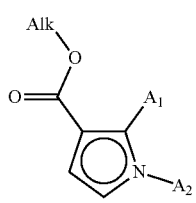

(III)

wherein Alk represents a linear or branched (C$_1$-C$_6$)alkyl, to obtain the compound of formula (IV):

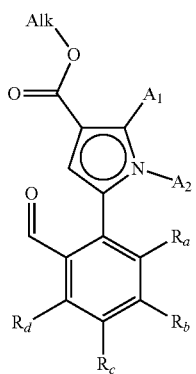

(IV)

the aldehyde function of which compound of formula (IV) is oxidized to a carboxylic acid to form a compound of formula (V):

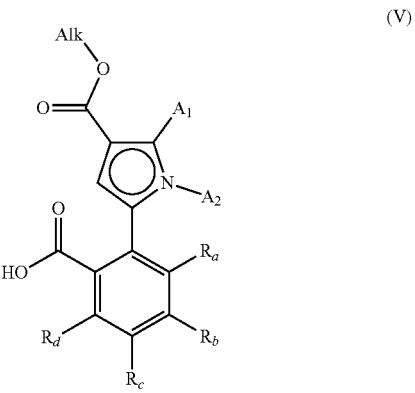

(V)

which compound of formula (V) is then subjected to peptide coupling with a compound of formula (VI):

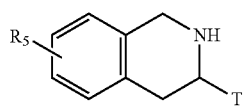

(VI)

to yield a compound of formula (VII):

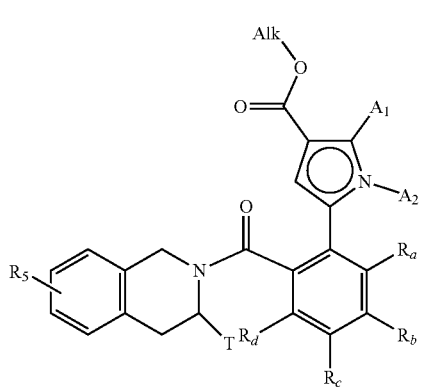

(VII)

the ester function of which compound of formula (VII) is hydrolyzed to yield the corresponding carboxylic acid or carboxylate, which may be converted into an acid derivative, including an acyl chloride or anhydride, which compound is then coupled with an amine NHR$_3$R$_4$, to yield the compound of formula (I), which compound of formula (I) may be purified according to a conventional separation technique, which is converted, if desired, into its addition salts with a pharmaceutically acceptable acid or base and which is optionally separated into its isomers according to a conventional separation technique, wherein, at any time considered appropriate in the course of the above-described process, certain groups of the reagents or intermediates of synthesis may be protected and then deprotected according to the requirements of synthesis.

2. The process according to claim 1, wherein one of the groups $R_3$ or $R_4$ of the amine $NHR_3R_4$ is substituted by a hydroxy function, which hydroxyl function is subjected to a protection reaction prior to any coupling with the carboxylic acid formed from the compound of formula (VII), or with a corresponding acid derivative thereof, and wherein the resulting protected compound of formula (I) undergoes a deprotection reaction and is then optionally converted into one of its addition salts with a pharmaceutically acceptable acid or base.

3. The process according to claim 1, wherein $A_1$ represents a hydrogen atom or a methyl group.

4. The process according to claim 1, wherein $A_2$ represents a linear or branched $(C_1-C_6)$alkyl group optionally substituted by a group selected from halogen, hydroxy, linear or branched $(C_1-C_6)$alkoxy, NR'R" and morpholine.

5. The process according to claim 1, wherein $A_2$ represents a linear or branched $(C_1-C_6)$polyhaloalkyl group or a cyclopropyl group.

6. The process according to claim 1, wherein $A_1$ and $A_2$ both represent a methyl group.

7. The process according to claim 1, wherein T represents methyl, aminomethyl, (morpholin-4-yl)methyl, (4-methylpipérazin-1-yl)methyl, 2-(morpholin-4-yl)ethyl, [2-(morpholin-4-yl)ethoxy]methyl, hydroxymethyl, [2-(dimethylamino)ethoxy]methyl, hexahydropyrazino[2, 1-c][1,4] oxazin-8 (1H)-ylmethyl, 1-oxa-6-azaspiro [3.3]hept-6-ylmethyl, 3-(morpholin-4-yl)propyl or trifluoromethyl.

8. The process according to claim 1, wherein $R_a$ and $R_d$ each represent a hydrogen atom and ($R_b,R_c$), together with the carbon atoms carrying them, form a 1,3-dioxolane group or a 1,4-dioxane group; or $R_a$, $R_c$ and $R_d$ each represent a hydrogen atom and $R_b$ represents a hydrogen atom, a halogen atom, or a methoxy group.

9. The process according to claim 1, wherein $R_a$ and $R_d$ each represent a hydrogen atom, $R_b$ represents a hydrogen or halogen atom and $R_c$ represents a hydroxy or methoxy group; or $R_a$ and $R_d$ each represent a hydrogen atom, $R_b$ represents a hydroxy or methoxy group and $R_c$ represents a halogen atom.

10. The process according to claim 1, wherein $R_a$, $R_b$ and $R_d$ each represent a hydrogen atom and $R_c$ represents a group selected from $R_7$—CO—NH—$(C_0-C_6)$alkyl-, $R_7$—$SO_2$—NH—$(C_0-C_6)$alkyl-, $R_7$—NH—CO—NH—$(C_0-C_6)$alkyl- and $R_7$—O—CO—NH—$(C_0-C_6)$alkyl-.

11. The process according to claim 1, wherein $R_4$ represents phenyl, 4-hydroxyphenyl, 3-fluoro-4-hydroxyphenyl, 2-hydroxypyrimidine or 3-hydroxypyridine.

12. The process according to claim 1, wherein $R_3$ represents an aryl or heteroaryl group.

13. The process according to claim 1, wherein $R_3$ represents a group selected from methyl, phenyl, 1H-pyrazole, 1H-indole, 1H-indazole, pyridine, pyrimidine, 1H-pyrrolo[2,3-b]pyridine, 2,3-dihydro-1H-pyrrolo[2,3-b]pyridine, 1H-benzimidazole, 1H-pyrrole, 1H-pyrrolo[2,3-c]pyridine, 1H-pyrrolo[3,2-b]pyridine, 5H-pyrrolo[3,2-d]pyrimidine, thiophene, pyrazine, 1H-pyrazolo[3,4-b]pyridine, 1,2-oxazole, and 1H-pyrazolo[1,5-a]pyrimidine, those groups optionally having one or more substituents selected from halogen, linear or branched $(C_1-C_6)$alkyl, linear or branched $(C_1-C_6)$alkoxy, cyano, cyclopropyl, oxetane, tetrahydrofuran, —CO—O—$CH_3$, trideuteriomethyl, 2-(morpholin-4-yl)ethyl and 2-(morpholin-4-yl)ethoxy.

14. The process according to claim 11, wherein $R_3$ represents a linear or branched $(C_1-C_6)$alkyl or a heteroaryl optionally substituted by a linear or branched $(C_1-C_6)$alkyl, and $R_4$ represents a 4-hydroxyphenyl group.

15. The process according to claim 1, wherein the compound of formula (I) is selected from:

5-(5-chloro-2-{[(3S)-3-(morpholin-4-ylmethyl)-3,4-dihydroisoquinolin-2(1H)-yl]-carbonyl}phenyl)-N-(4-hydroxyphenyl)-1,2-dimethyl-N-(1-methyl-1H-pyrazol-4-yl)-1H-pyrrole-3-carboxamide, 5-(5-chloro-2-{[(3R)-3-methyl-3,4-dihydroisoquinolin-2(1H)-yl]carbonyl}phenyl)-N-(4-hydroxyphenyl)-1,2-dimethyl-N-(pyridin-4-yl)-1H-pyrrole-3-carboxamide, N-(4-hydroxyphenyl)-1,2-dimethyl-N-(1-methyl-1H-pyrazol-4-yl)-5-(6-{[(3S)-3-(morpholin-4-ylmethyl)-3,4-dihydroisoquinolin-2(1H)-yl]carbonyl}-1,3-benzodioxol-5-yl)-1H-pyrrole-3-carboxamide, N-(4-hydroxyphenyl)-1,2-dimethyl-5-(6-{[(3R)-3-methyl-3,4-dihydroisoquinolin-2(1H)-yl]carbonyl}-1,3-benzodioxol-5-yl)-N-(pyridin-4-yl)-1H-pyrrole-3-carboxamide, 5-(5-fluoro-2-{[(3S)-3-(morpholin-4-ylmethyl)-3,4-dihydroisoquinolin-2(1H)-yl]-carbonyl}phenyl)-N-(4-hydroxyphenyl)-1,2-dimethyl-N-(1-methyl-1H-pyrazol-4-yl)-1H-pyrrole-3-carboxamide, 5-(5-chloro-2-{[(3S)-3-(morpholin-4-ylmethyl)-3,4-dihydroisoquinolin-2(1H)-yl]-carbonyl}phenyl)-N-(4-hydroxyphenyl)-1,2-dimethyl-N-(1-methyl-1H-pyrrolo[2,3-b]pyridin-5-yl)-1H-pyrrole-3-carboxamide, 5-(5-chloro-2-{[(3S)-3-(morpholin-4-ylmethyl)-3,4-dihydroisoquinolin-2(1H)-yl]-carbonyl}phenyl)-N-(4-hydroxyphenyl)-1,2-dimethyl-N-(pyridin-4-yl)-1H-pyrrole-3-carboxamide, 5-(5-chloro-2-{[(3S)-3-(morpholin-4-ylmethyl)-3,4-dihydroisoquinolin-2(1H)-yl]-carbonyl}phenyl)-N-(5-cyano-1-methyl-1H-pyrrol-3-yl)-N-(4-hydroxyphenyl)-1,2-dimethyl-1H-pyrrole-3-carboxamide, N-(5-cyano-1-methyl-1H-pyrrol-3-yl)-5-(5-fluoro-2-{[(3S)-3-(morpholin-4-yl-methyl)-3,4-dihydroisoquinolin-2(1H)-yl]carbonyl}phenyl)-N-(4-hydroxyphenyl)-1,2-dimethyl-1H-pyrrole-3-carboxamide, 5-(5-chloro-2-{[(3S)-3-(morpholin-4-ylmethyl)-3,4-dihydroisoquinolin-2(1H)-yl]-carbonyl}phenyl)-N-(5-cyano-1,2-dimethyl-1H-pyrrol-3-yl)-N-(4-hydroxyphenyl)-1,2-dimethyl-1H-pyrrole-3-carboxamide, 5-(5-chloro-2-{[(3S)-3-(morpholin-4-ylmethyl)-3,4-dihydroisoquinolin-2(1H)-yl]-carbonyl}phenyl)-N-(4-hydroxyphenyl)-1,2-dimethyl-N-(1-methyl-2,3-dihydro-1H-pyrrolo[2,3-b]pyridin-5-yl)-1H-pyrrole-3-carboxamide, N-(5-cyano-1,2-dimethyl-1H-pyrrol-3-yl)-5-(5-fluoro-2-{[(3S)-3-(morpholin-4-yl-methyl)-3,4-dihydroisoquinolin-2(1H)-yl]carbonyl}phenyl)-N-(4-hydroxyphenyl)-1,2-dimethyl-1H-pyrrole-3-carboxamide, and 5-(5-chloro-2-{[(3S)-3-(morpholin-4-ylmethyl)-3,4-dihydroisoquinolin-2(1H)-yl]-carbonyl}phenyl)-N-[5-cyano-2-methyl-1-(trideuteriomethyl)-1H-pyrrol-3-yl]-N-(4-hydroxyphenyl)-1,2-dimethyl-1H-pyrrole-3-carboxamide, or an enantiomer, a diastereoisomer, or an addition salt thereof with a pharmaceutically acceptable acid or base.

\* \* \* \* \*

UNITED STATES PATENT AND TRADEMARK OFFICE
CERTIFICATE OF CORRECTION

PATENT NO. : 10,688,101 B2
APPLICATION NO. : 16/271171
DATED : June 23, 2020
INVENTOR(S) : Arnaud Le Tiran et al.

It is certified that error appears in the above-identified patent and that said Letters Patent is hereby corrected as shown below:

On the Title Page

Item (73):
Column 1, under "Assignee": Laboratories should read Laboratoires.

Signed and Sealed this
Twenty-fifth Day of August, 2020

Andrei Iancu
*Director of the United States Patent and Trademark Office*